US012590166B2

(12) United States Patent
Fan et al.

(10) Patent No.: US 12,590,166 B2
(45) Date of Patent: \*Mar. 31, 2026

(54) CD20 BINDING MOLECULES AND USES THEREOF

(71) Applicants: Legend Biotech Ireland Limited, Dublin (IE); Legend Biotech USA Inc., Somerset, NJ (US)

(72) Inventors: Xiaohu Fan, Edmonton (CA); Zhe Zhou, Nanjing (CN); Qiuchuan Zhuang, Nanjing (CN); Xu Fang, Nanjing (CN); Hongbo Pan, Nanjing (CN); Min Wei, Nanjing (CN); Jianrui Zhu, Nanjing (CN)

(73) Assignees: Legend Biotech Ireland Limited, Dublin (IE); Legend Biotech USA Inc., Somerset, NJ (US)

( * ) Notice: Subject to any disclaimer, the term of this patent is extended or adjusted under 35 U.S.C. 154(b) by 551 days.

This patent is subject to a terminal disclaimer.

(21) Appl. No.: 18/015,690

(22) PCT Filed: Jul. 16, 2021

(86) PCT No.: PCT/CN2021/106886
§ 371 (c)(1),
(2) Date: Jan. 11, 2023

(87) PCT Pub. No.: WO2022/012680
PCT Pub. Date: Jan. 20, 2022

(65) Prior Publication Data
US 2023/0272104 A1 Aug. 31, 2023

(30) Foreign Application Priority Data
Jul. 16, 2020 (WO) ................ PCT/CN2020/102463

(51) Int. Cl.
| | |
|---|---|
| *C07K 16/28* | (2006.01) |
| *A61K 40/11* | (2025.01) |
| *A61K 40/31* | (2025.01) |
| *A61K 40/42* | (2025.01) |
| *A61P 35/00* | (2006.01) |
| *C07K 14/725* | (2006.01) |
| *C12N 5/0783* | (2010.01) |

(52) U.S. Cl.
CPC .......... *C07K 16/2887* (2013.01); *A61K 40/11* (2025.01); *A61K 40/31* (2025.01); *A61K 40/4221* (2025.01); *A61P 35/00* (2018.01); *C07K 14/7051* (2013.01); *C12N 5/0636* (2013.01); *A61K 2239/31* (2023.05); *A61K 2239/38* (2023.05); *A61K 2239/48* (2023.05); *C07K 2317/20* (2013.01); *C07K 2317/565* (2013.01); *C07K 2317/569* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| RE30,985 E | 6/1982 | Cartaya | |
| 4,496,689 A | 1/1985 | Mitra | |
| 4,526,938 A | 7/1985 | Churchill et al. | |
| 4,560,655 A | 12/1985 | Baker | |
| 4,640,835 A | 2/1987 | Shimizu et al. | |
| 4,657,760 A | 4/1987 | Kung et al. | |
| 4,657,866 A | 4/1987 | Kumar | |
| 4,670,417 A | 6/1987 | Iwashita et al. | |
| 4,690,915 A | 9/1987 | Rosenberg | |
| 4,767,704 A | 8/1988 | Cleveland et al. | |
| 4,791,192 A | 12/1988 | Nakagawa et al. | |
| 4,816,567 A | 3/1989 | Cabilly et al. | |
| 4,927,762 A | 5/1990 | Darfler | |
| 5,112,946 A | 5/1992 | Maione | |
| 5,122,469 A | 6/1992 | Mather et al. | |
| 5,128,326 A | 7/1992 | Balazs et al. | |
| 5,206,344 A | 4/1993 | Katre et al. | |
| 5,208,020 A | 5/1993 | Chari et al. | |
| 5,225,212 A | 7/1993 | Martin et al. | |
| 5,225,539 A | 7/1993 | Winter | |
| 5,264,365 A | 11/1993 | Georgiou et al. | |
| 5,336,603 A | 8/1994 | Capon et al. | |
| 5,349,053 A | 9/1994 | Landolfi | |
| 5,359,046 A | 10/1994 | Capon et al. | |

(Continued)

FOREIGN PATENT DOCUMENTS

| | | |
|---|---|---|
| CA | 2992372 A1 | 1/2017 |
| CN | 106939048 A | 7/2017 |

(Continued)

OTHER PUBLICATIONS

Extended European Search Report in European Appln. No. 21841791. 3, mailed on Nov. 12, 2024, 22 pages.
Partial Supplementary European Search Report in European Appln. No. 21841791.3, mailed on Aug. 22, 2024, 21 pages.
Allen et al., "Acute eosinophilic pneumonia as a reversible cause of noninfectious respiratory failure," N. Engl. J. Med., Aug. 31, 1989, 321(9):569-574.
Altschul et al., "Basic local alignment search tool," Journal of Molecular Biology, Oct. 1990, 215(3):403-410.

(Continued)

*Primary Examiner* — Maher M Haddad

(74) *Attorney, Agent, or Firm* — Fish & Richardson P.C.

(57) ABSTRACT

The present disclosure provides single domain antibodies that bind to CD20, and chimeric antigen receptors comprising same. Further provided are engineered immune effector cells (such as T cells) comprising the chimeric antigen receptors. Pharmaceutical compositions, kits and methods of treating a disease or disorder are also provided.

20 Claims, 28 Drawing Sheets

Specification includes a Sequence Listing.

(56) References Cited

U.S. PATENT DOCUMENTS

| | | | |
|---|---|---|---|
| 5,416,064 | A | 5/1995 | Chari et al. |
| 5,447,851 | A | 9/1995 | Beutler et al. |
| 5,500,362 | A | 3/1996 | Robinson et al. |
| 5,508,192 | A | 4/1996 | Georgiou et al. |
| 5,530,101 | A | 6/1996 | Queen et al. |
| 5,545,807 | A | 8/1996 | Surani et al. |
| 5,565,332 | A | 10/1996 | Hoogenboom et al. |
| 5,585,089 | A | 12/1996 | Queen et al. |
| 5,605,793 | A | 2/1997 | Stemmer |
| 5,622,929 | A | 4/1997 | Willner et al. |
| 5,624,821 | A | 4/1997 | Winter et al. |
| 5,635,483 | A | 6/1997 | Pettit et al. |
| 5,639,635 | A | 6/1997 | Joly et al. |
| 5,648,237 | A | 7/1997 | Carter |
| 5,648,260 | A | 7/1997 | Winter et al. |
| 5,679,377 | A | 10/1997 | Bernsein et al. |
| 5,712,374 | A | 1/1998 | Kuntsmann et al. |
| 5,714,586 | A | 2/1998 | Kuntsmann et al. |
| 5,723,125 | A | 3/1998 | Chang et al. |
| 5,739,116 | A | 4/1998 | Hamann et al. |
| 5,766,886 | A | 6/1998 | Studnicka et al. |
| 5,767,285 | A | 6/1998 | Hamann et al. |
| 5,770,196 | A | 6/1998 | Studnicka |
| 5,770,701 | A | 6/1998 | McGahren et al. |
| 5,770,710 | A | 6/1998 | McGahren et al. |
| 5,773,001 | A | 6/1998 | Hamann et al. |
| 5,780,588 | A | 7/1998 | Pettit et al. |
| 5,783,181 | A | 7/1998 | Browne et al. |
| 5,811,238 | A | 9/1998 | Stemmer et al. |
| 5,821,123 | A | 10/1998 | Studnicka |
| 5,821,337 | A | 10/1998 | Carter et al. |
| 5,827,690 | A | 10/1998 | Meade et al. |
| 5,830,721 | A | 11/1998 | Stemmer et al. |
| 5,834,252 | A | 11/1998 | Stemmer et al. |
| 5,837,458 | A | 11/1998 | Minshull et al. |
| 5,844,095 | A | 12/1998 | Linsley et al. |
| 5,858,358 | A | 1/1999 | June et al. |
| 5,869,619 | A | 2/1999 | Studnicka et al. |
| 5,877,296 | A | 3/1999 | Hamann et al. |
| 5,883,223 | A | 3/1999 | Gray |
| 5,908,626 | A | 6/1999 | Chang et al. |
| 5,912,015 | A | 6/1999 | Bernsein et al. |
| 5,916,597 | A | 6/1999 | Lee et al. |
| 5,989,463 | A | 11/1999 | Tracy et al. |
| 6,027,888 | A | 2/2000 | Georgiou et al. |
| 6,054,297 | A | 4/2000 | Carter et al. |
| 6,075,181 | A | 6/2000 | Kucherlapati et al. |
| 6,083,715 | A | 7/2000 | Georgiou et al. |
| 6,150,584 | A | 11/2000 | Kucherlapati et al. |
| 6,194,551 | B1 | 2/2001 | Idusogie et al. |
| 6,352,694 | B1 | 3/2002 | June et al. |
| 6,407,213 | B1 | 6/2002 | Carter et al. |
| 6,534,055 | B1 | 3/2003 | June et al. |
| 6,602,684 | B1 | 8/2003 | Umana et al. |
| 6,630,579 | B2 | 10/2003 | Chari et al. |
| 6,639,055 | B1 | 10/2003 | Carter et al. |
| 6,692,964 | B1 | 2/2004 | June et al. |
| 6,719,971 | B1 | 4/2004 | Carter et al. |
| 6,737,056 | B1 | 5/2004 | Presta |
| 6,797,514 | B2 | 9/2004 | Berenson et al. |
| 6,800,738 | B1 | 10/2004 | Carter et al. |
| 6,867,041 | B2 | 3/2005 | Berenson et al. |
| 6,887,466 | B2 | 5/2005 | June et al. |
| 6,905,680 | B2 | 6/2005 | June et al. |
| 6,905,681 | B1 | 6/2005 | June et al. |
| 6,905,874 | B2 | 6/2005 | Berenson et al. |
| 6,989,250 | B2 | 1/2006 | Soderlind et al. |
| 7,052,906 | B1 | 5/2006 | Lawson et al. |
| 7,067,318 | B2 | 6/2006 | June et al. |
| 7,144,575 | B2 | 12/2006 | June et al. |
| 7,172,869 | B2 | 2/2007 | June et al. |
| 7,175,843 | B2 | 2/2007 | June et al. |
| 7,232,566 | B2 | 6/2007 | June et al. |
| 7,332,581 | B2 | 2/2008 | Presta |
| 7,371,826 | B2 | 5/2008 | Presta |
| 7,498,298 | B2 | 3/2009 | Doronina et al. |
| 7,741,465 | B1 | 6/2010 | Eshhar et al. |
| 7,985,840 | B2 | 7/2011 | Fuh et al. |
| 8,603,930 | B2 | 12/2013 | Doesburg et al. |
| 8,685,897 | B2 | 4/2014 | Bowers et al. |
| 8,754,287 | B2 | 6/2014 | Macdonald et al. |
| 2002/0164328 | A1 | 11/2002 | Shinkawa et al. |
| 2003/0115614 | A1 | 6/2003 | Kanda et al. |
| 2003/0157108 | A1 | 8/2003 | Presta |
| 2003/0170238 | A1 | 9/2003 | Gruenberg et al. |
| 2003/0186374 | A1 | 10/2003 | Hufton et al. |
| 2004/0005709 | A1 | 1/2004 | Hoogenboom et al. |
| 2004/0093621 | A1 | 5/2004 | Shitara et al. |
| 2004/0101519 | A1 | 5/2004 | June et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2005/0014934 | A1 | 1/2005 | Hinton et al. |
| 2005/0042664 | A1 | 2/2005 | Wu et al. |
| 2005/0123546 | A1 | 6/2005 | Umana et al. |
| 2006/0034810 | A1 | 2/2006 | Riley et al. |
| 2006/0121005 | A1 | 6/2006 | Berenson et al. |
| 2009/0075378 | A1 | 3/2009 | Horlick et al. |
| 2009/0307787 | A1 | 12/2009 | Grosveld et al. |
| 2010/0122358 | A1 | 5/2010 | Bruggemann |
| 2011/0183855 | A1 | 7/2011 | Horlick et al. |
| 2012/0028301 | A1 | 2/2012 | Horlick et al. |
| 2014/0094392 | A1 | 4/2014 | Bowers et al. |
| 2014/0170705 | A1 | 6/2014 | Bowers et al. |
| 2014/0287509 | A1 | 9/2014 | Sharei et al. |
| 2015/0289489 | A1 | 10/2015 | Macdonald et al. |
| 2015/0299317 | A1 | 10/2015 | Orentas et al. |
| 2018/0079822 | A1 | 3/2018 | Liu et al. |
| 2018/0094044 | A1 | 4/2018 | Roessig et al. |
| 2018/0230225 | A1 | 8/2018 | Fan et al. |
| 2019/0077871 | A1 | 3/2019 | Tavernier et al. |
| 2023/0192883 | A1 | 6/2023 | Fan et al. |
| 2023/0250184 | A1 | 8/2023 | Fan et al. |
| 2023/0257475 | A1* | 8/2023 | Fan .................. A61K 40/4211 |
| | | | 424/130.1 |

FOREIGN PATENT DOCUMENTS

| | | | |
|---|---|---|---|
| CN | 109069573 | | 12/2018 |
| CN | 105555310 | | 7/2019 |
| CN | 110396127 | A | 11/2019 |
| CN | 110396128 | A | 11/2019 |
| CN | 110885376 | A | 3/2020 |
| CN | 110922482 | A | 3/2020 |
| CN | 111217908 | A | 6/2020 |
| EP | 0239400 | | 9/1987 |
| EP | 0307434 | | 3/1989 |
| EP | 0367166 | | 5/1990 |
| EP | 0368684 | | 5/1990 |
| EP | 0394827 | | 10/1990 |
| EP | 0519596 | | 12/1992 |
| EP | 0592106 | | 4/1994 |
| EP | 0425235 | | 9/1996 |
| EP | 3293199 | A1 | 3/2018 |
| EP | 3564266 | A1 | 11/2019 |
| JP | 2018525033 | A | 9/2018 |
| WO | WO 1987/000195 | | 1/1987 |
| WO | WO 1988/007089 | | 9/1988 |
| WO | WO 1990/003430 | | 4/1990 |
| WO | WO 1991/005548 | | 5/1991 |
| WO | WO 1991/006570 | | 5/1991 |
| WO | WO 1991/009967 | | 7/1991 |
| WO | WO 1993/011794 | | 6/1993 |
| WO | WO 1993/017105 | | 9/1993 |
| WO | WO 1994/004678 | | 3/1994 |
| WO | WO 1994/011026 | | 5/1994 |
| WO | WO 1994/029351 | | 12/1994 |
| WO | WO 1996/004388 | | 2/1996 |
| WO | WO 1996/020698 | | 7/1996 |
| WO | WO 1996/022024 | | 7/1996 |
| WO | WO 1996/034103 | | 10/1996 |
| WO | WO 1997/030087 | | 8/1997 |
| WO | WO 1997/034631 | | 9/1997 |

(56) References Cited

FOREIGN PATENT DOCUMENTS

| WO | WO 1997/049805 | 12/1997 |
|----|----|----|
| WO | WO 1998/058964 | 12/1998 |
| WO | WO 1999/004813 | 2/1999 |
| WO | WO 1999/015154 | 4/1999 |
| WO | WO 1999/020253 | 4/1999 |
| WO | WO 1999/022764 | 5/1999 |
| WO | WO 1999/037681 | 7/1999 |
| WO | WO 1999/051642 | 10/1999 |
| WO | WO 2000/032776 | 6/2000 |
| WO | WO 2000/043507 | 7/2000 |
| WO | WO 2000/061739 | 10/2000 |
| WO | WO 2001/029246 | 4/2001 |
| WO | WO 2001/090190 | 11/2001 |
| WO | WO 2002/031140 | 4/2002 |
| WO | WO 2003/011878 | 2/2003 |
| WO | WO 2003/014161 | 2/2003 |
| WO | WO 2003/025020 | 3/2003 |
| WO | WO 2003/035694 | 5/2003 |
| WO | WO 2003/084570 | 10/2003 |
| WO | WO 2003/085107 | 10/2003 |
| WO | WO 2003/085119 | 10/2003 |
| WO | WO 2004/049794 | 6/2004 |
| WO | WO 2004/056312 | 7/2004 |
| WO | WO 2005/035586 | 4/2005 |
| WO | WO 2005/035778 | 4/2005 |
| WO | WO 2005/053742 | 6/2005 |
| WO | WO 2005/100402 | 10/2005 |
| WO | WO 2006/003388 | 1/2006 |
| WO | WO 2006/029879 | 3/2006 |
| WO | WO 2006/030220 | 3/2006 |
| WO | WO 2008/077546 | 7/2008 |
| WO | WO 2014/011988 A2 | 1/2014 |
| WO | WO 2015/158671 | 10/2015 |
| WO | WO 2016/014789 | 1/2016 |
| WO | WO 2016/102965 | 6/2016 |
| WO | WO 2017/009476 A1 | 1/2017 |
| WO | WO 2017/025038 A1 | 2/2017 |
| WO | WO 2017/133175 | 8/2017 |
| WO | WO 2017/153345 | 9/2017 |
| WO | WO 2017/153402 A1 | 9/2017 |
| WO | WO 2017/191476 A1 | 11/2017 |
| WO | WO 2018/028647 A1 | 2/2018 |
| WO | WO 2018/067992 | 4/2018 |
| WO | WO 2018/218876 A1 | 12/2018 |
| WO | WO 2019/126724 | 6/2019 |
| WO | WO 2019/126756 A1 | 6/2019 |
| WO | WO 2019/191704 A1 | 10/2019 |
| WO | WO 2020/014482 A1 | 1/2020 |
| WO | WO 2020/018922 A1 | 1/2020 |
| WO | WO 2020/087116 A1 | 5/2020 |
| WO | WO 2020/113234 A1 | 6/2020 |

OTHER PUBLICATIONS

Altschul et al., "Gapped BLAST and PSI-BLAST: a new generation of protein database search programs," Nucleic Acids Res., Sep. 1, 1997, 25(17):3389-3402.
Arie et al., "Chaperone function of FkpA, a heat shock prolyl isomerase, in the periplasm of Escherichia coli," Mol. Microbiol., 2001, 39(1):199-210.
Ashkenazi et al., "Protection against endotoxic shock by a tumor necrosis factor receptor immunoadhesin," PNAS USA, Dec. 1, 1991, 88: 10535-10539.
Baca et al., Antibody Humanization Using Monovalent Phage Display, J. Biol. Chem., Apr. 18, 1997, 272(16):10678-10684.
Barnes et al., "Methods for growth of cultured cells in serum-free medium," Anal. Biochem., Mar. 1980, 102(2):255-270.
Bass et al., "Hormone phage: an enrichment method for variant proteins with altered binding properties," Proteins, 1990, 8(4):309-314.
Beck et al., "Trends in glycosylation, glycoanalysis and glycoengineering of therapeutic antibodies and Fc-fusion proteins," Curr. Pharm. Biotechnol., Dec. 2008, 9(6):482-501 (21 pages).

Berg et al., "Selective Expansion of a Peripheral Blood CD8+ Memory T Cell Subset Expressing Both Granzyme B and L-Selectin During Primary Viral Infection in Renal Allograft Recipients," Transplant Proc., 1998, 30(8):3975-3977.
Bierer et al., "Cyclosporin A and FK506: molecular mechanisms of immunosuppression and probes for transplantation biology," Curr. Opin. Immun., 1993, 5:763-773.
Bird et al., "Single-chain antigen-binding proteins," Science, Oct. 21, 1988, 242(4877):423-426.
Bitter et al., "[33] Expression and Secretion Vectors for Yeast," Methods in Enzymol., 1987, 153:516-544.
Blaise et al., "Construction and diversification of yeast cell surface displayed libraries by yeast mating: application to the affinity maturation of Fab antibody fragments," Gene, Nov. 24, 2004, 342(2):211-218.
Boder et al., "Yeast surface display for screening combinatorial polypeptide libraries," Nat. Biotech., Jun. 1997, 15(6):553-557.
Boerner et al., "Production of antigen-specific human monoclonal antibodies from in vitro-primed human splenocytes," J. Immunol., Jul. 1, 1991, 147(1):86-95.
Bond et al., "A structure-based database of antibody variable domain diversity," J. Mol. Biol., May 6, 2005, 348(3):699-709.
Bothmann et al., "The periplasmic Escherichia coli peptidylprolyl cis,trans-isomerase FkpA. I. Increased functional expression of antibody fragments with and without cis-prolines," J. Biol. Chem., Jun. 2, 2000, 275(22):17100-17105.
Bradbury et al., "Antibodies from phage antibody libraries," J. Immunol. Methods, Jul. 2004, 290(1-2):29-49.
Brudno et al., "Chimeric antigen receptor T-cell therapies for lymphoma," Nature Reviews Clinical Oncology, Jan. 2018, 15(1):31-46.
Bruggemann et al., "Comparison of the effector functions of human immunoglobulins using a matched set of chimeric antibodies," J. Exp. Med., Nov. 1987, 166(5):1351-1361.
Bruggemann et al., "Production of human antibody repertoires in transgenic mice," Curr. Opin. Biotechnol., Aug. 1997, 8(4):455-458.
Caldas et al., "Design and synthesis of germline-based hemi-humanized single-chain Fv against the CD18 surface antigen, " Protein Eng., 2000, 13(5):353-360.
Carter et al., "Humanization of an anti-p185HER2 antibody for human cancer therapy," Proc. Natl. Acad Sci. USA, May 1992, 89:4285-4289.
Carter, "Review Article: Site-directed mutagenesis, " Biochem J., 1986, 237:1-7.
Chao et al., "Isolating and engineering human antibodies using yeast surface display," Nature Protocols, 2006, 1(2):755-768.
Chen et al., "Chaperone activity of DsbC," J Bio Chem, Jul. 9, 1999, 274(28):19601-19605.
Chen et al., "Selection and analysis of an optimized anti-VEGF antibody: crystal structure of an affinity-matured Fab in complex with antigen," J. Mol Biol., Nov. 5, 1999, 293(4):865-881.
Chothia et al., Canonical structures for the hypervariable regions of immunoglobulins, J Mal. Biol., Aug. 20, 1987, 196(4):901-917.
Chowdhury, Partha S., "Engineering hot spots for affinity enhancement of antibodies, " Methods Mol. Biol., 2003, 207:179-196.
Clackson et al., "Making antibody fragments using phage display libraries," Nature, Aug. 15, 1991, 352:624-628.
Clynes et al., "Fc receptors are required in passive and active immunity to melanoma," PNAS USA, Jan. 1998, 95:652-656.
Colberre-Garapin et al., "A new dominant hybrid selective marker for higher eukaryotic cells," J. Mol. Biol., Jul. 25, 1981, 150(1):1-14.
Colcher et al., "In Vivo Tumor Targeting of a Recombinant Single-Chain Antigen-Binding Protein," J. Nat. Cancer Inst., Jul. 18, 1990, 82(14):1191-1197.
Couto et al., "Anti-BA46 Monoclonal Antibody Mc3: Humanization Using a Novel Positional Consensus and in Vivo and in Vitro Characterization," Cancer Res., Apr. 15, 1995, 55(8): 1717-1722.
Couto et al., "Designing Human Consensus Antibodies with Minimal Positional Templates," Cancer Res., Dec. 1, 1995, 55(23 Supp):5973s-5977s.

(56)         References Cited

OTHER PUBLICATIONS

Cragg et al., "Antibody specificity controls in vivo effector mechanisms of anti-CD20 reagents," Blood, Apr. 2004, 103(7):2738-2743.

Cragg et al., "Complement-mediated lysis by anti-CD20 mAb correlates with segregation into lipid rafts," Blood, Feb. 2003, 101(3):1045-1052.

Crouse et al., "Expression and amplification of engineered mouse dihydrofolate reductase minigenes," Mol. Cell. Biol., Feb. 1983, 3(2):257-266.

Cunningham et al., "High-Resolution Epitope Mapping of hGH-Receptor Interactions by Alanine-Scanning Mutagenesis," Science, Jun. 2, 1989, 244: 1081-1085.

Dall'Acqua et al., "Antibody humanization by framework shuffling," Methods, 2005, 36:43-60 (19 pages).

Damschroder et al., "Framework shuffling of antibodies to reduce immunogenicity and manipulate functional and biophysical properties," Mol. Immunol., Jan. 22, 2007, 44:3049-3060.

Davies et al., "'Camelising' human antibody fragments: NMR studies on VH domains," FEBS Letters, 1994, 339: 285-290.

Davies et al., "Single antibody domains as small recognition units: design and in vitro antigen selection of camelized, human VH domains with improved protein stability," Protein Engineering, 1996, 9(6):531-537.

Davila et al., "CD19 CAR-Targeted T Cells Induce Long-Term Remission and B Cel 1Aplasia in an Immunocompetent Mouse Model of B Cell Acute Lymphoblastic Leukemia," PLoS One, Apr. 2013, 8(4): e61338 (14 pages).

De Groot et al., "Evolutionary deimmunization: An ancillary mechanism for self-tolerance?," Cell. Immunol., Dec. 2006, 244(2):148-153.

De Munter et al., "Nanobody Based Dual Specific CARs," Int. J. Mol. Sci., Jan. 30, 2018, 19(2):403 (11 pages).

Deschacht et al., "A Novel Promiscuous Class of Camelid Single-Domain Antibody Contributes to the Antigen-Binding Repertoire," J Immunol., May 15, 2010, 184(10):5696-5704.

Dubowchik et al., "Doxorubicin immunoconjugates containing bivalent, lysosomally-cleavable dipeptide linkages," Bioorg. Med. Chem. Lett., Jun. 3, 2002, 12(11):1529-1532.

Dufner et al., "Harnessing phage and ribosome display for antibody optimisation," Trends Biotechnol., Dec. 2006, 24(11):523-529.

Duncan et al., "The binding site for C1q on IgG," Nature, Apr. 21, 1988, 322(6166):738-740.

During et al., "Controlled Release of Dopamine from a Polymeric Brain Implant: In Vivo Characterization," Ann. Neurol., 1989, 25:351-356.

Feldhaus et al., "Flow Cytometric Isolation of Human Antibodies from a Nonimmune Saccharomyces cerevisiae Surface Display Library," Nat. Biotechnol., Jan. 2003, 21(2):163-170.

Foote et al., "Antibody Framework Resides Affecting the Conformation of the Hypervariable Loops," J. Mol. Biol. 1992, 224:487-499.

Fukuda et al, "Invitro evolution of single-chain antibodies using mRNA display," Nucleic Acids Res., 2006, 34(19):e127 (8 pages).

Garland et al, "The use of Teflon cell culture bags to expand functionally active CD8+ Cytotoxic T lymphocytes," J. Immunol Meth., 1999, 227(1-2):53-63.

Gazzano-Santoro et al., "A non-radioactive complement-dependent cytotoxicity assay for anti-CD20 monoclonal antibody," J Immunol. Methods, Mar. 28, 1997, 202(2):163-171.

GenBank Accession No. NM_021950.3, "Homo sapiens membrane spanning 4-domains A1 (MS4A1), transcript variant 3, mRNA," Jul. 6, 2019, 5 pages.

Graham et al., "Characteristics of a human cell line transformed by DNA from human adenovirus type 5," J. Gen Virol., Jul. 1977, 36(1):59-72.

Guex et al., Swiss-Model and the Swiss-Pdb Viewer: An environment for comparative protein modeling, Electrophoresis, 1997, 18:2714-2723.

Guyer et al., "Immunoglobulin binding by mouse intestinal epithelial cell receptors," J. Immunol., Aug. 1976, 117(2):587-593.

Haanen et al., "Selective Expansion of Cross-reactive CD8 Memory T Cells by Viral Variants, " J. Exp. Med., Nov. 1, 1999, 190(9):1319-1328.

Ham et al., "[5] Media and growth requirements," Meth. Enz., 1979, 58:44-93.

Hamers-Casterman et al., "Naturally occurring antibodies devoid of light chains," Nature, Jun. 3, 1993, 363:446-448.

Hansson et al., "Evolution of differential substrate specificities in Mu class glutathione transferases probed by DNA shuffling," J. Mol. Biol., Mar. 26, 1999, 287(2):265-276.

Hara et al., "Overproduction of penicillin-binding protein 7 suppresses thermosensitive growth defect at low osmolarity due to an spr mutation of Escherichia coli," Microbial Drug Resistance, Spring 1996, 2(1):63-72.

Harayama, S., "Artificial evolution by DNA shuffling," Trends Biotechnol., Feb. 1998, 16(2):76-82.

Hellstrom et al., "Antitumor effects of L6, an IgG2a antibody that reacts with most human carcinomas," Proc. Nat'l Acad. Sci. USA, Sep. 1986, 83:7059-7063.

Hellstrom et al., "Strong antitumor activities of IgG3 antibodies to a human melanoma-associated ganglioside," PNAS USA, Mar. 1985, 82: 1499-1502.

Henderson et al., "Comparison of the effects of FK-506, cyclosporin A and Rapamycin on IL-2 production, " Immun., 1991, 73:316-321.

Hermans et al., "The VITAL assay: a versatile fluorometric technique for assessing CTL- and NKT-mediated cytotoxicity against multiple targets in vitro and in vivo," J. Immunological Methods, Feb. 1, 2004, 285(1):25-40.

Hinman et al., "Preparation and characterization of monoclonal antibody conjugates of the calicheamicins: a novel and potent family of antitumor antibiotics," Cancer Res., Jul. 15, 1993, 53(14):3336-3342.

Ho et al., "In Vitro Antibody Evolution Targeting Germline Hot Spots to Increase Activity of an Anti-CD22 Immunotoxin*," J Biol. Chem., Jan. 7, 2005, 280:607-617.

Holt et al., "Domain antibodies: proteins for therapy," Trends Biotechnol., Nov. 2003, 21(11):484-490.

Honegger et al., "Yet Another Numbering Scheme for Immunoglobulin Variable Domains: An Automatic Modelinga nd Analysis Tool," J. Mol. Biol., 2001, 309:657-670.

Hoogenboom et al., "By-passing Immunisation Human Antibodies from Synthetic Repertoires of Germline VH Gene Segments Rearranged in Vitro," J. Mol. Biol., 1992, 227:381-388.

Hoogenboom et al., "Overview of antibody phage-display technology and its applications," Methods Mol. Biology, 2002, 178:1-37.

Hoogenboom, Hennie, "Selecting and screening recombinant antibody libraries," Nat. Biotechnol., Sep. 2005, 23(9):1105-1116.

Howard et al., "Intracerebral drug delivery in rats with lesion-induced memory deficits," J. Neurosurg., 1989, 71(1):105-112.

Huston et al., "Antigen recognition and targeted delivery by the single-chain Fv," Cell Biophysics, Jan. 1993, 22:189-224.

Idusogie et al., "Mapping of the C1q Binding Site on Rituxan, a Chimeric Antibody with a Human IgG1 Fc," J Imnnmol., 2000, 164(8):4178-4184.

Inouye et al., "Up-promoter mutations in the Ipp gene of Escherichia coli," Nucleic Acids Res., May 10, 1985, 13(9):3101-3109.

International Preliminary Report on Patentability in International Appln. No. PCT/CN2021/106886, mailed on Jan. 26, 2023, 8 pages.

International Search Report and Written Opinion in International Appln. No. PCT/CN2021/106886, mailed on Oct. 14, 2021, 13 pages.

Jakobovits, "Production of fully human antibodies by transgenic mice," Curr. Opin. Biotechnol., 1995, 6(5):561-566.

Jeffrey et al., "Dipeptide-based highly potent doxorubicin antibody conjugates," Bioorganic Med. Chem. Lett., Jan. 15, 2006, 16(2):358-362.

Jones et al., "Deimmunization of Monoclonal Antibodies," Methods Mol Biol., 2009, 525:405-423.

Jones et al., "Replacing the complementarity-determining regions in a human antibody with those from a mouse," Nature, May 29, 1986, 321:522-525.

(56)          References Cited

OTHER PUBLICATIONS

Kanda et al., "Comparison of cell lines for stable production of fucose-negative antibodies with enhanced ADCC," Biotechnol. Bioeng., Jul. 5, 2006, 94(4):680-688.
Karlin et al., "Applications and statistics for multiple high-scoring segments in molecular sequences," Proc. Natl. Acad. Sci. U.S.A., Jun. 1993, 90:5873-5877.
Karlin et al., "Methods for assessing the statistical significance of molecular sequence features by using general scoring schemes," PNAS U.S.A., Mar. 1990, 87:2264-2268.
Kashmiri et al., "SDR grafting—a new approach to antibody humanization," Methods, May 2005, 36(1):25-34 (11 pages).
Kim et al., "Identifying amino acid residues that influence plasma clearance of murine IgG1 fragments by site-directed mutagenesis," J Immunol., 1994, 24:542-548.
King et al., "Monoclonal antibody conjugates of doxorubicin prepared with branched peptide linkers: inhibition of aggregation by methoxytriethyleneglycol chains," J. Med. Chem., Sep. 12, 2002, 45(19):4336-4343.
Kochenderfer et al., "Construction and Pre-clinical Evaluation of an Anti-CD19 Chimeric Antigen Receptor," J. Immunotherapy, Sep. 2009, 32(7):689-702 (Author Manuscript, 26 pages).
Kohler et al., "Continuous cultures of fused cells secreting antibody of predefined specificity," Nature, Aug. 1975, 256(5517):495-497.
Kratz et al., "Prodrugs of anthracyclines in cancer chemotherapy," Current Med. Chem., 2006, 13(5):477-523.
Langer et al., "Chemical and Physical Structure of Polymers as Carriers for Controlled Release of Bioactive Agents: A Review," J. Macromol Sci. Rev. Macromol. Chem., 1983, 23(1):61-126.
Langer, "New Methods of Drug Delivery," Science, Sep. 28, 1990, 249: 1527-1533.
Lazar et al., "A molecular immunology approach to antibody humanization and functional optimization," Mol. Immunol., 2007, 44:1986-1998.
Lefranc et al., "IMGT unique numbering for immunoglobulin and T cell receptor variable domains and Ig superfamily V-like domains," Dev. Comp. Immunol., Jan. 2003, 27(1):55-77.
Levy et al., "Inhibition of Calcification of Bioprosthetic Heart Valves by Local Controlled-Release Diphosphonate," Science, Apr. 12, 1985, 228: 190-192.
Li et al., "Construction and characterization of a humanized anti-human CD3 monoclonal antibody 12F6 with effective immunoregulation functions," Immunology, 2005, 116:487-498.
Li et al., "Human antibodies for immunotherapy development generated via a human B cell hybridoma technology," Proc. Natl. Acad Sci. USA, Mar. 7, 2006, 103:3557-3562.
Liu et al., "Calcineurin Is a Common Target of Cyclophilin-Cyclosporin A and FKBP-FK506 Complexes," Cell, Aug. 23, 1991, 66:807-815.
Liu et al., "Selection and characterization of single domain antibodies against human CD20," Mol. Immunol., Sep. 15, 2016, 78:146-154.
Lode et al., "Targeted therapy with a novel enediyene antibiotic calicheamicin theta(I)1 effectively suppresses growth and dissemination of liver metastases in a syngeneic model of murine neuroblastoma," Cancer Res., Jul. 15, 1998, 58(14):2925-2928.
Logan et al., "Adenovirus tripartite leader sequence enhances translation of mRNAs late after infection," Proc. Natl. Acad. Sci. USA, Jun. 1984, 81:3655-3659.
Lorenzo et al., "PCR-Based Method for the Introduction of Mutations in Genes Cloned and Expressed in Vaccinia Virus," Biotechniques, Feb. 1998, 24(2):308-313.
Lowy et al., "Isolation of Transforming DNA: Cloning the Hamster aprt Gene," Cell, Dec. 1980, 22:817-823.
Lu et al., "Tailoring in Vitro Selection for a Picomolar Affinity Human Antibody Directed against Vascular Endothelial Growth Factor Receptor 2 for Enhanced Neutralizing Activity*," J. Biol. Chem., Oct. 31, 2005, 278(44):43496-43507.

Marks et al., "By-Passing Immunization: Building High Affinity Human Antibodies by Chain Shuffling," Bio/Technology, 10:779-783 (1992).
Marks et al., "By-passing immunization: Human antibodies from V-gene libraries displayed on phage," J Mol. Biol., Dec. 5, 1991, 222(3):581-597.
Mather et al., "Culture of testicular cells in hormone-supplemented serum-free medium," Annals N Y Acad Sci., 1982, 383:44-68.
Mather, "Establishment and characterization of two distinct mouse testicular epithelial cell lines, "Biol. Reprod., Aug. 1980, 23(1):243-252.
McCafferty et al., Phage antibodies: filamentous phage displaying antibody variable domains, Nature, Dec. 6, 1990, 348:552-554.
Merrifield, R. B., "Solid Phase Peptide Synthesis. I. The Synthesis of a Tetrapeptide," J. Am. Chem. Soc., Jul. 1963, 85(14):2149-2154.
Milone,"Chimeric Receptors Containing CD137 Signal Transduction Domains Mediate Enhanced Survival of T Cells and Increased Antileukemic Efficacy In Vivo," Molecular Therapy, Aug. 2009, 17(8):1453-1464.
Morea et al., "Antibody Modeling: Implications for Engineering and Design," Methods, 2000, 20(3):267-279.
Morgan et al., "Human gene therapy," Annu. Rev. Biochem., 1993, 62:191-217.
Morrison et al., "Chimeric human antibody molecules: Mouse antigen-binding domains with human constant region domains," Proc. Natl. Acad Sci. USA, Nov. 1984, 81:6851-6855.
Mulligan et al., "Selection for animal cells that express the *Escherichia coli* gene coding for xanthine-guanine phosphoribosyltransferase," Proc. Natl. Acad. Sci. USA, Apr. 1981, 78(4):2072-2076.
Mulligan, R.C., "The basic science of gene therapy," Science, May 14, 1993, 260(5110):926-932.
Munson et al., "Ligand: a versatile computerized approach for characterization of ligand-binding systems," Anal. Biochem., Sep. 1980, 107(1):220-239.
Muyldermans, Serge, "Single domain camel antibodies: current status," Reviews Mol Biotech., 2001, 74:277-302 (2001).
Myers et al., "Optimal alignments in linear space," Cabios, Mar. 1988, 4(1):11-17.
Nagy et al., "Stability of cytotoxic luteinizing hormone-releasing hormone conjugate (AN-152) containing doxorubicin 14-O-hemiglutarate in mouse and human serum in vitro: implications for the design of preclinical studies," Proc. Natl. Acad Sci. USA, Jan. 18, 2000, 97(2):829-834.
Ning et al., "Intratumoral radioimmunotherapy of a human colon cancer xenograft using a sustained-release gel," Radiotherapy & Oncology, May 1996, 39(2):179-189.
O'Hare et al., "Transformation of mouse fibroblasts to methotrexate resistance by a recombinant plasmid expressing a prokaryotic dihydrofolate reductase.," Proc. Natl. Acad. Sci. USA, Mar. 1981, 78(3):1527-1531.
Okazaki et al., "Fucose depletion from human IgG1 oligosaccharide enhances binding enthalpy and association rate between IgG1 and FcgammaRIIIa," J Mol. Biol., Mar. 5, 2004, 336(5): 1239-1249.
Padlan et al., "Identification of specificity-determining residues in antibodies," Faseb J., Jan. 1995, 9(1):133-139.
Padlan, "A possible procedure for reducing the immunogenicity of antibody variable domains while preserving their ligand-binding properties, " Mal. Immunol., Apr.-May 1991, 28(4-5):489-498.
Pardon et al., "A general protocol for the generation of Nanobodies for structural biology," Nature Protocol, Mar. 2014, 9(3):674-693.
Patten et al., "Applications of DNA shuffling to pharmaceuticals and vaccines," Curr. Opinion Biotechnol., Dec. 1997, 8(6):724-733.
Pedersen et al., "Comparison of Surface Accessible Residues in Human and Murine Immunoglobulin Fv Domains: Implication for Humanization of Murine Antibodies," J. Mol. Biol., 1994, 235(3):959-973.
Petkova et al., "Enhanced half-life of genetically engineered human IgG1 antibodies in a humanized FcRn mouse model: potential application in humorally mediated autoimmune disease," Int'l. Immunol., 2006, 18(12): 1759-1769.
Pluckthun et al., "Expression of functional antibody Fv and Fab fragments in *Escherichia coli*," 1989, Meth. Enzymol., 178:497-515.

(56)          References Cited

OTHER PUBLICATIONS

Pluckthun, "Mono-and bivalent antibody fragments produced in *Escherichia coli*: engineering, folding and antigen binding," Immunol. Revs., Dec. 1992, 130:151-188.
Presta et al., "Humanization of an antibody directed against IgE," J Immunol., 1993, 151(5):2623-2632.
Presta, Leonard G., "Antibody engineering," Curr. Op. Struct. Biol., 1992, 2:593-596.
Quiroz et al., "Engineering antibody fragments: replicating the immune system and beyond," Revista Ingenieria Biomedica, 2010, 4(7):39-51.
Rabinovich et al., "Synthetic Messenger RNA as a Tool for Gene Therapy," Human Gene Therapy, Oct. 2006, 17:1027-1035.
Ramm et al., "The periplasmic *Escherichia coli* peptidylprolyl cis, trans-isomerase FkpA. II. Isomerase-independent chaperone activity in vitro," J. Biol. Chem., Jun. 2, 2000, 275(22):17106-17113.
Riechmann et al., "Reshaping human antibodies for therapy," Nature, Mar. 1988, 332:323-327.
Riechmann et al., "Single domain antibodies: comparison of camel VH and camelised human VH domains," J. Immunol. Meth., 1999, 231: 25-38.
Riechmann, "Rearrangement of the Former VL Interface in the Solution Structure of a Camelised, Single Antibody VH Domain," J. Mol. Biol., Jun. 28, 1996, 259(5): 957-969.
Ripka et al. "Two Chinese hamster ovary glycosylation mutants affected in the conversion of GDP-mannose to GDP-fucose," Arch. Biochern. Biophys., Sep. 1986, 249(2):533-545.
Rivollier et al., "Immature dendritic cell transdifferentiation into osteoclasts: a novel pathway sustained by the rheumatoid arthritis microenvironment," Blood, Dec. 15, 2004, 104(13):4029-4037.
Roguska et al., "Humanization of murine monoclonal antibodies through variable domain resurfacing," PNAS, Feb. 1994, 91:969-973.
Roguska et al., "A comparison of two murine monoclonal antibodies humanized by CDR-grafting and variable domain resurfacing," Protein Eng., 1996, 9(10):895-904.
Rosenberg, "Cell transfer immunotherapy for metastatic solid cancer—what clinicians need to know," Nat Rev Clin Oncol., Aug. 2, 2011, 8(10):577-585 (Author Manuscript, 23 pages).
Ruther et al., "Easy identification of cDNA clones," EMBO, Oct. 1983, 2(10):1791-1794.
Sali et al., "Comparative Protein Modelling by Satisfaction of Spatial Restraints," J. Mol. Biol., 1993, 234:779-815.
Sandhu, J.S., "A rapid procedure for the humanization of monoclonal antibodies," Gene, Dec. 15, 1994, 150(2):409-410.
Santerre et al., "Expression of prokaryotic genes for hygromycin B and G418 resistance as dominant-selection markers in mouse L cells," Gene, Oct. 1984, 30(1-3):147-156.
Schlapschy et al., "Functional humanization of an anti-CD30 Fab fragment for the immunotherapy of Hodgkin's lymphoma using an in vitro evolution approach," Protein Eng. Des. Sel., Dec. 2004, 17(12):847-860.
Shanehbandi et al., "CD20-based Immunotherapy of B-cell Derived Hematologic Malignancies, " Current Cancer Drug Targets, 2017, 17(5): 423-444.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol. Chem., Mar. 2, 2001, 276(9):6591-6604.
Shusta et al., "Yeast polypeptide fusion surface display levels predict thermal stability and soluble secretion efficiency," J. Mol. Biol., Oct. 8, 1999, 292(5):949-956.
Siebenlist et al., "*E. coli* RNA Polymerase Interacts Homologously with Two Different Promoters, " Cell, Jun. 1980, 20: 269-281.
Simmons et al., "Expression of full-length immunoglobulins in *Escherichia coli*: rapid and efficient production of aglycosylated antibodies, " J. Immunol. Methods, May 2002, 263(1-2):133-147.
Sims et al., "A humanized CD18 antibody can block function without cell destruction," J Immunol., Aug. 15, 1993, 151(4):2296-2308.

Skerra et al., "Bacterial expression of immunoglobulin fragments," Curr. Opinion in Immunol., Apr. 1993, 5(2):256-262.
Streltsov et al., "Structure of a shark IgNAR antibody variable domain and modeling of an early-developmental isotype," Protein Sci., 2005, 14:2901-2909.
Studnicka et al., "Human-engineered monoclonal antibodies retains full specific binding activity by preserving non-CDR complementarity-modulating residues," Protein Engineering, 1994, 7(6):805-814.
Tan et al., ""Superhumanized" Antibodies: Reduction of Immunogenic Potential by Complementarity-Determining Region Grafting with Human Germline Sequences: Application to an Anti-CD281," J.Immunol., Jul. 15, 2002, 169(2): 1119-1125.
Taylor et al., "A transgenic mouse that expresses adiversity of human sequence heavy and light chain immunoglobulins," Nucl. Acids Res., 1992, 20(23):6287-6295.
Terpe, "Overview of tag protein fusions: from molecular and biochemical fundamentals to commercial systems," Appl. Microbiol. Biotechnol., Jan. 2003, 60(5):523-533.
Themeli et al., "Generation of tumor-targeted human T lymphocytes from induced pluripotent stem cells for cancer therapy," Nat Biotechnol., 2013, available online Aug. 11, 2023, 31(10):928-933 (Advance Online Publication 8 pages).
Thorpe et al., "The preparation and cytotoxic properties of antibody-toxin conjugates," Immunol. Rev., 1982, 62:119-158.
Tolstoshev, P., "Gene therapy, concepts, current trials and future directions," Annu. Rev Pharmacol. Toxicol., 1993, 32:573-596.
Torgov et al., "Generation of an intensely potent anthracycline by a monoclonal antibody-beta-galactosidase conjugate," Bioconjug. Chem., May-Jun. 2005, 16(3):717-721.
Traunecker et al., "Soluble CD4 molecules neutralize human immunodeficiency virus type 1," Nature, Jan. 1988, 331(6151):84-86.
Tsukahara et al., "CD19 target-engineered T-cells accumulate at tumor lesions in human B-cell lymphoma xenograft mouse models," Biochem Biophys Res Commun., 2013, 438(1):84-89.
Ui-Tei et al., "Sensitive assay of RNA interference in *Drosophila* and Chinese hamster cultured cells using firefly luciferase gene as target," FEBS Letters, 2000, 479:79-82.
Urlaub et al., "Isolation of Chinese hamster cell mutants deficient in dihydrofolate reductase activity," PNAS USA, Jul. 1980, 77(7):4216-4220.
van Dijk et al., "Human antibodies as next generation therapeutics," Curr. Opin. Chemical Biolo., 2001, 5:368-374.
Van Heeke et al., "Expression of human asparagine synthetase in *Escherichia coli*," J. Biol. Chem., Apr. 5, 1989, 24(10):5503-5509.
Verhoeyen et al., "Reshaping Human Antibodies: Grafting an Antilysozyme Activity," Science, 1988, 239:1534-1136.
Vie et al., "Human fusion proteins between interleukin 2 and IgM heavy chain are cytotoxic for cells expressing the interleukin 2 receptor," Proc. Natl. Acad. Sci. USA, Dec. 1992, 89(23):11337-11341.
Vincke et al., "General Strategy to Humanize a Camelid Single-domain Antibody and Identification of a Universal Humanized Nanobody Scaffold," J. Biol. Chem, Jan. 30, 2009, available online Nov. 14, 2008, 284(5):3273-3284.
Vitetta et al., "Redesigning nature's poisons to create anti-tumor reagents," Science, Nov. 20, 1987, 238(4830):1098-1104 (9 pages).
Walsh, "Post-translational modifications of protein biopharmaceuticals," Drug Discov. Today, Sep. 2010, 15(17-18):773-780.
Ward et al., "Binding activities of a repertoire of single immunoglobulin variable from *Escherichia coli*," Nature, Oct. 12, 1989, 341:544-546.
Waterhouse et al., "Combinatorial infection and in vivo recombination: a strategy for making large phageantibody repertoires," Nucl. Acids Res., 1993, 21(9):2265-2266.
Wells et al., "Cassette mutagenesis: an efficient method for generation of multiple mutations at defined sites," Gene, 1985, 34(2-3):315-323.
Whitelegg et al., "WAM: an improved algorithm for modelling antibodies on the WEB," Protein Eng., 2000, 13(12):819-824.
Wigler et al., "Transfer of Purified Herpes Virus Thymidine Kinase Gene to Cultured Mouse Cells," Cell, May 1977, 11:223-232.

(56)                    References Cited

OTHER PUBLICATIONS

Wigler et al., "Transformation of mammalian cells with an ampli-fiable dominant-acting gene," Proc Natl Acad Sci U S A, Jun. 1980, 77(6):3567-3570.
Wilson et al., "The use of mRNA display to select high-affinity protein-binding peptides," Proc. Natl. Acad. Sci. USA, Mar. 27, 2001, 98(7):3750-3755.
Wright et al., "Effect of glycosylation on antibody function: impli-cations for genetic engineering, " TIBTECH, Jan. 1997, 15(1):26-32.
Wu et al., "Delivery systems for gene therapy," Biotherapy, 1991, 3(1):87-95.
Yamane-Ohnuki et al., "Establishment of FUT8 knockout Chinese hamster ovary cells: An ideal host cell line for producing completely defucosylated antibodies with enhanced antibody-dependent cellu-lar cytotoxicity," Biotech. Bioeng., 2004, 87(5):614-622.
Yaniv, M., "Enhancing elements for activation of eukaryotic pro-moters," Nature, May 6, 1982, 297(5861):17-18.
Yu et al., "Next generation chimeric antigen receptor T cells: safety strategies to overcome toxicity, " Molecular Cancer, 2019, 18(1):125 (13 pages).
Zheng et al., "Administration of noncytolytic IL-10/Fc in murine models of lipopolysaccharide-induced septic shock and allogeneic islet transplantation," J. Immunol., May 15, 1995, 154(10):5590-5600.
Zoller et al., "Oligonucleotide-directed mutagenesis using M13-derived vectors: an efficient and general procedure for the produc-tion of point mutations in any fragment of DNA," Nucl. Acids Res., Oct. 25, 1982, 10(20):6487-6500.
Carter et al., "Signaling by the CD19/CD21 complex on B cells," Curr Dir Autoimmun., 2004, 7:4-32.
Dorner et al., "Targeting CD22 as a strategy for treating systemic autoimmune diseases," Ther Clin Risk Manag, 2007, 3(5):953-959.
Extended European Search Report in European Appln. No. 21842411. 7, mailed on Oct. 23, 2024, 22 pages.
Extended European Search Report in European Appln. No. 21843054. 4, mailed on Nov. 12, 2024, 16 pages.
Extended European Search Report in European Appln. No. 21843275. 5, mailed on Feb. 13, 2025, 19 pages.
GenBank Accession No. NM_001770.5, "*Homo sapiens* CD19 molecule (CD19), transcript variant 2, mRNA," Jun. 26, 2019, 6 pages.
GenBank Accession No. NM_001771.3, "*Homo sapiens* CD22 molecule (CD22), transcript variant 1, mRNA, " Oct. 21, 2018, 6 pages.

International Preliminary Report on Patentability in International Appln. No. PCT/CN2021/106889, mailed on Jan. 26, 2023, 8 pages.
International Preliminary Report on Patentability in International Appln. No. PCT/CN2021/106891, mailed on Jan. 26, 2023, 7 pages.
International Preliminary Report on Patentability in International Appln. No. PCT/CN2021/106892, mailed on Jan. 26, 2023, 7 pages.
International Search Report and Written Opinion in International Appln. No. PCT/CN2021/106889, mailed on Oct. 14, 2021, 12 pages.
International Search Report and Written Opinion in International Appln. No. PCT/CN2021/106891, mailed on Oct. 25, 2021, 10 pages.
International Search Report and Written Opinion in International Appln. No. PCT/CN2021/106892, mailed on Oct. 25, 2021, 10 pages.
Jayaraman et al., "CAR-T design: Elements and their synergistic function," EBioMedicine, Aug. 2020, available online Jul. 30, 2020, 58:102931, 12 pages.
Kulemzin et al., "Engineering Chimeric Antigen Receptors," Acta Naturae, Jan.-Mar. 2017, 9(1):6-14.
Lindner et al., "Chimeric antigen receptor signaling: Functional consequences and design implications," Sci Adv, May 2020, 6(21):eaaz3223, 8 pages.
Majzner et al., "Tumor Antigen Escape from CAR T-cell Therapy," Cancer Discov, Oct. 2018, 8(10):1219-1226.
Nitschke, Lars, "The role of CD22 and other inhibitory co-receptors in B-cell activation," Curr. Opin. Immunol, Jun. 2005, 17(3):290-297.
Partial Supplementary European Search Report in European Appln. No. 21842411.7, mailed on Aug. 1, 2024, 22 pages.
Partial Supplementary European Search Report in European Appln. No. 21843054.4, mailed on Aug. 22, 2024, 16 pages.
Partial Supplementary European Search Report in European Appln. No. 21843275.5, mailed Aug. 28, 2024, 18 pages.
Steinfeld et al., "Epratuzumab (humanised anti-CD22 antibody) in autoimmune diseases," Expert. Opin. Biol. Ther., Sep. 2006, 6(9):943-949.
Sterner et al., "CAR-T cell therapy: current limitations and potential strategies," Blood Cancer, Apr. 2021, 11(4):69, 11 pages.
Walsh et al., "Multi-Specific CAR Targeting to Prevent Antigen Espace," Curr Hematol Malig Rep, Oct. 2019, 14(5):451-459.
Wang et al., "CD19: a biomarker for B cell development, lymphoma diagnosis and therapy," Exp Hematol Oncol., Nov. 29, 2012, 1(1): 36 (7 pages).
Zhou et al., "Structure of the genes encoding the CD19 antigen of human and mouse B lymphocytes," Immunogenetics., 1992, 35(2): 102-111.

* cited by examiner

FIG. 6

SEQUENCE LISTING

```
<160> NUMBER OF SEQ ID NOS: 200

<210> SEQ ID NO 1
<211> LENGTH: 10
<212> TYPE: PRT
<213> ORGANISM: Artificial Sequence
<220> FEATURE:
<223> OTHER INFORMATION: CDR1 (Kabat) of VHH-273, VHH-283, huVHH-253,
      huVHH-256, 2082H1, 2082H2, 2082H3, 2082H4, 2082H5, and 2082H6

<400> SEQUENCE: 1

Gly Arg Thr Phe Ser Ser Tyr Asn Met Gly
1               5                   10

<210> SEQ ID NO 2
<211> LENGTH: 17
<212> TYPE: PRT
<213> ORGANISM: Artificial Sequence
<220> FEATURE:
<223> OTHER INFORMATION: CDR2 (Kabat) of VHH-273, huVHH-256, 2082H1,
      2082H2, 2082H3, 2082H4, 2082H5, and 2082H6

<400> SEQUENCE: 2

Val Val Asp Trp Ser Gly Gly Ser Pro Tyr Tyr Ala Asp Ser Val Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: CDR3 (Kabat) of VHH-273, huVHH-253, huVHH-256,
      2082H1, 2082H2, 2082H3, 2082H4, 2082H5, and 2082H6

<400> SEQUENCE: 3

Arg Val Gln Tyr Gly Ser Ser Trp Ser Gly Asp Tyr
1               5                   10
```

```
<210> SEQ ID NO 4
<211> LENGTH: 8
<212> TYPE: PRT
<213> ORGANISM: Artificial Sequence
<220> FEATURE:
<223> OTHER INFORMATION: CDR1 (IMGT) of VHH-273, VHH-283, huVHH-253,
      huVHH-256, 2082H1, 2082H2, 2082H3, 2082H4, 2082H5, and 2082H6

<400> SEQUENCE: 4

Gly Arg Thr Phe Ser Ser Tyr Asn
1               5

<210> SEQ ID NO 5
<211> LENGTH: 9
<212> TYPE: PRT
<213> ORGANISM: Artificial Sequence
<220> FEATURE:
<223> OTHER INFORMATION: CDR2 (IMGT) of VHH-273

<400> SEQUENCE: 5

Val Val Asp Trp Ser Gly Gly Ser Pro
1               5

<210> SEQ ID NO 6
<211> LENGTH: 14
<212> TYPE: PRT
<213> ORGANISM: Artificial Sequence
<220> FEATURE:
<223> OTHER INFORMATION: CDR3 (IMGT) of VHH-273, huVHH-253, huVHH-256,
      2082H1, 2082H3, and 2082H6

<400> SEQUENCE: 6

Ala Gly Arg Val Gln Tyr Gly Ser Ser Trp Ser Gly Asp Tyr
1               5                   10

<210> SEQ ID NO 7
<211> LENGTH: 17
<212> TYPE: PRT
<213> ORGANISM: Artificial Sequence
<220> FEATURE:
<223> OTHER INFORMATION: CDR2 (Kabat) of VHH-283

<400> SEQUENCE: 7

Ala Ile Ser Trp Ser Gly Gly Ser Pro Tyr Tyr Ala Ser Ser Val Arg
1               5                   10                  15

Gly

<210> SEQ ID NO 8
<211> LENGTH: 12
<212> TYPE: PRT
<213> ORGANISM: Artificial Sequence
<220> FEATURE:
<223> OTHER INFORMATION: CDR3 (Kabat) of VHH-283, VHH-313, and huVHH-260

<400> SEQUENCE: 8

Pro Ile Glu Tyr Gly Ser Ser Trp Ser Ala Asp Tyr
1               5                   10

<210> SEQ ID NO 9
<211> LENGTH: 8
<212> TYPE: PRT
<213> ORGANISM: Artificial Sequence
<220> FEATURE:
<223> OTHER INFORMATION: CDR2 (IMGT) of VHH-283, VHH-313, and huVHH-260

<400> SEQUENCE: 9
```

-continued

```
Ile Ser Trp Ser Gly Gly Ser Pro
1               5

<210> SEQ ID NO 10
<211> LENGTH: 14
<212> TYPE: PRT
<213> ORGANISM: Artificial Sequence
<220> FEATURE:
<223> OTHER INFORMATION: CDR3 (IMGT) of VHH-283, VHH-313, and huVHH-260

<400> SEQUENCE: 10

Ala Ala Pro Ile Glu Tyr Gly Ser Ser Trp Ser Ala Asp Tyr
1               5                   10

<210> SEQ ID NO 11
<211> LENGTH: 10
<212> TYPE: PRT
<213> ORGANISM: Artificial Sequence
<220> FEATURE:
<223> OTHER INFORMATION: CDR1 (Kabat) of VHH-313 and huVHH-260

<400> SEQUENCE: 11

Gly Arg Thr Ile Ser Ser Tyr Ser Met Gly
1               5                   10

<210> SEQ ID NO 12
<211> LENGTH: 17
<212> TYPE: PRT
<213> ORGANISM: Artificial Sequence
<220> FEATURE:
<223> OTHER INFORMATION: CDR2 (Kabat) of VHH-313 and huVHH-260

<400> SEQUENCE: 12

Ala Ile Ser Trp Ser Gly Gly Ser Pro Tyr Tyr Ala Asp Ser Val Lys
1               5                   10                  15

Gly

<210> SEQ ID NO 13
<211> LENGTH: 8
<212> TYPE: PRT
<213> ORGANISM: Artificial Sequence
<220> FEATURE:
<223> OTHER INFORMATION: CDR1 (IMGT) of VHH-313 and huVHH-260

<400> SEQUENCE: 13

Gly Arg Thr Ile Ser Ser Tyr Ser
1               5

<210> SEQ ID NO 14
<211> LENGTH: 10
<212> TYPE: PRT
<213> ORGANISM: Artificial Sequence
<220> FEATURE:
<223> OTHER INFORMATION: CDR1 (Kabat) of VHH-440 and VHH-653

<400> SEQUENCE: 14

Ala Tyr Ile Arg Val Phe Tyr Leu Met Gly
1               5                   10

<210> SEQ ID NO 15
<211> LENGTH: 16
<212> TYPE: PRT
<213> ORGANISM: Artificial Sequence
<220> FEATURE:
<223> OTHER INFORMATION: CDR2 (Kabat) of VHH-440
```

<400> SEQUENCE: 15

Arg Val Thr Ala Asp Gly Phe Thr Asn His Ala Ala Ser Val Lys Gly
1               5                   10                  15

<210> SEQ ID NO 16
<211> LENGTH: 10
<212> TYPE: PRT
<213> ORGANISM: Artificial Sequence
<220> FEATURE:
<223> OTHER INFORMATION: CDR3 (Kabat) of VHH-440, VHH-466, VHH-653,
      huVHH-836, huVHH-840, huVHH-843, and huVHH-846

<400> SEQUENCE: 16

Gly Arg Thr Trp Asn Ser Gly Phe Glu Tyr
1               5                   10

<210> SEQ ID NO 17
<211> LENGTH: 8
<212> TYPE: PRT
<213> ORGANISM: Artificial Sequence
<220> FEATURE:
<223> OTHER INFORMATION: CDR1 (IMGT) of VHH-440 and VHH-653

<400> SEQUENCE: 17

Ala Tyr Ile Arg Val Phe Tyr Leu
1               5

<210> SEQ ID NO 18
<211> LENGTH: 7
<212> TYPE: PRT
<213> ORGANISM: Artificial Sequence
<220> FEATURE:
<223> OTHER INFORMATION: CDR2 (IMGT) of VHH-440

<400> SEQUENCE: 18

Val Thr Ala Asp Gly Phe Thr
1               5

<210> SEQ ID NO 19
<211> LENGTH: 12
<212> TYPE: PRT
<213> ORGANISM: Artificial Sequence
<220> FEATURE:
<223> OTHER INFORMATION: CDR3 (IMGT) of VHH-440, VHH-466, VHH-653,
      huVHH-836, huVHH-840, huVHH-843, and huVHH-846

<400> SEQUENCE: 19

Ala Ala Gly Arg Thr Trp Asn Ser Gly Phe Glu Tyr
1               5                   10

<210> SEQ ID NO 20
<211> LENGTH: 10
<212> TYPE: PRT
<213> ORGANISM: Artificial Sequence
<220> FEATURE:
<223> OTHER INFORMATION: CDR1 (Kabat) of VHH-466, huVHH-836, huVHH-840,
      huVHH-843, and huVHH-846

<400> SEQUENCE: 20

Ala Asp Ile Arg Leu Phe Tyr Leu Met Gly
1               5                   10

<210> SEQ ID NO 21
<211> LENGTH: 16
<212> TYPE: PRT
<213> ORGANISM: Artificial Sequence
<220> FEATURE:

<223> OTHER INFORMATION: CDR2 (Kabat) of VHH-466

<400> SEQUENCE: 21

Arg Val Asn Ala Asp Asp Ser Ile Asn Tyr Val Ala Ser Val Lys Gly
1               5                   10                  15

<210> SEQ ID NO 22
<211> LENGTH: 8
<212> TYPE: PRT
<213> ORGANISM: Artificial Sequence
<220> FEATURE:
<223> OTHER INFORMATION: CDR1 (IMGT) of VHH-466, huVHH-836, huVHH-840,
      huVHH-843, and huVHH-846

<400> SEQUENCE: 22

Ala Asp Ile Arg Leu Phe Tyr Leu
1               5

<210> SEQ ID NO 23
<211> LENGTH: 7
<212> TYPE: PRT
<213> ORGANISM: Artificial Sequence
<220> FEATURE:
<223> OTHER INFORMATION: CDR2 (IMGT) of VHH-466, huVHH-840, and
      huVHH-843, huVHH-846

<400> SEQUENCE: 23

Val Asn Ala Asp Asp Ser Ile
1               5

<210> SEQ ID NO 24
<211> LENGTH: 10
<212> TYPE: PRT
<213> ORGANISM: Artificial Sequence
<220> FEATURE:
<223> OTHER INFORMATION: CDR1 (Kabat) of VHH-496, huVHH-746, and
      huVHH-750, huVHH-753

<400> SEQUENCE: 24

Gly Phe Thr Phe Ser Asn Tyr Pro Met Thr
1               5                   10

<210> SEQ ID NO 25
<211> LENGTH: 17
<212> TYPE: PRT
<213> ORGANISM: Artificial Sequence
<220> FEATURE:
<223> OTHER INFORMATION: CDR2 (Kabat) of VHH-496, huVHH-746, huVHH-750,
      and huVHH-753

<400> SEQUENCE: 25

Asp Ile Thr Ser Gly Gly Asp Arg Pro Tyr Tyr Ala Asp Ser Val Lys
1               5                   10                  15

Gly

<210> SEQ ID NO 26
<211> LENGTH: 5
<212> TYPE: PRT
<213> ORGANISM: Artificial Sequence
<220> FEATURE:
<223> OTHER INFORMATION: CDR3 (Kabat) of VHH-496, huVHH-746, huVHH-750,
      and huVHH-753

<400> SEQUENCE: 26

Trp Asp Arg Thr Leu
1               5

-continued

<210> SEQ ID NO 27
<211> LENGTH: 8
<212> TYPE: PRT
<213> ORGANISM: Artificial Sequence
<220> FEATURE:
<223> OTHER INFORMATION: CDR1 (IMGT) of VHH-496, huVHH-746, huVHH-750,
      and huVHH-753

<400> SEQUENCE: 27

Gly Phe Thr Phe Ser Asn Tyr Pro
1               5

<210> SEQ ID NO 28
<211> LENGTH: 8
<212> TYPE: PRT
<213> ORGANISM: Artificial Sequence
<220> FEATURE:
<223> OTHER INFORMATION: CDR2 (IMGT) of VHH-496, huVHH-746, huVHH-750,
      and huVHH-753

<400> SEQUENCE: 28

Ile Thr Ser Gly Gly Asp Arg Pro
1               5

<210> SEQ ID NO 29
<211> LENGTH: 7
<212> TYPE: PRT
<213> ORGANISM: Artificial Sequence
<220> FEATURE:
<223> OTHER INFORMATION: CDR3 (IMGT) of VHH-496, huVHH-746, huVHH-750,
      and huVHH-753

<400> SEQUENCE: 29

Ala Thr Trp Asp Arg Thr Leu
1               5

<210> SEQ ID NO 30
<211> LENGTH: 16
<212> TYPE: PRT
<213> ORGANISM: Artificial Sequence
<220> FEATURE:
<223> OTHER INFORMATION: CDR2 (Kabat) of VHH-653

<400> SEQUENCE: 30

Arg Val Asn Ala Asp Gly Ile Thr Asn His Ala Ala Ser Val Lys Gly
1               5                   10                  15

<210> SEQ ID NO 31
<211> LENGTH: 7
<212> TYPE: PRT
<213> ORGANISM: Artificial Sequence
<220> FEATURE:
<223> OTHER INFORMATION: CDR2 (IMGT) of VHH-653

<400> SEQUENCE: 31

Val Asn Ala Asp Gly Ile Thr
1               5

<210> SEQ ID NO 32
<211> LENGTH: 17
<212> TYPE: PRT
<213> ORGANISM: Artificial Sequence
<220> FEATURE:
<223> OTHER INFORMATION: CDR2 (Kabat) of huVHH-253

<400> SEQUENCE: 32

Ala Val Asp Trp Ser Gly Gly Ser Pro Tyr Tyr Ala Asp Ser Val Lys

-continued

```
1               5               10              15

Gly

<210> SEQ ID NO 33
<211> LENGTH: 8
<212> TYPE: PRT
<213> ORGANISM: Artificial Sequence
<220> FEATURE:
<223> OTHER INFORMATION: CDR2 (IMGT) of huVHH-253, huVHH-256, 2082H1,
      2082H2, 2082H3, 2082H4, 2082H5, and 2082H6

<400> SEQUENCE: 33

Val Asp Trp Ser Gly Gly Ser Pro
1               5

<210> SEQ ID NO 34
<211> LENGTH: 16
<212> TYPE: PRT
<213> ORGANISM: Artificial Sequence
<220> FEATURE:
<223> OTHER INFORMATION: CDR2 (Kabat) of huVHH-836

<400> SEQUENCE: 34

Arg Val Asn Ala Asp Asp Ser Ile Ser Tyr Ala Asp Ser Val Lys Gly
1               5               10              15

<210> SEQ ID NO 35
<211> LENGTH: 8
<212> TYPE: PRT
<213> ORGANISM: Artificial Sequence
<220> FEATURE:
<223> OTHER INFORMATION: CDR2 (IMGT) of huVHH-836

<400> SEQUENCE: 35

Val Asn Ala Asp Asp Ser Ile Ser
1               5

<210> SEQ ID NO 36
<211> LENGTH: 16
<212> TYPE: PRT
<213> ORGANISM: Artificial Sequence
<220> FEATURE:
<223> OTHER INFORMATION: CDR2 (Kabat) of huVHH-840

<400> SEQUENCE: 36

Phe Val Asn Ala Asp Asp Ser Ile Tyr Tyr Ala Asp Ser Val Lys Gly
1               5               10              15

<210> SEQ ID NO 37
<211> LENGTH: 16
<212> TYPE: PRT
<213> ORGANISM: Artificial Sequence
<220> FEATURE:
<223> OTHER INFORMATION: CDR2 (Kabat) of huVHH-843

<400> SEQUENCE: 37

Arg Val Asn Ala Asp Asp Ser Ile Asn Tyr Val Asp Ser Val Lys Gly
1               5               10              15

<210> SEQ ID NO 38
<211> LENGTH: 16
<212> TYPE: PRT
<213> ORGANISM: Artificial Sequence
<220> FEATURE:
<223> OTHER INFORMATION: CDR2 (Kabat) of huVHH-846

<400> SEQUENCE: 38
```

```
Phe Val Asn Ala Asp Asp Ser Ile Asn Tyr Ala Asp Ser Val Lys Gly
1               5                   10                  15

<210> SEQ ID NO 39
<211> LENGTH: 14
<212> TYPE: PRT
<213> ORGANISM: Artificial Sequence
<220> FEATURE:
<223> OTHER INFORMATION: CDR3 (IMGT) of 2082H2 and 2082H5

<400> SEQUENCE: 39

Ala Lys Arg Val Gln Tyr Gly Ser Ser Trp Ser Gly Asp Tyr
1               5                   10

<210> SEQ ID NO 40
<211> LENGTH: 14
<212> TYPE: PRT
<213> ORGANISM: Artificial Sequence
<220> FEATURE:
<223> OTHER INFORMATION: CDR3 (IMGT) of 2082H4

<400> SEQUENCE: 40

Ala Ala Arg Val Gln Tyr Gly Ser Ser Trp Ser Gly Asp Tyr
1               5                   10

<210> SEQ ID NO 41
<211> LENGTH: 121
<212> TYPE: PRT
<213> ORGANISM: Artificial Sequence
<220> FEATURE:
<223> OTHER INFORMATION: VHH-273 (amino acid)

<400> SEQUENCE: 41

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Asn Met Gly Trp Phe Arg Gln Ala Pro Gly Lys Glu Arg Glu Phe Val
            35                  40                  45

Ala Val Val Asp Trp Ser Gly Gly Ser Pro Tyr Tyr Ala Asp Ser Val
        50                  55                  60

Lys Gly Arg Phe Thr Ile Ser Arg Asp Asn Gly Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gly Arg Val Gln Tyr Gly Ser Ser Trp Ser Gly Asp Tyr Trp Gly
            100                 105                 110

Gln Gly Thr Gln Val Thr Val Ser Ser
        115                 120

<210> SEQ ID NO 42
<211> LENGTH: 121
<212> TYPE: PRT
<213> ORGANISM: Artificial Sequence
<220> FEATURE:
<223> OTHER INFORMATION: VHH-283 (amino acid)

<400> SEQUENCE: 42

Gln Val Lys Leu Glu Glu Ser Gly Gly Gly Ser Val Gln Ala Gly Gly
1               5                   10                  15

Ser Leu Arg Leu Ser Cys Ala Ala Ser Gly Arg Thr Phe Ser Ser Tyr
            20                  25                  30
```

-continued

```
Asn Met Gly Trp Phe Arg Gln Ala Pro Gly Lys Glu Arg Glu Phe Val
    35                  40                  45

Ala Ala Ile Ser Trp Ser Gly Gly Ser Pro Tyr Tyr Ala Ser Ser Val
    50                  55                  60

Arg Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Pro Ile Glu Tyr Gly Ser Ser Trp Ser Ala Asp Tyr Trp Gly
            100                 105                 110

Gln Gly Thr Gln Val Thr Val Ser Ser
        115                 120

<210> SEQ ID NO 43
<211> LENGTH: 121
<212> TYPE: PRT
<213> ORGANISM: Artificial Sequence
<220> FEATURE:
<223> OTHER INFORMATION: VHH-313 (amino acid)

<400> SEQUENCE: 43

Asp Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Ile Ser Ser Tyr
            20                  25                  30

Ser Met Gly Trp Phe Arg Gln Ala Pro Gly Lys Glu Arg Arg Phe Val
        35                  40                  45

Ala Ala Ile Ser Trp Ser Gly Gly Ser Pro Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Pro Ile Glu Tyr Gly Ser Ser Trp Ser Ala Asp Tyr Trp Gly
            100                 105                 110

Gln Gly Thr Gln Val Thr Val Ser Ser
        115                 120

<210> SEQ ID NO 44
<211> LENGTH: 118
<212> TYPE: PRT
<213> ORGANISM: Artificial Sequence
<220> FEATURE:
<223> OTHER INFORMATION: VHH-440 (amino acid)

<400> SEQUENCE: 44

Gln Val His Leu Met Glu Ser Gly Gly Gly Ser Val Gln Ala Gly Gly
1               5                   10                  15

Ser Leu Arg Leu Ser Cys Gln Ala Ser Ala Tyr Ile Arg Val Phe Tyr
            20                  25                  30

Leu Met Gly Trp Phe Arg Gln Ala Pro Gly Lys Glu Arg Glu Glu Val
        35                  40                  45

Ala Arg Val Thr Ala Asp Gly Phe Thr Asn His Ala Ala Ser Val Lys
    50                  55                  60

Gly Arg Phe Thr Ile Ser Lys Asp Asn Ala Lys Asn Thr Leu Tyr Leu
65                  70                  75                  80

Gln Met Asp Ser Met Lys Ser Glu Asp Thr Ala Val Tyr Tyr Cys Ala
```

-continued 85                    90                    95

Ala Gly Arg Thr Trp Asn Ser Gly Phe Glu Tyr Trp Gly Gln Gly Thr
            100                   105                   110

Gln Val Thr Val Ser Ser
        115

<210> SEQ ID NO 45
<211> LENGTH: 118
<212> TYPE: PRT
<213> ORGANISM: Artificial Sequence
<220> FEATURE:
<223> OTHER INFORMATION: VHH-466 (amino acid)

<400> SEQUENCE: 45

Gln Val His Leu Val Glu Ser Gly Gly Gly Ser Val Gln Ala Gly Gly
1                   5                    10                   15

Ser Leu Arg Leu Ser Cys Gln Ala Ser Ala Asp Ile Arg Leu Phe Tyr
            20                   25                   30

Leu Met Gly Trp Phe Arg Gln Ala Pro Gly Lys Glu Arg Glu Glu Val
        35                   40                   45

Ala Arg Val Asn Ala Asp Asp Ser Ile Asn Tyr Val Ala Ser Val Lys
    50                   55                   60

Gly Arg Phe Thr Ile Ser Lys Asp Asn Ala Lys Asn Thr Leu Tyr Leu
65                   70                   75                   80

Gln Met Asp Ser Leu Lys Pro Glu Asp Thr Ala Thr Tyr Tyr Cys Ala
                85                   90                   95

Ala Gly Arg Thr Trp Asn Ser Gly Phe Glu Tyr Trp Gly Gln Gly Thr
            100                   105                   110

Gln Val Thr Val Ser Ser
        115

<210> SEQ ID NO 46
<211> LENGTH: 114
<212> TYPE: PRT
<213> ORGANISM: Artificial Sequence
<220> FEATURE:
<223> OTHER INFORMATION: VHH-496 (amino acid)

<400> SEQUENCE: 46

Gln Ile Gln Leu Val Glu Ser Gly Gly Gly Leu Val Gln Pro Gly Gly
1                   5                    10                   15

Ser Leu Arg Leu Ser Cys Ala Ala Ser Gly Phe Thr Phe Ser Asn Tyr
            20                   25                   30

Pro Met Thr Trp Leu Arg Gln Ala Pro Gly Lys Gly Leu Glu Ser Val
        35                   40                   45

Ser Asp Ile Thr Ser Gly Gly Asp Arg Pro Tyr Ala Asp Ser Val
    50                   55                   60

Lys Gly Arg Phe Thr Ile Ser Arg Asp Asn Ala Lys Asn Met Leu Tyr
65                   70                   75                   80

Leu Glu Met Asn Ser Leu Lys Thr Glu Asp Thr Ala Val Tyr Tyr Cys
                85                   90                   95

Ala Thr Trp Asp Arg Thr Leu Thr Gly Gln Gly Thr Gln Val Thr Val
            100                   105                   110

Ser Ser

<210> SEQ ID NO 47
<211> LENGTH: 118
<212> TYPE: PRT

<213> ORGANISM: Artificial Sequence
<220> FEATURE:
<223> OTHER INFORMATION: VHH-653 (amino acid)

<400> SEQUENCE: 47

Gln Val Lys Leu Val Glu Ser Gly Gly Gly Ser Val Gln Ala Gly Gly
1               5                   10                  15

Ser Leu Arg Leu Ser Cys Gln Ala Ser Ala Tyr Ile Arg Val Phe Tyr
            20                  25                  30

Leu Met Gly Trp Phe Arg Gln Ala Pro Gly Lys Glu Arg Glu Glu Val
        35                  40                  45

Ala Arg Val Asn Ala Asp Gly Ile Thr Asn His Ala Ala Ser Val Lys
    50                  55                  60

Gly Arg Phe Thr Ile Ser Lys Asp Asn Ala Lys Asn Thr Leu Tyr Leu
65                  70                  75                  80

Gln Met Asp Ser Leu Lys Pro Glu Asp Thr Ala Val Tyr Tyr Cys Ala
            85                  90                  95

Ala Gly Arg Thr Trp Asn Ser Gly Phe Glu Tyr Trp Gly Gln Gly Thr
            100                 105                 110

Gln Val Thr Val Ser Ser
        115

<210> SEQ ID NO 48
<211> LENGTH: 121
<212> TYPE: PRT
<213> ORGANISM: Artificial Sequence
<220> FEATURE:
<223> OTHER INFORMATION: huVHH-253 (amino acid)

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Asn Met Gly Trp Phe Arg Gln Ala Pro Gly Lys Gly Leu Glu Trp Val
        35                  40                  45

Ala Ala Val Asp Trp Ser Gly Gly Ser Pro Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
            85                  90                  95

Ala Gly Arg Val Gln Tyr Gly Ser Ser Trp Ser Gly Asp Tyr Trp Gly
            100                 105                 110

Gln Gly Thr Leu Val Thr Val Ser Ser
        115                 120

<210> SEQ ID NO 49
<211> LENGTH: 121
<212> TYPE: PRT
<213> ORGANISM: Artificial Sequence
<220> FEATURE:
<223> OTHER INFORMATION: huVHH-256 (amino acid)

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

```
Asn Met Gly Trp Phe Arg Gln Ala Pro Gly Lys Gly Leu Glu Phe Val
        35              40              45

Ala Val Val Asp Trp Ser Gly Gly Ser Pro Tyr Tyr Ala Asp Ser Val
    50              55              60

Lys Gly Arg Phe Thr Ile Ser Arg Asp Asn Ser Lys Asn Thr Val Tyr
65              70              75              80

Leu Gln Met Ser Ser Leu Arg Ala Glu Asp Thr Ala Val Tyr Tyr Cys
            85              90              95

Ala Gly Arg Val Gln Tyr Gly Ser Ser Trp Ser Gly Asp Tyr Trp Gly
            100             105             110

Gln Gly Thr Leu Val Thr Val Ser Ser
        115             120
```

```
<210> SEQ ID NO 50
<211> LENGTH: 121
<212> TYPE: PRT
<213> ORGANISM: Artificial Sequence
<220> FEATURE:
<223> OTHER INFORMATION: huVHH-260 (amino acid)
```

```
<400> SEQUENCE: 50
```

```
Asp Val Gln Leu Leu Glu Ser Gly Gly Gly Leu Val Gln Pro Gly Gly
1               5               10              15

Ser Leu Arg Leu Ser Cys Ala Ala Ser Gly Arg Thr Ile Ser Ser Tyr
            20              25              30

Ser Met Gly Trp Phe Arg Gln Ala Pro Gly Lys Gly Leu Glu Phe Val
        35              40              45

Ala Ala Ile Ser Trp Ser Gly Gly Ser Pro Tyr Tyr Ala Asp Ser Val
    50              55              60

Lys Gly Arg Phe Thr Ile Ser Arg Asp Asn Ala Lys Asn Thr Val Tyr
65              70              75              80

Leu Gln Met Asn Ser Leu Arg Ala Glu Asp Thr Ala Val Tyr Tyr Cys
            85              90              95

Ala Ala Pro Ile Glu Tyr Gly Ser Ser Trp Ser Ala Asp Tyr Trp Gly
            100             105             110

Gln Gly Thr Leu Val Thr Val Ser Ser
        115             120
```

```
<210> SEQ ID NO 51
<211> LENGTH: 114
<212> TYPE: PRT
<213> ORGANISM: Artificial Sequence
<220> FEATURE:
<223> OTHER INFORMATION: huVHH-746 (amino acid)
```

```
<400> SEQUENCE: 51
```

```
Gln Ile Gln Leu Leu Glu Ser Gly Gly Gly Leu Val Gln Pro Gly Gly
1               5               10              15

Ser Leu Arg Leu Ser Cys Ala Ala Ser Gly Phe Thr Phe Ser Asn Tyr
            20              25              30

Pro Met Thr Trp Ile Arg Gln Ala Pro Gly Lys Gly Leu Glu Ser Val
        35              40              45

Ser Asp Ile Thr Ser Gly Gly Asp Arg Pro Tyr Tyr Ala Asp Ser Val
    50              55              60

Lys Gly Arg Phe Thr Ile Ser Arg Asp Asn Ala Lys Asn Met Leu Tyr
65              70              75              80

Leu Gln Met Asn Ser Leu Arg Ala Glu Asp Thr Ala Val Tyr Tyr Cys
```

-continued

|  | 85 |  | 90 |  | 95 |
|---|---|---|---|---|---|

Ala Thr Trp Asp Arg Thr Leu Trp Gly Gln Gly Thr Met Val Thr Val
             100                 105                 110

Ser Ser

<210> SEQ ID NO 52
<211> LENGTH: 114
<212> TYPE: PRT
<213> ORGANISM: Artificial Sequence
<220> FEATURE:
<223> OTHER INFORMATION: huVHH-750 (amino acid)

<400> SEQUENCE: 52

Gln Ile Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Pro Met Thr Trp Leu Arg Gln Ala Pro Gly Lys Gly Leu Glu Ser Val
        35                  40                  45

Ser Asp Ile Thr Ser Gly Gly Asp Arg Pro Tyr Tyr Ala Asp Ser Val
    50                  55                  60

Lys Gly Arg Phe Thr Ile Ser Arg Asp Asn Ala Lys Asn Met Leu Tyr
65                  70                  75                  80

Leu Gln Met Asn Ser Leu Arg Ala Glu Asp Thr Ala Val Tyr Tyr Cys
                85                  90                  95

Ala Thr Trp Asp Arg Thr Leu Thr Gly Gln Gly Thr Met Val Thr Val
            100                 105                 110

Ser Ser

<210> SEQ ID NO 53
<211> LENGTH: 114
<212> TYPE: PRT
<213> ORGANISM: Artificial Sequence
<220> FEATURE:
<223> OTHER INFORMATION: huVHH-753 (amino acid)

<400> SEQUENCE: 53

Gln Ile Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Pro Met Thr Trp Leu Arg Gln Ala Pro Gly Lys Gly Leu Glu Ser Val
        35                  40                  45

Ser Asp Ile Thr Ser Gly Gly Asp Arg Pro Tyr Tyr Ala Asp Ser Val
    50                  55                  60

Lys Gly Arg Phe Thr Ile Ser Arg Asp Asn Ala Lys Asn Met Leu Tyr
65                  70                  75                  80

Leu Gln Met Asn Ser Leu Arg Ala Glu Asp Thr Ala Val Tyr Tyr Cys
                85                  90                  95

Ala Thr Trp Asp Arg Thr Leu Thr Gly Gln Gly Thr Leu Val Thr Val
            100                 105                 110

Ser Ser

<210> SEQ ID NO 54
<211> LENGTH: 118
<212> TYPE: PRT
<213> ORGANISM: Artificial Sequence
<220> FEATURE:

<223> OTHER INFORMATION: huVHH-836 (amino acid)

<400> SEQUENCE: 54

```
Glu Val Gln Leu Val Glu Ser Gly Gly Gly Leu Val Gln Pro Gly Gly
1               5                   10                  15

Ser Leu Arg Leu Ser Cys Ala Ala Ser Ala Asp Ile Arg Leu Phe Tyr
            20                  25                  30

Leu Met Gly Trp Phe Arg Gln Ala Pro Gly Lys Gly Leu Val Trp Val
        35                  40                  45

Ala Arg Val Asn Ala Asp Asp Ser Ile Ser Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Gly Arg Thr Trp Asn Ser Gly Phe Glu Tyr Trp Gly Gln Gly Thr
            100                 105                 110

Leu Val Thr Val Ser Ser
        115
```

<210> SEQ ID NO 55
<211> LENGTH: 118
<212> TYPE: PRT
<213> ORGANISM: Artificial Sequence
<220> FEATURE:
<223> OTHER INFORMATION: huVHH-840 (amino acid)

<400> SEQUENCE: 55

```
Gln Val Gln Leu Gln Glu Ser Gly Gly Gly Val Val Gln Pro Gly Gly
1               5                   10                  15

Ser Leu Arg Leu Ser Cys Ala Ala Ser Ala Asp Ile Arg Leu Phe Tyr
            20                  25                  30

Leu Met Gly Trp Phe Arg Gln Ala Pro Gly Lys Gly Leu Glu Trp Val
        35                  40                  45

Ala Phe Val Asn Ala Asp Asp Ser Ile Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Gly Arg Thr Trp Asn Ser Gly Phe Glu Tyr Trp Gly Gln Gly Thr
            100                 105                 110

Leu Val Thr Val Ser Ser
        115
```

<210> SEQ ID NO 56
<211> LENGTH: 118
<212> TYPE: PRT
<213> ORGANISM: Artificial Sequence
<220> FEATURE:
<223> OTHER INFORMATION: huVHH-843 (amino acid)

<400> SEQUENCE: 56

```
Gln Val His Leu Val Glu Ser Gly Gly Gly Leu Val Gln Pro Gly Gly
1               5                   10                  15

Ser Leu Arg Leu Ser Cys Gln Ala Ser Ala Asp Ile Arg Leu Phe Tyr
            20                  25                  30

Leu Met Gly Trp Phe Arg Gln Ala Pro Gly Lys Gly Leu Val Trp Val
```

-continued

```
              35                  40                  45

Ala Arg Val Asn Ala Asp Asp Ser Ile Asn Tyr Val Asp Ser Val Lys
    50                  55                  60

Gly Arg Phe Thr Ile Ser Lys Asp Asn Ala Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Gly Arg Thr Trp Asn Ser Gly Phe Glu Tyr Trp Gly Gln Gly Thr
            100                 105                 110

Leu Val Thr Val Ser Ser
        115
```

<210> SEQ ID NO 57
<211> LENGTH: 118
<212> TYPE: PRT
<213> ORGANISM: Artificial Sequence
<220> FEATURE:
<223> OTHER INFORMATION: huVHH-846 (amino acid)

<400> SEQUENCE: 57

```
Gln Val His Leu Gln Glu Ser Gly Gly Gly Val Val Gln Pro Gly Gly
1               5                  10                  15

Ser Leu Arg Leu Ser Cys Gln Ala Ser Ala Asp Ile Arg Leu Phe Tyr
                20                  25                  30

Leu Met Gly Trp Phe Arg Gln Ala Pro Gly Lys Gly Leu Glu Trp Val
            35                  40                  45

Ala Phe Val Asn Ala Asp Asp Ser Ile Asn Tyr Ala Asp Ser Val Lys
    50                  55                  60

Gly Arg Phe Thr Ile Ser Lys Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Ala Gly Arg Thr Trp Asn Ser Gly Phe Glu Tyr Trp Gly Gln Gly Thr
            100                 105                 110

Leu Val Thr Val Ser Ser
        115
```

<210> SEQ ID NO 58
<211> LENGTH: 121
<212> TYPE: PRT
<213> ORGANISM: Artificial Sequence
<220> FEATURE:
<223> OTHER INFORMATION: 2082H1 (amino acid)

<400> SEQUENCE: 58

```
Glu Val Gln Leu Val Glu Ser Gly Gly Gly Leu Val Gln Pro Gly Gly
1               5                  10                  15

Ser Leu Arg Leu Ser Cys Ala Ala Ser Gly Arg Thr Phe Ser Ser Tyr
                20                  25                  30

Asn Met Gly Trp Phe Arg Gln Ala Pro Gly Lys Gly Leu Glu Phe Val
            35                  40                  45

Ala Val Val Asp Trp Ser Gly Gly Ser Pro Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Gly Arg Val Gln Tyr Gly Ser Ser Trp Ser Gly Asp Tyr Trp Gly
            100                 105                 110

Gln Gly Thr Leu Val Thr Val Ser Ser
        115                 120

<210> SEQ ID NO 59
<211> LENGTH: 121
<212> TYPE: PRT
<213> ORGANISM: Artificial Sequence
<220> FEATURE:
<223> OTHER INFORMATION: 2082H2 (amino acid)

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Asn Met Gly Trp Phe Arg Gln Ala Pro Gly Lys Gly Leu Glu Phe Val
        35                  40                  45

Ala Val Val Asp Trp Ser Gly Gly Ser Pro Tyr Tyr Ala Asp Ser Val
    50                  55                  60

Lys Gly Arg Phe Thr Ile Ser Leu Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Val Gln Tyr Gly Ser Ser Trp Ser Gly Asp Tyr Trp Gly
            100                 105                 110

Gln Gly Thr Leu Val Thr Val Ser Ser
        115                 120

<210> SEQ ID NO 60
<211> LENGTH: 121
<212> TYPE: PRT
<213> ORGANISM: Artificial Sequence
<220> FEATURE:
<223> OTHER INFORMATION: 2082H3 (amino acid)

<400> SEQUENCE: 60

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Asn Met Gly Trp Val Arg Gln Ala Pro Gly Lys Gly Leu Glu Trp Val
        35                  40                  45

Ala Val Val Asp Trp Ser Gly Gly Ser Pro Tyr Tyr Ala Asp Ser Val
    50                  55                  60

Lys Gly Arg Phe Thr Ile Ser Arg Asp Asn Gly Lys Asn Thr Val Tyr
65                  70                  75                  80

Leu Gln Met Asn Ser Leu Lys Pro Glu Asp Thr Ala Val Tyr Tyr Cys
                85                  90                  95

Ala Gly Arg Val Gln Tyr Gly Ser Ser Trp Ser Gly Asp Tyr Trp Gly
            100                 105                 110

Gln Gly Thr Gln Val Thr Val Ser Ser
        115                 120

<210> SEQ ID NO 61
<211> LENGTH: 121
<212> TYPE: PRT
<213> ORGANISM: Artificial Sequence
```

<220> FEATURE:
<223> OTHER INFORMATION: 2082H4 (amino acid)

<400> SEQUENCE: 61

```
Gln Val Gln Leu Val Glu Ser Gly Gly Gly Ser Val Gln Ala Gly Gly
1               5                   10                  15

Ser Leu Arg Leu Ser Cys Ser Ala Ser Gly Arg Thr Phe Ser Ser Tyr
            20                  25                  30

Asn Met Gly Trp Val Arg Gln Ala Pro Gly Lys Gly Leu Glu Trp Val
        35                  40                  45

Ala Val Val Asp Trp Ser Gly Gly Ser Pro Tyr Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Ala Ala Arg Val Gln Tyr Gly Ser Ser Trp Ser Gly Asp Tyr Trp Gly
            100                 105                 110

Gln Gly Thr Gln Val Thr Val Ser Ser
        115                 120
```

<210> SEQ ID NO 62
<211> LENGTH: 121
<212> TYPE: PRT
<213> ORGANISM: Artificial Sequence
<220> FEATURE:
<223> OTHER INFORMATION: 2082H5 (amino acid)

<400> SEQUENCE: 62

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Asn Met Gly Trp Val Arg Gln Ala Pro Gly Lys Gly Leu Glu Trp Val
        35                  40                  45

Ser Val Val Asp Trp Ser Gly Gly Ser Pro Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Val Gln Tyr Gly Ser Ser Trp Ser Gly Asp Tyr Trp Gly
            100                 105                 110

Gln Gly Thr Leu Val Thr Val Ser Ser
        115                 120
```

<210> SEQ ID NO 63
<211> LENGTH: 121
<212> TYPE: PRT
<213> ORGANISM: Artificial Sequence
<220> FEATURE:
<223> OTHER INFORMATION: 2082H6 (amino acid)

<400> SEQUENCE: 63

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30
```

```
Asn Met Gly Trp Phe Arg Gln Ala Pro Gly Lys Glu Arg Glu Phe Val
        35                  40                  45
```

```
Ala Val Val Asp Trp Ser Gly Gly Ser Pro Tyr Tyr Ala Asp Ser Val
    50                  55                  60
```

```
Lys Gly Arg Phe Thr Ile Ser Arg Asp Asn Ser Lys Asn Thr Val Tyr
65                  70                  75                  80
```

```
Leu Gln Met Asn Ser Leu Lys Ala Glu Asp Thr Ala Val Tyr Tyr Cys
                85                  90                  95
```

```
Ala Gly Arg Val Gln Tyr Gly Ser Ser Trp Ser Gly Asp Tyr Trp Gly
            100                 105                 110
```

```
Gln Gly Thr Leu Val Thr Val Ser Ser
        115                 120
```

<210> SEQ ID NO 64
<211> LENGTH: 363
<212> TYPE: DNA
<213> ORGANISM: Artificial Sequence
<220> FEATURE:
<223> OTHER INFORMATION: VHH-273 (nucleic acid)

<400> SEQUENCE: 64

```
gaagtccagc tggtggaatc cgggggaggc ctggtgcagg caggaggctc cctgcggctg      60
tcttgcgcag caagcggaag gaccttcagc tcctacaaca tgggctggtt taggcaggca     120
ccaggcaagg agagggagtt cgtggcagtg gtggactggt ctggaggcag cccttactat     180
gccgattccg tgaagggccg gtttaccatc agccgggaca cggcaagaa tacagtgtat      240 ctgcagatga cagcctgaa gcccgaggat acagccgtgt actattgtgc cggccgggtg     300
cagtacgggt caagctggtc tggggattat tggggggcagg ggactcaggt cactgtctca    360
tca                                                                    363
```

<210> SEQ ID NO 65
<211> LENGTH: 363
<212> TYPE: DNA
<213> ORGANISM: Artificial Sequence
<220> FEATURE:
<223> OTHER INFORMATION: VHH-283 (nucleic acid)

<400> SEQUENCE: 65

```
caggtcaaac tggaggaatc tggggggaggc agcgtgcagg caggaggcag cctgcggctg      60
tcctgcgccg cctctggcag gaccttcagc tcctacaaca tgggctggtt taggcaggca     120
ccaggcaagg agagggagtt cgtggcagca atctcctggt ctggaggcag cccctactat     180
gcctctagcg tgcgggggccg gttcaccatc tcccgggaca cgccaagaa tacagtgtat      240 ctgcagatga cagcctgaa gcccgaggat acagccgtgt actattgtgc cgcccctatc     300
gagtacggct cttcttggtc agcagattat tggggacagg gcactcaggt cacagtctca    360
tca                                                                    363
```

<210> SEQ ID NO 66
<211> LENGTH: 363
<212> TYPE: DNA
<213> ORGANISM: Artificial Sequence
<220> FEATURE:
<223> OTHER INFORMATION: VHH-313 (nucleic acid)

<400> SEQUENCE: 66

```
gatgtgcagc tggtggagag cggcggcggg ttggtgcaag ccggtggttc gctgcggttg      60
tcatgcgccg cttccggacg tacaatctct agctactcca tgggctggtt ccgccaggcc     120
```

```
cctggtaagg agcgcaggtt tgtcgcggcc atctcctggt ctggagggtc gccctattac    180
gcggacagcg tgaagggccg cttcaccatc agccgtgaca acgccaagaa cacggtttac    240
ctgcagatga actccctcaa acctgaagac accgccgtgt actactgtgc tgcaccaatt    300
gagtacggct ccagttggtc tgcggactat tggggccagg gcacccaggt caccgtgtcc    360
tct                                                                   363
```

```
<210> SEQ ID NO 67
<211> LENGTH: 354
<212> TYPE: DNA
<213> ORGANISM: Artificial Sequence
<220> FEATURE:
<223> OTHER INFORMATION: VHH-440 (nucleic acid)

<400> SEQUENCE: 67
caggtccacc tgatggagag cggaggcggc tccgtgcagg ccggaggtag tctgcgcctg     60
tcatgccagg cctccgccta cattcgagtg ttctacctga tgggctggtt ccgccaggcc    120
ccggggaagg agcgcgagga ggtggctcgt gtcactgcgg acggcttcac caaccatgca    180
gcttctgtga agggccgctt caccatctcc aaggacaacg cgaagaacac gctgtacttg    240
cagatggatt ctatgaaaag cgaagacact gccgtgtact actgtgccgc tgggcggacc    300
tggaactccg gttttgagta ttggggccag ggcacccagg tcaccgtgtc gtcc          354
```

```
<210> SEQ ID NO 68
<211> LENGTH: 354
<212> TYPE: DNA
<213> ORGANISM: Artificial Sequence
<220> FEATURE:
<223> OTHER INFORMATION: VHH-466 (nucleic acid)

<400> SEQUENCE: 68
caggtccact tggtggagag cggtggaggc tccgtgcagg ccggaggttc tctccgtctc     60
tcatgccagg cctccgcgga catccgcctg ttttacctga tgggctggtt ccgccaagca    120
cccgggaagg agcgcgagga ggtggctcgg gttaacgcgg atgacagcat taactacgtg    180
gcgagtgtaa agggccgctt caccatctcc aaggacaacg ccaagaacac gctgtacttg    240
cagatggatt ctcttaaacc ggaagacacc gccacttact actgtgctgc tgggcgaacc    300
tggaactccg gcttcgagta ttggggccag ggcacccagg tcaccgtgag ctcg          354
```

```
<210> SEQ ID NO 69
<211> LENGTH: 342
<212> TYPE: DNA
<213> ORGANISM: Artificial Sequence
<220> FEATURE:
<223> OTHER INFORMATION: VHH-496 (nucleic acid)

<400> SEQUENCE: 69
cagatccagc tggtggagag tggaggcggc ttggtgcagc caggggggctc cctacgcctg     60 tcatgcgctg cttctggctt cacgttcagc aactacccga tgacctggct ccgccaggcc    120
cccgggaaag gcctcgagag cgtgtccgac atcacctccg gtggtgatcg gccctattac    180
gcggactcgg tgaagggcag gtttacaatt tctcgcgaca acgccaagaa tatgctgtac    240
ctggagatga actccctgaa gactgaagac accgccgtgt actactgtgc cacctgggat    300
cgcaccctga cgggacaagg cacccaggtc accgttagct cg                        342
```

```
<210> SEQ ID NO 70
```

```
<211> LENGTH: 354
<212> TYPE: DNA
<213> ORGANISM: Artificial Sequence
<220> FEATURE:
<223> OTHER INFORMATION: VHH-653 (nucleic acid)

<400> SEQUENCE: 70
caggtgaagc tggtggagag cggtgggggc tccgtgcagg ccggaggtag ccttcgcctg      60
tcatgccagg cctccgccta cattcgggtg ttttacctga tgggctggtt ccgccaggcc     120
ccggggaagg agcgcgagga ggtggcacga gtcaacgcgg acggcatcac caaccatgca     180
gcttccgtaa aaggccgctt caccatctcc aaggacaacg ccaagaacac gctatacctc     240
cagatggatt ctctgaagcc cgaggacacc gccgtgtact actgtgctgc gggacgtact     300
tggaactccg gcttcgaata ttggggccag ggcacccagg tcactgtcag ttcc           354

<210> SEQ ID NO 71
<211> LENGTH: 363
<212> TYPE: DNA
<213> ORGANISM: Artificial Sequence
<220> FEATURE:
<223> OTHER INFORMATION: huVHH-253 (nucleic acid)

<400> SEQUENCE: 71
gaggtgcagc tggtggagag cggcggcggt ttggtgcagc caggaggctc cctccgcctg      60
tcatgcgccg cttccggccg caccttcagc agctacaaca tgggctggtt ccgccaggcc     120
cccggcaaag gcctggagtg ggtcgcggcc gtggattggt ctggcggttc ccctattac      180 gcggactccg tgaagggccg cttcaccatc tcccgcgaca actccaagaa cacggtgtac     240
ctgcagatga actctctgcg cgccgaggac accgccgtct actactgtgc cggccgagtg     300
cagtacggct ccagttggtc tggggactat tggggccagg gcaccctggt gaccgtgtcg     360
tcc                                                                    363

<210> SEQ ID NO 72
<211> LENGTH: 363
<212> TYPE: DNA
<213> ORGANISM: Artificial Sequence
<220> FEATURE:
<223> OTHER INFORMATION: huVHH-256 (nucleic acid)

<400> SEQUENCE: 72
gaggtgcagc tggtggagag cggaggcggt ttggtgcagc caggggggttc tctgcgcctg     60 agctgtgctg cttccggtcg tacgttcagc agctacaaca tgggctggtt ccgccaggcc     120
cccggcaaag gcctggagtt cgtcgccgtg gtggactggt ctggcggctc ccctattac      180 gcggactccg tgaagggccg cttcaccatc tcccgcgaca actccaagaa cacggtgtac     240
ctgcagatgt cttctcttcg cgccgaggac accgccgtct actactgcgc cggccgagtg     300
cagtacggct ccagttggtc tggtgattat tggggccagg gcaccctggt gaccgtgtcg     360
tcc                                                                    363

<210> SEQ ID NO 73
<211> LENGTH: 363
<212> TYPE: DNA
<213> ORGANISM: Artificial Sequence
<220> FEATURE:
<223> OTHER INFORMATION: huVHH-260 (nucleic acid)

<400> SEQUENCE: 73
gacgtgcagc tgctggagag cggaggcggg ctggtgcagc caggggggttc tcttcgcctg     60
```

```
tcatgcgccg cttccggtcg caccatctct agctactcca tgggctggtt ccgccaggcc        120
cccggcaaag gcctcgagtt cgtcgcggcc atcagttggt ctggcggctc ccctattac         180 gcggactccg tgaagggccg cttcaccatc tcccgcgaca acgccaagaa cacggtctac        240
ctgcagatga actccctgcg cgccgaggac accgccgtgt actactgtgc tgctcctatt        300
gagtacggct ccagttggtc tgcggactat tggggccagg gcaccctggt caccgtgtcg        360
tcc                                                                     363
```

<210> SEQ ID NO 74
<211> LENGTH: 342
<212> TYPE: DNA
<213> ORGANISM: Artificial Sequence
<220> FEATURE:
<223> OTHER INFORMATION: huVHH-746 (nucleic acid)

<400> SEQUENCE: 74

```
cagatccagc tgctggagag tggcggcggg ctggtgcagc cgggaggctc cctgcgcctg         60
tcatgcgccg cttccggctt cacgttcagc aactacccaa tgacctggat ccgccaggcc        120
cccggcaaag gcctcgagag cgtgtccgac atcacctccg gtggtgatag gccctattac        180
gcggactccg tgaagggccg cttcaccatc tctcgcgaca acgccaagaa catgctgtac        240
ctgcagatga actccctccg cgccgaggac accgccgtgt actactgtgc cacctgggac        300
cgcacccttt ggggccaggg caccatggtg accgtgagct cc                          342
```

<210> SEQ ID NO 75
<211> LENGTH: 342
<212> TYPE: DNA
<213> ORGANISM: Artificial Sequence
<220> FEATURE:
<223> OTHER INFORMATION: huVHH-750 (nucleic acid)

<400> SEQUENCE: 75

```
cagatccagc tggtggagag cggaggcggt ttggtgcagc cgggcggctc cctgcgcctg         60
agctgtgctg cttccggctt cacattttca aattatccaa tgacctggct ccgccaggcc        120
cccggcaagg gcctggagtc cgtgtccgac atcacctccg gtggggacag gccctattac        180
gcggacagcg tcaaaggccg cttcaccatc tctcgcgaca acgccaagaa catgctgtac        240
ctgcagatga actccttacg cgccgaggac accgccgtgt actactgcgc cacctgggac        300
cgcaccctga ccggccaggg caccatggtg accgtgagct cc                          342
```

<210> SEQ ID NO 76
<211> LENGTH: 342
<212> TYPE: DNA
<213> ORGANISM: Artificial Sequence
<220> FEATURE:
<223> OTHER INFORMATION: huVHH-753 (nucleic acid)

<400> SEQUENCE: 76

```
cagatccagc tggtggagag cggcggcggt ttggtgcagc cgggaggctc cctgcgcctg         60
tcatgcgccg cttccggctt caccttttca aattacccaa tgacctggct ccgccaggcc        120
cccggcaaag gcctggagtc cgtgtccgac atcacctccg gtggggacag gccctattac        180
gcggacagcg tgaagggccg cttcaccatc tctcgcgaca acgccaagaa catgctttac        240
ctgcagatga actccttacg cgccgaggac accgccgtgt actactgtgc cacctgggac        300
cgcaccctca ctggacaggg caccctggtc accgtgtcgt cc                          342
```

-continued

<210> SEQ ID NO 77
<211> LENGTH: 354
<212> TYPE: DNA
<213> ORGANISM: Artificial Sequence
<220> FEATURE:
<223> OTHER INFORMATION: huVHH-836 (nucleic acid)

<400> SEQUENCE: 77
gaggtgcagc tggtggagag cggtggcggt ctggtgcagc cgggaggctc cttgcgtcta      60
tcatgcgccg cttccgcgga catccgcctg ttttacctga tgggctggtt ccgccaggcc     120
cccgggaaag ggttggtttg ggtcgcccga gtcaacgcgg atgacagcat ttcttacgcg     180
gatagtgtga agggccgctt caccatctcc cgcgacaacg ccaagaacac gctctacctc     240
cagatgaact ccctgcgcgc cgaggacacc gccgtatact actgtgctgc aggacggacc     300
tggaactccg gcttcgagta ctggggccag ggcactcttg tcaccgtgag ctcg           354

<210> SEQ ID NO 78
<211> LENGTH: 354
<212> TYPE: DNA
<213> ORGANISM: Artificial Sequence
<220> FEATURE:
<223> OTHER INFORMATION: huVHH-840 (nucleic acid)

<400> SEQUENCE: 78
caggtgcagc tgcaggagag cggaggaggt gtggtgcagc caggcggctc cttgcgcctg      60
tcatgcgccg ctagtgcgga catccgactc ttttacctga tgggctggtt ccgccaggcc     120
ccggggaaag gtctcgagtg ggtcgccttc gtgaacgcag atgacagcat ttactacgcg     180
gattccgtaa agggccgctt caccatctct cgggacaact ccaagaacac gctgtacctc     240
cagatgaaca gcctacgtgc cgaggacact gccgtgtact actgtgccgc tgggcgcacc     300
tggaactccg gcttcgagta ctggggccaa ggcaccctgg tgaccgtgtc gtct           354

<210> SEQ ID NO 79
<211> LENGTH: 354
<212> TYPE: DNA
<213> ORGANISM: Artificial Sequence
<220> FEATURE:
<223> OTHER INFORMATION: huVHH-843 (nucleic acid)

<400> SEQUENCE: 79
caggtccact tggtggagag cggaggtggt ctggtgcagc caggggggctc cctacgcctg      60 tcatgccagg cctccgcgga catccgactc ttttacctaa tgggctggtt ccgccaggcc     120
cccgggaaag gccttgtttg ggtcgcacgg gtcaacgcgg atgacagcat taactacgtg     180
gattctgtga agggccgctt caccatctcc aaggacaacg ccaagaacac gctgtacctg     240
cagatgaact ccctgcgcgc cgaggacacc gccgtgtact actgtgctgc tggacgtacc     300
tggaactccg gcttcgagta ttggggccag ggcaccctgg taacagtgtc gtcg           354

<210> SEQ ID NO 80
<211> LENGTH: 354
<212> TYPE: DNA
<213> ORGANISM: Artificial Sequence
<220> FEATURE:
<223> OTHER INFORMATION: huVHH-846 (nucleic acid)

<400> SEQUENCE: 80
caggtccact tgcaggagag cggcgggggt gtggtgcagc cgggaggctc ccttcgtctc      60
tcatgccaag cctcggcgga catccggctt ttttacctga tgggctggtt ccgccaggcc     120

-continued

```
cccgggaagg gactggagtg ggttgccttc gtgaacgctg atgacagcat taactacgcg      180
gattccgtga agggccgctt caccatctct aaggacaaca gcaaaaacac tctgtacctc      240
cagatgaact ccctgcgcgc tgaagacacc gccgtgtact actgtgctgc aggtcgcacc      300
tggaactccg gcttcgagta ttggggccag ggcaccctgg tgacggtgtc cagt            354
```

<210> SEQ ID NO 81
<211> LENGTH: 367
<212> TYPE: PRT
<213> ORGANISM: Artificial Sequence
<220> FEATURE:
<223> OTHER INFORMATION: VHH-273 CAR (amino acid)

<400> SEQUENCE: 81

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Ser Ser Tyr Asn Met Gly Trp Phe Arg Gln Ala Pro Gly Lys
    50                  55                  60

Glu Arg Glu Phe Val Ala Val Val Asp Trp Ser Gly Gly Ser Pro Tyr
65                  70                  75                  80

Tyr Ala Asp Ser Val Lys Gly Arg Phe Thr Ile Ser Arg Asp Asn Gly
                85                  90                  95

Lys Asn Thr Val Tyr Leu Gln Met Asn Ser Leu Lys Pro Glu Asp Thr
            100                 105                 110

Ala Val Tyr Tyr Cys Ala Gly Arg Val Gln Tyr Gly Ser Ser Trp Ser
        115                 120                 125

Gly Asp Tyr Trp Gly Gln Gly Thr Gln Val Thr Val Ser Ser Thr Ser
    130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
    210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Gln Gln Gly Gln
                260                 265                 270

Asn Gln Leu Tyr Asn Glu Leu Asn Leu Gly Arg Arg Glu Glu Tyr Asp
            275                 280                 285

Val Leu Asp Lys Arg Arg Gly Arg Asp Pro Glu Met Gly Gly Lys Pro
        290                 295                 300

Arg Arg Lys Asn Pro Gln Glu Gly Leu Tyr Asn Glu Leu Gln Lys Asp
305                 310                 315                 320
```

-continued

```
Lys Met Ala Glu Ala Tyr Ser Glu Ile Gly Met Lys Gly Glu Arg Arg
            325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365

<210> SEQ ID NO 82
<211> LENGTH: 367
<212> TYPE: PRT
<213> ORGANISM: Artificial Sequence
<220> FEATURE:
<223> OTHER INFORMATION: VHH-283 CAR (amino acid)

<400> SEQUENCE: 82

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Ser
            20                  25                  30

Val Gln Ala Gly Gly Ser Leu Arg Leu Ser Cys Ala Ala Ser Gly Arg
        35                  40                  45

Thr Phe Ser Ser Tyr Asn Met Gly Trp Phe Arg Gln Ala Pro Gly Lys
    50                  55                  60

Glu Arg Glu Phe Val Ala Ala Ile Ser Trp Ser Gly Gly Ser Pro Tyr
65                  70                  75                  80

Tyr Ala Ser Ser Val Arg Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Ala Val Tyr Tyr Cys Ala Ala Pro Ile Glu Tyr Gly Ser Ser Trp Ser
            115                 120                 125

Ala Asp Tyr Trp Gly Gln Gly Thr Gln Val Thr Val Ser Ser Thr Ser
        130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
            195                 200                 205

Ile Thr Leu Tyr Cys Lys Arg Gly Arg Lys Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Gln Gln Gly Gln
                260                 265                 270

Asn Gln Leu Tyr Asn Glu Leu Asn Leu Gly Arg Arg Glu Glu Tyr Asp
            275                 280                 285

Val Leu Asp Lys Arg Arg Gly Arg Asp Pro Glu Met Gly Gly Lys Pro
        290                 295                 300

Arg Arg Lys Asn Pro Gln Glu Gly Leu Tyr Asn Glu Leu Gln Lys Asp
305                 310                 315                 320
```

-continued

```
Lys Met Ala Glu Ala Tyr Ser Glu Ile Gly Met Lys Gly Glu Arg Arg
            325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365

<210> SEQ ID NO 83
<211> LENGTH: 367
<212> TYPE: PRT
<213> ORGANISM: Artificial Sequence
<220> FEATURE:
<223> OTHER INFORMATION: VHH-313 CAR (amino acid)

<400> SEQUENCE: 83

Met Ala Leu Pro Val Thr Ala Leu Leu Leu Pro Leu Ala Leu Leu Leu
1               5                   10                  15

His Ala Ala Arg Pro Asp Val Gln Leu Val Glu Ser Gly Gly Gly Leu
            20                  25                  30

Val Gln Ala Gly Gly Ser Leu Arg Leu Ser Cys Ala Ala Ser Gly Arg
            35                  40                  45

Thr Ile Ser Ser Tyr Ser Met Gly Trp Phe Arg Gln Ala Pro Gly Lys
        50                  55                  60

Glu Arg Arg Phe Val Ala Ala Ile Ser Trp Ser Gly Gly Ser Pro Tyr
65                  70                  75                  80

Tyr Ala Asp Ser Val Lys Gly Arg Phe Thr Ile Ser Arg Asp Asn Ala
            85                  90                  95

Lys Asn Thr Val Tyr Leu Gln Met Asn Ser Leu Lys Pro Glu Asp Thr
            100                 105                 110

Ala Val Tyr Tyr Cys Ala Ala Pro Ile Glu Tyr Gly Ser Ser Trp Ser
            115                 120                 125

Ala Asp Tyr Trp Gly Gln Gly Thr Gln Val Thr Val Ser Ser Thr Ser
        130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
            165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
            195                 200                 205

Ile Thr Leu Tyr Cys Lys Arg Gly Arg Lys Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu Arg
            245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
            275                 280                 285

Val Leu Asp Lys Arg Arg Gly Arg Asp Pro Glu Met Gly Gly Lys Pro
        290                 295                 300

Arg Arg Lys Asn Pro Gln Glu Gly Leu Tyr Asn Glu Leu Gln Lys Asp
305                 310                 315                 320
```

-continued

```
Lys Met Ala Glu Ala Tyr Ser Glu Ile Gly Met Lys Gly Glu Arg Arg
            325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
            355                 360                 365

<210> SEQ ID NO 84
<211> LENGTH: 364
<212> TYPE: PRT
<213> ORGANISM: Artificial Sequence
<220> FEATURE:
<223> OTHER INFORMATION: VHH-440 CAR (amino acid)

<400> SEQUENCE: 84

Met Ala Leu Pro Val Thr Ala Leu Leu Leu Pro Leu Ala Leu Leu Leu
1               5                   10                  15

His Ala Ala Arg Pro Gln Val His Leu Met Glu Ser Gly Gly Gly Ser
            20                  25                  30

Val Gln Ala Gly Gly Ser Leu Arg Leu Ser Cys Gln Ala Ser Ala Tyr
            35                  40                  45

Ile Arg Val Phe Tyr Leu Met Gly Trp Phe Arg Gln Ala Pro Gly Lys
            50                  55                  60

Glu Arg Glu Glu Val Ala Arg Val Thr Ala Asp Gly Phe Thr Asn His
65                  70                  75                  80

Ala Ala Ser Val Lys Gly Arg Phe Thr Ile Ser Lys Asp Asn Ala Lys
            85                  90                  95

Asn Thr Leu Tyr Leu Gln Met Asp Ser Met Lys Ser Glu Asp Thr Ala
            100                 105                 110

Val Tyr Tyr Cys Ala Ala Gly Arg Thr Trp Asn Ser Gly Phe Glu Tyr
            115                 120                 125

Trp Gly Gln Gly Thr Gln Val Thr Val Ser Ser Thr Ser Thr Thr Thr
            130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
            165                 170                 175

His Thr Arg Gly Leu Asp Phe Ala Cys Asp Ile Tyr Ile Trp Ala Pro
            180                 185                 190

Leu Ala Gly Thr Cys Gly Val Leu Leu Leu Ser Leu Val Ile Thr Leu
            195                 200                 205

Tyr Cys Lys Arg Gly Arg Lys Lys Leu Leu Tyr Ile Phe Lys Gln Pro
            210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
            245                 250                 255

Ser Arg Ser Ala Asp Ala Pro Ala Tyr Gln Gln Gly Gln Asn Gln Leu
            260                 265                 270

Tyr Asn Glu Leu Asn Leu Gly Arg Arg Glu Glu Tyr Asp Val Leu Asp
            275                 280                 285

Lys Arg Arg Gly Arg Asp Pro Glu Met Gly Gly Lys Pro Arg Arg Lys
            290                 295                 300

Asn Pro Gln Glu Gly Leu Tyr Asn Glu Leu Gln Lys Asp Lys Met Ala
305                 310                 315                 320
```

-continued

```
Glu Ala Tyr Ser Glu Ile Gly Met Lys Gly Glu Arg Arg Arg Gly Lys
                325             330             335

Gly His Asp Gly Leu Tyr Gln Gly Leu Ser Thr Ala Thr Lys Asp Thr
            340             345             350

Tyr Asp Ala Leu His Met Gln Ala Leu Pro Pro Arg
        355             360

<210> SEQ ID NO 85
<211> LENGTH: 364
<212> TYPE: PRT
<213> ORGANISM: Artificial Sequence
<220> FEATURE:
<223> OTHER INFORMATION: VHH-466 CAR (amino acid)

<400> SEQUENCE: 85

Met Ala Leu Pro Val Thr Ala Leu Leu Leu Pro Leu Ala Leu Leu Leu
1               5               10              15

His Ala Ala Arg Pro Gln Val His Leu Val Glu Ser Gly Gly Gly Ser
            20              25              30

Val Gln Ala Gly Gly Ser Leu Arg Leu Ser Cys Gln Ala Ser Ala Asp
        35              40              45

Ile Arg Leu Phe Tyr Leu Met Gly Trp Phe Arg Gln Ala Pro Gly Lys
    50              55              60

Glu Arg Glu Glu Val Ala Arg Val Asn Ala Asp Asp Ser Ile Asn Tyr
65              70              75              80

Val Ala Ser Val Lys Gly Arg Phe Thr Ile Ser Lys Asp Asn Ala Lys
            85              90              95

Asn Thr Leu Tyr Leu Gln Met Asp Ser Leu Lys Pro Glu Asp Thr Ala
            100             105             110

Thr Tyr Tyr Cys Ala Ala Gly Arg Thr Trp Asn Ser Gly Phe Glu Tyr
            115             120             125

Trp Gly Gln Gly Thr Gln Val Thr Val Ser Ser Thr Ser Thr Thr Thr
    130             135             140

Pro Ala Pro Arg Pro Pro Thr Pro Ala Pro Thr Ile Ala Ser Gln Pro
145             150             155             160

Leu Ser Leu Arg Pro Glu Ala Cys Arg Pro Ala Ala Gly Gly Ala Val
            165             170             175

His Thr Arg Gly Leu Asp Phe Ala Cys Asp Ile Tyr Ile Trp Ala Pro
            180             185             190

Leu Ala Gly Thr Cys Gly Val Leu Leu Leu Ser Leu Val Ile Thr Leu
            195             200             205

Tyr Cys Lys Arg Gly Arg Lys Lys Leu Leu Tyr Ile Phe Lys Gln Pro
    210             215             220

Phe Met Arg Pro Val Gln Thr Thr Gln Glu Glu Asp Gly Cys Ser Cys
225             230             235             240

Arg Phe Pro Glu Glu Glu Glu Gly Gly Cys Glu Leu Arg Val Lys Phe
            245             250             255

Ser Arg Ser Ala Asp Ala Pro Ala Tyr Gln Gln Gly Gln Asn Gln Leu
            260             265             270

Tyr Asn Glu Leu Asn Leu Gly Arg Arg Glu Glu Tyr Asp Val Leu Asp
        275             280             285

Lys Arg Arg Gly Arg Asp Pro Glu Met Gly Gly Lys Pro Arg Arg Lys
    290             295             300

Asn Pro Gln Glu Gly Leu Tyr Asn Glu Leu Gln Lys Asp Lys Met Ala
305             310             315             320
```

-continued

```
Glu Ala Tyr Ser Glu Ile Gly Met Lys Gly Glu Arg Arg Arg Gly Lys
            325                     330                     335

Gly His Asp Gly Leu Tyr Gln Gly Leu Ser Thr Ala Thr Lys Asp Thr
            340                     345                     350

Tyr Asp Ala Leu His Met Gln Ala Leu Pro Pro Arg
            355                     360

<210> SEQ ID NO 86
<211> LENGTH: 360
<212> TYPE: PRT
<213> ORGANISM: Artificial Sequence
<220> FEATURE:
<223> OTHER INFORMATION: VHH-496 CAR (amino acid)

<400> SEQUENCE: 86

Met Ala Leu Pro Val Thr Ala Leu Leu Leu Pro Leu Ala Leu Leu Leu
1               5                   10                  15

His Ala Ala Arg Pro Gln Ile Gln Leu Val Glu Ser Gly Gly Gly Leu
            20                  25                  30

Val Gln Pro Gly Gly Ser Leu Arg Leu Ser Cys Ala Ala Ser Gly Phe
            35                  40                  45

Thr Phe Ser Asn Tyr Pro Met Thr Trp Leu Arg Gln Ala Pro Gly Lys
            50                  55                  60

Gly Leu Glu Ser Val Ser Asp Ile Thr Ser Gly Gly Asp Arg Pro Tyr
65                  70                  75                  80

Tyr Ala Asp Ser Val Lys Gly Arg Phe Thr Ile Ser Arg Asp Asn Ala
            85                  90                  95

Lys Asn Met Leu Tyr Leu Glu Met Asn Ser Leu Lys Thr Glu Asp Thr
            100                 105                 110

Ala Val Tyr Tyr Cys Ala Thr Trp Asp Arg Thr Leu Thr Gly Gln Gly
            115                 120                 125

Thr Gln Val Thr Val Ser Ser Thr Ser Thr Thr Thr Pro Ala Pro Arg
            130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
            165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Lys Arg
            195                 200                 205

Gly Arg Lys Lys Leu Leu Tyr Ile Phe Lys Gln Pro Phe Met Arg Pro
            210                 215                 220

Val Gln Thr Thr Gln Glu Glu Asp Gly Cys Ser Cys Arg Phe Pro Glu
225                 230                 235                 240

Glu Glu Glu Gly Gly Cys Glu Leu Arg Val Lys Phe Ser Arg Ser Ala
            245                 250                 255

Asp Ala Pro Ala Tyr Gln Gln Gly Gln Asn Gln Leu Tyr Asn Glu Leu
            260                 265                 270

Asn Leu Gly Arg Arg Glu Glu Tyr Asp Val Leu Asp Lys Arg Arg Gly
            275                 280                 285

Arg Asp Pro Glu Met Gly Gly Lys Pro Arg Arg Lys Asn Pro Gln Glu
            290                 295                 300

Gly Leu Tyr Asn Glu Leu Gln Lys Asp Lys Met Ala Glu Ala Tyr Ser
305                 310                 315                 320
```

-continued

```
Glu Ile Gly Met Lys Gly Glu Arg Arg Arg Gly Lys Gly His Asp Gly
                325             330             335

Leu Tyr Gln Gly Leu Ser Thr Ala Thr Lys Asp Thr Tyr Asp Ala Leu
            340             345             350

His Met Gln Ala Leu Pro Pro Arg
        355             360

<210> SEQ ID NO 87
<211> LENGTH: 364
<212> TYPE: PRT
<213> ORGANISM: Artificial Sequence
<220> FEATURE:
<223> OTHER INFORMATION: VHH-653 CAR (amino acid)

<400> SEQUENCE: 87

Met Ala Leu Pro Val Thr Ala Leu Leu Leu Pro Leu Ala Leu Leu Leu
1               5               10              15

His Ala Ala Arg Pro Gln Val Lys Leu Val Glu Ser Gly Gly Gly Ser
            20              25              30

Val Gln Ala Gly Gly Ser Leu Arg Leu Ser Cys Gln Ala Ser Ala Tyr
        35              40              45

Ile Arg Val Phe Tyr Leu Met Gly Trp Phe Arg Gln Ala Pro Gly Lys
    50              55              60

Glu Arg Glu Glu Val Ala Arg Val Asn Ala Asp Gly Ile Thr Asn His
65              70              75              80

Ala Ala Ser Val Lys Gly Arg Phe Thr Ile Ser Lys Asp Asn Ala Lys
            85              90              95

Asn Thr Leu Tyr Leu Gln Met Asp Ser Leu Lys Pro Glu Asp Thr Ala
            100             105             110

Val Tyr Tyr Cys Ala Ala Gly Arg Thr Trp Asn Ser Gly Phe Glu Tyr
            115             120             125

Trp Gly Gln Gly Thr Gln Val Thr Val Ser Ser Thr Ser Thr Thr Thr
    130             135             140

Pro Ala Pro Arg Pro Pro Thr Pro Ala Pro Thr Ile Ala Ser Gln Pro
145             150             155             160

Leu Ser Leu Arg Pro Glu Ala Cys Arg Pro Ala Ala Gly Gly Ala Val
            165             170             175

His Thr Arg Gly Leu Asp Phe Ala Cys Asp Ile Tyr Ile Trp Ala Pro
            180             185             190

Leu Ala Gly Thr Cys Gly Val Leu Leu Leu Ser Leu Val Ile Thr Leu
            195             200             205

Tyr Cys Lys Arg Gly Arg Lys Lys Leu Leu Tyr Ile Phe Lys Gln Pro
    210             215             220

Phe Met Arg Pro Val Gln Thr Thr Gln Glu Glu Asp Gly Cys Ser Cys
225             230             235             240

Arg Phe Pro Glu Glu Glu Glu Gly Gly Cys Glu Leu Arg Val Lys Phe
            245             250             255

Ser Arg Ser Ala Asp Ala Pro Ala Tyr Gln Gln Gly Gln Asn Gln Leu
            260             265             270

Tyr Asn Glu Leu Asn Leu Gly Arg Arg Glu Glu Tyr Asp Val Leu Asp
            275             280             285

Lys Arg Arg Gly Arg Asp Pro Glu Met Gly Gly Lys Pro Arg Arg Lys
    290             295             300

Asn Pro Gln Glu Gly Leu Tyr Asn Glu Leu Gln Lys Asp Lys Met Ala
305             310             315             320
```

-continued

```
Glu Ala Tyr Ser Glu Ile Gly Met Lys Gly Glu Arg Arg Arg Gly Lys
            325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
            355                 360

<210> SEQ ID NO 88
<211> LENGTH: 367
<212> TYPE: PRT
<213> ORGANISM: Artificial Sequence
<220> FEATURE:
<223> OTHER INFORMATION: huVHH-253 CAR (amino acid)

<400> SEQUENCE: 88

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Gly Arg
            35                  40                  45

Thr Phe Ser Ser Tyr Asn Met Gly Trp Phe Arg Gln Ala Pro Gly Lys
            50                  55                  60

Gly Leu Glu Trp Val Ala Ala Val Asp Trp Ser Gly Gly Ser Pro Tyr
65                  70                  75                  80

Tyr Ala Asp Ser Val Lys Gly Arg Phe Thr Ile Ser Arg Asp Asn Ser
                85                  90                  95

Lys Asn Thr Val Tyr Leu Gln Met Asn Ser Leu Arg Ala Glu Asp Thr
            100                 105                 110

Ala Val Tyr Tyr Cys Ala Gly Arg Val Gln Tyr Gly Ser Ser Trp Ser
            115                 120                 125

Gly Asp Tyr Trp Gly Gln Gly Thr Leu Val Thr Val Ser Ser Thr Ser
            130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
            165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
            195                 200                 205

Ile Thr Leu Tyr Cys Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Gly Gly Cys Glu Leu Arg
            245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
            275                 280                 285

Val Leu Asp Lys Arg Arg Gly Arg Asp Pro Glu Met Gly Gly Lys Pro
            290                 295                 300

Arg Arg Lys Asn Pro Gln Glu Gly Leu Tyr Asn Glu Leu Gln Lys Asp
305                 310                 315                 320
```

```
Lys Met Ala Glu Ala Tyr Ser Glu Ile Gly Met Lys Gly Glu Arg Arg
            325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365
```

<210> SEQ ID NO 89
<211> LENGTH: 367
<212> TYPE: PRT
<213> ORGANISM: Artificial Sequence
<220> FEATURE:
<223> OTHER INFORMATION: huVHH-256 CAR (amino acid)

<400> SEQUENCE: 89

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Gly Arg
        35                  40                  45

Thr Phe Ser Ser Tyr Asn Met Gly Trp Phe Arg Gln Ala Pro Gly Lys
    50                  55                  60

Gly Leu Glu Phe Val Ala Val Val Asp Trp Ser Gly Gly Ser Pro Tyr
65                  70                  75                  80

Tyr Ala Asp Ser Val Lys Gly Arg Phe Thr Ile Ser Arg Asp Asn Ser
                85                  90                  95

Lys Asn Thr Val Tyr Leu Gln Met Ser Ser Leu Arg Ala Glu Asp Thr
            100                 105                 110

Ala Val Tyr Tyr Cys Ala Gly Arg Val Gln Tyr Gly Ser Ser Trp Ser
            115                 120                 125

Gly Asp Tyr Trp Gly Gln Gly Thr Leu Val Thr Val Ser Ser Thr Ser
        130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
                165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
            195                 200                 205

Ile Thr Leu Tyr Cys Lys Arg Gly Arg Lys Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
                245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
            275                 280                 285

Val Leu Asp Lys Arg Arg Gly Arg Asp Pro Glu Met Gly Gly Lys Pro
        290                 295                 300

Arg Arg Lys Asn Pro Gln Glu Gly Leu Tyr Asn Glu Leu Gln Lys Asp
305                 310                 315                 320
```

-continued

```
Lys Met Ala Glu Ala Tyr Ser Glu Ile Gly Met Lys Gly Glu Arg Arg
                325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365

<210> SEQ ID NO 90
<211> LENGTH: 367
<212> TYPE: PRT
<213> ORGANISM: Artificial Sequence
<220> FEATURE:
<223> OTHER INFORMATION: huVHH-260 CAR (amino acid)

<400> SEQUENCE: 90

Met Ala Leu Pro Val Thr Ala Leu Leu Leu Pro Leu Ala Leu Leu Leu
1               5                   10                  15

His Ala Ala Arg Pro Asp Val Gln Leu Leu Glu Ser Gly Gly Gly Leu
            20                  25                  30

Val Gln Pro Gly Gly Ser Leu Arg Leu Ser Cys Ala Ala Ser Gly Arg
        35                  40                  45

Thr Ile Ser Ser Tyr Ser Met Gly Trp Phe Arg Gln Ala Pro Gly Lys
        50                  55                  60

Gly Leu Glu Phe Val Ala Ala Ile Ser Trp Ser Gly Gly Ser Pro Tyr
65                  70                  75                  80

Tyr Ala Asp Ser Val Lys Gly Arg Phe Thr Ile Ser Arg Asp Asn Ala
            85                  90                  95

Lys Asn Thr Val Tyr Leu Gln Met Asn Ser Leu Arg Ala Glu Asp Thr
            100                 105                 110

Ala Val Tyr Tyr Cys Ala Ala Pro Ile Glu Tyr Gly Ser Ser Trp Ser
        115                 120                 125

Ala Asp Tyr Trp Gly Gln Gly Thr Leu Val Thr Val Ser Ser Thr Ser
        130                 135                 140

Thr Thr Thr Pro Ala Pro Arg Pro Pro Thr Pro Ala Pro Thr Ile Ala
145                 150                 155                 160

Ser Gln Pro Leu Ser Leu Arg Pro Glu Ala Cys Arg Pro Ala Ala Gly
            165                 170                 175

Gly Ala Val His Thr Arg Gly Leu Asp Phe Ala Cys Asp Ile Tyr Ile
            180                 185                 190

Trp Ala Pro Leu Ala Gly Thr Cys Gly Val Leu Leu Leu Ser Leu Val
        195                 200                 205

Ile Thr Leu Tyr Cys Lys Arg Gly Arg Lys Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu Arg
            245                 250                 255

Val Lys Phe Ser Arg Ser Ala Asp Ala Pro Ala Tyr Gln Gln Gly Gln
            260                 265                 270

Asn Gln Leu Tyr Asn Glu Leu Asn Leu Gly Arg Arg Glu Glu Tyr Asp
            275                 280                 285

Val Leu Asp Lys Arg Arg Gly Arg Asp Pro Glu Met Gly Gly Lys Pro
        290                 295                 300

Arg Arg Lys Asn Pro Gln Glu Gly Leu Tyr Asn Glu Leu Gln Lys Asp
305                 310                 315                 320
```

-continued

```
Lys Met Ala Glu Ala Tyr Ser Glu Ile Gly Met Lys Gly Glu Arg Arg
            325                 330                 335

Arg Gly Lys Gly His Asp Gly Leu Tyr Gln Gly Leu Ser Thr Ala Thr
            340                 345                 350

Lys Asp Thr Tyr Asp Ala Leu His Met Gln Ala Leu Pro Pro Arg
        355                 360                 365

<210> SEQ ID NO 91
<211> LENGTH: 360
<212> TYPE: PRT
<213> ORGANISM: Artificial Sequence
<220> FEATURE:
<223> OTHER INFORMATION: huVHH-746 CAR (amino acid)

<400> SEQUENCE: 91

Met Ala Leu Pro Val Thr Ala Leu Leu Leu Pro Leu Ala Leu Leu Leu
1               5                   10                  15

His Ala Ala Arg Pro Gln Ile Gln Leu Leu Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Ser Asn Tyr Pro Met Thr Trp Ile Arg Gln Ala Pro Gly Lys
        50                  55                  60

Gly Leu Glu Ser Val Ser Asp Ile Thr Ser Gly Gly Asp Arg Pro Tyr
65                  70                  75                  80

Tyr Ala Asp Ser Val Lys Gly Arg Phe Thr Ile Ser Arg Asp Asn Ala
                85                  90                  95

Lys Asn Met Leu Tyr Leu Gln Met Asn Ser Leu Arg Ala Glu Asp Thr
            100                 105                 110

Ala Val Tyr Tyr Cys Ala Thr Trp Asp Arg Thr Leu Trp Gly Gln Gly
            115                 120                 125

Thr Met Val Thr Val Ser Ser Thr Ser Thr Thr Thr Pro Ala Pro Arg
        130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Lys Arg
            195                 200                 205

Gly Arg Lys Lys Leu Leu Tyr Ile Phe Lys Gln Pro Phe Met Arg Pro
        210                 215                 220

Val Gln Thr Thr Gln Glu Glu Asp Gly Cys Ser Cys Arg Phe Pro Glu
225                 230                 235                 240

Glu Glu Glu Gly Gly Cys Glu Leu Arg Val Lys Phe Ser Arg Ser Ala
                245                 250                 255

Asp Ala Pro Ala Tyr Gln Gln Gly Gln Asn Gln Leu Tyr Asn Glu Leu
            260                 265                 270

Asn Leu Gly Arg Arg Glu Glu Tyr Asp Val Leu Asp Lys Arg Arg Gly
        275                 280                 285

Arg Asp Pro Glu Met Gly Gly Lys Pro Arg Arg Lys Asn Pro Gln Glu
        290                 295                 300

Gly Leu Tyr Asn Glu Leu Gln Lys Asp Lys Met Ala Glu Ala Tyr Ser
305                 310                 315                 320
```

-continued

Glu Ile Gly Met Lys Gly Glu Arg Arg Arg Gly Lys Gly His Asp Gly
                325                     330                     335

Leu Tyr Gln Gly Leu Ser Thr Ala Thr Lys Asp Thr Tyr Asp Ala Leu
                340                     345                     350

His Met Gln Ala Leu Pro Pro Arg
                355                     360

<210> SEQ ID NO 92
<211> LENGTH: 360
<212> TYPE: PRT
<213> ORGANISM: Artificial Sequence
<220> FEATURE:
<223> OTHER INFORMATION: huVHH-750 CAR (amino acid)

<400> SEQUENCE: 92

Met Ala Leu Pro Val Thr Ala Leu Leu Leu Pro Leu Ala Leu Leu Leu
1                   5                       10                      15

His Ala Ala Arg Pro Gln Ile Gln Leu Val Glu Ser Gly Gly Gly Leu
                20                      25                      30

Val Gln Pro Gly Gly Ser Leu Arg Leu Ser Cys Ala Ala Ser Gly Phe
                35                      40                      45

Thr Phe Ser Asn Tyr Pro Met Thr Trp Leu Arg Gln Ala Pro Gly Lys
                50                      55                      60

Gly Leu Glu Ser Val Ser Asp Ile Thr Ser Gly Gly Asp Arg Pro Tyr
65                      70                      75                      80

Tyr Ala Asp Ser Val Lys Gly Arg Phe Thr Ile Ser Arg Asp Asn Ala
                85                      90                      95

Lys Asn Met Leu Tyr Leu Gln Met Asn Ser Leu Arg Ala Glu Asp Thr
                100                     105                     110

Ala Val Tyr Tyr Cys Ala Thr Trp Asp Arg Thr Leu Thr Gly Gln Gly
                115                     120                     125

Thr Met Val Thr Val Ser Ser Thr Ser Thr Thr Thr Pro Ala Pro Arg
                130                     135                     140

Pro Pro Thr Pro Ala Pro Thr Ile Ala Ser Gln Pro Leu Ser Leu Arg
145                     150                     155                     160

Pro Glu Ala Cys Arg Pro Ala Ala Gly Gly Ala Val His Thr Arg Gly
                165                     170                     175

Leu Asp Phe Ala Cys Asp Ile Tyr Ile Trp Ala Pro Leu Ala Gly Thr
                180                     185                     190

Cys Gly Val Leu Leu Leu Ser Leu Val Ile Thr Leu Tyr Cys Lys Arg
                195                     200                     205

Gly Arg Lys Lys Leu Leu Tyr Ile Phe Lys Gln Pro Phe Met Arg Pro
                210                     215                     220

Val Gln Thr Thr Gln Glu Glu Asp Gly Cys Ser Cys Arg Phe Pro Glu
225                     230                     235                     240

Glu Glu Glu Gly Gly Cys Glu Leu Arg Val Lys Phe Ser Arg Ser Ala
                245                     250                     255

Asp Ala Pro Ala Tyr Gln Gln Gly Gln Asn Gln Leu Tyr Asn Glu Leu
                260                     265                     270

Asn Leu Gly Arg Arg Glu Glu Tyr Asp Val Leu Asp Lys Arg Arg Gly
                275                     280                     285

Arg Asp Pro Glu Met Gly Gly Lys Pro Arg Arg Lys Asn Pro Gln Glu
                290                     295                     300

Gly Leu Tyr Asn Glu Leu Gln Lys Asp Lys Met Ala Glu Ala Tyr Ser
305                     310                     315                     320

-continued

Glu Ile Gly Met Lys Gly Glu Arg Arg Arg Gly Lys Gly His Asp Gly
                325             330             335

Leu Tyr Gln Gly Leu Ser Thr Ala Thr Lys Asp Thr Tyr Asp Ala Leu
            340             345             350

His Met Gln Ala Leu Pro Pro Arg
        355             360

<210> SEQ ID NO 93
<211> LENGTH: 360
<212> TYPE: PRT
<213> ORGANISM: Artificial Sequence
<220> FEATURE:
<223> OTHER INFORMATION: huVHH-753 CAR (amino acid)

<400> SEQUENCE: 93

Met Ala Leu Pro Val Thr Ala Leu Leu Leu Pro Leu Ala Leu Leu Leu
1               5               10              15

His Ala Ala Arg Pro Gln Ile Gln Leu Val Glu Ser Gly Gly Gly Leu
            20              25              30

Val Gln Pro Gly Gly Ser Leu Arg Leu Ser Cys Ala Ala Ser Gly Phe
        35              40              45

Thr Phe Ser Asn Tyr Pro Met Thr Trp Leu Arg Gln Ala Pro Gly Lys
    50              55              60

Gly Leu Glu Ser Val Ser Asp Ile Thr Ser Gly Gly Asp Arg Pro Tyr
65              70              75              80

Tyr Ala Asp Ser Val Lys Gly Arg Phe Thr Ile Ser Arg Asp Asn Ala
            85              90              95

Lys Asn Met Leu Tyr Leu Gln Met Asn Ser Leu Arg Ala Glu Asp Thr
        100             105             110

Ala Val Tyr Tyr Cys Ala Thr Trp Asp Arg Thr Leu Thr Gly Gln Gly
        115             120             125

Thr Leu Val Thr Val Ser Ser Thr Ser Thr Thr Thr Pro Ala Pro Arg
    130             135             140

Pro Pro Thr Pro Ala Pro Thr Ile Ala Ser Gln Pro Leu Ser Leu Arg
145             150             155             160

Pro Glu Ala Cys Arg Pro Ala Ala Gly Gly Ala Val His Thr Arg Gly
            165             170             175

Leu Asp Phe Ala Cys Asp Ile Tyr Ile Trp Ala Pro Leu Ala Gly Thr
            180             185             190

Cys Gly Val Leu Leu Leu Ser Leu Val Ile Thr Leu Tyr Cys Lys Arg
        195             200             205

Gly Arg Lys Lys Leu Leu Tyr Ile Phe Lys Gln Pro Phe Met Arg Pro
    210             215             220

Val Gln Thr Thr Gln Glu Glu Asp Gly Cys Ser Cys Arg Phe Pro Glu
225             230             235             240

Glu Glu Glu Gly Gly Cys Glu Leu Arg Val Lys Phe Ser Arg Ser Ala
            245             250             255

Asp Ala Pro Ala Tyr Gln Gln Gly Gln Asn Gln Leu Tyr Asn Glu Leu
            260             265             270

Asn Leu Gly Arg Arg Glu Glu Tyr Asp Val Leu Asp Lys Arg Arg Gly
        275             280             285

Arg Asp Pro Glu Met Gly Gly Lys Pro Arg Arg Lys Asn Pro Gln Glu
    290             295             300

Gly Leu Tyr Asn Glu Leu Gln Lys Asp Lys Met Ala Glu Ala Tyr Ser
305             310             315             320

-continued

Glu Ile Gly Met Lys Gly Glu Arg Arg Arg Gly Lys Gly His Asp Gly
             325                 330                 335

Leu Tyr Gln Gly Leu Ser Thr Ala Thr Lys Asp Thr Tyr Asp Ala Leu
             340                 345                 350

His Met Gln Ala Leu Pro Pro Arg
         355                 360

<210> SEQ ID NO 94
<211> LENGTH: 364
<212> TYPE: PRT
<213> ORGANISM: Artificial Sequence
<220> FEATURE:
<223> OTHER INFORMATION: huVHH-836 CAR (amino acid)

<400> SEQUENCE: 94

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
             20                  25                  30

Val Gln Pro Gly Gly Ser Leu Arg Leu Ser Cys Ala Ala Ser Ala Asp
         35                  40                  45

Ile Arg Leu Phe Tyr Leu Met Gly Trp Phe Arg Gln Ala Pro Gly Lys
     50                  55                  60

Gly Leu Val Trp Val Ala Arg Val Asn Ala Asp Asp Ser Ile Ser Tyr
65                  70                  75                  80

Ala Asp Ser Val Lys Gly Arg Phe Thr Ile Ser Arg Asp Asn Ala Lys
                 85                  90                  95

Asn Thr Leu Tyr Leu Gln Met Asn Ser Leu Arg Ala Glu Asp Thr Ala
             100                 105                 110

Val Tyr Tyr Cys Ala Ala Gly Arg Thr Trp Asn Ser Gly Phe Glu Tyr
             115                 120                 125

Trp Gly Gln Gly Thr Leu Val Thr Val Ser Ser Thr Ser Thr Thr Thr
     130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
             165                 170                 175

His Thr Arg Gly Leu Asp Phe Ala Cys Asp Ile Tyr Ile Trp Ala Pro
             180                 185                 190

Leu Ala Gly Thr Cys Gly Val Leu Leu Leu Ser Leu Val Ile Thr Leu
             195                 200                 205

Tyr Cys Lys Arg Gly Arg Lys Lys Leu Leu Tyr Ile Phe Lys Gln Pro
     210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
             245                 250                 255

Ser Arg Ser Ala Asp Ala Pro Ala Tyr Gln Gln Gly Gln Asn Gln Leu
             260                 265                 270

Tyr Asn Glu Leu Asn Leu Gly Arg Arg Glu Glu Tyr Asp Val Leu Asp
             275                 280                 285

Lys Arg Arg Gly Arg Asp Pro Glu Met Gly Gly Lys Pro Arg Arg Lys
     290                 295                 300

Asn Pro Gln Glu Gly Leu Tyr Asn Glu Leu Gln Lys Asp Lys Met Ala
305                 310                 315                 320

```
Glu Ala Tyr Ser Glu Ile Gly Met Lys Gly Glu Arg Arg Arg Gly Lys
            325             330             335

Gly His Asp Gly Leu Tyr Gln Gly Leu Ser Thr Ala Thr Lys Asp Thr
            340             345             350

Tyr Asp Ala Leu His Met Gln Ala Leu Pro Pro Arg
            355             360
```

<210> SEQ ID NO 95
<211> LENGTH: 364
<212> TYPE: PRT
<213> ORGANISM: Artificial Sequence
<220> FEATURE:
<223> OTHER INFORMATION: huVHH-840 CAR (amino acid)

<400> SEQUENCE: 95

```
Met Ala Leu Pro Val Thr Ala Leu Leu Leu Pro Leu Ala Leu Leu Leu
1                5                10              15

His Ala Ala Arg Pro Gln Val Gln Leu Gln Glu Ser Gly Gly Gly Val
            20              25              30

Val Gln Pro Gly Gly Ser Leu Arg Leu Ser Cys Ala Ala Ser Ala Asp
            35              40              45

Ile Arg Leu Phe Tyr Leu Met Gly Trp Phe Arg Gln Ala Pro Gly Lys
        50              55              60

Gly Leu Glu Trp Val Ala Phe Val Asn Ala Asp Asp Ser Ile Tyr Tyr
65              70              75              80

Ala Asp Ser Val Lys Gly Arg Phe Thr Ile Ser Arg Asp Asn Ser Lys
                85              90              95

Asn Thr Leu Tyr Leu Gln Met Asn Ser Leu Arg Ala Glu Asp Thr Ala
            100             105             110

Val Tyr Tyr Cys Ala Ala Gly Arg Thr Trp Asn Ser Gly Phe Glu Tyr
            115             120             125

Trp Gly Gln Gly Thr Leu Val Thr Val Ser Ser Thr Ser Thr Thr Thr
        130             135             140

Pro Ala Pro Arg Pro Pro Thr Pro Ala Pro Thr Ile Ala Ser Gln Pro
145             150             155             160

Leu Ser Leu Arg Pro Glu Ala Cys Arg Pro Ala Ala Gly Gly Ala Val
                165             170             175

His Thr Arg Gly Leu Asp Phe Ala Cys Asp Ile Tyr Ile Trp Ala Pro
            180             185             190

Leu Ala Gly Thr Cys Gly Val Leu Leu Leu Ser Leu Val Ile Thr Leu
            195             200             205

Tyr Cys Lys Arg Gly Arg Lys Lys Leu Leu Tyr Ile Phe Lys Gln Pro
        210             215             220

Phe Met Arg Pro Val Gln Thr Thr Gln Glu Glu Asp Gly Cys Ser Cys
225             230             235             240

Arg Phe Pro Glu Glu Glu Glu Gly Gly Cys Glu Leu Arg Val Lys Phe
                245             250             255

Ser Arg Ser Ala Asp Ala Pro Ala Tyr Gln Gln Gly Gln Asn Gln Leu
            260             265             270

Tyr Asn Glu Leu Asn Leu Gly Arg Arg Glu Glu Tyr Asp Val Leu Asp
            275             280             285

Lys Arg Arg Gly Arg Asp Pro Glu Met Gly Gly Lys Pro Arg Arg Lys
        290             295             300

Asn Pro Gln Glu Gly Leu Tyr Asn Glu Leu Gln Lys Asp Lys Met Ala
305             310             315             320
```

```
Glu Ala Tyr Ser Glu Ile Gly Met Lys Gly Glu Arg Arg Arg Gly Lys
            325             330             335

Gly His Asp Gly Leu Tyr Gln Gly Leu Ser Thr Ala Thr Lys Asp Thr
            340             345             350

Tyr Asp Ala Leu His Met Gln Ala Leu Pro Pro Arg
        355             360
```

<210> SEQ ID NO 96
<211> LENGTH: 364
<212> TYPE: PRT
<213> ORGANISM: Artificial Sequence
<220> FEATURE:
<223> OTHER INFORMATION: huVHH-843 CAR (amino acid)

<400> SEQUENCE: 96

```
Met Ala Leu Pro Val Thr Ala Leu Leu Leu Pro Leu Ala Leu Leu Leu
1               5               10              15

His Ala Ala Arg Pro Gln Val His Leu Val Glu Ser Gly Gly Gly Leu
            20              25              30

Val Gln Pro Gly Gly Ser Leu Arg Leu Ser Cys Gln Ala Ser Ala Asp
            35              40              45

Ile Arg Leu Phe Tyr Leu Met Gly Trp Phe Arg Gln Ala Pro Gly Lys
        50              55              60

Gly Leu Val Trp Val Ala Arg Val Asn Ala Asp Asp Ser Ile Asn Tyr
65              70              75              80

Val Asp Ser Val Lys Gly Arg Phe Thr Ile Ser Lys Asp Asn Ala Lys
                85              90              95

Asn Thr Leu Tyr Leu Gln Met Asn Ser Leu Arg Ala Glu Asp Thr Ala
            100             105             110

Val Tyr Tyr Cys Ala Ala Gly Arg Thr Trp Asn Ser Gly Phe Glu Tyr
            115             120             125

Trp Gly Gln Gly Thr Leu Val Thr Val Ser Ser Thr Ser Thr Thr Thr
        130             135             140

Pro Ala Pro Arg Pro Pro Thr Pro Ala Pro Thr Ile Ala Ser Gln Pro
145             150             155             160

Leu Ser Leu Arg Pro Glu Ala Cys Arg Pro Ala Ala Gly Gly Ala Val
            165             170             175

His Thr Arg Gly Leu Asp Phe Ala Cys Asp Ile Tyr Ile Trp Ala Pro
            180             185             190

Leu Ala Gly Thr Cys Gly Val Leu Leu Leu Ser Leu Val Ile Thr Leu
            195             200             205

Tyr Cys Lys Arg Gly Arg Lys Lys Leu Leu Tyr Ile Phe Lys Gln Pro
        210             215             220

Phe Met Arg Pro Val Gln Thr Thr Gln Glu Glu Asp Gly Cys Ser Cys
225             230             235             240

Arg Phe Pro Glu Glu Glu Glu Gly Gly Cys Glu Leu Arg Val Lys Phe
            245             250             255

Ser Arg Ser Ala Asp Ala Pro Ala Tyr Gln Gln Gly Gln Asn Gln Leu
            260             265             270

Tyr Asn Glu Leu Asn Leu Gly Arg Arg Glu Glu Tyr Asp Val Leu Asp
            275             280             285

Lys Arg Arg Gly Arg Asp Pro Glu Met Gly Gly Lys Pro Arg Arg Lys
        290             295             300

Asn Pro Gln Glu Gly Leu Tyr Asn Glu Leu Gln Lys Asp Lys Met Ala
305             310             315             320
```

-continued

```
Glu Ala Tyr Ser Glu Ile Gly Met Lys Gly Glu Arg Arg Arg Gly Lys
            325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
            355                 360
```

```
<210> SEQ ID NO 97
<211> LENGTH: 364
<212> TYPE: PRT
<213> ORGANISM: Artificial Sequence
<220> FEATURE:
<223> OTHER INFORMATION: huVHH-846 CAR (amino acid)

<400> SEQUENCE: 97

Met Ala Leu Pro Val Thr Ala Leu Leu Leu Pro Leu Ala Leu Leu Leu
1               5                   10                  15

His Ala Ala Arg Pro Gln Val His Leu Gln Glu Ser Gly Gly Gly Val
            20                  25                  30

Val Gln Pro Gly Gly Ser Leu Arg Leu Ser Cys Gln Ala Ser Ala Asp
            35                  40                  45

Ile Arg Leu Phe Tyr Leu Met Gly Trp Phe Arg Gln Ala Pro Gly Lys
            50                  55                  60

Gly Leu Glu Trp Val Ala Phe Val Asn Ala Asp Asp Ser Ile Asn Tyr
65                  70                  75                  80

Ala Asp Ser Val Lys Gly Arg Phe Thr Ile Ser Lys Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Ala Gly Arg Thr Trp Asn Ser Gly Phe Glu Tyr
            115                 120                 125

Trp Gly Gln Gly Thr Leu Val Thr Val Ser Ser Thr Ser Thr Thr Thr
            130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
                165                 170                 175

His Thr Arg Gly Leu Asp Phe Ala Cys Asp Ile Tyr Ile Trp Ala Pro
            180                 185                 190

Leu Ala Gly Thr Cys Gly Val Leu Leu Leu Ser Leu Val Ile Thr Leu
            195                 200                 205

Tyr Cys Lys Arg Gly Arg Lys Lys Leu Leu Tyr Ile Phe Lys Gln Pro
            210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
                245                 250                 255

Ser Arg Ser Ala Asp Ala Pro Ala Tyr Gln Gln Gly Gln Asn Gln Leu
            260                 265                 270

Tyr Asn Glu Leu Asn Leu Gly Arg Arg Glu Glu Tyr Asp Val Leu Asp
            275                 280                 285

Lys Arg Arg Gly Arg Asp Pro Glu Met Gly Gly Lys Pro Arg Arg Lys
            290                 295                 300

Asn Pro Gln Glu Gly Leu Tyr Asn Glu Leu Gln Lys Asp Lys Met Ala
305                 310                 315                 320
```

-continued

```
Glu Ala Tyr Ser Glu Ile Gly Met Lys Gly Glu Arg Arg Arg Gly Lys
            325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
        355                 360

<210> SEQ ID NO 98
<211> LENGTH: 491
<212> TYPE: PRT
<213> ORGANISM: Artificial Sequence
<220> FEATURE:
<223> OTHER INFORMATION: Bi-VHH1 CAR (amino acid)

<400> SEQUENCE: 98

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Ser Ser Tyr Asn Met Gly Trp Phe Arg Gln Ala Pro Gly Lys
    50                  55                  60

Glu Arg Glu Phe Val Ala Val Val Asp Trp Ser Gly Gly Ser Pro Tyr
65                  70                  75                  80

Tyr Ala Asp Ser Val Lys Gly Arg Phe Thr Ile Ser Arg Asp Asn Gly
                85                  90                  95

Lys Asn Thr Val Tyr Leu Gln Met Asn Ser Leu Lys Pro Glu Asp Thr
            100                 105                 110

Ala Val Tyr Tyr Cys Ala Gly Arg Val Gln Tyr Gly Ser Ser Trp Ser
            115                 120                 125

Gly Asp Tyr Trp Gly Gln Gly Thr Gln Val Thr Val Ser Ser Gly Gly
        130                 135                 140

Gly Gly Ser Gly Gly Gly Gly Ser Gln Ile Gln Leu Val Glu Ser Gly
145                 150                 155                 160

Gly Gly Leu Val Gln Pro Gly Gly Ser Leu Arg Leu Ser Cys Ala Ala
            165                 170                 175

Ser Gly Phe Thr Phe Ser Asn Tyr Pro Met Thr Trp Leu Arg Gln Ala
            180                 185                 190

Pro Gly Lys Gly Leu Glu Ser Val Ser Asp Ile Thr Ser Gly Gly Asp
            195                 200                 205

Arg Pro Tyr Tyr Ala Asp Ser Val Lys Gly Arg Phe Thr Ile Ser Arg
    210                 215                 220

Asp Asn Ala Lys Asn Met Leu Tyr Leu Glu Met Asn Ser Leu Lys Thr
225                 230                 235                 240

Glu Asp Thr Ala Val Tyr Tyr Cys Ala Thr Trp Asp Arg Thr Leu Thr
            245                 250                 255

Gly Gln Gly Thr Gln Val Thr Val Ser Ser Thr Ser Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320
```

-continued

```
Ala Gly Thr Cys Gly Val Leu Leu Leu Ser Leu Val Ile Thr Leu Tyr
              325                 330                 335

Cys Lys Arg Gly Arg Lys Lys Leu Leu Tyr Ile Phe Lys Gln Pro Phe
              340                 345                 350

Met Arg Pro Val Gln Thr Thr Gln Glu Glu Asp Gly Cys Ser Cys Arg
              355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
              405                 410                 415

Arg Arg Gly Arg Asp Pro Glu Met Gly Gly Lys Pro Arg Arg Lys Asn
              420                 425                 430

Pro Gln Glu Gly Leu Tyr Asn Glu Leu Gln Lys Asp Lys Met Ala Glu
              435                 440                 445

Ala Tyr Ser Glu Ile Gly Met Lys Gly Glu Arg Arg Arg Gly Lys Gly
              450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
              485                 490
```

<210> SEQ ID NO 99
<211> LENGTH: 491
<212> TYPE: PRT
<213> ORGANISM: Artificial Sequence
<220> FEATURE:
<223> OTHER INFORMATION: Bi-VHH2 CAR (amino acid)

<400> SEQUENCE: 99

```
Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Ser
              20                  25                  30

Val Gln Ala Gly Gly Ser Leu Arg Leu Ser Cys Ala Ala Ser Gly Arg
              35                  40                  45

Thr Phe Ser Ser Tyr Asn Met Gly Trp Phe Arg Gln Ala Pro Gly Lys
    50                  55                  60

Glu Arg Glu Phe Val Ala Ala Ile Ser Trp Ser Gly Gly Ser Pro Tyr
65                  70                  75                  80

Tyr Ala Ser Ser Val Arg Gly Arg Phe Thr Ile Ser Arg Asp Asn Ala
              85                  90                  95

Lys Asn Thr Val Tyr Leu Gln Met Asn Ser Leu Lys Pro Glu Asp Thr
              100                 105                 110

Ala Val Tyr Tyr Cys Ala Ala Pro Ile Glu Tyr Gly Ser Ser Trp Ser
              115                 120                 125

Ala Asp Tyr Trp Gly Gln Gly Thr Gln Val Thr Val Ser Ser Gly Gly
    130                 135                 140

Gly Gly Ser Gly Gly Gly Gly Ser Gln Ile Gln Leu Val Glu Ser Gly
145                 150                 155                 160

Gly Gly Leu Val Gln Pro Gly Gly Ser Leu Arg Leu Ser Cys Ala Ala
              165                 170                 175

Ser Gly Phe Thr Phe Ser Asn Tyr Pro Met Thr Trp Leu Arg Gln Ala
              180                 185                 190
```

-continued

```
Pro Gly Lys Gly Leu Glu Ser Val Ser Asp Ile Thr Ser Gly Gly Asp
        195                 200                 205

Arg Pro Tyr Tyr Ala Asp Ser Val Lys Gly Arg Phe Thr Ile Ser Arg
        210                 215                 220

Asp Asn Ala Lys Asn Met Leu Tyr Leu Glu Met Asn Ser Leu Lys Thr
225                 230                 235                 240

Glu Asp Thr Ala Val Tyr Tyr Cys Ala Thr Trp Asp Arg Thr Leu Thr
                245                 250                 255

Gly Gln Gly Thr Gln Val Thr Val Ser Ser Thr Ser Thr Thr Thr Pro
                260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
        290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
                340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
        370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
                420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
        450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490
```

<210> SEQ ID NO 100
<211> LENGTH: 495
<212> TYPE: PRT
<213> ORGANISM: Artificial Sequence
<220> FEATURE:
<223> OTHER INFORMATION: Bi-VHH3 CAR (amino acid)

<400> SEQUENCE: 100

```
Met Ala Leu Pro Val Thr Ala Leu Leu Leu Pro Leu Ala Leu Leu Leu
1               5                   10                  15

His Ala Ala Arg Pro Asp Val Gln Leu Val Glu Ser Gly Gly Gly Leu
                20                  25                  30

Val Gln Ala Gly Gly Ser Leu Arg Leu Ser Cys Ala Ala Ser Gly Arg
        35                  40                  45

Thr Ile Ser Ser Tyr Ser Met Gly Trp Phe Arg Gln Ala Pro Gly Lys
        50                  55                  60
```

-continued

```
Glu Arg Arg Phe Val Ala Ala Ile Ser Trp Ser Gly Gly Ser Pro Tyr
65                  70                  75                  80

Tyr Ala Asp Ser Val Lys Gly Arg Phe Thr Ile Ser Arg Asp Asn Ala
                85                  90                  95

Lys Asn Thr Val Tyr Leu Gln Met Asn Ser Leu Lys Pro Glu Asp Thr
            100                 105                 110

Ala Val Tyr Tyr Cys Ala Ala Pro Ile Glu Tyr Gly Ser Ser Trp Ser
        115                 120                 125

Ala Asp Tyr Trp Gly Gln Gly Thr Gln Val Thr Val Ser Ser Gly Gly
    130                 135                 140

Gly Gly Ser Gly Gly Gly Gly Ser Gln Val His Leu Met Glu Ser Gly
145                 150                 155                 160

Gly Gly Ser Val Gln Ala Gly Gly Ser Leu Arg Leu Ser Cys Gln Ala
                165                 170                 175

Ser Ala Tyr Ile Arg Val Phe Tyr Leu Met Gly Trp Phe Arg Gln Ala
            180                 185                 190

Pro Gly Lys Glu Arg Glu Glu Val Ala Arg Val Thr Ala Asp Gly Phe
            195                 200                 205

Thr Asn His Ala Ala Ser Val Lys Gly Arg Phe Thr Ile Ser Lys Asp
    210                 215                 220

Asn Ala Lys Asn Thr Leu Tyr Leu Gln Met Asp Ser Met Lys Ser Glu
225                 230                 235                 240

Asp Thr Ala Val Tyr Tyr Cys Ala Ala Gly Arg Thr Trp Asn Ser Gly
                245                 250                 255

Phe Glu Tyr Trp Gly Gln Gly Thr Gln Val Thr Val Ser Ser Thr Ser
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
            355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
            435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
```

-continued

```
            485                 490                 495

<210> SEQ ID NO 101
<211> LENGTH: 490
<212> TYPE: PRT
<213> ORGANISM: Artificial Sequence
<220> FEATURE:
<223> OTHER INFORMATION: Bi-VHH4 (G4S)1 CAR (amino acid)

<400> SEQUENCE: 101

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Ser Ser Tyr Asn Met Gly Trp Phe Arg Gln Ala Pro Gly Lys
    50                  55                  60

Glu Arg Glu Phe Val Ala Val Val Asp Trp Ser Gly Gly Ser Pro Tyr
65                  70                  75                  80

Tyr Ala Asp Ser Val Lys Gly Arg Phe Thr Ile Ser Arg Asp Asn Gly
                85                  90                  95

Lys Asn Thr Val Tyr Leu Gln Met Asn Ser Leu Lys Pro Glu Asp Thr
            100                 105                 110

Ala Val Tyr Tyr Cys Ala Gly Arg Val Gln Tyr Gly Ser Ser Trp Ser
            115                 120                 125

Gly Asp Tyr Trp Gly Gln Gly Thr Gln Val Thr Val Ser Ser Gly Gly
        130                 135                 140

Gly Gly Ser Gln Val Lys Leu Val Glu Ser Gly Gly Gly Ser Val Gln
145                 150                 155                 160

Ala Gly Gly Ser Leu Arg Leu Ser Cys Gln Ala Ser Ala Tyr Ile Arg
                165                 170                 175

Val Phe Tyr Leu Met Gly Trp Phe Arg Gln Ala Pro Gly Lys Glu Arg
            180                 185                 190

Glu Glu Val Ala Arg Val Asn Ala Asp Gly Ile Thr Asn His Ala Ala
            195                 200                 205

Ser Val Lys Gly Arg Phe Thr Ile Ser Lys Asp Asn Ala Lys Asn Thr
        210                 215                 220

Leu Tyr Leu Gln Met Asp Ser Leu Lys Pro Glu Asp Thr Ala Val Tyr
225                 230                 235                 240

Tyr Cys Ala Ala Gly Arg Thr Trp Asn Ser Gly Phe Glu Tyr Trp Gly
                245                 250                 255

Gln Gly Thr Gln Val Thr Val Ser Ser Thr Ser Thr Thr Thr Pro Ala
            260                 265                 270

Pro Arg Pro Pro Thr Pro Ala Pro Thr Ile Ala Ser Gln Pro Leu Ser
            275                 280                 285

Leu Arg Pro Glu Ala Cys Arg Pro Ala Ala Gly Gly Ala Val His Thr
        290                 295                 300

Arg Gly Leu Asp Phe Ala Cys Asp Ile Tyr Ile Trp Ala Pro Leu Ala
305                 310                 315                 320

Gly Thr Cys Gly Val Leu Leu Leu Ser Leu Val Ile Thr Leu Tyr Cys
                325                 330                 335

Lys Arg Gly Arg Lys Lys Leu Leu Tyr Ile Phe Lys Gln Pro Phe Met
            340                 345                 350

Arg Pro Val Gln Thr Thr Gln Glu Glu Asp Gly Cys Ser Cys Arg Phe
```

-continued

```
            355                 360                 365

Pro Glu Glu Glu Glu Gly Gly Cys Glu Leu Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415

Arg Gly Arg Asp Pro Glu Met Gly Gly Lys Pro Arg Arg Lys Asn Pro
                420                 425                 430

Gln Glu Gly Leu Tyr Asn Glu Leu Gln Lys Asp Lys Met Ala Glu Ala
                435                 440                 445

Tyr Ser Glu Ile Gly Met Lys Gly Glu Arg Arg Arg Gly Lys Gly His
    450                 455                 460

Asp Gly Leu Tyr Gln Gly Leu Ser Thr Ala Thr Lys Asp Thr Tyr Asp
465                 470                 475                 480

Ala Leu His Met Gln Ala Leu Pro Pro Arg
                485                 490
```

```
<210> SEQ ID NO 102
<211> LENGTH: 495
<212> TYPE: PRT
<213> ORGANISM: Artificial Sequence
<220> FEATURE:
<223> OTHER INFORMATION: Bi-VHH4 (G4S)2 CAR (amino acid)

<400> SEQUENCE: 102

Met Ala Leu Pro Val Thr Ala Leu Leu Leu Pro Leu Ala Leu Leu Leu
1                   5                   10                  15

His Ala Ala Arg Pro Glu Val Gln Leu Val Glu Ser Gly Gly Gly Leu
                20                  25                  30

Val Gln Ala Gly Gly Ser Leu Arg Leu Ser Cys Ala Ala Ser Gly Arg
                35                  40                  45

Thr Phe Ser Ser Tyr Asn Met Gly Trp Phe Arg Gln Ala Pro Gly Lys
    50                  55                  60

Glu Arg Glu Phe Val Ala Val Val Asp Trp Ser Gly Gly Ser Pro Tyr
65                  70                  75                  80

Tyr Ala Asp Ser Val Lys Gly Arg Phe Thr Ile Ser Arg Asp Asn Gly
                85                  90                  95

Lys Asn Thr Val Tyr Leu Gln Met Asn Ser Leu Lys Pro Glu Asp Thr
                100                 105                 110

Ala Val Tyr Tyr Cys Ala Gly Arg Val Gln Tyr Gly Ser Ser Trp Ser
                115                 120                 125

Gly Asp Tyr Trp Gly Gln Gly Thr Gln Val Thr Val Ser Ser Gly Gly
    130                 135                 140

Gly Gly Ser Gly Gly Gly Gly Ser Gln Val Lys Leu Val Glu Ser Gly
145                 150                 155                 160

Gly Gly Ser Val Gln Ala Gly Gly Ser Leu Arg Leu Ser Cys Gln Ala
                165                 170                 175

Ser Ala Tyr Ile Arg Val Phe Tyr Leu Met Gly Trp Phe Arg Gln Ala
                180                 185                 190

Pro Gly Lys Glu Arg Glu Glu Val Ala Arg Val Asn Ala Asp Gly Ile
                195                 200                 205

Thr Asn His Ala Ala Ser Val Lys Gly Arg Phe Thr Ile Ser Lys Asp
    210                 215                 220

Asn Ala Lys Asn Thr Leu Tyr Leu Gln Met Asp Ser Leu Lys Pro Glu
```

```
225              230              235              240

Asp Thr Ala Val Tyr Tyr Cys Ala Ala Gly Arg Thr Trp Asn Ser Gly
             245              250              255

Phe Glu Tyr Trp Gly Gln Gly Thr Gln Val Thr Val Ser Ser Thr Ser
             260              265              270

Thr Thr Thr Pro Ala Pro Arg Pro Thr Pro Ala Pro Thr Ile Ala
             275              280              285

Ser Gln Pro Leu Ser Leu Arg Pro Glu Ala Cys Arg Pro Ala Ala Gly
             290              295              300

Gly Ala Val His Thr Arg Gly Leu Asp Phe Ala Cys Asp Ile Tyr Ile
305              310              315              320

Trp Ala Pro Leu Ala Gly Thr Cys Gly Val Leu Leu Leu Ser Leu Val
             325              330              335

Ile Thr Leu Tyr Cys Lys Arg Gly Arg Lys Lys Leu Leu Tyr Ile Phe
             340              345              350

Lys Gln Pro Phe Met Arg Pro Val Gln Thr Thr Gln Glu Glu Asp Gly
             355              360              365

Cys Ser Cys Arg Phe Pro Glu Glu Glu Gly Gly Cys Glu Leu Arg
             370              375              380

Val Lys Phe Ser Arg Ser Ala Asp Ala Pro Ala Tyr Gln Gln Gly Gln
385              390              395              400

Asn Gln Leu Tyr Asn Glu Leu Asn Leu Gly Arg Arg Glu Glu Tyr Asp
             405              410              415

Val Leu Asp Lys Arg Arg Gly Arg Asp Pro Glu Met Gly Gly Lys Pro
             420              425              430

Arg Arg Lys Asn Pro Gln Glu Gly Leu Tyr Asn Glu Leu Gln Lys Asp
             435              440              445

Lys Met Ala Glu Ala Tyr Ser Glu Ile Gly Met Lys Gly Glu Arg Arg
             450              455              460

Arg Gly Lys Gly His Asp Gly Leu Tyr Gln Gly Leu Ser Thr Ala Thr
465              470              475              480

Lys Asp Thr Tyr Asp Ala Leu His Met Gln Ala Leu Pro Pro Arg
             485              490              495
```

```
<210> SEQ ID NO 103
<211> LENGTH: 500
<212> TYPE: PRT
<213> ORGANISM: Artificial Sequence
<220> FEATURE:
<223> OTHER INFORMATION: Bi-VHH4 (G4S)3 CAR (amino acid)

<400> SEQUENCE: 103
```

```
Met Ala Leu Pro Val Thr Ala Leu Leu Leu Pro Leu Ala Leu Leu Leu
1               5               10              15

His Ala Ala Arg Pro Glu Val Gln Leu Val Glu Ser Gly Gly Gly Leu
             20              25              30

Val Gln Ala Gly Gly Ser Leu Arg Leu Ser Cys Ala Ala Ser Gly Arg
             35              40              45

Thr Phe Ser Ser Tyr Asn Met Gly Trp Phe Arg Gln Ala Pro Gly Lys
             50              55              60

Glu Arg Glu Phe Val Ala Val Val Asp Trp Ser Gly Gly Ser Pro Tyr
65              70              75              80

Tyr Ala Asp Ser Val Lys Gly Arg Phe Thr Ile Ser Arg Asp Asn Gly
             85              90              95

Lys Asn Thr Val Tyr Leu Gln Met Asn Ser Leu Lys Pro Glu Asp Thr
```

-continued

```
             100                 105                 110
Ala Val Tyr Tyr Cys Ala Gly Arg Val Gln Tyr Gly Ser Ser Trp Ser
             115                 120                 125

Gly Asp Tyr Trp Gly Gln Gly Thr Gln Val Thr Val Ser Ser Gly Gly
    130                 135                 140

Gly Gly Ser Gly Gly Gly Ser Gly Gly Gly Gly Ser Gln Val Lys
145                 150                 155                 160

Leu Val Glu Ser Gly Gly Gly Ser Val Gln Ala Gly Gly Ser Leu Arg
             165                 170                 175

Leu Ser Cys Gln Ala Ser Ala Tyr Ile Arg Val Phe Tyr Leu Met Gly
             180                 185                 190

Trp Phe Arg Gln Ala Pro Gly Lys Glu Arg Glu Glu Val Ala Arg Val
             195                 200                 205

Asn Ala Asp Gly Ile Thr Asn His Ala Ala Ser Val Lys Gly Arg Phe
    210                 215                 220

Thr Ile Ser Lys Asp Asn Ala Lys Asn Thr Leu Tyr Leu Gln Met Asp
225                 230                 235                 240

Ser Leu Lys Pro Glu Asp Thr Ala Val Tyr Tyr Cys Ala Ala Gly Arg
             245                 250                 255

Thr Trp Asn Ser Gly Phe Glu Tyr Trp Gly Gln Gly Thr Gln Val Thr
             260                 265                 270

Val Ser Ser Thr Ser Thr Thr Thr Pro Ala Pro Arg Pro Pro Thr Pro
             275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
             325                 330                 335

Leu Leu Ser Leu Val Ile Thr Leu Tyr Cys Lys Arg Gly Arg Lys Lys
             340                 345                 350

Leu Leu Tyr Ile Phe Lys Gln Pro Phe Met Arg Pro Val Gln Thr Thr
             355                 360                 365

Gln Glu Glu Asp Gly Cys Ser Cys Arg Phe Pro Glu Glu Glu Glu Gly
    370                 375                 380

Gly Cys Glu Leu Arg Val Lys Phe Ser Arg Ser Ala Asp Ala Pro Ala
385                 390                 395                 400

Tyr Gln Gln Gly Gln Asn Gln Leu Tyr Asn Glu Leu Asn Leu Gly Arg
             405                 410                 415

Arg Glu Glu Tyr Asp Val Leu Asp Lys Arg Arg Gly Arg Asp Pro Glu
             420                 425                 430

Met Gly Gly Lys Pro Arg Arg Lys Asn Pro Gln Glu Gly Leu Tyr Asn
             435                 440                 445

Glu Leu Gln Lys Asp Lys Met Ala Glu Ala Tyr Ser Glu Ile Gly Met
    450                 455                 460

Lys Gly Glu Arg Arg Arg Gly Lys Gly His Asp Gly Leu Tyr Gln Gly
465                 470                 475                 480

Leu Ser Thr Ala Thr Lys Asp Thr Tyr Asp Ala Leu His Met Gln Ala
             485                 490                 495

Leu Pro Pro Arg
             500
```

<210> SEQ ID NO 104

<211> LENGTH: 505
<212> TYPE: PRT
<213> ORGANISM: Artificial Sequence
<220> FEATURE:
<223> OTHER INFORMATION: Bi-VHH4 (G4S)4 CAR (amino acid)

<400> SEQUENCE: 104

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
                20                  25                  30

Val Gln Ala Gly Gly Ser Leu Arg Leu Ser Cys Ala Ala Ser Gly Arg
            35                  40                  45

Thr Phe Ser Ser Tyr Asn Met Gly Trp Phe Arg Gln Ala Pro Gly Lys
        50                  55                  60

Glu Arg Glu Phe Val Ala Val Val Asp Trp Ser Gly Gly Ser Pro Tyr
65                  70                  75                  80

Tyr Ala Asp Ser Val Lys Gly Arg Phe Thr Ile Ser Arg Asp Asn Gly
                85                  90                  95

Lys Asn Thr Val Tyr Leu Gln Met Asn Ser Leu Lys Pro Glu Asp Thr
            100                 105                 110

Ala Val Tyr Tyr Cys Ala Gly Arg Val Gln Tyr Gly Ser Ser Trp Ser
        115                 120                 125

Gly Asp Tyr Trp Gly Gln Gly Thr Gln Val Thr Val Ser Ser Gly Gly
    130                 135                 140

Gly Gly Ser Gly Gly Gly Gly Ser Gly Gly Gly Gly Ser Gly Gly Gly
145                 150                 155                 160

Gly Ser Gln Val Lys Leu Val Glu Ser Gly Gly Gly Ser Val Gln Ala
                165                 170                 175

Gly Gly Ser Leu Arg Leu Ser Cys Gln Ala Ser Ala Tyr Ile Arg Val
            180                 185                 190

Phe Tyr Leu Met Gly Trp Phe Arg Gln Ala Pro Gly Lys Glu Arg Glu
        195                 200                 205

Glu Val Ala Arg Val Asn Ala Asp Gly Ile Thr Asn His Ala Ala Ser
    210                 215                 220

Val Lys Gly Arg Phe Thr Ile Ser Lys Asp Asn Ala Lys Asn Thr Leu
225                 230                 235                 240

Tyr Leu Gln Met Asp Ser Leu Lys Pro Glu Asp Thr Ala Val Tyr Tyr
                245                 250                 255

Cys Ala Ala Gly Arg Thr Trp Asn Ser Gly Phe Glu Tyr Trp Gly Gln
            260                 265                 270

Gly Thr Gln Val Thr Val Ser Ser Thr Ser Thr Thr Thr Pro Ala Pro
        275                 280                 285

Arg Pro Pro Thr Pro Ala Pro Thr Ile Ala Ser Gln Pro Leu Ser Leu
    290                 295                 300

Arg Pro Glu Ala Cys Arg Pro Ala Ala Gly Gly Ala Val His Thr Arg
305                 310                 315                 320

Gly Leu Asp Phe Ala Cys Asp Ile Tyr Ile Trp Ala Pro Leu Ala Gly
                325                 330                 335

Thr Cys Gly Val Leu Leu Leu Ser Leu Val Ile Thr Leu Tyr Cys Lys
            340                 345                 350

Arg Gly Arg Lys Lys Leu Leu Tyr Ile Phe Lys Gln Pro Phe Met Arg
        355                 360                 365

Pro Val Gln Thr Thr Gln Glu Glu Asp Gly Cys Ser Cys Arg Phe Pro
    370                 375                 380
```

```
Glu Glu Glu Glu Gly Gly Cys Glu Leu Arg Val Lys Phe Ser Arg Ser
385             390             395             400

Ala Asp Ala Pro Ala Tyr Gln Gln Gly Gln Asn Gln Leu Tyr Asn Glu
            405             410             415

Leu Asn Leu Gly Arg Arg Glu Glu Tyr Asp Val Leu Asp Lys Arg Arg
            420             425             430

Gly Arg Asp Pro Glu Met Gly Gly Lys Pro Arg Arg Lys Asn Pro Gln
            435             440             445

Glu Gly Leu Tyr Asn Glu Leu Gln Lys Asp Lys Met Ala Glu Ala Tyr
    450             455             460

Ser Glu Ile Gly Met Lys Gly Glu Arg Arg Arg Gly Lys Gly His Asp
465             470             475             480

Gly Leu Tyr Gln Gly Leu Ser Thr Ala Thr Lys Asp Thr Tyr Asp Ala
            485             490             495

Leu His Met Gln Ala Leu Pro Pro Arg
            500             505
```

```
<210> SEQ ID NO 105
<211> LENGTH: 510
<212> TYPE: PRT
<213> ORGANISM: Artificial Sequence
<220> FEATURE:
<223> OTHER INFORMATION: Bi-VHH4 (G4S)5 CAR (amino acid)

<400> SEQUENCE: 105
```

```
Met Ala Leu Pro Val Thr Ala Leu Leu Leu Pro Leu Ala Leu Leu Leu
1               5               10              15

His Ala Ala Arg Pro Glu Val Gln Leu Val Glu Ser Gly Gly Gly Leu
            20              25              30

Val Gln Ala Gly Gly Ser Leu Arg Leu Ser Cys Ala Ala Ser Gly Arg
            35              40              45

Thr Phe Ser Ser Tyr Asn Met Gly Trp Phe Arg Gln Ala Pro Gly Lys
    50              55              60

Glu Arg Glu Phe Val Ala Val Val Asp Trp Ser Gly Gly Ser Pro Tyr
65              70              75              80

Tyr Ala Asp Ser Val Lys Gly Arg Phe Thr Ile Ser Arg Asp Asn Gly
            85              90              95

Lys Asn Thr Val Tyr Leu Gln Met Asn Ser Leu Lys Pro Glu Asp Thr
            100             105             110

Ala Val Tyr Tyr Cys Ala Gly Arg Val Gln Tyr Gly Ser Ser Trp Ser
            115             120             125

Gly Asp Tyr Trp Gly Gln Gly Thr Gln Val Thr Val Ser Ser Gly Gly
    130             135             140

Gly Gly Ser Gly Gly Gly Gly Ser Gly Gly Gly Gly Ser Gly Gly Gly
145             150             155             160

Gly Ser Gly Gly Gly Gly Ser Gln Val Lys Leu Val Glu Ser Gly Gly
            165             170             175

Gly Ser Val Gln Ala Gly Gly Ser Leu Arg Leu Ser Cys Gln Ala Ser
            180             185             190

Ala Tyr Ile Arg Val Phe Tyr Leu Met Gly Trp Phe Arg Gln Ala Pro
            195             200             205

Gly Lys Glu Arg Glu Glu Val Ala Arg Val Asn Ala Asp Gly Ile Thr
    210             215             220

Asn His Ala Ala Ser Val Lys Gly Arg Phe Thr Ile Ser Lys Asp Asn
225             230             235             240
```

-continued

```
Ala Lys Asn Thr Leu Tyr Leu Gln Met Asp Ser Leu Lys Pro Glu Asp
            245                 250                 255

Thr Ala Val Tyr Tyr Cys Ala Ala Gly Arg Thr Trp Asn Ser Gly Phe
            260                 265                 270

Glu Tyr Trp Gly Gln Gly Thr Gln Val Thr Val Ser Ser Thr Ser Thr
            275                 280                 285

Thr Thr Pro Ala Pro Arg Pro Pro Thr Pro Ala Pro Thr Ile Ala Ser
    290                 295                 300

Gln Pro Leu Ser Leu Arg Pro Glu Ala Cys Arg Pro Ala Ala Gly Gly
305                 310                 315                 320

Ala Val His Thr Arg Gly Leu Asp Phe Ala Cys Asp Ile Tyr Ile Trp
            325                 330                 335

Ala Pro Leu Ala Gly Thr Cys Gly Val Leu Leu Leu Ser Leu Val Ile
            340                 345                 350

Thr Leu Tyr Cys Lys Arg Gly Arg Lys Lys Leu Leu Tyr Ile Phe Lys
            355                 360                 365

Gln Pro Phe Met Arg Pro Val Gln Thr Thr Gln Glu Glu Asp Gly Cys
    370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
            405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
            435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
            485                 490                 495

Asp Thr Tyr Asp Ala Leu His Met Gln Ala Leu Pro Pro Arg
            500                 505                 510
```

<210> SEQ ID NO 106
<211> LENGTH: 619
<212> TYPE: PRT
<213> ORGANISM: Artificial Sequence
<220> FEATURE:
<223> OTHER INFORMATION: Tri-VHH CAR (amino acid)

<400> SEQUENCE: 106

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Ala Gly Gly Ser Leu Arg Leu Ser Cys Ala Ala Ser Gly Arg
        35                  40                  45

Thr Phe Ser Ser Tyr Asn Met Gly Trp Phe Arg Gln Ala Pro Gly Lys
    50                  55                  60

Glu Arg Glu Phe Val Ala Val Val Asp Trp Ser Gly Gly Ser Pro Tyr
65                  70                  75                  80

Tyr Ala Asp Ser Val Lys Gly Arg Phe Thr Ile Ser Arg Asp Asn Gly
            85                  90                  95
```

```
Lys Asn Thr Val Tyr Leu Gln Met Asn Ser Leu Lys Pro Glu Asp Thr
            100                 105                 110

Ala Val Tyr Tyr Cys Ala Gly Arg Val Gln Tyr Gly Ser Ser Trp Ser
            115                 120                 125

Gly Asp Tyr Trp Gly Gln Gly Thr Gln Val Thr Val Ser Ser Gly Gly
    130                 135                 140

Gly Gly Ser Gly Gly Gly Gly Ser Gln Ile Gln Leu Val Glu Ser Gly
145                 150                 155                 160

Gly Gly Leu Val Gln Pro Gly Gly Ser Leu Arg Leu Ser Cys Ala Ala
                165                 170                 175

Ser Gly Phe Thr Phe Ser Asn Tyr Pro Met Thr Trp Leu Arg Gln Ala
            180                 185                 190

Pro Gly Lys Gly Leu Glu Ser Val Ser Asp Ile Thr Ser Gly Gly Asp
            195                 200                 205

Arg Pro Tyr Tyr Ala Asp Ser Val Lys Gly Arg Phe Thr Ile Ser Arg
    210                 215                 220

Asp Asn Ala Lys Asn Met Leu Tyr Leu Glu Met Asn Ser Leu Lys Thr
225                 230                 235                 240

Glu Asp Thr Ala Val Tyr Tyr Cys Ala Thr Trp Asp Arg Thr Leu Thr
                245                 250                 255

Gly Gln Gly Thr Gln Val Thr Val Ser Ser Gly Gly Gly Gly Ser Gly
                260                 265                 270

Gly Gly Gly Ser Gln Val His Leu Met Glu Ser Gly Gly Gly Ser Val
            275                 280                 285

Gln Ala Gly Gly Ser Leu Arg Leu Ser Cys Gln Ala Ser Ala Tyr Ile
    290                 295                 300

Arg Val Phe Tyr Leu Met Gly Trp Phe Arg Gln Ala Pro Gly Lys Glu
305                 310                 315                 320

Arg Glu Glu Val Ala Arg Val Thr Ala Asp Gly Phe Thr Asn His Ala
                325                 330                 335

Ala Ser Val Lys Gly Arg Phe Thr Ile Ser Lys Asp Asn Ala Lys Asn
            340                 345                 350

Thr Leu Tyr Leu Gln Met Asp Ser Met Lys Ser Glu Asp Thr Ala Val
            355                 360                 365

Tyr Tyr Cys Ala Ala Gly Arg Thr Trp Asn Ser Gly Phe Glu Tyr Trp
    370                 375                 380

Gly Gln Gly Thr Gln Val Thr Val Ser Ser Thr Ser Thr Thr Thr Pro
385                 390                 395                 400

Ala Pro Arg Pro Pro Thr Pro Ala Pro Thr Ile Ala Ser Gln Pro Leu
            405                 410                 415

Ser Leu Arg Pro Glu Ala Cys Arg Pro Ala Ala Gly Gly Ala Val His
            420                 425                 430

Thr Arg Gly Leu Asp Phe Ala Cys Asp Ile Tyr Ile Trp Ala Pro Leu
            435                 440                 445

Ala Gly Thr Cys Gly Val Leu Leu Leu Ser Leu Val Ile Thr Leu Tyr
            450                 455                 460

Cys Lys Arg Gly Arg Lys Lys Leu Leu Tyr Ile Phe Lys Gln Pro Phe
465                 470                 475                 480

Met Arg Pro Val Gln Thr Thr Gln Glu Glu Asp Gly Cys Ser Cys Arg
                485                 490                 495

Phe Pro Glu Glu Glu Glu Gly Gly Cys Glu Leu Arg Val Lys Phe Ser
            500                 505                 510
```

-continued

Arg Ser Ala Asp Ala Pro Ala Tyr Gln Gln Gly Gln Asn Gln Leu Tyr
        515                 520                 525

Asn Glu Leu Asn Leu Gly Arg Arg Glu Glu Tyr Asp Val Leu Asp Lys
        530                 535                 540

Arg Arg Gly Arg Asp Pro Glu Met Gly Gly Lys Pro Arg Arg Lys Asn
545                 550                 555                 560

Pro Gln Glu Gly Leu Tyr Asn Glu Leu Gln Lys Asp Lys Met Ala Glu
                565                 570                 575

Ala Tyr Ser Glu Ile Gly Met Lys Gly Glu Arg Arg Arg Gly Lys Gly
                580                 585                 590

His Asp Gly Leu Tyr Gln Gly Leu Ser Thr Ala Thr Lys Asp Thr Tyr
        595                 600                 605

Asp Ala Leu His Met Gln Ala Leu Pro Pro Arg
        610                 615

<210> SEQ ID NO 107
<211> LENGTH: 489
<212> TYPE: PRT
<213> ORGANISM: Artificial Sequence
<220> FEATURE:
<223> OTHER INFORMATION: Leu16 scFv CAR (amino acid)

<400> SEQUENCE: 107

Met Ala Leu Pro Val Thr Ala Leu Leu Leu Pro Leu Ala Leu Leu Leu
1               5                   10                  15

His Ala Ala Arg Pro Asp Ile Val Leu Thr Gln Ser Pro Ala Ile Leu
                20                  25                  30

Ser Ala Ser Pro Gly Glu Lys Val Thr Met Thr Cys Arg Ala Ser Ser
        35                  40                  45

Ser Val Asn Tyr Met Asp Trp Tyr Gln Lys Lys Pro Gly Ser Ser Pro
        50                  55                  60

Lys Pro Trp Ile Tyr Ala Thr Ser Asn Leu Ala Ser Gly Val Pro Ala
65                  70                  75                  80

Arg Phe Ser Gly Ser Gly Ser Gly Thr Ser Tyr Ser Leu Thr Ile Ser
                85                  90                  95

Arg Val Glu Ala Glu Asp Ala Ala Thr Tyr Tyr Cys Gln Gln Trp Ser
                100                 105                 110

Phe Asn Pro Pro Thr Phe Gly Gly Gly Thr Lys Leu Glu Ile Lys Gly
        115                 120                 125

Gly Gly Gly Ser Gly Gly Gly Gly Ser Gly Gly Gly Gly Ser Glu Val
        130                 135                 140

Gln Leu Gln Gln Ser Gly Ala Glu Leu Val Lys Pro Gly Ala Ser Val
145                 150                 155                 160

Lys Met Ser Cys Lys Ala Ser Gly Tyr Thr Phe Thr Ser Tyr Asn Met
                165                 170                 175

His Trp Val Lys Gln Thr Pro Gly Gln Gly Leu Glu Trp Ile Gly Ala
                180                 185                 190

Ile Tyr Pro Gly Asn Gly Asp Thr Ser Tyr Asn Gln Lys Phe Lys Gly
        195                 200                 205

Lys Ala Thr Leu Thr Ala Asp Lys Ser Ser Ser Thr Ala Tyr Met Gln
        210                 215                 220

Leu Ser Ser Leu Thr Ser Glu Asp Ser Ala Asp Tyr Tyr Cys Ala Arg
225                 230                 235                 240

Ser Asn Tyr Tyr Gly Ser Ser Tyr Trp Phe Phe Asp Val Trp Gly Ala
                245                 250                 255

```
Gly Thr Thr Val Thr Val Ser Ser Thr Ser Thr Thr Thr Pro Ala Pro
            260             265             270

Arg Pro Pro Thr Pro Ala Pro Thr Ile Ala Ser Gln Pro Leu Ser Leu
        275             280             285

Arg Pro Glu Ala Cys Arg Pro Ala Ala Gly Gly Ala Val His Thr Arg
        290             295             300

Gly Leu Asp Phe Ala Cys Asp Ile Tyr Ile Trp Ala Pro Leu Ala Gly
305             310             315             320

Thr Cys Gly Val Leu Leu Leu Ser Leu Val Ile Thr Leu Tyr Cys Lys
                325             330             335

Arg Gly Arg Lys Lys Leu Leu Tyr Ile Phe Lys Gln Pro Phe Met Arg
            340             345             350

Pro Val Gln Thr Thr Gln Glu Glu Asp Gly Cys Ser Cys Arg Phe Pro
        355             360             365

Glu Glu Glu Glu Gly Gly Cys Glu Leu Arg Val Lys Phe Ser Arg Ser
        370             375             380

Ala Asp Ala Pro Ala Tyr Gln Gln Gly Gln Asn Gln Leu Tyr Asn Glu
385             390             395             400

Leu Asn Leu Gly Arg Arg Glu Glu Tyr Asp Val Leu Asp Lys Arg Arg
            405             410             415

Gly Arg Asp Pro Glu Met Gly Gly Lys Pro Arg Arg Lys Asn Pro Gln
            420             425             430

Glu Gly Leu Tyr Asn Glu Leu Gln Lys Asp Lys Met Ala Glu Ala Tyr
            435             440             445

Ser Glu Ile Gly Met Lys Gly Glu Arg Arg Arg Gly Lys Gly His Asp
        450             455             460

Gly Leu Tyr Gln Gly Leu Ser Thr Ala Thr Lys Asp Thr Tyr Asp Ala
465             470             475             480

Leu His Met Gln Ala Leu Pro Pro Arg
            485
```

<210> SEQ ID NO 108
<211> LENGTH: 1104
<212> TYPE: DNA
<213> ORGANISM: Artificial Sequence
<220> FEATURE:
<223> OTHER INFORMATION: VHH-273 CAR (nucleic acid)

<400> SEQUENCE: 108

```
atggccctgc ccgtaacagc tctgctccta ccattggcac tgctgctgca tgccgccagg      60
cctgaagtcc agctggtgga atccgggggga ggcctggtgc aggcaggagg ctccctgcgg     120
ctgtcttgcg cagcaagcgg aaggaccttc agctcctaca acatgggctg gtttaggcag     180
gcaccaggca aggagaggga gttcgtggca gtggtggact ggtctggagg cagcccttac     240
tatgccgatt ccgtgaaggg ccggtttacc atcagccggg acaacggcaa gaatacagtg     300
tatctgcaga tgaacagcct gaagcccgag gatacagccg tgtactattg tgccggccgg     360
gtgcagtacg ggtcaagctg gtctggggat tattggggggc aggggactca ggtcactgtc     420
tcatcaacta gtaccacgac gccagcgccg cgaccaccaa caccggcgcc caccatcgcg     480
tcgcagcccc tgtccctgcg cccagaggcg tgccggccag cggcggggggg cgcagtgcac     540 acgaggggggc tggacttcgc ctgtgatatc tacatctggg cgcccttggc cgggacttgt     600 gggggtcctttc tcctgtcact ggttatcacc ctttactgca aacggggcag aaagaaactc     660
ctgtatatat tcaaacaacc atttatgaga ccagtacaaa ctactcaaga ggaagatggc     720
```

-continued

```
tgtagctgcc gatttccaga agaagaagaa ggaggatgtg aactgagagt gaagttcagc      780
aggagcgcag acgcccccgc gtaccagcag ggccagaacc agctctataa cgagctcaat      840
ctaggacgaa gagaggagta cgatgttttg gacaagagac gtggccggga ccctgagatg      900
gggggaaagc cgagaaggaa gaaccctcag gaaggcctgt acaatgaact gcagaaagat      960
aagatggcgg aggcctacag tgagattggg atgaaaggcg agcgccggag gggcaagggg    1020
cacgatggcc tttaccaggg tctcagtaca gccaccaagg acacctacga cgcccttcac    1080
atgcaggccc tgcccctcg ctaa                                             1104
```

<210> SEQ ID NO 109
<211> LENGTH: 1104
<212> TYPE: DNA
<213> ORGANISM: Artificial Sequence
<220> FEATURE:
<223> OTHER INFORMATION: VHH-283 CAR (nucleic acid)

<400> SEQUENCE: 109

```
atggccctgc ccgtaacagc tctgctccta ccattggcac tgctgctgca tgccgccagg       60
cctcaggtca aactggagga atctggggga ggcagcgtgc aggcaggagg cagcctgcgg      120
ctgtcctgcg ccgcctctgg caggaccttc agctcctaca acatgggctg gtttaggcag      180
gcaccaggca aggagaggga gttcgtggca gcaatctcct ggtctggagg cagcccctac      240
tatgcctcta gcgtgcgggg ccggttcacc atctcccggg acaacgccaa gaatacagtg      300
tatctgcaga tgaacagcct gaagcccgag gatacagccg tgtactattg cgccgcccct      360
atcgagtacg gctcttcttg gtcagcagat tattggggac agggcactca ggtcacagtc      420
tcatcaacta gtaccacgac gccagcgccg cgaccaccaa caccggcgcc caccatcgcg      480
tcgcagcccc tgtccctgcg cccagaggcg tgccggccag cggcgggggg cgcagtgcac      540 acgaggggc tggacttcgc ctgtgatatc tacatctggg cgcccttggc cgggacttgt      600
ggggtccttc tcctgtcact ggttatcacc ctttactgca acggggcag aaagaaactc      660 ctgtatatat tcaaacaacc atttatgaga ccagtacaaa ctactcaaga ggaagatggc      720
tgtagctgcc gatttccaga agaagaagaa ggaggatgtg aactgagagt gaagttcagc      780
aggagcgcag acgcccccgc gtaccagcag ggccagaacc agctctataa cgagctcaat      840
ctaggacgaa gagaggagta cgatgttttg gacaagagac gtggccggga ccctgagatg      900
gggggaaagc cgagaaggaa gaaccctcag gaaggcctgt acaatgaact gcagaaagat      960
aagatggcgg aggcctacag tgagattggg atgaaaggcg agcgccggag gggcaagggg    1020
cacgatggcc tttaccaggg tctcagtaca gccaccaagg acacctacga cgcccttcac    1080
atgcaggccc tgcccctcg ctaa                                             1104
```

<210> SEQ ID NO 110
<211> LENGTH: 1104
<212> TYPE: DNA
<213> ORGANISM: Artificial Sequence
<220> FEATURE:
<223> OTHER INFORMATION: VHH-313 CAR (nucleic acid)

<400> SEQUENCE: 110

```
atggccctgc ccgtaacagc tctgctccta ccattggcac tgctgctgca tgccgccagg       60
cctgatgtgc agctggtgga gagcggcggc gggttggtgc aagccggtgg ttcgctgcgg      120
ttgtcatgcg ccgcttccgg acgtacaatc tctagctact ccatgggctg gttccgccag      180
gcccctggta aggagcgcag gtttgtcgcg gccatctcct ggtctggagg gtcgccctat      240
```

-continued

```
tacgcggaca gcgtgaaggg ccgcttcacc atcagccgtg acaacgccaa gaacacggtt      300
tacctgcaga tgaactccct caaacctgaa gacaccgccg tgtactactg tgctgcacca      360
attgagtacg gctccagttg gtctgcggac tattggggcc agggcaccca ggtcaccgtg      420
tcctctacta gtaccacgac gccagcgccg cgaccaccaa caccggcgcc caccatcgcg      480
tcgcagcccc tgtccctgcg cccagaggcg tgccggccag cggcgggggg cgcagtgcac      540
acgagggggc tggacttcgc ctgtgatatc tacatctggg cgcccttggc cgggacttgt      600
ggggtccttc tcctgtcact ggttatcacc ctttactgca aacggggcag aaagaaactc      660
ctgtatatat tcaaacaacc atttatgaga ccagtacaaa ctactcaaga ggaagatggc      720
tgtagctgcc gatttccaga agaagaagaa ggaggatgtg aactgagagt gaagttcagc      780
aggagcgcag acgcccccgc gtaccagcag ggccagaacc agctctataa cgagctcaat      840
ctaggacgaa gagaggagta cgatgttttg gacaagagac gtggccggga ccctgagatg      900
gggggaaagc cgagaaggaa gaaccctcag gaaggcctgt acaatgaact gcagaaagat      960
aagatggcgg aggcctacag tgagattggg atgaaaggcg agcgccggag gggcaagggg     1020
cacgatggcc tttaccaggg tctcagtaca gccaccaagg acacctacga cgcccttcac     1080
atgcaggccc tgccccctcg ctaa                                            1104
```

```
<210> SEQ ID NO 111
<211> LENGTH: 1095
<212> TYPE: DNA
<213> ORGANISM: Artificial Sequence
<220> FEATURE:
<223> OTHER INFORMATION: VHH-440 CAR (nucleic acid)

<400> SEQUENCE: 111
```

```
atggccctgc ccgtaacagc tctgctccta ccattggcac tgctgctgca tgccgccagg       60
cctcaggtcc acctgatgga gagcggaggc ggctccgtgc aggccggagg tagtctgcgc      120
ctgtcatgcc aggcctccgc ctacattcga gtgttctacc tgatgggctg gttccgccag      180
gccccgggga aggagcgcga ggaggtggct cgtgtcactg cggacggctt caccaaccat      240
gcagcttctg tgaagggccg cttcaccatc tccaaggaca cgcgaagaa cacgctgtac      300 ttgcagatgg attctatgaa aagcgaagac actgccgtgt actactgtgc cgctgggcgg      360
acctggaact ccggttttga gtattggggc agggcaccc aggtcaccgt gtcgtccact      420
agtaccacga cgccagcgcc gcgaccacca caccggcgc ccaccatcgc gtcgcagccc      480
ctgtccctgc cccagaggc gtgccggcca gcggcggggg gcgcagtgca cacgaggggg      540
ctggacttcg cctgtgatat ctacatctgg gcgcccttgg ccgggacttg tggggtcctt      600
ctcctgtcac tggttatcac cctttactgc aaacggggca gaaagaaact cctgtatata      660
ttcaaacaac catttatgag accagtacaa actactcaag aggaagatgg ctgtagctgc      720
cgatttccag aagaagaaga aggaggatgt gaactgagag tgaagttcag caggagcgca      780
gacgcccccg cgtaccagca gggccagaac cagctctata cgagctcaa tctaggacga      840 agagaggagt acgatgtttt ggacaagaga cgtggccggg accctgagat gggggggaaag      900 ccgagaagga agaaccctca ggaaggcctg tacaatgaac tgcagaaaga taagatggcg      960
gaggcctaca gtgagattgg gatgaaaggc gagcgccgga ggggcaaggg gcacgatggc     1020
ctttaccagg gtctcagtac agccaccaag gacacctacg acgcccttca catgcaggcc     1080 ctgcccccte gctaa                                                      1095
```

<210> SEQ ID NO 112
<211> LENGTH: 1095
<212> TYPE: DNA
<213> ORGANISM: Artificial Sequence
<220> FEATURE:
<223> OTHER INFORMATION: VHH-466 CAR (nucleic acid)

<400> SEQUENCE: 112

```
atggccctgc ccgtaacagc tctgctccta ccattggcac tgctgctgca tgccgccagg      60
cctcaggtcc acttggtgga gagcggtgga ggctccgtgc aggccggagg ttctctccgt     120
ctctcatgcc aggcctccgc ggacatccgc ctgttttacc tgatgggctg gttccgccaa     180
gcacccggga aggagcgcga ggaggtggct cgggttaacg cggatgacag cattaactac     240
gtggcgagtg taaagggccg cttcaccatc tccaaggaca cgccaagaa cacgctgtac      300 ttgcagatgg attctcttaa accggaagac accgccactt actactgtgc tgctgggcga     360
acctggaact ccggcttcga gtattggggc caggcaccc aggtcaccgt gagctcgact      420
agtaccacga cgccagcgcc gcgaccacca acaccggcgc ccaccatcgc gtcgcagccc     480
ctgtccctgc gcccagaggc gtgccggcca gcggcggggg gcgcagtgca cacgaggggg     540
ctggacttcg cctgtgatat ctacatctgg gcgcccttgg ccgggacttg tggggtcctt     600
ctcctgtcac tggttatcac cctttactgc aaacgggca gaaagaaact cctgtatata     660
ttcaaacaac catttatgag accagtacaa actactcaag aggaagatgg ctgtagctgc     720
cgatttccag aagaagaaga aggaggatgt gaactgagag tgaagttcag caggagcgca     780
gacgcccccg cgtaccagca gggccagaac cagctctata cgagctcaa tctaggacga     840 agagaggagt acgatgtttt ggacaagaga cgtggccggg accctgagat ggggggaaag     900
ccgagaagga agaaccctca ggaaggcctg tacaatgaac tgcagaaaga taagatggcg     960
gaggcctaca gtgagattgg gatgaaaggc gagcgccgga ggggcaaggg gcacgatggc    1020
ctttaccagg gtctcagtac agccaccaag gacacctacg acgcccttca catgcaggcc    1080 ctgcccctc gctaa                                                     1095
```

<210> SEQ ID NO 113
<211> LENGTH: 1083
<212> TYPE: DNA
<213> ORGANISM: Artificial Sequence
<220> FEATURE:
<223> OTHER INFORMATION: VHH-496 CAR (nucleic acid)

<400> SEQUENCE: 113

```
atggccctgc ccgtaacagc tctgctccta ccattggcac tgctgctgca tgccgccagg      60
cctcagatcc agctggtgga gagtggaggc ggcttggtgc agccaggggg ctccctacgc     120
ctgtcatgcg ctgcttctgg cttcacgttc agcaactacc gatgacctg ctccgccag      180 gcccccggga aaggcctcga gagcgtgtcc gacatcacct ccggtggtga tcggccctat     240
tacgcggact cggtgaaggg caggtttaca atttctcgcg acaacgccaa gaatatgctg     300
tacctggaga tgaactccct gaagactgaa gacaccgccg tgtactactg tgccacctgg     360
gatcgcaccc tgacgggaca aggcacccag gtcaccgtta gctcgactag taccacgacg     420
ccagcgccgc gaccaccaac accggcgccc accatcgcgt cgcagcccct gtccctgcgc     480
ccagaggcgt gccggccagc ggcggggggc gcagtgcaca cgaggggggct ggacttcgcc    540 tgtgatatct acatctgggc gcccttggcc gggacttgtg ggtccttct cctgtcactg      600 gttatcaccc tttactgcaa acggggcaga aagaaactcc tgtatatatt caaacaacca     660
```

-continued

```
tttatgagac cagtacaaac tactcaagag gaagatggct gtagctgccg atttccagaa      720
gaagaagaag gaggatgtga actgagagtg aagttcagca ggagcgcaga cgcccccgcg      780
taccagcagg gccagaacca gctctataac gagctcaatc taggacgaag agaggagtac      840
gatgttttgg acaagagacg tggccgggac cctgagatgg ggggaaagcc gagaaggaag      900
aaccctcagg aaggcctgta caatgaactg cagaaagata agatggcgga ggcctacagt      960
gagattggga tgaaaggcga cgccggagg ggcaagggc acgatggcct ttaccagggt      1020
ctcagtacag ccaccaagga cacctacgac gcccttcaca tgcaggccct gccccctcgc      1080
taa                                                                    1083
```

<210> SEQ ID NO 114
<211> LENGTH: 1095
<212> TYPE: DNA
<213> ORGANISM: Artificial Sequence
<220> FEATURE:
<223> OTHER INFORMATION: VHH-653 CAR (nucleic acid)

<400> SEQUENCE: 114

```
atggccctgc ccgtaacagc tctgctccta ccattggcac tgctgctgca tgccgccagg       60
cctcaggtga agctggtgga gagcggtggg ggctccgtgc aggccggagg tagccttcgc      120
ctgtcatgcc aggcctccgc ctacattcgg gtgttttacc tgatgggctg gttccgccag      180
gccccgggga aggagcgcga ggaggtggca cgagtcaacg cggacggcat caccaaccat      240
gcagcttccg taaaaggccg cttcaccatc tccaaggaca cgccaagaa cacgctatac       300 ctccagatgg attctctgaa gcccgaggac accgccgtgt actactgtgc tgcgggacgt      360
acttggaact ccggcttcga atattggggc caggcaccc aggtcactgt cagttccact       420
agtaccacga cgccagcgcc gcgaccacca acaccggcgc ccaccatcgc gtcgcagccc      480
ctgtccctgc gcccagaggc gtgccggcca gcggcggggg gcgcagtgca cacgaggggg      540
ctggacttcg cctgtgatat ctacatctgg gcgcccttgg ccgggacttg tggggtcctt      600
ctcctgtcac tggttatcac cctttactgc aaacggggca gaaagaaact cctgtatata      660
ttcaaacaac catttatgag accagtacaa actactcaag aggaagatgg ctgtagctgc      720
cgatttccag aagaagaaga aggaggatgt gaactgagag tgaagttcag caggagcgca      780 gacgccccg cgtaccagca gggccagaac cagctctata cgagctcaa tctaggacga      840 agagaggagt acgatgtttt ggacaagaga cgtggccggg accctgagat ggggggaaag      900
ccgagaagga agaaccctca ggaaggcctg tacaatgaac tgcagaaaga taagatggcg      960
gaggcctaca gtgagattgg gatgaaaggc gagcgccgga ggggcaaggg cacgatggcc     1020
ctttaccagg gtctcagtac agccaccaag gacacctacg acgcccttca catgcaggcc     1080
ctgccccctc gctaa                                                       1095
```

<210> SEQ ID NO 115
<211> LENGTH: 1104
<212> TYPE: DNA
<213> ORGANISM: Artificial Sequence
<220> FEATURE:
<223> OTHER INFORMATION: huVHH-253 CAR (nucleic acid)

<400> SEQUENCE: 115

```
atggccctgc ccgtaacagc tctgctccta ccattggcac tgctgctgca tgccgccagg       60
cctgaggtgc agctggtgga gagcggcggc ggtttggtgc agccaggagg ctccctccgc      120
```

-continued

```
ctgtcatgcg ccgcttccgg ccgcaccttc agcagctaca acatgggctg gttccgccag        180 gccccggca aaggcctgga gtgggtcgcg gccgtggatt ggtctggcgg ttccccctat        240
tacgcggact ccgtgaaggg ccgcttcacc atctcccgcg acaactccaa gaacacggtg        300
tacctgcaga tgaactctct gcgcgccgag gacaccgccg tctactactg tgccggccga        360
gtgcagtacg gctccagttg gtctggggac tattggggcc agggcaccct ggtgaccgtg        420
tcgtccacta gtaccacgac gccagcgccg cgaccaccaa caccggcgcc caccatcgcg        480
tcgcagcccc tgtccctgcg cccagaggcg tgccggccag cggcggggggg cgcagtgcac       540 acgagggggc tggacttcgc ctgtgatatc tacatctggg cgcccttggc cgggacttgt        600
ggggtccttc tcctgtcact ggttatcacc ctttactgca aacggggcag aaagaaactc        660
ctgtatatat tcaaacaacc atttatgaga ccagtacaaa ctactcaaga ggaagatggc        720
tgtagctgcc gatttccaga agaagaagaa ggaggatgtg aactgagagt gaagttcagc        780
aggagcgcag acgcccccgc gtaccagcag ggccagaacc agctctataa cgagctcaat        840
ctaggacgaa gagaggagta cgatgttttg gacaagagac gtggccggga ccctgagatg        900
gggggaaagc cgagaaggaa gaaccctcag gaaggcctgt acaatgaact gcagaaagat        960
aagatggcgg aggcctacag tgagattggg atgaaaggcg agcgccggag gggcaagggg       1020
cacgatggcc tttaccaggg tctcagtaca gccaccaagg acacctacga cgcccttcac       1080
atgcaggccc tgccccctcg ctaa                                            1104
```

<210> SEQ ID NO 116
<211> LENGTH: 1104
<212> TYPE: DNA
<213> ORGANISM: Artificial Sequence
<220> FEATURE:
<223> OTHER INFORMATION: huVHH-256 CAR (nucleic acid)

<400> SEQUENCE: 116

```
atggccctgc ccgtaacagc tctgctccta ccattggcac tgctgctgca tgccgccagg         60
cctgaggtgc agctggtgga gagcggaggc ggtttggtgc agccagggggg ttctctgcgc        120 ctgagctgtg ctgcttccgg tcgtacgttc agcagctaca acatgggctg gttccgccag        180 gccccggca aaggcctgga gttcgtcgcc gtggtggact ggtctggcgg ctcccccctat        240 tacgcggact ccgtgaaggg ccgcttcacc atctcccgcg acaactccaa gaacacggtg        300
tacctgcaga tgtcttctct tcgcgccgag gacaccgccg tctactactg cgccggccga        360
gtgcagtacg gctccagttg gtctggtgat tattggggcc agggcaccct ggtgaccgtg        420
tcgtccacta gtaccacgac gccagcgccg cgaccaccaa caccggcgcc caccatcgcg        480
tcgcagcccc tgtccctgcg cccagaggcg tgccggccag cggcggggggg cgcagtgcac       540 acgagggggc tggacttcgc ctgtgatatc tacatctggg cgcccttggc cgggacttgt        600
ggggtccttc tcctgtcact ggttatcacc ctttactgca aacggggcag aaagaaactc        660
ctgtatatat tcaaacaacc atttatgaga ccagtacaaa ctactcaaga ggaagatggc        720
tgtagctgcc gatttccaga agaagaagaa ggaggatgtg aactgagagt gaagttcagc        780
aggagcgcag acgcccccgc gtaccagcag ggccagaacc agctctataa cgagctcaat        840
ctaggacgaa gagaggagta cgatgttttg gacaagagac gtggccggga ccctgagatg        900
gggggaaagc cgagaaggaa gaaccctcag gaaggcctgt acaatgaact gcagaaagat        960
aagatggcgg aggcctacag tgagattggg atgaaaggcg agcgccggag gggcaagggg       1020
cacgatggcc tttaccaggg tctcagtaca gccaccaagg acacctacga cgcccttcac       1080
```

-continued

```
atgcaggccc tgcccctcg ctaa                                            1104

<210> SEQ ID NO 117
<211> LENGTH: 1104
<212> TYPE: DNA
<213> ORGANISM: Artificial Sequence
<220> FEATURE:
<223> OTHER INFORMATION: huVHH-260 CAR (nucleic acid)

<400> SEQUENCE: 117
atggccctgc ccgtaacagc tctgctccta ccattggcac tgctgctgca tgccgccagg      60
cctgacgtgc agctgctgga gagcggaggc gggctggtgc agccaggggg ttctcttcgc     120
ctgtcatgcg ccgcttccgg tcgcaccatc tctagctact ccatgggctg gttccgccag     180 gccccggca aaggcctcga gttcgtcgcg gccatcagtt ggtctggcgg ctccccctat     240
tacgcggact ccgtgaaggg ccgcttcacc atctcccgcg acaacgccaa gaacacggtc     300
tacctgcaga tgaactccct gcgcgccgag gacaccgccg tgtactactg tgctgctcct     360
attgagtacg ctccagttg tctgcggac tattggggcc agggcaccct ggtcaccgtg      420
tcgtccacta gtaccacgac gccagcgccg cgaccaccaa caccggcgcc caccatcgcg     480
tcgcagcccc tgtccctgcg cccagaggcg tgccggccag cggcggggg cgcagtgcac      540 acgagggggc tggacttcgc ctgtgatatc tacatctggg cgcccttggc cgggacttgt     600
ggggtccttc tcctgtcact ggttatcacc ctttactgca acgggcag aaagaaactc       660 ctgtatatat tcaaacaacc atttatgaga ccagtacaaa ctactcaaga ggaagatggc     720
tgtagctgcc gatttccaga agaagaagaa ggaggatgtg aactgagagt gaagttcagc     780
aggagcgcag acgcccccgc gtaccagcag ggccagaacc agctctataa cgagctcaat     840
ctaggacgaa gagaggagta cgatgttttg gacaagagac gtggccggga ccctgagatg     900
gggggaaagc cgagaaggaa gaaccctcag gaaggcctgt acaatgaact gcagaaagat     960
aagatggcgg aggcctacag tgagattggg atgaaaggcg agcgccggag gggcaagggg    1020
cacgatggcc tttaccaggg tctcagtaca gccaccaagg acacctacga cgcccttcac    1080
atgcaggccc tgcccctcg ctaa                                           1104

<210> SEQ ID NO 118
<211> LENGTH: 1083
<212> TYPE: DNA
<213> ORGANISM: Artificial Sequence
<220> FEATURE:
<223> OTHER INFORMATION: huVHH-746 CAR (nucleic acid)

<400> SEQUENCE: 118
atggccctgc ccgtaacagc tctgctccta ccattggcac tgctgctgca tgccgccagg      60
cctcagatcc agctgctgga gagtggcggc gggctggtgc agccgggagg ctccctgcgc     120
ctgtcatgcg ccgcttccgg cttcacgttc agcaactacc caatgacctg gatccgccag     180 gccccggca aaggcctcga gagcgtgtcc gacatcacct ccggtggtga taggccctat     240
tacgcggact ccgtgaaggg ccgcttcacc atctctcgcg acaacgccaa gaacatgctg     300
tacctgcaga tgaactccct ccgcgccgag gacaccgccg tgtactactg tgccaccctgg     360 gaccgcaccc tttggggcca gggcaccatg gtgaccgtga gctccactag taccacgacg     420
ccagcgccgc gaccaccaac accggcgccc accatcgcgt cgcagcccct gtccctgcgc     480
ccagaggcgt gccggccagc ggcgggggc gcagtgcaca cgaggggct ggacttcgcc      540
```

```
tgtgatatct acatctgggc gcccttggcc gggacttgtg gggtccttct cctgtcactg      600
gttatcaccc tttactgcaa acggggcaga aagaaactcc tgtatatatt caaacaacca      660
tttatgagac cagtacaaac tactcaagag gaagatggct gtagctgccg atttccagaa      720
gaagaagaag gaggatgtga actgagagtg aagttcagca ggagcgcaga cgcccccgcg      780
taccagcagg gccagaacca gctctataac gagctcaatc taggacgaag agaggagtac      840
gatgttttgg acaagagacg tggccgggac cctgagatgg ggggaaagcc gagaaggaag      900
aaccctcagg aaggcctgta caatgaactg cagaaagata agatggcgga ggcctacagt      960
gagattggga tgaaaggcga cgcgcggagg ggcaaggggc acgatggcct ttaccagggt      1020
ctcagtacag ccaccaagga cacctacgac gcccttcaca tgcaggccct gccccctcgc      1080
taa                                                                    1083

<210> SEQ ID NO 119
<211> LENGTH: 1083
<212> TYPE: DNA
<213> ORGANISM: Artificial Sequence
<220> FEATURE:
<223> OTHER INFORMATION: huVHH-750 CAR (nucleic acid)

<400> SEQUENCE: 119
atggccctgc ccgtaacagc tctgctccta ccattggcac tgctgctgca tgccgccagg       60
cctcagatcc agctggtgga gagcggaggc ggtttggtgc agccgggcgg ctccctgcgc      120
ctgagctgtg ctgcttccgg cttcacattt tcaaattatc caatgacctg gctccgccag      180 gccccccggca aaggcctgga gtccgtgtcc gacatcacct ccggtgggga caggcccctat      240 tacgcggaca gcgtcaaagg ccgcttcacc atctctcgcg acaacgccaa gaacatgctg      300
tacctgcaga tgaactcctt acgcgccgag gacaccgccg tgtactactg cgccacctgg      360
gaccgcaccc tgaccggcca gggcaccatg gtgaccgtga gctccactag taccacgacg      420
ccagcgccgc gaccaccaac accggcgccc accatcgcgt cgcagcccct gtccctgcgc      480
ccagaggcgt gccggccagc ggcggggggc gcagtgcaca cgagggggct ggacttcgcc      540
tgtgatatct acatctgggc gcccttggcc gggacttgtg gggtccttct cctgtcactg      600
gttatcaccc tttactgcaa acggggcaga aagaaactcc tgtatatatt caaacaacca      660
tttatgagac cagtacaaac tactcaagag gaagatggct gtagctgccg atttccagaa      720
gaagaagaag gaggatgtga actgagagtg aagttcagca ggagcgcaga cgcccccgcg      780
taccagcagg gccagaacca gctctataac gagctcaatc taggacgaag agaggagtac      840
gatgttttgg acaagagacg tggccgggac cctgagatgg ggggaaagcc gagaaggaag      900
aaccctcagg aaggcctgta caatgaactg cagaaagata agatggcgga ggcctacagt      960
gagattggga tgaaaggcga cgcgcggagg ggcaaggggc acgatggcct ttaccagggt      1020
ctcagtacag ccaccaagga cacctacgac gcccttcaca tgcaggccct gccccctcgc      1080
taa                                                                    1083

<210> SEQ ID NO 120
<211> LENGTH: 1083
<212> TYPE: DNA
<213> ORGANISM: Artificial Sequence
<220> FEATURE:
<223> OTHER INFORMATION: huVHH-753 CAR (nucleic acid)

<400> SEQUENCE: 120
atggccctgc ccgtaacagc tctgctccta ccattggcac tgctgctgca tgccgccagg       60
```

-continued

```
cctcagatcc agctggtgga gagcggcggc ggtttggtgc agccgggagg ctccctgcgc      120
ctgtcatgcg ccgcttccgg cttcaccttt tcaaattacc caatgacctg gctccgccag      180 gccccggca aaggcctgga gtccgtgtcc gacatcacct ccggtgggga caggccctat        240
tacgcggaca gcgtgaaggg ccgcttcacc atctctcgcg acaacgccaa gaacatgctt      300
tacctgcaga tgaactcctt acgcgccgag gacaccgccg tgtactactg tgccacctgg      360
gaccgcaccc tcactggaca gggcaccctg gtcaccgtgt cgtccactag taccacgacg       420
ccagcgccgc gaccaccaac accggcgccc accatcgcgt cgcagcccct gtccctgcgc      480
ccagaggcgt gccggccagc ggcggggggc gcagtgcaca cgaggggct ggacttcgcc         540 tgtgatatct acatctgggc gcccttggcc gggacttgtg gggtccttct cctgtcactg      600
gttatcaccc tttactgcaa acggggcaga aagaaactcc tgtatatatt caaacaacca      660
tttatgagac cagtacaaac tactcaagag gaagatggct gtagctgccg atttccagaa      720
gaagaagaag gaggatgtga actgagagtg aagttcagca ggagcgcaga cgcccccgcg      780
taccagcagg gccagaacca gctctataac gagctcaatc taggacgaag agaggagtac       840
gatgttttgg acaagagacg tggccgggac cctgagatgg ggggaaagcc gagaaggaag      900
aaccctcagg aaggcctgta caatgaactg cagaaagata agatggcgga ggcctacagt       960
gagattggga tgaaaggcga gcgccggagg gcaagggc acgatggcct ttaccagggt          1020
ctcagtacag ccaccaagga cacctacgac gcccttcaca tgcaggccct gccccctcgc     1080
taa                                                                                          1083
```

```
<210> SEQ ID NO 121
<211> LENGTH: 1095
<212> TYPE: DNA
<213> ORGANISM: Artificial Sequence
<220> FEATURE:
<223> OTHER INFORMATION: huVHH-836 CAR (nucleic acid)

<400> SEQUENCE: 121
```

```
atggccctgc ccgtaacagc tctgctccta ccattggcac tgctgctgca tgccgccagg       60
cctgaggtgc agctggtgga gagcggtggc ggtctggtgc agccgggagg ctcccttgcgt     120 ctatcatgcg ccgcttccgc ggacatccgc ctgtttttacc tgatgggctg gttccgccag      180
gcccccggga aagggttggt ttgggtcgcc cgagtcaacg cggatgacag catttcttac       240
gcggatagtg tgaagggccg cttcaccatc tcccgcgaca cgccaagaa cacgctctac        300 ctccagatga actccctgcg cgccgaggac accgccgtat actactgtgc tgcaggacgg      360
acctggaact ccggcttcga gtactggggc agggcactc ttgtcaccgt gagctcgact         420
agtaccacga cgccagcgcc gcgaccacca acaccggcgc ccaccatcgc gtcgcagccc      480
ctgtccctgc gcccagaggc gtgccggcca gcggcggggg gcgcagtgca cacgaggggg     540
ctggacttcg cctgtgatat ctacatctgg gcgcccttgg ccgggacttg tggggtcctt        600
ctcctgtcac tggttatcac cctttactgc aaacggggca gaaagaaact cctgtatata      660
ttcaaacaac catttatgag accagtacaa actactcaag aggaagatgg ctgtagctgc       720
cgatttccag aagaagaaga aggaggatgt gaactgagag tgaagttcag caggagcgca      780 gacgccccg cgtaccagca gggccagaac cagctctata cgagctcaa tctaggacga         840 agagaggagt acgatgtttt ggacaagaga cgtggccggg accctgagat ggggggaaag     900
ccgagaagga agaaccctca ggaaggcctg tacaatgaac tgcagaaaga taagatggcg     960
```

-continued

```
gaggcctaca gtgagattgg gatgaaaggc gagcgccgga ggggcaaggg gcacgatggc     1020
ctttaccagg gtctcagtac agccaccaag gacacctacg acgcccttca catgcaggcc     1080
ctgccccctc gctaa                                                     1095

<210> SEQ ID NO 122
<211> LENGTH: 1095
<212> TYPE: DNA
<213> ORGANISM: Artificial Sequence
<220> FEATURE:
<223> OTHER INFORMATION: huVHH-840 CAR (nucleic acid)

<400> SEQUENCE: 122
atggccctgc ccgtaacagc tctgctccta ccattggcac tgctgctgca tgccgccagg       60
cctcaggtgc agctgcagga gagcggagga ggtgtggtgc agccaggcgg ctccttgcgc      120
ctgtcatgcg ccgctagtgc ggacatccga ctctttttacc tgatgggctg gttccgccag      180
gccccgggga aggtctcga  gtgggtcgcc ttcgtgaacg cagatgacag catttactac      240
gcggattccg taaagggccg cttcaccatc tctcgggaca actccaagaa cacgctgtac      300
ctccagatga cagcctacg tgccgaggac actgccgtgt actactgtgc cgctgggcgc      360
acctggaact ccggcttcga gtactggggc caaggcaccc tggtgaccgt gtcgtctact      420
agtaccacga cgccagcgcc gcgaccacca acaccggcgc ccaccatcgc gtcgcagccc      480
ctgtccctgc gcccagaggc gtgccggcca cgggcggggg gcgcagtgca cacgaggggg      540
ctggacttcg cctgtgatat ctacatctgg gcgcccttgg ccgggacttg tggggtcctt      600
ctcctgtcac tggttatcac cctttactgc aaacggggca gaaagaaact cctgtatata      660
ttcaaacaac catttatgag accagtacaa actactcaag aggaagatgg ctgtagctgc      720
cgatttccag aagaagaaga aggaggatgt gaactgagag tgaagttcag caggagcgca      780
gacgcccccg cgtaccagca gggccagaac cagctctata cgagctcaa  tctaggacga      840 agagaggagt acgatgtttt ggacaagaga cgtggccggg accctgagat ggggggaaag      900
ccgagaagga agaaccctca ggaaggcctg tacaatgaac tgcagaaaga taagatggcg      960
gaggcctaca gtgagattgg gatgaaaggc gagcgccgga ggggcaaggg gcacgatggc     1020
ctttaccagg gtctcagtac agccaccaag gacacctacg acgcccttca catgcaggcc     1080
ctgccccctc gctaa                                                     1095

<210> SEQ ID NO 123
<211> LENGTH: 1095
<212> TYPE: DNA
<213> ORGANISM: Artificial Sequence
<220> FEATURE:
<223> OTHER INFORMATION: huVHH-843 CAR (nucleic acid)

<400> SEQUENCE: 123
atggccctgc ccgtaacagc tctgctccta ccattggcac tgctgctgca tgccgccagg       60
cctcaggtcc acttggtgga gagcggaggt ggtctggtgc agccaggggg ctccctacgc      120
ctgtcatgcc aggcctccgc ggacatccga ctcttttacc taatgggctg gttccgccag      180
gccccgggga aggccttgt  ttgggtcgca cgggtcaacg cggatgacag cattaactac      240
gtggattctg tgaagggccg cttcaccatc tccaaggaca acgccaagaa cacgctgtac      300
ctgcagatga actccctgcg cgccgaggac accgccgtgt actactgtgc tgctggacgt      360
acctggaact ccggcttcga gtattggggc caggcaccc  tggtaacagt gtcgtcgact      420
agtaccacga cgccagcgcc gcgaccacca acaccggcgc ccaccatcgc gtcgcagccc      480
```

```
ctgtccctgc gcccagaggc gtgccggcca gcggcggggg gcgcagtgca cacgagggggg      540 ctggacttcg cctgtgatat ctacatctgg gcgcccttgg ccgggacttg tggggtcctt      600
ctcctgtcac tggttatcac cctttactgc aaacggggca gaaagaaact cctgtatata      660
ttcaaacaac catttatgag accagtacaa actactcaag aggaagatgg ctgtagctgc      720
cgatttccag aagaagaaga aggaggatgt gaactgagag tgaagttcag caggagcgca      780 gacgccccg cgtaccagca gggccagaac cagctctata cgagctcaa tctaggacga        840 agagaggagt acgatgtttt ggacaagaga cgtggccggg accctgagat ggggggaaag      900
ccgagaagga agaaccctca ggaaggcctg tacaatgaac tgcagaaaga taagatggcg      960
gaggcctaca gtgagattgg gatgaaaggc gagcgccgga ggggcaaggg gcacgatggc     1020
ctttaccagg gtctcagtac agccaccaag gacacctacg acgcccttca catgcaggcc     1080 ctgcccccctc gctaa                                                     1095
```

<210> SEQ ID NO 124
<211> LENGTH: 1095
<212> TYPE: DNA
<213> ORGANISM: Artificial Sequence
<220> FEATURE:
<223> OTHER INFORMATION: huVHH-846 CAR (nucleic acid)

<400> SEQUENCE: 124

```
atggccctgc ccgtaacagc tctgctccta ccattggcac tgctgctgca tgccgccagg       60
cctcaggtcc acttgcagga gagcggcggg ggtgtggtgc agccgggagg ctcccttcgt      120
ctctcatgcc aagcctcggc ggacatccgg cttttttacc tgatgggctg gttccgccag      180
gcccccggga agggactgga gtgggttgcc ttcgtgaacg ctgatgacag cattaactac      240
gcggattccg tgaagggccg cttcaccatc tctaaggaca acagcaaaaa cactctgtac      300
ctccagatga actccctgcg cgctgaagac accgccgtgt actactgtgc tgcaggtcgc      360
acctggaact ccggcttcga gtattggggc cagggcaccc tggtgacggt gtccagtact      420
agtaccacga cgccagcgcc gcgaccacca acaccggcgc ccaccatcgc gtcgcagccc      480
ctgtccctgc gcccagaggc gtgccggcca gcggcggggg gcgcagtgca cacgagggggg      540 ctggacttcg cctgtgatat ctacatctgg gcgcccttgg ccgggacttg tggggtcctt      600
ctcctgtcac tggttatcac cctttactgc aaacggggca gaaagaaact cctgtatata      660
ttcaaacaac catttatgag accagtacaa actactcaag aggaagatgg ctgtagctgc      720
cgatttccag aagaagaaga aggaggatgt gaactgagag tgaagttcag caggagcgca      780 gacgccccg cgtaccagca gggccagaac cagctctata cgagctcaa tctaggacga        840 agagaggagt acgatgtttt ggacaagaga cgtggccggg accctgagat ggggggaaag      900
ccgagaagga agaaccctca ggaaggcctg tacaatgaac tgcagaaaga taagatggcg      960
gaggcctaca gtgagattgg gatgaaaggc gagcgccgga ggggcaaggg gcacgatggc     1020
ctttaccagg gtctcagtac agccaccaag gacacctacg acgcccttca catgcaggcc     1080 ctgcccccctc gctaa                                                     1095
```

<210> SEQ ID NO 125
<211> LENGTH: 1476
<212> TYPE: DNA
<213> ORGANISM: Artificial Sequence
<220> FEATURE:
<223> OTHER INFORMATION: Bi-VHH1 CAR (nucleic acid)

-continued

```
<400> SEQUENCE: 125
atggccctgc ccgtaacagc tctgctccta ccattggcac tgctgctgca tgccgccagg      60
cctgaggtgc agttggtgga gagtggggggt ggtctggtgc aggccggcgg ttctctgcgc     120
ctgagctgtg ctgcatccgg acgtacgttc tctagctaca acatgggctg gttccgccag     180
gctcccggca aggagcgcga gttcgtcgcg gtggtcgatt ggtctggcgg ctcccccctat    240 tacgcggaca gtgttaaggg cagatttaca atttcccgcg acaacggcaa aaacacggtc     300
tacctgcaga tgaactccct caagcctgaa gacactgccg tgtactactg cgccggccgc     360
gtgcaatacg gcagcagttg gtctggtgat tattgggggcc agggcaccca ggtcaccgtg    420
tcgtccggcg gcggcggctc gggcggaggt ggctcccaga tccagctggt ggagagcgga     480
ggcggtttgg tacagccagg tggcagcctt cgtctgtcat gcgcagcttc cggcttcacc     540 tttttcaaatt acccaatgac ctggctccgc caggcccccg ggaaagggct ggagagcgtg     600
tccgacatca cctccggtgg ggacaggccc tattacgcgg actcggtgaa ggggcgcttc      660
accatctctc gggacaacgc caagaacatg ctttacttgg agatgaacag cctgaagacc      720
gaggacaccg ccgtgtacta ctgtgccacc tgggatcgaa ctctgactgg acaggggacc      780
caggttacag tctcgtctac tagtaccacg acgccagcgc cgcgaccacc aacaccggcg     840
cccaccatcg cgtcgcagcc cctgtccctg cgcccagagg cgtgccggcc agcggcgggg     900
ggcgcagtgc acacgagggg gctggacttc gcctgtgata tctacatctg ggcgcccttg     960
gccgggactt gtgggggtcct tctcctgtca ctggttatca ccctttactg caaacggggc    1020
agaaagaaac tcctgtatat attcaaacaa ccatttatga ccagtacaa aactactcaa     1080 gaggaagatg gctgtagctg ccgatttcca gaagaagaag aaggaggatg tgaactgaga     1140
gtgaagttca gcaggagcgc agacgccccc gcgtaccagc agggccagaa ccagctctat     1200
aacgagctca atctaggacg aagagaggag tacgatgttt tggacaagag acgtggccgg     1260
gaccctgaga tggggggaaa gccgagaagg aagaaccctc aggaaggcct gtacaatgaa      1320
ctgcagaaag ataagatggc ggaggcctac agtgagattg ggatgaaagg cgagcgccgg    1380
aggggcaagg ggcacgatgg cctttaccag ggtctcagta cagccaccaa ggacacctac     1440
gacgcccttc acatgcaggc cctgccccct cgctaa                              1476

<210> SEQ ID NO 126
<211> LENGTH: 1476
<212> TYPE: DNA
<213> ORGANISM: Artificial Sequence
<220> FEATURE:
<223> OTHER INFORMATION: Bi-VHH2 CAR (nucleic acid)

<400> SEQUENCE: 126
atggccctgc ccgtaacagc tctgctccta ccattggcac tgctgctgca tgccgccagg      60
cctcaggtga agctggagga atccggtggt ggatccgtgc aggccggcgg gagcctgcgc     120
ctgtcctgtg cagctagcgg ccgcaccttc tctagctaca acatgggctg gttccgccag     180
gccccaggca aggagcgcga gttcgtcgcg gccattagtt ggtctggggg ttctcccctat    240 tacgcttcat ccgtgcgcgg ccgcttcacc atctctcggg acaacgcgaa gaacacggtt     300
tacctgcaga tgaactcgtt gaagcctgaa gacaccgccg tgtactactg cgccgcaccg     360
attgagtacg ctccagttg gtctgctgat tattggggcc aagggaccca ggtcaccgtg      420
tcgtcgggcg gcgaggctc cggggggtggg ggctcccaga tccagctggt ggagagcgga     480
ggcggtcttg tgcagccggg aggctctctg aggttgtcgt gtgctgcgtc aggcttcaca     540
```

```
tttagcaact acccaatgac ctggctccga caggccccg gcaaaggtct ggagagcgta        600
tccgacatca cctccggcgg tgatagaccc tattacgcgg acagcgtcaa gggccgtttt        660
actatctccc gcgacaacgc caagaatatg ctttacctcg agatgaactc cctcaaaact        720
gaggacacag ccgtgtacta ctgcgccacc tgggaccgca ccctgaccgg ccagggcacc        780
caggtcactg tgagctctac tagtaccacg acgccagcgc cgcgaccacc aacaccggcg        840
cccaccatcg cgtcgcagcc cctgtccctg cgcccagagg cgtgccggcc agcggcgggg        900
ggcgcagtgc acacgagggg gctggacttc gcctgtgata tctacatctg ggcgcccttg        960
gccgggactt gtggggtcct tctcctgtca ctggttatca ccctttactg caaacggggc       1020
agaaagaaac tcctgtatat attcaaacaa ccatttatga gaccagtaca aactactcaa       1080
gaggaagatg gctgtagctg ccgatttcca gaagaagaag aaggaggatg tgaactgaga       1140
gtgaagttca gcaggagcgc agacgccccc gcgtaccagc agggccagaa ccagctctat       1200
aacgagctca atctaggacg aagagaggag tacgatgttt tggacaagag acgtggccgg       1260
gaccctgaga tggggggaaa gccgagaagg aagaaccctc aggaaggcct gtacaatgaa       1320
ctgcagaaag ataagatggc ggaggcctac agtgagattg ggatgaaagg cgagcgccgg       1380
aggggcaagg ggcacgatgg cctttaccag ggtctcagta cagccaccaa ggacacctac       1440 gacgccttc acatgcaggc cctgcccccct cgctaa                                 1476
```

```
<210> SEQ ID NO 127
<211> LENGTH: 1488
<212> TYPE: DNA
<213> ORGANISM: Artificial Sequence
<220> FEATURE:
<223> OTHER INFORMATION: Bi-VHH3 CAR (nucleic acid)

<400> SEQUENCE: 127
```

```
atggccctgc ccgtaacagc tctgctccta ccattggcac tgctgctgca tgccgccagg         60
cctgacgtgc agctggtgga gagcggtggt ggcttggtgc aggccggcgg tagcctccgc        120
ctgagctgtg ccgcgagcgg ccgcaccatc tcgagctact ccatgggctg gttccgccag        180
gcacctggca aggagcggag gtttgtcgca gccatcagtt ggtctggtgg gagtccctat        240
tacgcggact ccgtgaaggg ccgcttcacc atctcacgcg acaacgccaa gaacacggta        300
tacctgcaga tgaactccct gaagcctgag gacaccgccg tgtactactg tgccgccccc        360
attgagtacg ctccagctg tctgcggac tattggggcc aaggcaccca ggtcaccgtc        420
agctccggcg gcgtggctc tggcggaggg gggtcccagg ttcatctgat ggagtcgggt        480
ggggggtccg tgcaggccgg tggatctctg cgcttgtcat gccaggcttc tgcctacatc        540
cgcgtgttct acctgatggg atggttcaga caggctccgg aaaagagcg cgaggaggtg        600 gctcgagtga ccgcggacgg cttcaccaac cacgccgctt ccgttaaggg ccgtttttacg        660 atttccaagg acaacgcgaa aaacactctt taccttcaga tggattctat gaagagcgaa        720
gatactgctg tctactactg cgccgctggc cgtacctgga actccggatt cgaatattgg        780
ggccagggca cccaggtgac cgtgtcctcg actagtacca cgacgccagc cgcgcgacca        840
ccaacaccgg cgcccaccat cgcgtcgcag cccctgtccc tgcgcccaga ggcgtgccgg        900
ccagcggcgg ggggcgcagt gcacacgagg gggctggact cgcctgtga tatctacatc        960 tgggcgccct tggccgggac ttgtggggtc cttctcctgt cactggttat caccctttac       1020
tgcaaacggg gcagaaagaa actcctgtat atattcaaac aaccatttat gagaccagta       1080
```

-continued

```
caaactactc aagaggaaga tggctgtagc tgccgatttc cagaagaaga agaaggagga    1140
tgtgaactga gagtgaagtt cagcaggagc gcagacgccc ccgcgtacca gcagggccag    1200
aaccagctct ataacgagct caatctagga cgaagagagg agtacgatgt tttggacaag    1260
agacgtggcc gggaccctga gatggggga aagccgagaa ggaagaaccc tcaggaaggc    1320
ctgtacaatg aactgcagaa agataagatg gcggaggcct acagtgagat tgggatgaaa    1380
ggcgagcgcc ggagggggcaa ggggcacgat ggcctttacc agggtctcag tacagccacc    1440
aaggacacct acgacgccct tcacatgcag gccctgcccc tcgctaa                  1488
```

<210> SEQ ID NO 128
<211> LENGTH: 1473
<212> TYPE: DNA
<213> ORGANISM: Artificial Sequence
<220> FEATURE:
<223> OTHER INFORMATION: Bi-VHH4 (G4S)1 CAR (nucleic acid)

<400> SEQUENCE: 128

```
atggccctgc ccgtaacagc tctgctccta ccattggcac tgctgctgca tgccgccagg     60
cctgaagtgc agctggtgga gagcggaggc ggcctcgttc aggctggcgg ctcgctccgc    120
ctgtcttgtg ccgcttctgg ccgcaccttc tcgagctaca acatgggctg gttcagacag    180
gccccaggca aagagcgcga gttcgtcgcg gtggtcgact ggtctggtgg tagcccctat    240
tacgcggaca gtgtaaaagg tcgcttcacc atctcgcggg acaacggtaa gaacaccgtg    300
tacctgcaga tgaactccct caagcctgag gacaccgccg tctactactg cgctggtcgt    360
gtgcagtacg gcagcagttg gtccggtgat tattggggac agggggacccca ggtgaccgtg    420 tcctctgggg gggaggcag ccaggtcaag ctggtggagt ccggcggagg ctcagttcag    480
gccggtggct ctttgcgtct gtcctgtcaa gcgagcgcct catccgcgt gttctacctg    540 atggggtggt tccgccaggc acccgggaag gagcgggagg aggtggctcg cgtcaacgcg    600
gacggcatca ccaaccacgc cgcttccgtg aagggcaggt ttacgatttc caaggacaac    660
gccaagaata ctctttacct tcagatggat ccctgaagc cggaagatac tgcagtgtac    720
tactgcgccg ccggccgcac ctggaactcc ggcttcgagt actggggcca gggcacccag    780
gtcaccgtgt cctcgactag taccacgacg ccagcgccgc gaccaccaac accggcgccc    840
accatcgcgt cgcagcccct gtccctgcgc ccagaggcgt gccggccagc ggcggggggc    900
gcagtgcaca cgagggggct ggacttcgcc tgtgatatct acatctgggc gcccttggcc    960
gggacttgtg gggtccttct cctgtcactg gttatcaccc tttactgcaa acggggcaga   1020
aagaaactcc tgtatatatt caaacaacca tttatgagac cagtacaaac tactcaagag   1080
gaagatggct gtagctgccg atttccagaa gaagaagaag gaggatgtga actgagagtg   1140
aagttcagca ggagcgcaga cgcccccgcg taccagcagg ccagaaccca gctctataac   1200
gagctcaatc taggacgaag agaggagtac gatgtttgg acaagagacg tggccgggac   1260
cctgagatgg ggggaaagcc gagaaggaag aaccctcagg aaggcctgta caatgaactg   1320
cagaaagata agatggcgga ggcctacagt gagattggga tgaaaggcga gcgccggagg   1380 ggcaagggc acgatggcct ttaccagggt ctcagtacag ccaccaagga cacctacgac   1440
gcccttcaca tgcaggccct gccccctcgc taa                                1473
```

<210> SEQ ID NO 129
<211> LENGTH: 1488
<212> TYPE: DNA
<213> ORGANISM: Artificial Sequence
<220> FEATURE:
<223> OTHER INFORMATION: Bi-VHH4 (G4S)2 CAR (nucleic acid)

<400> SEQUENCE: 129

```
atggccctgc ccgtaacagc tctgctccta ccattggcac tgctgctgca tgccgccagg      60
cctgaagtgc agctggtgga gagcggaggc ggcctcgtgc aggcgggagg ctcgctgcgc     120
ctgagctgcg ccgcatcagg tcgtacgttc agcagctaca acatggggtg gttcagacag     180
gccccggca aagagaggga gttcgtcgcg gtggtggatt ggtctggtgg gtcccccctat     240
tacgcggact ccgttaaggg tcgttttacc atctcgcggg acaacggtaa aaacactgtc     300
tacctccaga tgaactccct gaagccggaa gacactgcag tgtactactg tgctgggcgg     360
gtgcagtacg gctccagttg gtctggggat tattggggcc aggggaccca ggtcaccgtg     420
tcgtctggcg gtggaggttc cggaggcggc ggttcccagg taaagctggt ggagagcggc     480
gggggcagcg tacaggccgg cggctccctg cgcctgtcgt gccaggcctc cgcctacatt     540
cgagtgttct acctgatggg ctggttccgc caggccccag gcaaggagcg cgaggaggtg     600
gctcgcgtca cgcggacggg catcaccaac cacgccgctt ccgtgaaggg ccgcttcacc     660
atctccaagg acaatgccaa gaacacgctg tacctgcaga tggattctct taagcctgag     720
gacaccgccg tgtactactg tgcggcgggc cgcacctgga actctggctt tgagtattgg     780
ggtcagggga cccaggttac agtgtccagt actagtacca cgacgccagc cgcgcgacca     840
ccaacaccgg cgcccaccat cgcgtcgcag cccctgtccc tgcgcccaga ggcgtgccgg     900
ccagcggcgg ggggcgcagt gcacacgagg gggctggact cgcctgtga tatctacatc     960
tgggcgccct tggccgggac ttgtgggtc cttctcctgt cactggttat cacccttac    1020
tgcaaacggg gcagaaagaa actcctgtat atattcaaac aaccatttat gagaccagta    1080
caaactactc aagaggaaga tggctgtagc tgccgatttc cagaagaaga agaaggagga    1140
tgtgaactga gagtgaagtt cagcaggagc gcagacgccc ccgcgtacca gcagggccag    1200
aaccagctct ataacgagct caatctagga cgaagagagg agtacgatgt tttggacaag    1260
agacgtggcc gggaccctga gatggggggga aagccgagaa ggaagaaccc tcaggaaggc    1320
ctgtacaatg aactgcagaa agataagatg gcggaggcct acagtgagat tgggatgaaa    1380
ggcgagcgcc ggagggggcaa ggggcacgat ggcctttacc agggtctcag tacagccacc    1440
aaggacacct acgacgccct tcacatgcag gccctgcccc ctcgctaa               1488
```

<210> SEQ ID NO 130
<211> LENGTH: 1503
<212> TYPE: DNA
<213> ORGANISM: Artificial Sequence
<220> FEATURE:
<223> OTHER INFORMATION: Bi-VHH4 (G4S)3 CAR (nucleic acid)

<400> SEQUENCE: 130

```
atggccctgc ccgtaacagc tctgctccta ccattggcac tgctgctgca tgccgccagg      60
cctgaagtgc agctggtgga gagcggtggg ggcttggtgc aagctggtgg atcgctgcga     120
ctctcgtgcg ccgcgtccgg ccgcacgttt tcaagctaca acatgggctg gttccgccag     180
gccccgggca aggagcgcga gttcgtcgca gtggtcgact ggtctggtgg ctctcccctat     240
tacgcggaca cgtcaaggg ccggtttact atctcccgcg acaacggcaa aaacaccgtg     300
tacctgcaga tgaactcctt aaagcccgag gacaccgctg tctattactg cgcgggacgg     360
gttcagtacg gctccagttg gtctggggac tattggggcc aggggaccca ggtgacagta     420
```

-continued

```
tctagcggcg gtggaggctc gggcggtggc ggatcgggtg gcggggggag ccaggttaag      480
ctggtggaga gtggcggggg atccgtgcag gccggcggca gccttcgtct ttcctgtcag      540
gcctccgcct acatccgcgt gttctacctg atgggctggt tcaggcaggc ccctggaaag      600
gagcgcgagg aggtggcgcg tgtcaacgcg gacggcatca ccaaccatgc cgcatccgtg      660
aagggtcgct tcaccatttc caaggacaac gccaaaaata cgctgtactt gcagatggat      720
tctctgaagc ctgaagatac tgccgtgtac tactgtgccg ctgggcgcac ctggaactcc      780
ggcttcgagt actgggccca gggtacccag gtgaccgtga gctctactag taccacgacg      840
ccagcgccgc gaccaccaac accgcgcccc accatcgcgt cgcagcccct gtccctgcgc      900
ccagaggcgt gccggccagc ggcggggggc gcagtgcaca cgaggggggct ggacttcgcc      960 tgtgatatct acatctgggc gcccttggcc gggacttgtg gggtccttct cctgtcactg     1020
gttatcaccc tttactgcaa acgggggcaga aagaaactcc tgtatatatt caaacaacca     1080
tttatgagac cagtacaaac tactcaagag gaagatggct gtagctgccg atttccagaa     1140
gaagaagaag gaggatgtga actgagagtg aagttcagca ggagcgcaga cgcccccgcg     1200
taccagcagg gccagaacca gctctataac gagctcaatc taggacgaag agaggagtac     1260
gatgttttgg acaagagacg tggccgggac cctgagatgg ggggaaagcc gagaaggaag     1320
aaccctcagg aaggcctgta caatgaactg cagaaagata agatggcgga ggcctacagt     1380
gagattggga tgaaaggcga gcgccggagg ggcaagggggc acgatggcct ttaccagggt     1440
ctcagtacag ccaccaagga cacctacgac gcccttcaca tgcaggccct gcccctcgc      1500 taa                                                                    1503
```

```
<210> SEQ ID NO 131
<211> LENGTH: 1518
<212> TYPE: DNA
<213> ORGANISM: Artificial Sequence
<220> FEATURE:
<223> OTHER INFORMATION: Bi-VHH4 (G4S)4 CAR (nucleic acid)

<400> SEQUENCE: 131
```

```
atggccctgc ccgtaacagc tctgctccta ccattggcac tgctgctgca tgccgccagg       60
cctgaagtgc agctggtgga gagcggtggt ggcctagtac aggctggcgg gtcgctgcgc      120
ctgtcttgtg ctgcatccgg acgcacgttc tcgagctaca acatgggctg gttcagacaa      180
gccccgggca aggagcgcga gttcgtcgct gtggtcgact ggtctggcgg ctctccctat      240
tacgcggaca cgtcaaggg gaggtttacc atctcccgcg acaacggtaa aaacacggtt      300
tacttgcaga tgaactccct gaagcctgaa gacactgccg tgtactactg cgctggacgt      360
gtgcagtacg gctccagttg gtctggtgat tattgggggc aggggaccca ggtcaccgta      420
tcctccggag gcggaggcag cggaggtggc gggtccggcg gcggcggctc cggcggtggg      480
ggttcacagg tgaagctggt ggagagtgga ggtggcagcg tgcaggccgg cggctccctt      540
cggctctcgt gtcaggccag cgcctacatc cgagtgttct atctgatggg ctggttccgc      600
caggccccag gcaaagagag ggaggaggtg gcacgtgtca cgcggacgg catcaccaac      660 catgccgctt ccgttaaggg gcgcttcacc atttccaagg acaacgccaa gaatacactg      720
tacctgcaga tggattctct caagccggag gacaccgccg tgtactactg cgcggcgggc      780
cgcacctgga atagcggctt tgagtactgg ggccagggta cccaggtcac cgtgtcctcg      840
actagtacca cgacgccagc gccgcgacca ccaacaccgg cgccaccat cgcgtcgcag      900 cccctgtccc tgcgcccaga ggcgtgccgg ccagcggcgg ggggcgcagt gcacacgagg      960
```

-continued

```
gggctggact tcgcctgtga tatctacatc tgggcgccct tggccgggac ttgtggggtc   1020
cttctcctgt cactggttat cacccttttac tgcaaacggg gcagaaagaa actcctgtat   1080
atattcaaac aaccatttat gagaccagta caaactactc aagaggaaga tggctgtagc   1140
tgccgatttc cagaagaaga agaaggagga tgtgaactga gagtgaagtt cagcaggagc   1200
gcagacgccc ccgcgtacca gcagggccag aaccagctct ataacgagct caatctagga   1260
cgaagagagg agtacgatgt tttggacaag agacgtggcc gggaccctga gatgggggga   1320
aagccgagaa ggaagaaccc tcaggaaggc ctgtacaatg aactgcagaa agataagatg   1380
gcggaggcct acagtgagat tgggatgaaa ggcgagcgcc ggagggggcaa ggggcacgat   1440 ggcctttacc agggtctcag tacagccacc aaggacacct acgacgccct tcacatgcag   1500
gccctgcccc ctcgctaa                                                  1518
```

```
<210> SEQ ID NO 132
<211> LENGTH: 1533
<212> TYPE: DNA
<213> ORGANISM: Artificial Sequence
<220> FEATURE:
<223> OTHER INFORMATION: Bi-VHH4 (G4S)5 CAR (nucleic acid)

<400> SEQUENCE: 132
```

```
atggccctgc ccgtaacagc tctgctccta ccattggcac tgctgctgca tgccgccagg     60
cctgaagtcc agctggtgga gagtggcggg gggttagttc aagctggcgg ctcccttcgt    120
ctttcatgcg ctgcgtccgg tcgtactttt tcaagctaca acatgggctg gttccgccag    180
gcccccggga aggagcgcga gttcgtcgcc gtggtggact ggtctggcgg cagcccctat    240
tacgcggaca cgcgttaaagg ccgcttcacc atttctcggg acaatggcaa aaacacggtg    300
tacctgcaga tgaactccct caagccggaa gatacagcag tctactactg cgctggccga    360
gtgcagtacg gctccagttg gtctggagat tattggggtc agggaaccca ggtcaccgtg    420
tccagcgggg gtggaggctc gggggggaggc ggatcgggcg gcggtgggtc tggcggaggc    480
ggttctggcg ggggggttc ccaggtgaag ctggtggaga gcggcggtgg ctctgtgcag    540
gccggtggct ccttgcgcct gagctgtcag gctagcgcct acatccgcgt gttctacctg    600
atggggtggt tcagacaggc ccctggcaag gagagggagg aggtggctcg cgtcaacgcg    660
gacggtatca ccaaccacgc cgcttcggta aagggacggt ttaccatctc caaggacaac    720
gccaagaaca cgctgtacct ccagatggat tctctgaagc ctgaggacac cgcagtgtac    780
tattgtgctg caggccgcac ctggaactcc ggcttcgagt actggggcca gggcacccag    840
gtcaccgtgt cctccactag taccacgacg ccagcgccgc gaccaccaac accggcgccc    900
accatcgcgt cgcagcccct gtccctgcgc ccagaggcgt gccggccagc ggcggggggc    960
gcagtgcaca cgagggggct ggacttcgcc tgtgatatct acatctgggc gcccttggcc   1020
gggacttgtg ggtccttct cctgtcactg gttatcaccc tttactgcaa acggggcaga   1080
aagaaactcc tgtatatatt caaacaacca tttatgagac cagtacaaac tactcaagag   1140
gaagatggct gtagctgccg atttccagaa gaagaagaag aggatgtga actgagagtg   1200 aagttcagca ggagcgcaga cgcccccgcg taccagcagg ccagaacca gctctataac   1260 gagctcaatc taggacgaag agaggagtac gatgttttgg acaagagacg tggccgggac   1320
cctgagatgg ggggaaagcc gagaaggaag aaccctcagg aaggcctgta caatgaactg   1380
cagaaagata agatggcgga ggcctacagt gagattggga tgaaaggcga gcgccggagg   1440
```

-continued

```
ggcaaggggc acgatggcct ttaccagggt ctcagtacag ccaccaagga cacctacgac    1500
gcccttcaca tgcaggccct gcccctcgc taa                                  1533

<210> SEQ ID NO 133
<211> LENGTH: 1860
<212> TYPE: DNA
<213> ORGANISM: Artificial Sequence
<220> FEATURE:
<223> OTHER INFORMATION: Tri-VHH CAR (nucleic acid)

<400> SEQUENCE: 133
atggccctgc ccgtaacagc tctgctccta ccattggcac tgctgctgca tgccgccagg      60
cctgaggtgc agctggtgga gagcggaggt gggctggtgc aggccggtgg ctcgctgcgc     120
ctgtcatgcg cagcctctgg ccgcaccttc tctagctaca acatgggctg gttcagacaa     180
gcgcctggca aggagaggga gttcgtcgca gtggtcgatt ggtctggagg ctcccctttat    240 tacgcggact cggtaaaggg ccgttttacg atttcccgcg acaacggcaa aaacaccgtg     300
tacttgcaga tgaactccct caagcccgaa gacaccgccg tctactactg tgccggccga     360
gtgcagtacg gctcctcttg gtctggtgat tattggggcc agggcaccca ggtgaccgtc     420
tcgtcggggg ggggtgggtc cggaggcggg ggttctcaaa ttcagttggt ggagagtgga     480
ggcggcctcg ttcagccggg cggctcctta cgcctttcat gcgcagcttc cggttttacg     540
ttctccaact accctatgac ctggctccgc caggcccccg gaagggact ggagagcgtg      600 agtgacatca ccagcggtgg ggacaggccc tattacgcgg acagcgtgaa gggccgcttc     660
accatctctc gtgacaatgc taagaatatg ctgtacctgg atgaacag cctgaagaca      720 gaggacaccg cggtgtacta ctgtgctacc tgggaccgca ctctgaccgg tcagggcacc     780
caggttacag tcagctccgg aggcggcggc tccggcgggg gtggctccca ggtccacctg     840
atggagagcg gcggaggctc agtgcaggct ggggttctc ttcgcctgag ctgtcaggcc      900
agtgcctaca tccgcgtgtt ctacctgatg gggtggttcc gccaggcgcc aggtaaagag     960
cgcgaggagg tggctcgggt aacagcggac ggcttcacca accatgccgc tagcgtgaaa    1020
ggccgtttta ctatctccaa ggacaacgcc aagaacacgc tgtatctgca gatggattct    1080
atgaagtccg aagatactgc cgtgtactac tgcgctgctg gccgcacctg gaactccggc    1140
ttcgagtact ggggccaggg gacccaggtc accgtgtcgt ccactagtac cacgacgcca    1200
gcgccgcgac caccaacacc ggcgcccacc atcgcgtcgc agcccctgtc cctgcgccca    1260
gaggcgtgcc ggcagcggc ggggggcgca gtgcacacga gggggctgga cttcgcctgt     1320
gatatctaca tctgggcgcc cttggccggg acttgtgggg tccttctcct gtcactggtt    1380
atcacccttt actgcaaacg gggcagaaag aaactcctgt atatattcaa acaaccattt    1440
atgagaccag tacaaactac tcaagaggaa gatggctgta gctgccgatt ccagaagaa     1500 gaagaaggag gatgtgaact gagagtgaag ttcagcagga gcgcagacgc ccccgcgtac    1560
cagcagggcc agaaccagct ctataacgag ctcaatctag gacgaagaga ggagtacgat    1620
gttttggaca gagacgtgg ccgggaccct gagatggggg gaaagccgag aaggaagaac      1680
cctcaggaag gcctgtacaa tgaactgcag aaagataaga tggcggaggc ctacagtgag    1740
attgggatga aaggcgagcg ccggaggggc aaggggcacg atggccttta ccagggtctc    1800
agtacagcca ccaaggacac ctacgacgcc cttcacatgc aggccctgcc cctcgctaa     1860

<210> SEQ ID NO 134
<211> LENGTH: 2
```

-continued

```
<212> TYPE: PRT
<213> ORGANISM: Artificial Sequence
<220> FEATURE:
<223> OTHER INFORMATION: Exemplary peptide linker 1
<220> FEATURE:
<221> NAME/KEY: MISC_FEATURE
<222> LOCATION: (1)..(2)
<223> OTHER INFORMATION: can be repeated n times, where n is an integer
      including, e.g., 1, 2, 3, 4, 5, and 6

<400> SEQUENCE: 134

Gly Ser
1

<210> SEQ ID NO 135
<211> LENGTH: 5
<212> TYPE: PRT
<213> ORGANISM: Artificial Sequence
<220> FEATURE:
<223> OTHER INFORMATION: Exemplary peptide linker 2
<220> FEATURE:
<221> NAME/KEY: MISC_FEATURE
<222> LOCATION: (1)..(5)
<223> OTHER INFORMATION: can be repeated n times, where n is an integer
      including, e.g., 1, 2, 3, 4, 5, and 6

<400> SEQUENCE: 135

Gly Ser Gly Gly Ser
1               5

<210> SEQ ID NO 136
<211> LENGTH: 4
<212> TYPE: PRT
<213> ORGANISM: Artificial Sequence
<220> FEATURE:
<223> OTHER INFORMATION: Exemplary peptide linker 3
<220> FEATURE:
<221> NAME/KEY: MISC_FEATURE
<222> LOCATION: (1)..(4)
<223> OTHER INFORMATION: can be repeated n times, where n is an integer
      including, e.g., 1, 2, 3, 4, 5, and 6

<400> SEQUENCE: 136

Gly Gly Gly Ser
1

<210> SEQ ID NO 137
<211> LENGTH: 34
<212> TYPE: PRT
<213> ORGANISM: Artificial Sequence
<220> FEATURE:
<223> OTHER INFORMATION: Exemplary peptide linker 4

<400> SEQUENCE: 137

Gly Gly Gly Gly Ser Gly Gly Gly Gly Ser Gly Gly Gly Gly Gly Gly
1               5                   10                  15

Ser Gly Ser Gly Gly Gly Gly Ser Gly Gly Gly Gly Ser Gly Gly Gly
            20                  25                  30

Gly Ser

<210> SEQ ID NO 138
<211> LENGTH: 5
<212> TYPE: PRT
<213> ORGANISM: Artificial Sequence
<220> FEATURE:
<223> OTHER INFORMATION: Exemplary peptide linker 5
<220> FEATURE:
<221> NAME/KEY: MISC_FEATURE
<222> LOCATION: (1)..(5)
```

<223> OTHER INFORMATION: can be repeated n times, where n is an integer
      including, e.g., 1, 2, 3, 4, 5, and 6

<400> SEQUENCE: 138

Gly Gly Gly Gly Ser
1               5

<210> SEQ ID NO 139
<211> LENGTH: 5
<212> TYPE: PRT
<213> ORGANISM: Artificial Sequence
<220> FEATURE:
<223> OTHER INFORMATION: Exemplary peptide linker 6

<400> SEQUENCE: 139

Asp Gly Gly Gly Ser
1               5

<210> SEQ ID NO 140
<211> LENGTH: 5
<212> TYPE: PRT
<213> ORGANISM: Artificial Sequence
<220> FEATURE:
<223> OTHER INFORMATION: Exemplary peptide linker 7

<400> SEQUENCE: 140

Thr Gly Glu Lys Pro
1               5

<210> SEQ ID NO 141
<211> LENGTH: 4
<212> TYPE: PRT
<213> ORGANISM: Artificial Sequence
<220> FEATURE:
<223> OTHER INFORMATION: Exemplary peptide linker 8

<400> SEQUENCE: 141

Gly Gly Arg Arg
1

<210> SEQ ID NO 142
<211> LENGTH: 24
<212> TYPE: PRT
<213> ORGANISM: Artificial Sequence
<220> FEATURE:
<223> OTHER INFORMATION: Exemplary peptide linker 9

<400> SEQUENCE: 142

Gly Gly Gly Gly Ser Gly Gly Gly Gly Ser Gly Gly Gly Gly Gly Gly
1               5                   10                  15

Ser Gly Ser Gly Gly Gly Gly Ser
            20

<210> SEQ ID NO 143
<211> LENGTH: 14
<212> TYPE: PRT
<213> ORGANISM: Artificial Sequence
<220> FEATURE:
<223> OTHER INFORMATION: Exemplary peptide linker 10

<400> SEQUENCE: 143

Glu Gly Lys Ser Ser Gly Ser Gly Ser Glu Ser Lys Val Asp
1               5                   10

<210> SEQ ID NO 144
<211> LENGTH: 16

```
<212> TYPE: PRT
<213> ORGANISM: Artificial Sequence
<220> FEATURE:
<223> OTHER INFORMATION: Exemplary peptide linker 11

<400> SEQUENCE: 144

Lys Glu Ser Gly Ser Val Ser Ser Glu Gln Leu Ala Gln Phe Arg Ser
1               5                   10                  15

<210> SEQ ID NO 145
<211> LENGTH: 8
<212> TYPE: PRT
<213> ORGANISM: Artificial Sequence
<220> FEATURE:
<223> OTHER INFORMATION: Exemplary peptide linker 12

<400> SEQUENCE: 145

Gly Gly Arg Arg Gly Gly Gly Ser
1               5

<210> SEQ ID NO 146
<211> LENGTH: 9
<212> TYPE: PRT
<213> ORGANISM: Artificial Sequence
<220> FEATURE:
<223> OTHER INFORMATION: Exemplary peptide linker 13

<400> SEQUENCE: 146

Leu Arg Gln Arg Asp Gly Glu Arg Pro
1               5

<210> SEQ ID NO 147
<211> LENGTH: 12
<212> TYPE: PRT
<213> ORGANISM: Artificial Sequence
<220> FEATURE:
<223> OTHER INFORMATION: Exemplary peptide linker 14

<400> SEQUENCE: 147

Leu Arg Gln Lys Asp Gly Gly Gly Ser Glu Arg Pro
1               5                   10

<210> SEQ ID NO 148
<211> LENGTH: 16
<212> TYPE: PRT
<213> ORGANISM: Artificial Sequence
<220> FEATURE:
<223> OTHER INFORMATION: Exemplary peptide linker 15

<400> SEQUENCE: 148

Leu Arg Gln Lys Asp Gly Gly Gly Ser Gly Gly Gly Ser Glu Arg Pro
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Exemplary peptide linker 16

<400> SEQUENCE: 149

Gly Ser Thr Ser Gly Ser Gly Lys Pro Gly Ser Gly Glu Gly Ser Thr
1               5                   10                  15

<210> SEQ ID NO 150
<211> LENGTH: 14
<212> TYPE: PRT
```

```
<213> ORGANISM: Artificial Sequence
<220> FEATURE:
<223> OTHER INFORMATION: Exemplary peptide linker 17

<400> SEQUENCE: 150

Gly Ser Thr Ser Gly Ser Gly Lys Ser Ser Glu Gly Lys Gly
1               5                   10

<210> SEQ ID NO 151
<211> LENGTH: 18
<212> TYPE: PRT
<213> ORGANISM: Artificial Sequence
<220> FEATURE:
<223> OTHER INFORMATION: Exemplary peptide linker 18

<400> SEQUENCE: 151

Lys Glu Ser Gly Ser Val Ser Ser Glu Gln Leu Ala Gln Phe Arg Ser
1               5                   10                  15

Leu Asp

<210> SEQ ID NO 152
<211> LENGTH: 21
<212> TYPE: PRT
<213> ORGANISM: Artificial Sequence
<220> FEATURE:
<223> OTHER INFORMATION: Signal Peptide (CD8Alpha)

<400> SEQUENCE: 152

Met Ala Leu Pro Val Thr Ala Leu Leu Leu Pro Leu Ala Leu Leu Leu
1               5                   10                  15

His Ala Ala Arg Pro
            20

<210> SEQ ID NO 153
<211> LENGTH: 45
<212> TYPE: PRT
<213> ORGANISM: Artificial Sequence
<220> FEATURE:
<223> OTHER INFORMATION: Hinge (CD8Alpha)

<400> SEQUENCE: 153

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
            35                  40                  45

<210> SEQ ID NO 154
<211> LENGTH: 24
<212> TYPE: PRT
<213> ORGANISM: Artificial Sequence
<220> FEATURE:
<223> OTHER INFORMATION: Transmembrane domain (CD8Alpha)

<400> SEQUENCE: 154

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 155
<211> LENGTH: 42
<212> TYPE: PRT
```

<213> ORGANISM: Artificial Sequence
<220> FEATURE:
<223> OTHER INFORMATION: Co-stimulatory signaling domain (CD137)

<400> SEQUENCE: 155

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 156
<211> LENGTH: 112
<212> TYPE: PRT
<213> ORGANISM: Artificial Sequence
<220> FEATURE:
<223> OTHER INFORMATION: Primary intracellular signaling domain
      (CD3Zeta)

<400> SEQUENCE: 156

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 157
<211> LENGTH: 243
<212> TYPE: PRT
<213> ORGANISM: Artificial Sequence
<220> FEATURE:
<223> OTHER INFORMATION: Leu16 scFv

<400> SEQUENCE: 157

Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

Asp Trp Tyr Gln Lys Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Gly Gly Thr Lys Leu Glu Ile Lys Gly Gly Gly Gly Ser Gly
            100                 105                 110

Gly Gly Gly Ser Gly Gly Gly Gly Ser Glu Val Gln Leu Gln Gln Ser

```
            115                 120                 125

Gly Ala Glu Leu Val Lys Pro Gly Ala Ser Val Lys Met Ser Cys Lys
    130                 135                 140

Ala Ser Gly Tyr Thr Phe Thr Ser Tyr Asn Met His Trp Val Lys Gln
145                 150                 155                 160

Thr Pro Gly Gln Gly Leu Glu Trp Ile Gly Ala Ile Tyr Pro Gly Asn
                165                 170                 175

Gly Asp Thr Ser Tyr Asn Gln Lys Phe Lys Gly Lys Ala Thr Leu Thr
                180                 185                 190

Ala Asp Lys Ser Ser Ser Thr Ala Tyr Met Gln Leu Ser Ser Leu Thr
                195                 200                 205

Ser Glu Asp Ser Ala Asp Tyr Tyr Cys Ala Arg Ser Asn Tyr Tyr Gly
    210                 215                 220

Ser Ser Tyr Trp Phe Phe Asp Val Trp Gly Ala Gly Thr Thr Val Thr
225                 230                 235                 240

Val Ser Ser

<210> SEQ ID NO 158
<211> LENGTH: 242
<212> TYPE: PRT
<213> ORGANISM: Artificial Sequence
<220> FEATURE:
<223> OTHER INFORMATION: Rituximab scFv

<400> SEQUENCE: 158

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Gly Gly Gly Gly Ser Gly
            100                 105                 110

Gly Gly Gly Ser Gly Gly Gly Gly Ser Gln Val Gln Leu Gln Gln Pro
        115                 120                 125

Gly Ala Glu Leu Val Lys Pro Gly Ala Ser Val Lys Met Ser Cys Lys
    130                 135                 140

Ala Ser Gly Tyr Thr Phe Thr Ser Tyr Asn Met His Trp Val Lys Gln
145                 150                 155                 160

Thr Pro Gly Arg Gly Leu Glu Trp Ile Gly Ala Ile Tyr Pro Gly Asn
                165                 170                 175

Gly Asp Thr Ser Tyr Asn Gln Lys Phe Lys Gly Lys Ala Thr Leu Thr
                180                 185                 190

Ala Asp Lys Ser Ser Ser Thr Ala Tyr Met Gln Leu Ser Ser Leu Thr
                195                 200                 205

Ser Glu Asp Ser Ala Val Tyr Tyr Cys Ala Arg Ser Thr Tyr Tyr Gly
    210                 215                 220

Gly Asp Trp Tyr Phe Asn Val Trp Gly Ala Gly Thr Thr Val Thr Val
225                 230                 235                 240
```

-continued

Ser Ala

<210> SEQ ID NO 159
<211> LENGTH: 227
<212> TYPE: PRT
<213> ORGANISM: Artificial Sequence
<220> FEATURE:
<223> OTHER INFORMATION: human IgG1 Fc fragment sequence

<400> SEQUENCE: 159

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 160
<211> LENGTH: 9
<212> TYPE: DNA
<213> ORGANISM: Artificial Sequence
<220> FEATURE:
<223> OTHER INFORMATION: Kozak sequence

<400> SEQUENCE: 160 gccgccacc                                                                                              9

<210> SEQ ID NO 161
<211> LENGTH: 6
<212> TYPE: DNA
<213> ORGANISM: Artificial Sequence
<220> FEATURE:
<223> OTHER INFORMATION: EcoRI restriction site

<400> SEQUENCE: 161 gaattc                                                                    6

<210> SEQ ID NO 162
<211> LENGTH: 6
<212> TYPE: DNA
<213> ORGANISM: Artificial Sequence
<220> FEATURE:
<223> OTHER INFORMATION: SpeI restriction site

<400> SEQUENCE: 162 actagt                                                                    6

<210> SEQ ID NO 163
<211> LENGTH: 225
<212> TYPE: PRT
<213> ORGANISM: Artificial Sequence
<220> FEATURE:
<223> OTHER INFORMATION: Leu16 VH-CH1

<400> SEQUENCE: 163

Glu Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Asp Tyr Tyr Cys
                85                  90                  95

Ala Arg Ser Asn Tyr Tyr Gly Ser Ser Tyr Trp Phe Phe Asp Val Trp
                100                 105                 110

Gly Ala Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
    210                 215                 220

Cys
225

<210> SEQ ID NO 164
<211> LENGTH: 213
<212> TYPE: PRT
<213> ORGANISM: Artificial Sequence
<220> FEATURE:
<223> OTHER INFORMATION: Leu16 VL-CL

<400> SEQUENCE: 164

-continued

```
Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
            20                  25                  30

Asp Trp Tyr Gln Lys Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
            195                 200                 205

Asn Arg Gly Glu Cys
    210
```

```
<210> SEQ ID NO 165
<211> LENGTH: 8
<212> TYPE: PRT
<213> ORGANISM: Artificial Sequence
<220> FEATURE:
<223> OTHER INFORMATION: CDR1 (Kabat) of VHH-623

<400> SEQUENCE: 165

Gly Arg Thr Phe Ser Asn Tyr Ala
1               5
```

```
<210> SEQ ID NO 166
<211> LENGTH: 17
<212> TYPE: PRT
<213> ORGANISM: Artificial Sequence
<220> FEATURE:
<223> OTHER INFORMATION: CDR2 (Kabat) of VHH-623

<400> SEQUENCE: 166

Ala Ile Ser Trp Ser Gly Gly Ser Pro Tyr Tyr Ala Asp Ala Val Arg
1               5                   10                  15

Gly
```

```
<210> SEQ ID NO 167
<211> LENGTH: 12
<212> TYPE: PRT
<213> ORGANISM: Artificial Sequence
<220> FEATURE:
<223> OTHER INFORMATION: CDR3 (Kabat) of VHH-623
```

```
<400> SEQUENCE: 167

Gly Ile Tyr Tyr Gly Ser Asn Trp Ser Ser Glu Asn
1               5                   10

<210> SEQ ID NO 168
<211> LENGTH: 10
<212> TYPE: PRT
<213> ORGANISM: Artificial Sequence
<220> FEATURE:
<223> OTHER INFORMATION: CDR1 (IMGT) of VHH-623

<400> SEQUENCE: 168

Gly Arg Thr Phe Ser Asn Tyr Ala Ala Gly
1               5                   10

<210> SEQ ID NO 169
<211> LENGTH: 8
<212> TYPE: PRT
<213> ORGANISM: Artificial Sequence
<220> FEATURE:
<223> OTHER INFORMATION: CDR2 (IMGT) of VHH-623

<400> SEQUENCE: 169

Ile Ser Trp Ser Gly Gly Ser Pro
1               5

<210> SEQ ID NO 170
<211> LENGTH: 14
<212> TYPE: PRT
<213> ORGANISM: Artificial Sequence
<220> FEATURE:
<223> OTHER INFORMATION: CDR3 (IMGT) of VHH-623

<400> SEQUENCE: 170

Ala Ala Gly Ile Tyr Tyr Gly Ser Asn Trp Ser Ser Glu Asn
1               5                   10

<210> SEQ ID NO 171
<211> LENGTH: 10
<212> TYPE: PRT
<213> ORGANISM: Artificial Sequence
<220> FEATURE:
<223> OTHER INFORMATION: CDR1 (Kabat) of VHH-640

<400> SEQUENCE: 171

Gly Tyr Thr Trp Gln Thr Tyr Cys Met Ala
1               5                   10

<210> SEQ ID NO 172
<211> LENGTH: 16
<212> TYPE: PRT
<213> ORGANISM: Artificial Sequence
<220> FEATURE:
<223> OTHER INFORMATION: CDR2 (Kabat) of VHH-640

<400> SEQUENCE: 172

Val Ala Thr Gly Ser Arg Thr Thr Ser Tyr Ala Asp Ser Val Lys Gly
1               5                   10                  15

<210> SEQ ID NO 173
<211> LENGTH: 17
<212> TYPE: PRT
<213> ORGANISM: Artificial Sequence
<220> FEATURE:
<223> OTHER INFORMATION: CDR3 (Kabat) of VHH-640

<400> SEQUENCE: 173
```

-continued

Asp Pro Arg Arg Tyr Gly Ser Cys Pro Leu Ser Ala Ala Asn Phe Asn
1               5                   10                  15

Asn

<210> SEQ ID NO 174
<211> LENGTH: 8
<212> TYPE: PRT
<213> ORGANISM: Artificial Sequence
<220> FEATURE:
<223> OTHER INFORMATION: CDR1 (IMGT) of VHH-640

<400> SEQUENCE: 174

Gly Tyr Thr Trp Gln Thr Tyr Cys
1               5

<210> SEQ ID NO 175
<211> LENGTH: 8
<212> TYPE: PRT
<213> ORGANISM: Artificial Sequence
<220> FEATURE:
<223> OTHER INFORMATION: CDR2 (IMGT) of VHH-640

<400> SEQUENCE: 175

Val Ala Thr Gly Ser Arg Thr Thr
1               5

<210> SEQ ID NO 176
<211> LENGTH: 19
<212> TYPE: PRT
<213> ORGANISM: Artificial Sequence
<220> FEATURE:
<223> OTHER INFORMATION: CDR3 (IMGT) of VHH-640

<400> SEQUENCE: 176

Ala Ala Asp Pro Arg Arg Tyr Gly Ser Cys Pro Leu Ser Ala Ala Asn
1               5                   10                  15

Phe Asn Asn

<210> SEQ ID NO 177
<211> LENGTH: 10
<212> TYPE: PRT
<213> ORGANISM: Artificial Sequence
<220> FEATURE:
<223> OTHER INFORMATION: CDR1 (Kabat) of VHH-657

<400> SEQUENCE: 177

Ala Asn Ile Arg Val Phe Tyr Leu Met Gly
1               5                   10

<210> SEQ ID NO 178
<211> LENGTH: 16
<212> TYPE: PRT
<213> ORGANISM: Artificial Sequence
<220> FEATURE:
<223> OTHER INFORMATION: CDR2 (Kabat) of VHH-657

<400> SEQUENCE: 178

Arg Val Asn Ala Asp Gly Ile Thr Asn His Ala Ala Ser Val Lys Gly
1               5                   10                  15

<210> SEQ ID NO 179
<211> LENGTH: 10
<212> TYPE: PRT
<213> ORGANISM: Artificial Sequence
<220> FEATURE:

<223> OTHER INFORMATION: CDR3 (Kabat) of VHH-657

<400> SEQUENCE: 179

Gly Arg Thr Trp Asn Ser Gly Phe Glu Tyr
1               5                   10

<210> SEQ ID NO 180
<211> LENGTH: 8
<212> TYPE: PRT
<213> ORGANISM: Artificial Sequence
<220> FEATURE:
<223> OTHER INFORMATION: CDR1 (IMGT) of VHH-657

<400> SEQUENCE: 180

Ala Asn Ile Arg Val Phe Tyr Leu
1               5

<210> SEQ ID NO 181
<211> LENGTH: 7
<212> TYPE: PRT
<213> ORGANISM: Artificial Sequence
<220> FEATURE:
<223> OTHER INFORMATION: CDR2 (IMGT) of VHH-657

<400> SEQUENCE: 181

Val Asn Ala Asp Gly Ile Thr
1               5

<210> SEQ ID NO 182
<211> LENGTH: 12
<212> TYPE: PRT
<213> ORGANISM: Artificial Sequence
<220> FEATURE:
<223> OTHER INFORMATION: CDR3 (IMGT) of VHH-657

<400> SEQUENCE: 182

Ala Thr Gly Arg Thr Trp Asn Ser Gly Phe Glu Tyr
1               5                   10

<210> SEQ ID NO 183
<211> LENGTH: 121
<212> TYPE: PRT
<213> ORGANISM: Artificial Sequence
<220> FEATURE:
<223> OTHER INFORMATION: VHH-623 (amino acid)

<400> SEQUENCE: 183

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Ala Gly Trp Phe Arg Gln Ala Pro Gly Lys Glu Arg Glu Phe Val
        35                  40                  45

Ala Ala Ile Ser Trp Ser Gly Gly Ser Pro Tyr Tyr Ala Asp Ala Val
    50                  55                  60

Arg Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Ile Tyr Tyr Gly Ser Asn Trp Ser Ser Glu Asn Trp Gly
            100                 105                 110

Gln Gly Thr Gln Val Thr Val Ser Ser
            115                 120

```
<210> SEQ ID NO 184
<211> LENGTH: 125
<212> TYPE: PRT
<213> ORGANISM: Artificial Sequence
<220> FEATURE:
<223> OTHER INFORMATION: VHH-640 (amino acid)

<400> SEQUENCE: 184

Gln Val Lys Leu Val Glu Ser Gly Gly Gly Ser Val Gln Ala Gly Gly
1               5                   10                  15

Ser Leu Arg Leu Ser Cys Ala Ala Ser Gly Tyr Thr Trp Gln Thr Tyr
            20                  25                  30

Cys Met Ala Trp Phe Arg Gln Ala Pro Gly Lys Glu Arg Glu Gly Val
        35                  40                  45

Ala Val Ala Thr Gly Ser Arg Thr Thr Ser Tyr Ala Asp Ser Val Lys
    50                  55                  60

Gly Arg Phe Thr Ile Ser Lys Asp Tyr Ala Lys Asn Thr Leu Tyr Leu
65                  70                  75                  80

Gln Met Ser Ser Leu Glu Pro Glu Asp Thr Ala Met Tyr Tyr Cys Ala
                85                  90                  95

Ala Asp Pro Arg Arg Tyr Gly Ser Cys Pro Leu Ser Ala Ala Asn Phe
            100                 105                 110

Asn Asn Trp Gly Gln Gly Thr Gln Val Thr Val Ser Ser
            115                 120                 125

<210> SEQ ID NO 185
<211> LENGTH: 118
<212> TYPE: PRT
<213> ORGANISM: Artificial Sequence
<220> FEATURE:
<223> OTHER INFORMATION: VHH-657 (amino acid)

<400> SEQUENCE: 185

Gln Val Gln Leu Val Glu Ser Gly Gly Gly Ser Ala Gln Ala Gly Gly
1               5                   10                  15

Ser Leu Arg Leu Ser Cys Gln Ala Ser Ala Asn Ile Arg Val Phe Tyr
            20                  25                  30

Leu Met Gly Trp Phe Arg Gln Ala Pro Gly Lys Glu Arg Glu Glu Val
        35                  40                  45

Ala Arg Val Asn Ala Asp Gly Ile Thr Asn His Ala Ala Ser Val Lys
    50                  55                  60

Gly Arg Phe Thr Ile Ser Glu Asp Ser Pro Lys Asn Thr Leu Tyr Leu
65                  70                  75                  80

Gln Met Asp Ser Leu Lys Pro Glu Asp Thr Ala Val Tyr Tyr Cys Ala
                85                  90                  95

Thr Gly Arg Thr Trp Asn Ser Gly Phe Glu Tyr Trp Gly Gln Gly Thr
            100                 105                 110

Gln Val Thr Val Ser Ser
        115

<210> SEQ ID NO 186
<211> LENGTH: 363
<212> TYPE: DNA
<213> ORGANISM: Artificial Sequence
<220> FEATURE:
<223> OTHER INFORMATION: VHH-623 (nucleic acid)

<400> SEQUENCE: 186
```

-continued

```
caggtaaagc tggaggagag cggaggtggt ctggtgcaag ccggcggctc cctccgtctt        60
tcatgcgccg cttccggacg aacattttca aattatgcgg ctgggtggtt ccgccaggcc       120
ccgggcaagg agcgcgagtt cgtcgcagcc attagctggt ctggtggctc ccctattac        180 gcggacgccg tgcgcgggcg cttcaccatc tctcgggaca cgcgaaaaa cacggtgtac        240 ctgcagatga actccctgaa gccagaagat accgccgttt actactgtgc tgcaggcatc        300
tactacggca gcaactggtc ttcggagaac tggggccagg gcacccaggt caccgtgtcg        360
tcc                                                                     363

<210> SEQ ID NO 187
<211> LENGTH: 375
<212> TYPE: DNA
<213> ORGANISM: Artificial Sequence
<220> FEATURE:
<223> OTHER INFORMATION: VHH-640 (nucleic acid)

<400> SEQUENCE: 187
caggtgaagc tggtggagag cggagggggt tccgtgcagg ccggcggatc gctgcggttg        60
tcctgtgccg cttctggcta cacctggcaa acgtactgca tggcttggtt ccgccaggct       120
cccgggaagg agagggaggg cgtagctgtg gcgactggtt cccgcaccac aagctacgcg       180
gacagtgtta aaggccgttt taccatctcc aaggactatg ccaagaatac tctgtacctg       240
cagatgtctt ctctggagcc tgaagatacc gccatgtatt actgtgctgc ggacccgcgc       300
cgctacggct catgcccact cagcgcagcc aacttcaaca ctggggcca gggcacccag        360 gtcaccgtgt cctcg                                                        375

<210> SEQ ID NO 188
<211> LENGTH: 354
<212> TYPE: DNA
<213> ORGANISM: Artificial Sequence
<220> FEATURE:
<223> OTHER INFORMATION: VHH-657 (nucleic acid)

<400> SEQUENCE: 188
caggtgcagc tggtggagag cggagggggc tccgctcagg ccggaggctc gctgcgccta        60
tcatgccagg cctccgccaa cattcgagtg ttctacttga tgggctggtt ccgccaggcg       120
ccggggaagg agagggagga ggtggctcgc gtcaacgcgg acggcatcac caaccatgca       180
gcctccgtaa agggccgctt caccatctct gaggacagtc aaaaaacac tctttatctg        240 cagatggatt ctctgaagcc tgaagacacc gccgtgtact actgtgccac gggtcggacc        300
tggaactccg gttttgagta ctggggccag ggcacccagg tcactgtgag ctcg             354

<210> SEQ ID NO 189
<211> LENGTH: 367
<212> TYPE: PRT
<213> ORGANISM: Artificial Sequence
<220> FEATURE:
<223> OTHER INFORMATION: VHH-623 CAR (amino acid)

<400> SEQUENCE: 189

Met Ala Leu Pro Val Thr Ala Leu Leu Leu Pro Leu Ala Leu Leu Leu
1               5                   10                  15

His Ala Ala Arg Pro Gln Val Lys Leu Glu Glu Ser Gly Gly Gly Leu
                20                  25                  30

Val Gln Ala Gly Gly Ser Leu Arg Leu Ser Cys Ala Ala Ser Gly Arg
            35                  40                  45
```

-continued

```
Thr Phe Ser Asn Tyr Ala Ala Gly Trp Phe Arg Gln Ala Pro Gly Lys
    50              55              60
```

```
Glu Arg Glu Phe Val Ala Ala Ile Ser Trp Ser Gly Gly Ser Pro Tyr
65              70              75              80
```

```
Tyr Ala Asp Ala Val Arg Gly Arg Phe Thr Ile Ser Arg Asp Asn Ala
            85              90              95
```

```
Lys Asn Thr Val Tyr Leu Gln Met Asn Ser Leu Lys Pro Glu Asp Thr
            100             105             110
```

```
Ala Val Tyr Tyr Cys Ala Ala Gly Ile Tyr Tyr Gly Ser Asn Trp Ser
            115             120             125
```

```
Ser Glu Asn Trp Gly Gln Gly Thr Gln Val Thr Val Ser Ser Thr Ser
    130             135             140
```

```
Thr Thr Thr Pro Ala Pro Arg Pro Pro Thr Pro Ala Pro Thr Ile Ala
145             150             155             160
```

```
Ser Gln Pro Leu Ser Leu Arg Pro Glu Ala Cys Arg Pro Ala Ala Gly
            165             170             175
```

```
Gly Ala Val His Thr Arg Gly Leu Asp Phe Ala Cys Asp Ile Tyr Ile
            180             185             190
```

```
Trp Ala Pro Leu Ala Gly Thr Cys Gly Val Leu Leu Leu Ser Leu Val
            195             200             205
```

```
Ile Thr Leu Tyr Cys Lys Arg Gly Arg Lys Lys Leu Leu Tyr Ile Phe
    210             215             220
```

```
Lys Gln Pro Phe Met Arg Pro Val Gln Thr Thr Gln Glu Glu Asp Gly
225             230             235             240
```

```
Cys Ser Cys Arg Phe Pro Glu Glu Glu Glu Gly Gly Cys Glu Leu Arg
            245             250             255
```

```
Val Lys Phe Ser Arg Ser Ala Asp Ala Pro Ala Tyr Gln Gln Gly Gln
            260             265             270
```

```
Asn Gln Leu Tyr Asn Glu Leu Asn Leu Gly Arg Arg Glu Glu Tyr Asp
    275             280             285
```

```
Val Leu Asp Lys Arg Arg Gly Arg Asp Pro Glu Met Gly Gly Lys Pro
    290             295             300
```

```
Arg Arg Lys Asn Pro Gln Glu Gly Leu Tyr Asn Glu Leu Gln Lys Asp
305             310             315             320
```

```
Lys Met Ala Glu Ala Tyr Ser Glu Ile Gly Met Lys Gly Glu Arg Arg
            325             330             335
```

```
Arg Gly Lys Gly His Asp Gly Leu Tyr Gln Gly Leu Ser Thr Ala Thr
            340             345             350
```

```
Lys Asp Thr Tyr Asp Ala Leu His Met Gln Ala Leu Pro Pro Arg
            355             360             365
```

<210> SEQ ID NO 190
<211> LENGTH: 371
<212> TYPE: PRT
<213> ORGANISM: Artificial Sequence
<220> FEATURE:
<223> OTHER INFORMATION: VHH-640 CAR (amino acid)

<400> SEQUENCE: 190

```
Met Ala Leu Pro Val Thr Ala Leu Leu Leu Pro Leu Ala Leu Leu Leu
1               5               10              15
```

```
His Ala Ala Arg Pro Gln Val Lys Leu Val Glu Ser Gly Gly Gly Ser
            20              25              30
```

```
Val Gln Ala Gly Gly Ser Leu Arg Leu Ser Cys Ala Ala Ser Gly Tyr
    35              40              45
```

```
Thr Trp Gln Thr Tyr Cys Met Ala Trp Phe Arg Gln Ala Pro Gly Lys
    50                  55                  60

Glu Arg Glu Gly Val Ala Val Ala Thr Gly Ser Arg Thr Thr Ser Tyr
65                  70                  75                  80

Ala Asp Ser Val Lys Gly Arg Phe Thr Ile Ser Lys Asp Tyr Ala Lys
                85                  90                  95

Asn Thr Leu Tyr Leu Gln Met Ser Ser Leu Glu Pro Glu Asp Thr Ala
            100                 105                 110

Met Tyr Tyr Cys Ala Ala Asp Pro Arg Arg Tyr Gly Ser Cys Pro Leu
            115                 120                 125

Ser Ala Ala Asn Phe Asn Asn Trp Gly Gln Gly Thr Gln Val Thr Val
    130                 135                 140

Ser Ser Thr Ser Thr Thr Thr Pro Ala Pro Arg Pro Pro Thr Pro Ala
145                 150                 155                 160

Pro Thr Ile Ala Ser Gln Pro Leu Ser Leu Arg Pro Glu Ala Cys Arg
                165                 170                 175

Pro Ala Ala Gly Gly Ala Val His Thr Arg Gly Leu Asp Phe Ala Cys
            180                 185                 190

Asp Ile Tyr Ile Trp Ala Pro Leu Ala Gly Thr Cys Gly Val Leu Leu
            195                 200                 205

Leu Ser Leu Val Ile Thr Leu Tyr Cys Lys Arg Gly Arg Lys Lys Leu
    210                 215                 220

Leu Tyr Ile Phe Lys Gln Pro Phe Met Arg Pro Val Gln Thr Thr Gln
225                 230                 235                 240

Glu Glu Asp Gly Cys Ser Cys Arg Phe Pro Glu Glu Glu Glu Gly Gly
                245                 250                 255

Cys Glu Leu Arg Val Lys Phe Ser Arg Ser Ala Asp Ala Pro Ala Tyr
            260                 265                 270

Gln Gln Gly Gln Asn Gln Leu Tyr Asn Glu Leu Asn Leu Gly Arg Arg
            275                 280                 285

Glu Glu Tyr Asp Val Leu Asp Lys Arg Arg Gly Arg Asp Pro Glu Met
    290                 295                 300

Gly Gly Lys Pro Arg Arg Lys Asn Pro Gln Glu Gly Leu Tyr Asn Glu
305                 310                 315                 320

Leu Gln Lys Asp Lys Met Ala Glu Ala Tyr Ser Glu Ile Gly Met Lys
            325                 330                 335

Gly Glu Arg Arg Arg Gly Lys Gly His Asp Gly Leu Tyr Gln Gly Leu
            340                 345                 350

Ser Thr Ala Thr Lys Asp Thr Tyr Asp Ala Leu His Met Gln Ala Leu
            355                 360                 365

Pro Pro Arg
    370
```

<210> SEQ ID NO 191
<211> LENGTH: 364
<212> TYPE: PRT
<213> ORGANISM: Artificial Sequence
<220> FEATURE:
<223> OTHER INFORMATION: VHH-657 CAR (amino acid)

<400> SEQUENCE: 191

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Ser
            20                  25                  30
```

-continued

```
Ala Gln Ala Gly Gly Ser Leu Arg Leu Ser Cys Gln Ala Ser Ala Asn
        35                  40                  45

Ile Arg Val Phe Tyr Leu Met Gly Trp Phe Arg Gln Ala Pro Gly Lys
    50                  55                  60

Glu Arg Glu Glu Val Ala Arg Val Asn Ala Asp Gly Ile Thr Asn His
65                  70                  75                  80

Ala Ala Ser Val Lys Gly Arg Phe Thr Ile Ser Glu Asp Ser Pro Lys
                85                  90                  95

Asn Thr Leu Tyr Leu Gln Met Asp Ser Leu Lys Pro Glu Asp Thr Ala
            100                 105                 110

Val Tyr Tyr Cys Ala Thr Gly Arg Thr Trp Asn Ser Gly Phe Glu Tyr
            115                 120                 125

Trp Gly Gln Gly Thr Gln Val Thr Val Ser Ser Thr Ser Thr Thr Thr
    130                 135                 140

Pro Ala Pro Arg Pro Pro Thr Pro Ala Pro Thr Ile Ala Ser Gln Pro
145                 150                 155                 160

Leu Ser Leu Arg Pro Glu Ala Cys Arg Pro Ala Ala Gly Gly Ala Val
                165                 170                 175

His Thr Arg Gly Leu Asp Phe Ala Cys Asp Ile Tyr Ile Trp Ala Pro
            180                 185                 190

Leu Ala Gly Thr Cys Gly Val Leu Leu Leu Ser Leu Val Ile Thr Leu
            195                 200                 205

Tyr Cys Lys Arg Gly Arg Lys Lys Leu Leu Tyr Ile Phe Lys Gln Pro
    210                 215                 220

Phe Met Arg Pro Val Gln Thr Thr Gln Glu Glu Asp Gly Cys Ser Cys
225                 230                 235                 240

Arg Phe Pro Glu Glu Glu Glu Gly Gly Cys Glu Leu Arg Val Lys Phe
                245                 250                 255

Ser Arg Ser Ala Asp Ala Pro Ala Tyr Gln Gln Gly Gln Asn Gln Leu
            260                 265                 270

Tyr Asn Glu Leu Asn Leu Gly Arg Arg Glu Glu Tyr Asp Val Leu Asp
            275                 280                 285

Lys Arg Arg Gly Arg Asp Pro Glu Met Gly Gly Lys Pro Arg Arg Lys
    290                 295                 300

Asn Pro Gln Glu Gly Leu Tyr Asn Glu Leu Gln Lys Asp Lys Met Ala
305                 310                 315                 320

Glu Ala Tyr Ser Glu Ile Gly Met Lys Gly Glu Arg Arg Arg Gly Lys
                325                 330                 335

Gly His Asp Gly Leu Tyr Gln Gly Leu Ser Thr Ala Thr Lys Asp Thr
            340                 345                 350

Tyr Asp Ala Leu His Met Gln Ala Leu Pro Pro Arg
            355                 360
```

<210> SEQ ID NO 192
<211> LENGTH: 1104
<212> TYPE: DNA
<213> ORGANISM: Artificial Sequence
<220> FEATURE:
<223> OTHER INFORMATION: VHH-623 CAR (nucleic acid)

<400> SEQUENCE: 192
atggcgctgc ctgtgactgc tctgctgctc cccctggcct tgcttctaca cgccgctagg      60
cctcaggtaa agctggagga gagcggaggt ggtctggtgc aagccggcgg ctccctccgt     120
ctttcatgcg ccgcttccgg acgaacattt tcaaattatg cggctgggtg gttccgccag     180

-continued

```
gccccgggca aggagcgcga gttcgtcgca gccattagct ggtctggtgg ctccccctat      240
tacgcggacg ccgtgcgcgg cgcgcttcacc atctctcggg acaacgcgaa aaacacggtg      300
tacctgcaga tgaactccct gaagccagaa gataccgccg tttactactg tgctgcaggc      360
atctactacg gcagcaactg gtcttcggag aactgggggcc agggcaccca ggtcaccgtg      420
tcgtccacta gtaccacgac gccagcgccg cgaccaccaa caccggcgcc caccatcgcg      480
tcgcagcccc tgtccctgcg cccagaggcg tgccggccag cggcgggggg cgcagtgcac      540
acgagggggc tggacttcgc ctgtgatatc tacatctggg cgcccttggc cgggacttgt      600
ggggtccttc tcctgtcact ggttatcacc ctttactgca aacggggcag aaagaaactc      660
ctgtatatat tcaaacaacc atttatgaga ccagtacaaa ctactcaaga ggaagatggc      720
tgtagctgcc gatttccaga agaagaagaa ggaggatgtg aactgagagt gaagttcagc      780
aggagcgcag acgcccccgc gtaccagcag ggccagaacc agctctataa cgagctcaat      840
ctaggacgaa gagaggagta cgatgttttg gacaagagac gtggccggga ccctgagatg      900
gggggaaagc cgagaaggaa gaaccctcag gaaggcctgt acaatgaact gcagaaagat      960
aagatggcgg aggcctacag tgagattggg atgaaaggcg agcgccggag gggcaagggg     1020
cacgatggcc tttaccaggg tctcagtaca gccaccaagg acacctacga cgcccttcac     1080
atgcaggccc tgccccctcg ctaa                                            1104
```

<210> SEQ ID NO 193
<211> LENGTH: 1116
<212> TYPE: DNA
<213> ORGANISM: Artificial Sequence
<220> FEATURE:
<223> OTHER INFORMATION: VHH-640 CAR (nucleic acid)

<400> SEQUENCE: 193

```
atggcgcttc ccgtcacggc cctttttgctg cccctggcgc tgctgctcca cgccgcccga       60
cctcaggtga agctggtgga gagcggaggg ggttccgtgc aggccggcgg atcgctgcgg      120
ttgtcctgtg ccgcttctgg ctacacctgg caaacgtact gcatggcttg gttccgccag      180
gctcccggga aggagaggga gggcgtagct gtggcgactg gttcccgcac cacaagctac      240
gcggacagtg ttaaaggccg tttttaccatc tccaaggact atgccaagaa tactctgtac      300
ctgcagatgt cttctctgga gcctgaagat accgccatgt attactgtgc tgcggacccg      360
cgccgctacg gctcatgccc actcagcgca gccaacttca caactggggg ccagggcacc      420
caggtcaccg tgtcctcgac tagtaccacg acgccagcgc cgcgaccacc aacaccggcg      480
cccaccatcg cgtcgcagcc cctgtccctg cgcccagagg cgtgccggcc agcggcgggg      540
ggcgcagtgc acacgagggg gctggacttc gcctgtgata tctacatctg gcgcgccttg      600
gccgggactt gtggggtcct tctcctgtca ctggttatca cccttttactg caaacggggc      660 agaaagaaac tcctgtatat attcaaacaa ccatttatga ccagtacaa aactactcaa      720 gaggaagatg gctgtagctg ccgatttcca gaagaagaag aaggaggatg tgaactgaga      780
gtgaagttca gcaggagcgc agacgccccc gcgtaccagc agggccagaa ccagctctat      840
aacgagctca atctaggacg aagagaggag tacgatgttt tggacaagag acgtggccgg      900
gaccctgaga tggggggaaa gccgagaagg aagaaccctc aggaaggcct gtacaatgaa      960
ctgcagaaag ataagatggc ggaggcctac agtgagattg ggatgaaagg cgagcgccgg     1020
aggggcaagg ggcacgatgg cctttaccag ggtctcagta cagccaccaa ggacacctac     1080
gacgcccttc acatgcaggc cctgcccccct cgctaa                              1116
```

<210> SEQ ID NO 194
<211> LENGTH: 1095
<212> TYPE: DNA
<213> ORGANISM: Artificial Sequence
<220> FEATURE:
<223> OTHER INFORMATION: VHH-657 CAR (nucleic acid)

<400> SEQUENCE: 194

```
atggcgctgc ccgttacagc tctgctgctc cccctggcac ttttgctcca cgccgcgcgt      60
cctcaggtgc agctggtgga gagcggaggg ggctccgctc aggccggagg ctcgctgcgc     120
ctatcatgcc aggcctccgc caacattcga gtgttctact tgatgggctg gttccgccag     180
gcgccgggga aggagaggga ggaggtggct cgcgtcaacg cggacggcat caccaaccat     240
gcagcctccg taaagggccg cttcaccatc tctgaggaca gtccaaaaaa cactctttat     300
ctgcagatgg attctctgaa gcctgaagac accgccgtgt actactgtgc cacgggtcgg     360
acctggaact ccggttttga gtactggggc cagggcaccc aggtcactgt gagctcgact     420
agtaccacga cgccagcgcc gcgaccacca acaccggcgc ccaccatcgc gtcgcagccc     480
ctgtccctgc gcccagaggc gtgccggcca cggcgcgggg cgcagtgca cacgaggggg     540 ctggacttcg cctgtgatat ctacatctgg gcgcccttgg ccgggacttg tggggtcctt     600
ctcctgtcac tggttatcac cctttactgc aaacggggca gaaagaaact cctgtatata     660
ttcaaacaac catttatgag accagtacaa actactcaag aggaagatgg ctgtagctgc     720
cgatttccag aagaagaaga aggaggatgt gaactgagag tgaagttcag caggagcgca     780 gacgccccg cgtaccagca gggccagaac cagctctata cgagctcaa tctaggacga     840 agagaggagt acgatgtttt ggacaagaga cgtggccggg accctgagat ggggggaaag     900
ccgagaagga agaaccctca ggaaggcctg tacaatgaac tgcagaaaga taagatggcg     960
gaggcctaca gtgagattgg gatgaaaggc gagcgccgga ggggcaaggg cacgatggc     1020 ctttaccagg gtctcagtac agccaccaag gacacctacg acgcccttca catgcaggcc    1080
ctgccccctc gctaa                                                     1095
```

<210> SEQ ID NO 195
<211> LENGTH: 5
<212> TYPE: PRT
<213> ORGANISM: Artificial Sequence
<220> FEATURE:
<223> OTHER INFORMATION: CDR1 (Kabat with 5aa) of VHH-273, VHH-283,
     huVHH-253, huVHH-256, 2082H1, 2082H2, 2082H3, 2082H4, 2082H5, and
     2082H6

<400> SEQUENCE: 195

Ser Tyr Asn Met Gly
1               5

<210> SEQ ID NO 196
<211> LENGTH: 5
<212> TYPE: PRT
<213> ORGANISM: Artificial Sequence
<220> FEATURE:
<223> OTHER INFORMATION: CDR1 (Kabat with 5aa) of VHH-313 and huVHH-260

<400> SEQUENCE: 196

Ser Tyr Ser Met Gly
1               5

<210> SEQ ID NO 197

```
<211> LENGTH: 5
<212> TYPE: PRT
<213> ORGANISM: Artificial Sequence
<220> FEATURE:
<223> OTHER INFORMATION: CDR1 (Kabat with 5aa) of VHH-440, VHH-653,
      VHH-466, huVHH-836, huVHH-840, huVHH-843, huVHH-846 and VHH-657

<400> SEQUENCE: 197

Phe Tyr Leu Met Gly
1               5

<210> SEQ ID NO 198
<211> LENGTH: 5
<212> TYPE: PRT
<213> ORGANISM: Artificial Sequence
<220> FEATURE:
<223> OTHER INFORMATION: CDR1 (Kabat with 5aa) of VHH-496, huVHH-746,
      and huVHH-750, huVHH-753

<400> SEQUENCE: 198

Asn Tyr Pro Met Thr
1               5

<210> SEQ ID NO 199
<211> LENGTH: 5
<212> TYPE: PRT
<213> ORGANISM: Artificial Sequence
<220> FEATURE:
<223> OTHER INFORMATION: CDR1 (Kabat with 5aa) of VHH-623

<400> SEQUENCE: 199

Asn Tyr Ala Ala Gly
1               5

<210> SEQ ID NO 200
<211> LENGTH: 5
<212> TYPE: PRT
<213> ORGANISM: Artificial Sequence
<220> FEATURE:
<223> OTHER INFORMATION: CDR1 (Kabat with 5aa) of VHH-640

<400> SEQUENCE: 200

Thr Tyr Cys Met Ala
1               5
```

CD20 BINDING MOLECULES AND USES THEREOF

CROSS REFERENCE

This application is a national stage of International Application No. PCT/CN2021/106886, filed on Jul. 16, 2021, which claims benefit of priority of International Patent Application No. PCT/CN2020/102463. Both of the aforementioned applications are hereby incorporated by reference in their entireties.

SEQUENCE LISTING

This application incorporates by reference a Sequence Listing submitted with this application as a text file, entitled 14651-026-228_SEQ_LISTING.txt, created on Jul. 9, 2021, and is 236,191 bytes in size.

1. FIELD

The present disclosure relates to anti-CD20 single domain antibodies, chimeric antigen receptors, engineered immune effector cells, and methods of use thereof. The present disclosure further relates to activation and expansion of cells for therapeutic uses, especially to chimeric antigen receptor-based T cell immunotherapies.

2. BACKGROUND

CD20 is a surface antigen expressed at certain stages of B-cell differentiation. Targeting the CD20-positive B cells with therapeutic monoclonal antibodies (mAbs) has been an effectual strategy in the treatment of hematologic malignancies such as non-Hodgkin's lymphoma (NHL) and chronic lymphocytic leukemia (CLL). Initial success with Rituximab (RTX) has encouraged the creation and development of more effective CD20 based therapeutics. However, treatment with conventional mAbs has not been adequate to overcome the problems such as refractory/relapsed diseases (Shanehbandi et al., *Current Cancer Drug Targets*, 17(5): 423-444 (2007)).

Chimeric antigen receptor T (CAR-T) cell therapy is an emerging and effective cancer immunotherapy. Especially in hematological malignancies, CAR-T cells have achieved exciting results. Early clinical studies of CD20 CAR-T cells have been conducted, which indicate that CD20 CAR-T cells have encouraging therapeutic potential in B-cell NHLs (Brudno and Kochenderfer, *Nature Reviews Clinical Oncology*, 15: 31-46 (2018)). However, the application of CAR-T cells is obviously hampered by adverse effects, such as cytokines release syndrome and on-target off-tumor toxicity (Yu et al., *Molecular Cancer*, 18 (1): 125 (2019)).

Thus, improved CD20-binding molecules and engineered CD20-targeting cells are needed. For example, there is a need to develop stable and small-sized CD20 binding molecules for use in more effective or efficient CAR-T therapies.

3. SUMMARY

In one aspect, provided herein is an anti-CD20 single domain antibody (sdAb) comprising (i) a CDR1 comprising the amino acid sequence of SEQ ID NO: 1 or 195; a CDR2 comprising the amino acid sequence of SEQ ID NO: 2; and a CDR3 comprising the amino acid sequence of SEQ ID NO: 3; (ii) a CDR1 comprising the amino acid sequence of SEQ ID NO: 4; a CDR2 comprising the amino acid sequence of SEQ ID NO: 5; and a CDR3 comprising the amino acid sequence of SEQ ID NO: 6; (iii) a CDR1 comprising the amino acid sequence of SEQ ID NO: 1 or 195; a CDR2 comprising the amino acid sequence of SEQ ID NO: 7; and a CDR3 comprising the amino acid sequence of SEQ ID NO: 8; (iv) a CDR1 comprising the amino acid sequence of SEQ ID NO: 4; a CDR2 comprising the amino acid sequence of SEQ ID NO: 9; and a CDR3 comprising the amino acid sequence of SEQ ID NO: 10; (v) a CDR1 comprising the amino acid sequence of SEQ ID NO: 11 or 196; a CDR2 comprising the amino acid sequence of SEQ ID NO: 12; and a CDR3 comprising the amino acid sequence of SEQ ID NO: 8; (vi) a CDR1 comprising the amino acid sequence of SEQ ID NO: 13; a CDR2 comprising the amino acid sequence of SEQ ID NO: 9; and a CDR3 comprising the amino acid sequence of SEQ ID NO: 10; (vii) a CDR1 comprising the amino acid sequence of SEQ ID NO: 14 or 197; a CDR2 comprising the amino acid sequence of SEQ ID NO: 15; and a CDR3 comprising the amino acid sequence of SEQ ID NO: 16; (viii) a CDR1 comprising the amino acid sequence of SEQ ID NO: 17; a CDR2 comprising the amino acid sequence of SEQ ID NO: 18; and a CDR3 comprising the amino acid sequence of SEQ ID NO: 19; (ix) a CDR1 comprising the amino acid sequence of SEQ ID NO: 20 or 197; a CDR2 comprising the amino acid sequence of SEQ ID NO: 21; and a CDR3 comprising the amino acid sequence of SEQ ID NO: 16; (x) a CDR1 comprising the amino acid sequence of SEQ ID NO: 22; a CDR2 comprising the amino acid sequence of SEQ ID NO: 23; and a CDR3 comprising the amino acid sequence of SEQ ID NO: 19; (xi) a CDR1 comprising the amino acid sequence of SEQ ID NO: 24 or 198; a CDR2 comprising the amino acid sequence of SEQ ID NO: 25; and a CDR3 comprising the amino acid sequence of SEQ ID NO: 26; (xii) a CDR1 comprising the amino acid sequence of SEQ ID NO: 27; a CDR2 comprising the amino acid sequence of SEQ ID NO: 28; and a CDR3 comprising the amino acid sequence of SEQ ID NO: 29; (xiii) a CDR1 comprising the amino acid sequence of SEQ ID NO: 14 or 197; a CDR2 comprising the amino acid sequence of SEQ ID NO: 30; and a CDR3 comprising the amino acid sequence of SEQ ID NO: 16; (xiv) a CDR1 comprising the amino acid sequence of SEQ ID NO: 17; a CDR2 comprising the amino acid sequence of SEQ ID NO: 31; and a CDR3 comprising the amino acid sequence of SEQ ID NO: 19; (xv) a CDR1 comprising the amino acid sequence of SEQ ID NO: 1 or 195; a CDR2 comprising the amino acid sequence of SEQ ID NO: 32; and a CDR3 comprising the amino acid sequence of SEQ ID NO: 3; (xvi) a CDR1 comprising the amino acid sequence of SEQ ID NO: 4; a CDR2 comprising the amino acid sequence of SEQ ID NO: 33; and a CDR3 comprising the amino acid sequence of SEQ ID NO: 6; (xvii) a CDR1 comprising the amino acid sequence of SEQ ID NO: 20 or 197; a CDR2 comprising the amino acid sequence of SEQ ID NO: 34; and a CDR3 comprising the amino acid sequence of SEQ ID NO: 16; (xviii) a CDR1 comprising the amino acid sequence of SEQ ID NO: 22; a CDR2 comprising the amino acid sequence of SEQ ID NO: 35; and a CDR3 comprising the amino acid sequence of SEQ ID NO: 19; (xix) a CDR1 comprising the amino acid sequence of SEQ ID NO: 20 or 197; a CDR2 comprising the amino acid sequence of SEQ ID NO: 36; and a CDR3 comprising the amino acid sequence of SEQ ID NO: 16; (xx) a CDR1 comprising the amino acid sequence of SEQ ID NO: 20 or 197; a CDR2 comprising the amino acid sequence of SEQ ID NO: 37; and a CDR3 comprising the amino acid sequence of SEQ ID NO: 16; (xxi) a CDR1 comprising the amino acid sequence of SEQ ID NO: 20 or 197; a CDR2 comprising the amino acid sequence of SEQ ID NO: 38; and a CDR3 comprising the amino acid sequence of SEQ ID NO: 16; (xxii) a CDR1 comprising the amino acid sequence of SEQ ID NO: 4; a CDR2 comprising the amino acid sequence of SEQ ID NO: 33; and a CDR3 comprising the amino acid sequence of SEQ ID NO: 39; (xxiii) a CDR1 comprising the amino acid sequence of SEQ ID NO: 4; a CDR2 comprising the amino acid sequence of SEQ ID NO: 33; and a CDR3 comprising the amino acid sequence of SEQ ID NO: 40; (xxiv) a CDR1 comprising the amino acid sequence of SEQ ID NO: 165 or 199; a CDR2 comprising the amino acid sequence of SEQ ID NO: 166; and a CDR3 comprising the amino acid sequence of SEQ ID NO: 167; (xxv) a CDR1 comprising the amino acid sequence of SEQ ID NO: 168; a CDR2 comprising the amino acid sequence of SEQ ID NO: 169; and a CDR3 comprising the amino acid sequence of SEQ ID NO: 170; (xxvi) a CDR1 comprising the amino acid sequence of SEQ ID NO: 171 or 200; a CDR2 comprising the amino acid sequence of SEQ ID NO: 172; and a CDR3 comprising the amino acid sequence of SEQ ID NO: 173; (xxvii) a CDR1 comprising the amino acid sequence of SEQ ID NO: 174; a CDR2 comprising the amino acid sequence of SEQ ID NO: 175; and a CDR3 comprising the amino acid sequence of SEQ ID NO: 176; (xxviii) a CDR1 comprising the amino acid sequence of SEQ ID NO: 177 or 197; a CDR2 comprising the amino acid sequence of SEQ ID NO: 178; and a CDR3 comprising the amino acid sequence of SEQ ID NO: 179; or (xxix) a CDR1 comprising the amino acid sequence of SEQ ID NO: 180; a CDR2 comprising the amino acid sequence of SEQ ID NO: 181; and a CDR3 comprising the amino acid sequence of SEQ ID NO: 182.

In another aspect, provided herein is an anti-CD20 single domain antibody (sdAb) comprising: (i) a CDR1, a CDR2, and a CDR3 having the amino acid sequences of the CDR1, CDR2, and CDR3, respectively, as set forth in SEQ ID NO: 41; (ii) a CDR1, a CDR2, and a CDR3 having the amino acid sequences of the CDR1, CDR2, and CDR3, respectively, as set forth in SEQ ID NO: 42; (iii) a CDR1, a CDR2, and a CDR3 having the amino acid sequences of the CDR1, CDR2, and CDR3, respectively, as set forth in SEQ ID NO: 43; (iv) a CDR1, a CDR2, and a CDR3 having the amino acid sequences of the CDR1, CDR2, and CDR3, respectively, as set forth in SEQ ID NO: 44; (v) a CDR1, a CDR2, and a CDR3 having the amino acid sequences of the CDR1, CDR2, and CDR3, respectively, as set forth in SEQ ID NO: 45; (vi) a CDR1, a CDR2, and a CDR3 having the amino acid sequences of the CDR1, CDR2, and CDR3, respectively, as set forth in SEQ ID NO: 46; (vii) a CDR1, a CDR2, and a CDR3 having the amino acid sequences of the CDR1, CDR2, and CDR3, respectively, as set forth in SEQ ID NO: 47; (viii) a CDR1, a CDR2, and a CDR3 having the amino acid sequences of the CDR1, CDR2, and CDR3, respectively, as set forth in SEQ ID NO: 48; (ix) a CDR1, a CDR2, and a CDR3 having the amino acid sequences of the CDR1, CDR2, and CDR3, respectively, as set forth in SEQ ID NO: 49; (x) a CDR1, a CDR2, and a CDR3 having the amino acid sequences of the CDR1, CDR2, and CDR3, respectively, as set forth in SEQ ID NO: 50; (xi) a CDR1, a CDR2, and a CDR3 having the amino acid sequences of the CDR1, CDR2, and CDR3, respectively, as set forth in SEQ ID NO: 51; (xii) a CDR1, a CDR2, and a CDR3 having the amino acid sequences of the CDR1, CDR2, and CDR3, respectively, as set forth in SEQ ID NO: 52; (xiii) a CDR1, a CDR2, and a CDR3 having the amino acid sequences of the CDR1, CDR2, and CDR3, respectively, as set forth in SEQ ID NO: 53; (xiv) a CDR1, a CDR2, and a CDR3 having the amino acid sequences of the CDR1, CDR2, and CDR3, respectively, as set forth in SEQ ID NO: 54; (xv) a CDR1, a CDR2, and a CDR3 having the amino acid sequences of the CDR1, CDR2, and CDR3, respectively, as set forth in SEQ ID NO: 55; (xvi) a CDR1, a CDR2, and a CDR3 having the amino acid sequences of the CDR1, CDR2, and CDR3, respectively, as set forth in SEQ ID NO: 56; (xvii) a CDR1, a CDR2, and a CDR3 having the amino acid sequences of the CDR1, CDR2, and CDR3, respectively, as set forth in SEQ ID NO: 57; (xviii) a CDR1, a CDR2, and a CDR3 having the amino acid sequences of the CDR1, CDR2, and CDR3, respectively, as set forth in SEQ ID NO: 58; (xix) a CDR1, a CDR2, and a CDR3 having the amino acid sequences of the CDR1, CDR2, and CDR3, respectively, as set forth in SEQ ID NO: 59; (xx) a CDR1, a CDR2, and a CDR3 having the amino acid sequences of the CDR1, CDR2, and CDR3, respectively, as set forth in SEQ ID NO: 60; (xxi) a CDR1, a CDR2, and a CDR3 having the amino acid sequences of the CDR1, CDR2, and CDR3, respectively, as set forth in SEQ ID NO: 61; (xxii) a CDR1, a CDR2, and a CDR3 having the amino acid sequences of the CDR1, CDR2, and CDR3, respectively, as set forth in SEQ ID NO: 62; or (xxiii) a CDR1, a CDR2, and a CDR3 having the amino acid sequences of the CDR1, CDR2, and CDR3, respectively, as set forth in SEQ ID NO: 63; (xxiv) a CDR1, a CDR2, and a CDR3 having the amino acid sequences of the CDR1, CDR2, and CDR3, respectively, as set forth in SEQ ID NO: 183; (xxv) a CDR1, a CDR2, and a CDR3 having the amino acid sequences of the CDR1, CDR2, and CDR3, respectively, as set forth in SEQ ID NO: 184; or (xxvi) a CDR1, a CDR2, and a CDR3 having the amino acid sequences of the CDR1, CDR2, and CDR3, respectively, as set forth in SEQ ID NO: 185.

In some embodiments, the CDR1, CDR2 or CDR3 are determined according to the Kabat numbering scheme, the IMGT numbering scheme, the AbM numbering scheme, the Chothia numbering scheme, the Contact numbering scheme, or a combination thereof.

In some embodiments, the anti-CD20 sdAb provided herein further comprises one or more FR regions as set forth in SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184 and/or SEQ ID NO: 185.

In some embodiments, the anti-CD20 sdAb provided herein comprises the amino acid sequence of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184 or SEQ ID NO: 185.

In other embodiments, the anti-CD20 sdAb provided herein comprises or consists of an amino acid sequence having at least 75%, 80%, 85%, 90%, 95%, 96%, 97%, 98%, 99%, or more sequence identity with the sequence of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO:

58, SEQ ID NO: 59, SEQ ID NO: 60, SEQ ID NO: 61, SEQ ID NO: 62, SEQ ID NO: 63, SEQ ID NO: 183, SEQ ID NO: 184 or SEQ ID NO: 185.

In some embodiments, the anti-CD20 sdAb is a camelid sdAb. In some embodiments, the anti-CD20 sdAb is a humanized sdAb. In some embodiments, the anti-CD20 sdAb is a VHH domain. In some embodiments, the anti-CD20 sdAb is a humanized VHH domain.

In some embodiments, the anti-CD20 sdAb is genetically fused or chemically conjugated to an agent.

In another aspect, provided herein is a chimeric antigen receptor (CAR), comprising (a) an extracellular antigen binding domain comprising the anti-CD20 sdAb provided herein; (b) a transmembrane domain; and (c) an intracellular signaling domain. In some embodiments, the extracellular antigen binding domain further comprises one or more additional antigen binding domain(s). In some embodiments, the extracellular antigen binding domain further comprises one additional antigen binding domain. In other embodiments, the extracellular antigen binding domain further comprises two additional antigen binding domains. In some embodiments, the one or more additional antigen binding domain(s) bind to one or more antigen(s) selected from a group consisting of CD20, CD19, CD22, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the CD20 CAR is monospecific. In some embodiments, the CD20 CAR is monovalent. In some embodiments, the CD20 CAR is multivalent. In some embodiments, the extracellular antigen binding domain comprises at least two anti-CD20 sdAbs provided herein.

In some embodiments, provided herein is a multivalent (such as bivalent and trivalent) CAR comprising a polypeptide comprising: (a) an extracellular antigen binding domain comprising two or more single domain antibodies (sdAbs) specifically binding to CD20; (b) a transmembrane domain; and (c) an intracellular signaling domain. In some embodiments, the extracellular antigen binding domain comprises two single domain antibodies (sdAbs) specifically binding to CD20 provided herein. In other embodiments, the extracellular antigen binding domain comprises three single domain antibodies (sdAbs) specifically binding to CD20 provided herein.

In some embodiments according to any one of the CARS described above, the transmembrane domain is derived from a molecule selected from a group consisting of CD8α, CD4, CD28, CD137, CD80, CD86, CD152, and PD1. In some embodiments, the transmembrane domain is derived from CD8α.

In some embodiments according to any one of the CARs described above, the intracellular signaling domain comprises a primary intracellular signaling domain of an immune effector cell. In some embodiments, the primary intracellular signaling domain is derived from CD3ζ.

In other embodiments according to any one of the CARS described above, the intracellular signaling domain further comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the co-stimulatory signaling domain is derived from CD137.

In some embodiments, the CAR provided herein further comprises a hinge domain located between the C-terminus of the extracellular antigen binding domain and the N-terminus of the transmembrane domain. In some embodiments, the hinge domain is derived from CD8α.

In some embodiments, the CAR provided herein further comprises a signal peptide located at the N-terminus of the polypeptide. In some embodiments, the signal peptide is derived from CD8α.

In certain embodiments, provided herein is a chimeric antigen receptor (CAR), comprising (i) an amino acid sequence selected from the group consisting of SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 189, SEQ ID NO: 190, and SEQ ID NO: 191; or (ii) an amino acid sequence having at least 75%, 80%, 85%, 90%, 95%, 96%, 97%, 98%, 99%, or more sequence identity with the sequence of SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 189, SEQ ID NO: 190, or SEQ ID NO: 191.

In another aspect, provided herein is an isolated nucleic acid comprising a nucleic acid sequence encoding the anti-CD20 sdAb provided herein. In another aspect, provided herein is a vector comprising a nucleic acid encoding the anti-CD20 sdAb provided herein.

In yet another aspect, provided herein is an isolated nucleic acid comprising a nucleic acid sequence encoding the CAR provided herein. In another aspect, provided herein is a vector comprising a nucleic acid encoding the CAR provided herein.

In yet another aspect, provided herein is an engineered immune effector cell, comprising the CAR, the isolated nucleic acid, or the vector provided herein. In some embodiments, the engineered immune effector cell is a T cell or B cell.

In another aspect, provided herein is a pharmaceutical composition, comprising the anti-CD20 sdAb, the engineered immune effector cell, or the vector provided herein, and a pharmaceutically acceptable excipient.

In yet another aspect, provided herein is a method of treating a disease or disorder in a subject, comprising administering to the subject an effective amount of the anti-CD20 sdAb, the engineered immune effector cell, or the pharmaceutical composition provided herein. In some embodiments, the disease or disorder is a B cell associated disease or disorder and/or CD20 associated disease or disorder. In some embodiments, the disease or disorder is cancer. In other embodiments, the disease or disorder is a B cell malignancy. In some embodiments, the B cell malignancy is a B cell leukemia or B cell lymphoma. In some embodiments, the disease or disorder is selected from a group consisting of marginal zone lymphoma (e.g., splenic marginal zone lymphoma), diffuse large B cell lymphoma (DLBCL), mantle cell lymphoma (MCL), primary central nervous system (CNS) lymphoma, primary mediastinal B cell lymphoma (PMBL), small lymphocytic lymphoma (SLL), B cell prolymphocytic leukemia (B-PLL), follicular lymphoma (FL), burkitt lymphoma, primary intraocular lymphoma, chronic lymphocytic leukemia (CLL), acute lymphoblastic leukemia (ALL), hairy cell leukemia (HCL), precursor B lymphoblastic leukemia, non-hodgkin lymphoma (NHL), high-grade B-cell lymphoma (HGBL), and multiple myelomia (MM). In other embodiments, the disease or disorder is an autoimmune and/or inflammatory disease. In some embodiments, the autoimmune and/or inflammatory disease is associated with inappropriate or enhanced B cell numbers and/or activation.

4. BRIEF DESCRIPTION OF THE FIGURES

FIG. 6 shows IFN-γ release level of mono-, bi- and tri-VHH CAR-T cells compared to that of CD20 scFv CAR-T cells after co-culture with Raji.Luc or K562.Luc cells for 24 hours.

Figure 10A:
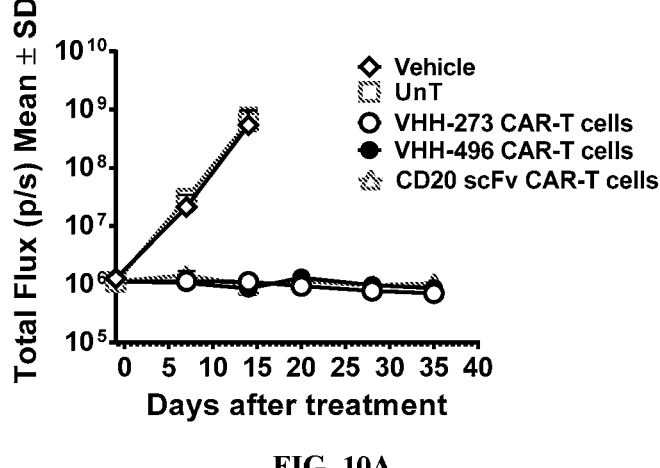
Figure 10B:
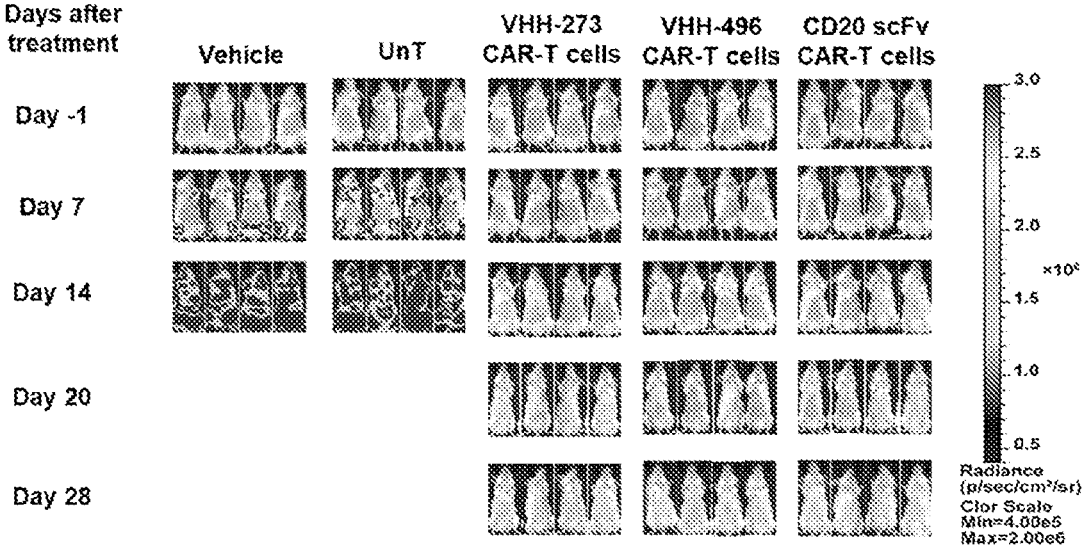
Figure 10C:
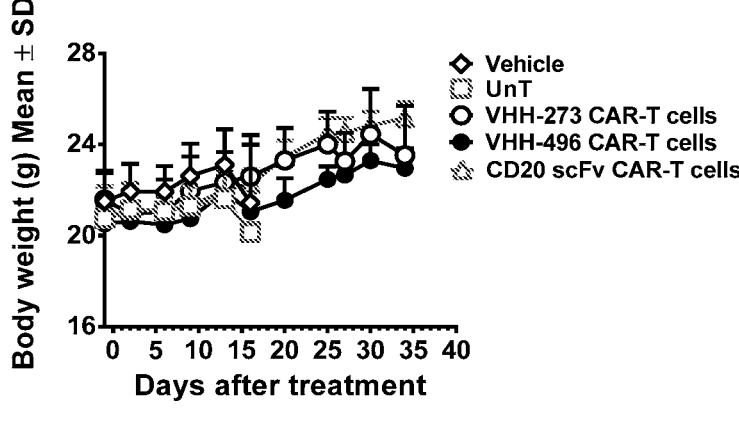
Figure 10D:
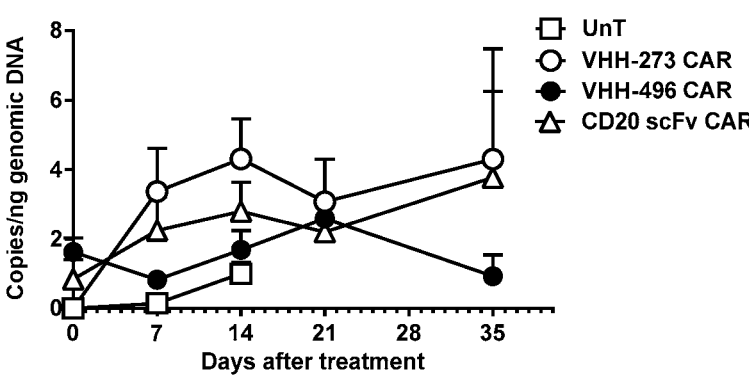
Figure 10E:
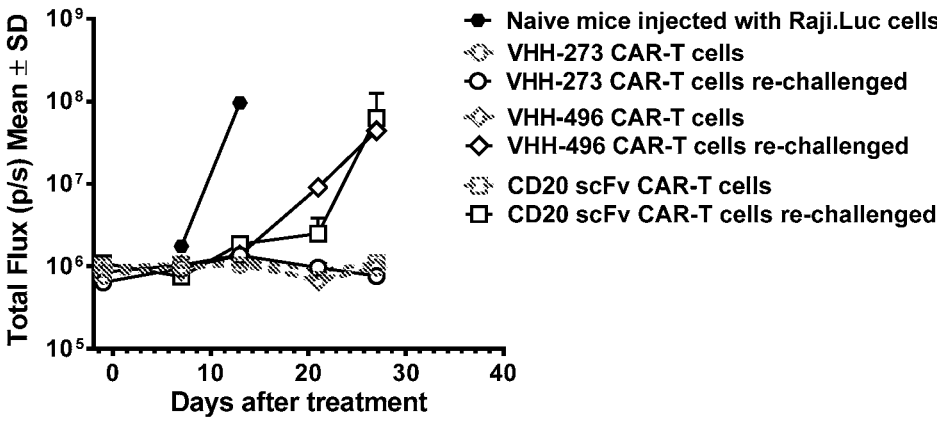
Figure 10F:
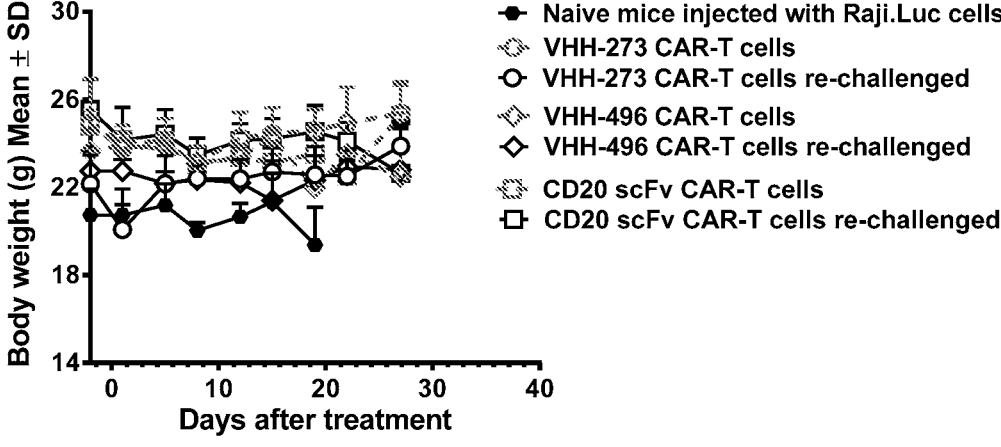

FIGS. 10A-10F show in vivo anti-tumor and re-challenging efficacy of VHH-273 CAR-T cells and VHH-496 CAR-T cells in a Raji xenograft NCG mouse model. Mice were assessed on a regular basis to monitor tumor growth by bioluminescence imaging (FIGS. 10A-10B), and body weight (FIG. 10C), as well as CAR copies in mouse peripheral blood (FIG. 10D). Then, mice at least 5 weeks tumor-free with undetectable CAR copy number (copies/ng of genomic DNA) in PBMC were selected for re-challenging assay. The Raji tumors were monitored weekly by bioluminescence imaging (FIG. 10E) and the mice body weight was measured (FIG. 10F).

Figures 11A, 11B:
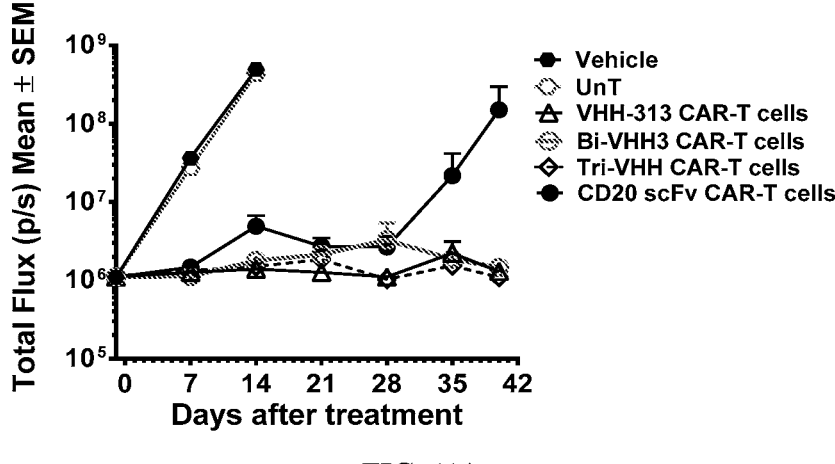
Figure 11C:
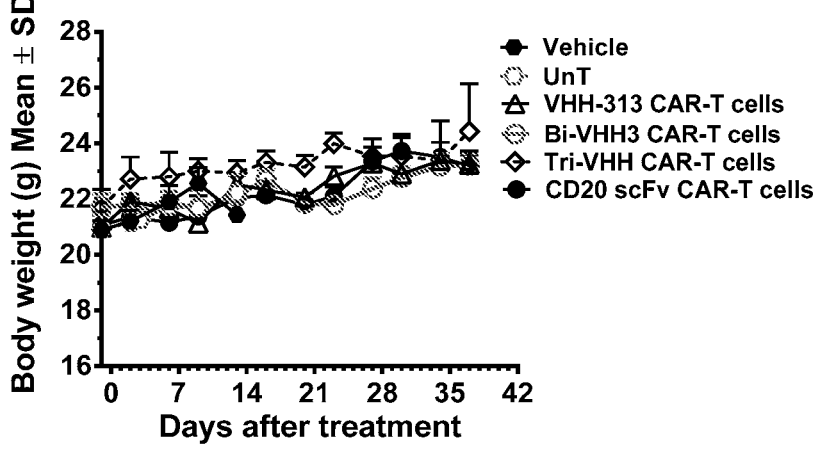
Figure 11D:
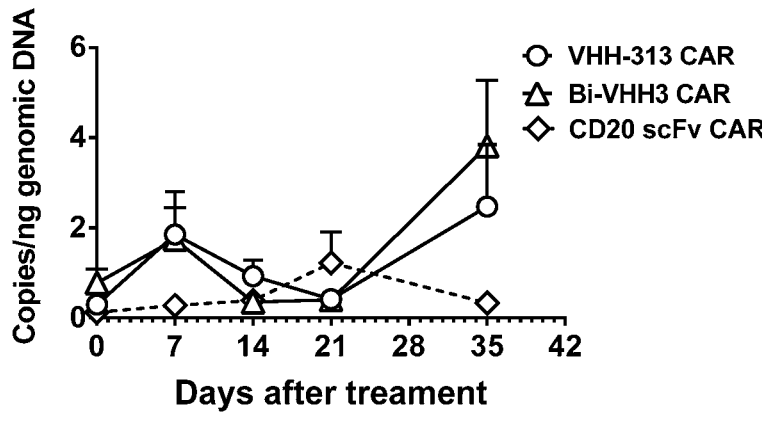

FIGS. 11A-11F show in vivo anti-tumor and re-challenging efficacy of mono-, bi- and tri-VHH CAR-T cells in a Rani xenograft NCG mouse model. Mice were assessed on a regular basis to monitor tumor growth by bioluminescence imaging (FIGS. 11A-11B), and body weight (FIG. 11C), as well as CAR copies in mouse peripheral blood (FIGS. 11D-11E; FIG. 11D is adopted from FIG. 11E and the scale of Y-axis is adjusted to enhance the resolution of copies/ng genomic DNA). Then, mice at least 6 weeks tumor-free were

Figure 11E:
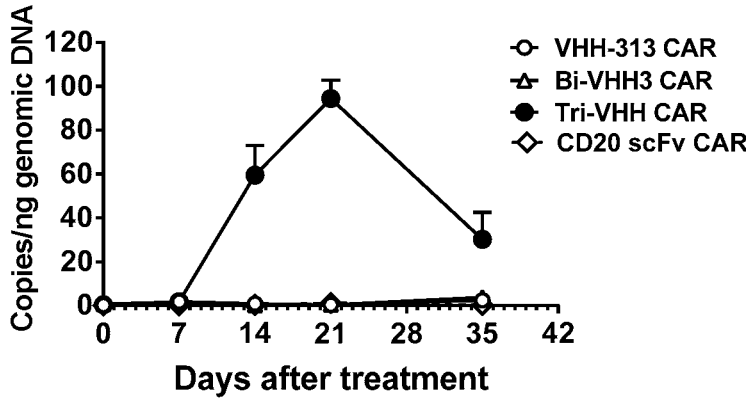
Figure 11F:
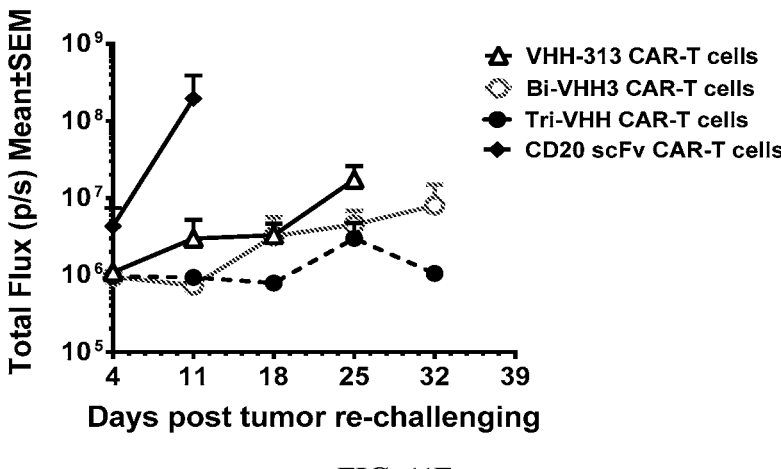

8 selected for re-challenging assay. The Raji tumors were monitored weekly by bioluminescence imaging (FIG. 11F).

FIGS. 12A-12E show the results from studies assessing binding affinities of anti-CD20 VHH-huIgG1 Fc mAbs. MFI=mean fluorescence intensity.

Figure 13A:
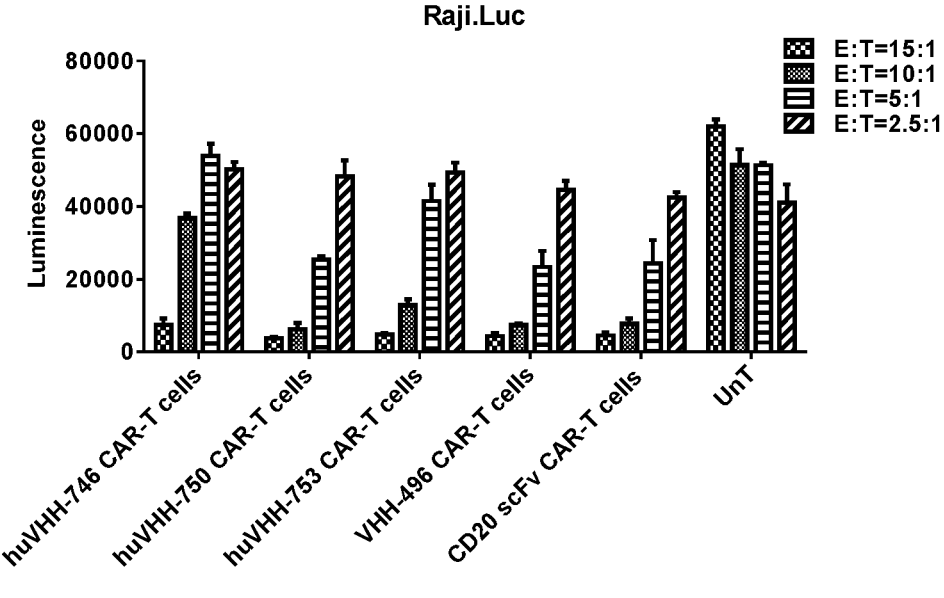
Figure 13B:
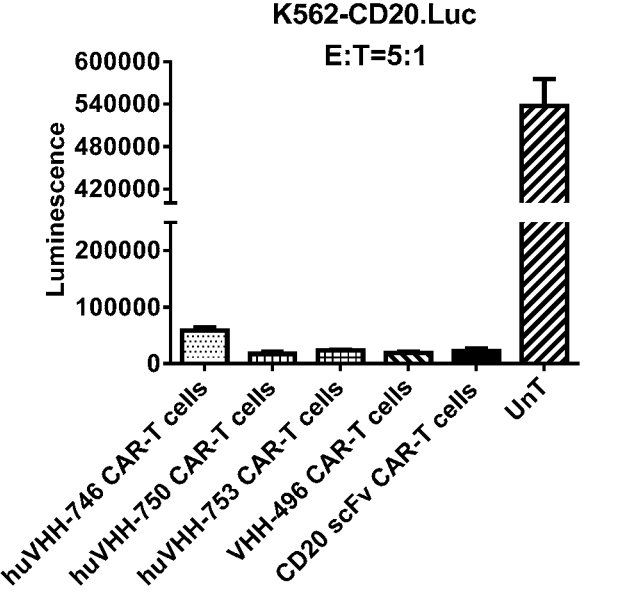
Figure 13C:
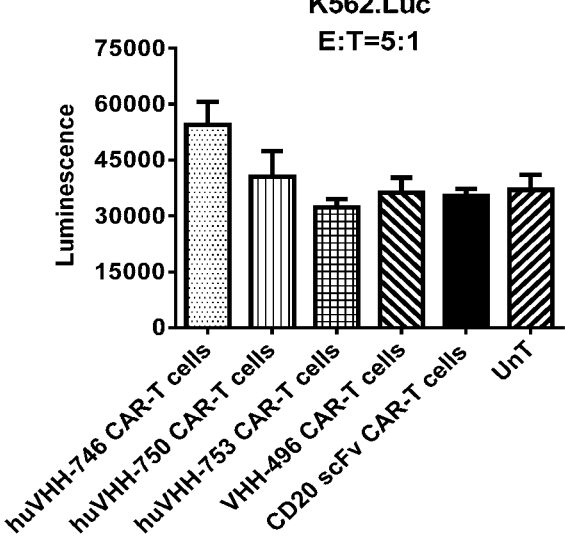
Figure 13D:
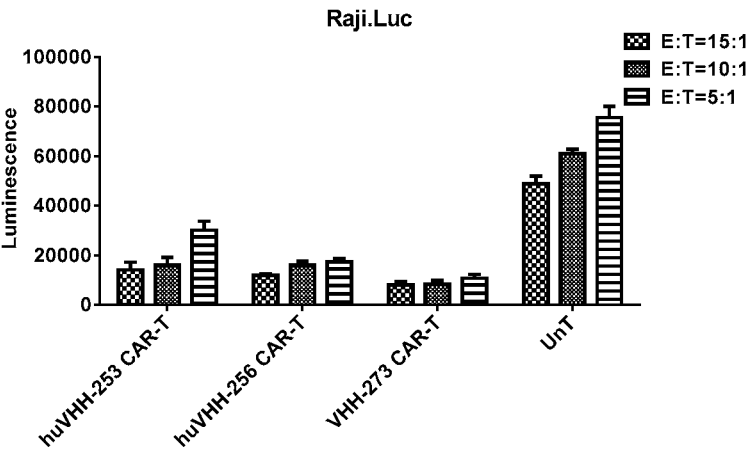
Figure 13E:
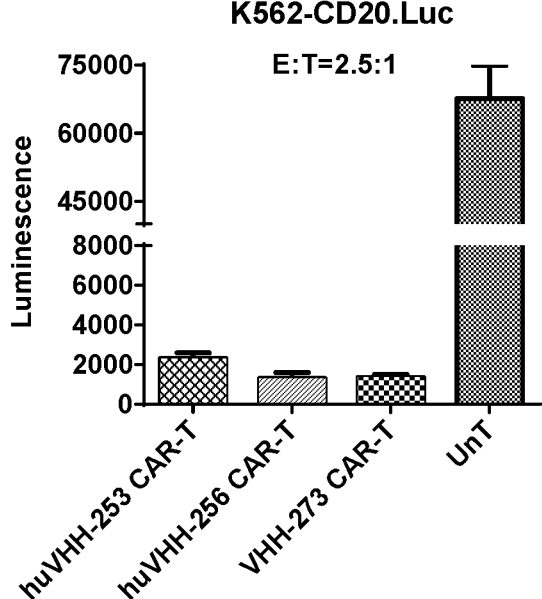
Figure 13F:
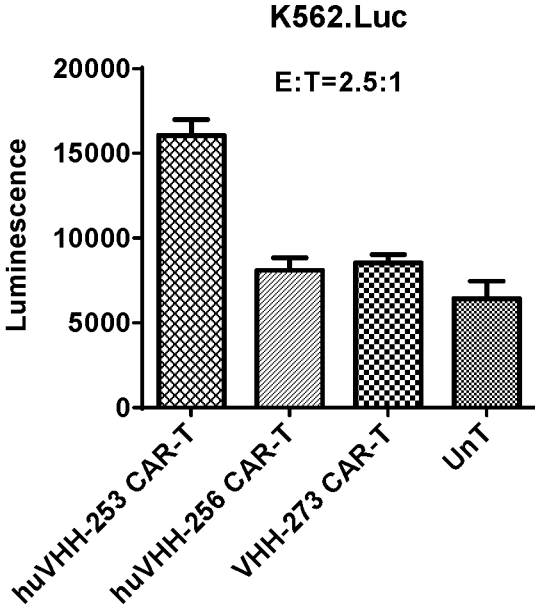
Figure 13G:
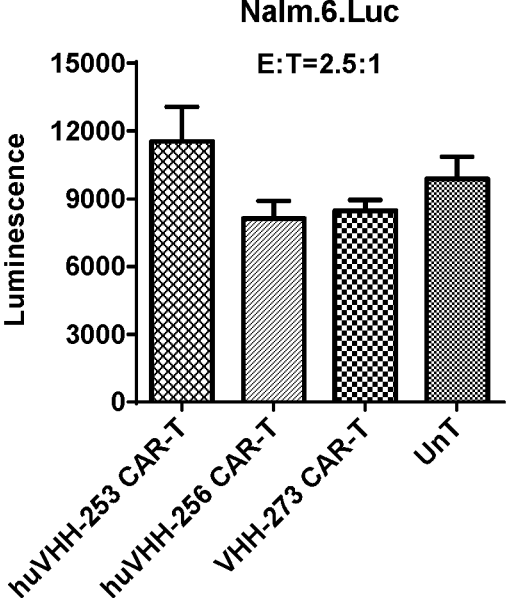
Figure 13H:
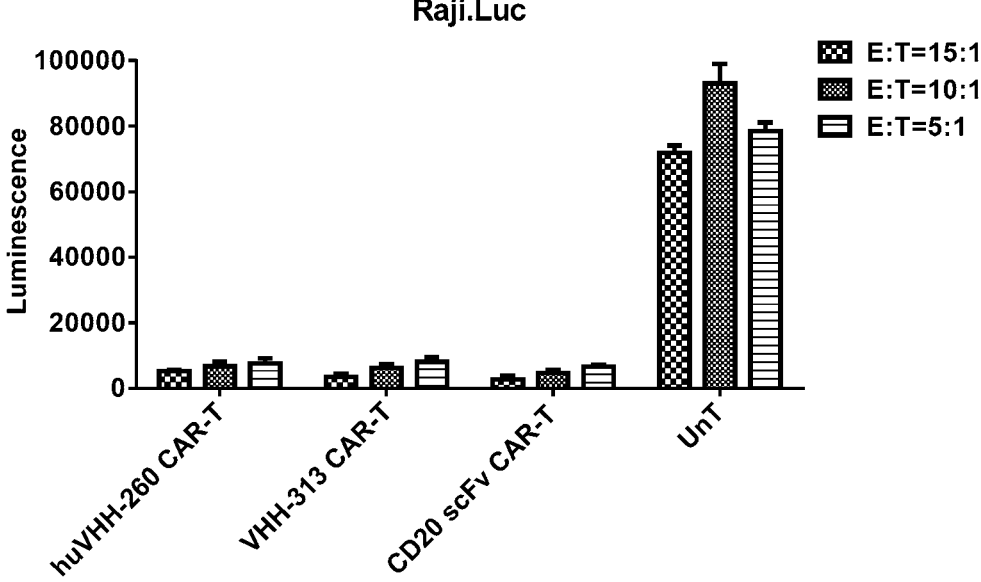
Figure 13I:
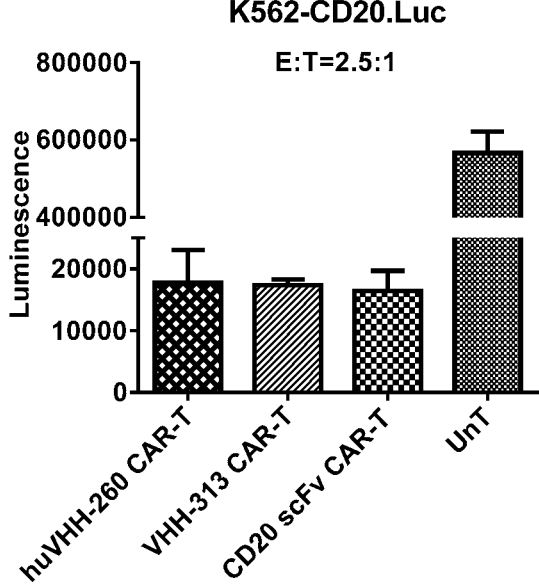
Figure 13J:
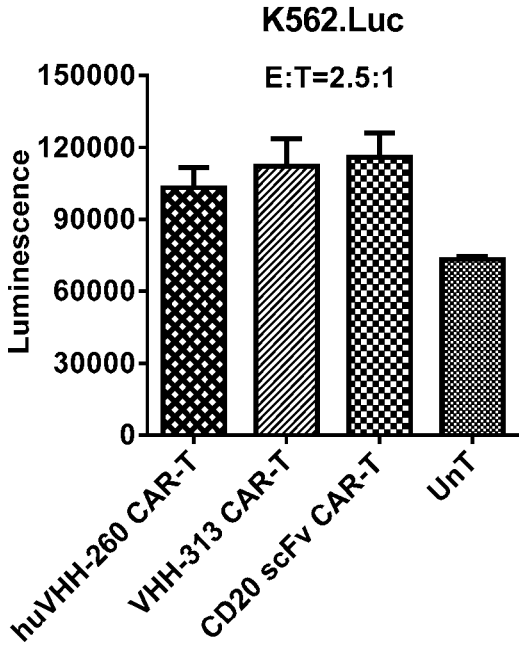
Figure 13K:
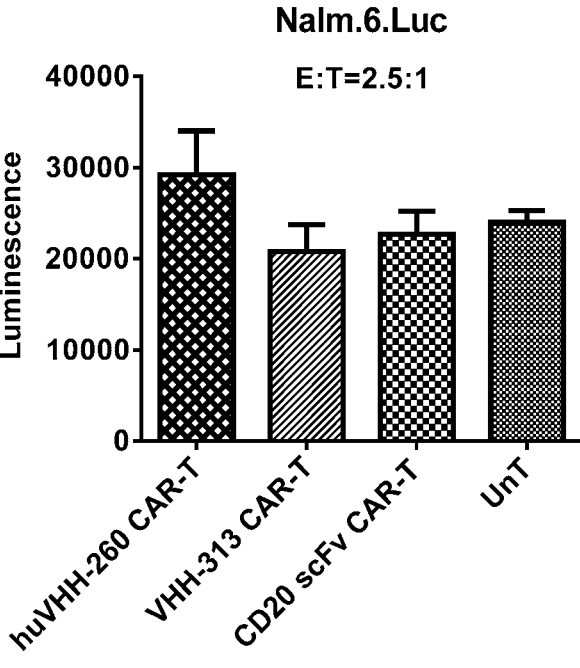

FIGS. 13A-13K show the cytotoxicity of the exemplary humanized CD20 VHH CAR-T cells against Raji.Luc cells, K652-CD20.Luc cells, K562.Luc cells and Nalm.6.Luc at different effector cells to target cells ratios (E:T) of 15:1, 10:1, 5:1 or 2.5:1. FIGS. 13A-13C show the cytotoxicity of huVHH-746 CAR-T cells, huVHH-750 CAR-T cells, and huVHH-753 CAR-T cells; FIGS. 13D-13G show the cytotoxicity of huVHH-253 CAR-T cells and huVHH-256 CAR-T cells; FIGS. 13H-13K show the cytotoxicity of huVHH-260 CAR-T cells.

5. DETAILED DESCRIPTION

The present disclosure is based in part on the novel single domain antibodies (e.g., VHH domains) that bind to CD20, chimeric antigen receptors or engineered cells comprising same, and improved properties thereof.

5.1. Definitions

Techniques and procedures described or referenced herein include those that are generally well understood and/or commonly employed using conventional methodology by those skilled in the art, such as, for example, the widely utilized methodologies described in Sambrook et al., Molecular Cloning: A Laboratory Manual (3d ed. 2001); Current Protocols in Molecular Biology (Ausubel et al. eds., 2003); Therapeutic Monoclonal Antibodies: From Bench to Clinic (An ed. 2009); Monoclonal Antibodies; *Methods and Protocols* (Albitar ed. 2010); and *Antibody Engineering* Vols 1 and 2 (Kontermann and Dübel eds., 2d ed. 2010). Unless otherwise defined herein, technical and scientific terms used in the present description have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

The term "antibody." "immunoglobulin," or "Ig" is used interchangeably herein, and is used in the broadest sense and specifically covers, for example, monoclonal antibodies (including agonist, antagonist, neutralizing antibodies, full length or intact monoclonal antibodies), antibody compositions with polyepitopic or monoepitopic specificity, polyclonal or monovalent antibodies, multivalent antibodies, multispecific antibodies (e.g., bispecific antibodies so long as they exhibit the desired biological activity), formed from at least two intact antibodies, single chain antibodies, and fragments thereof (e.g., domain antibodies), as described below. An antibody can be human, humanized, chimeric and/or affinity matured, as well as an antibody from other species, for example, mouse, rabbit, llama, etc. The term "antibody" is intended to include a polypeptide product of B cells within the immunoglobulin class of polypeptides that is able to bind to a specific molecular antigen and is composed of two identical pairs of polypeptide chains, wherein each pair has one heavy chain (about 50-70 kDa) and one light chain (about 25 kDa), each amino-terminal portion of each chain includes a variable region of about 100 to about 130 or more amino acids, and each carboxy-terminal portion of each chain includes a constant region. See. e.g., *Antibody Engineering* (Borrebaeck ed., 2d ed. 1995); and Kuby, *Immunology* (3d ed. 1997). Antibodies also include, but are not limited to, synthetic antibodies, recombinantly produced antibodies, single domain antibodies including from Camelidae species (e.g., llama or alpaca) or their humanized variants, intrabodies, anti-idiotypic (anti-Id) antibodies, and functional fragments (e.g., antigen-binding fragments) of any of the above, which refers to a portion of an antibody heavy or light chain polypeptide that retains some or all of the binding activity of the antibody from which the fragment was derived. Non-limiting examples of functional fragments (e.g., antigen-binding fragments) include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (dsFv), Fd fragments, Fv fragments, diabody, triabody, tetrabody, and minibody. In particular, antibodies provided herein include immunoglobulin molecules and immunologically active portions of immunoglobulin molecules, for example, antigen-binding domains or molecules that contain an antigen-binding site that binds to an antigen (e.g., one or more CDRs of an antibody). Such antibody fragments can be found in, for example, Harlow and Lane. *Antibodies; A Laboratory Manual* (1989); *Mol. Biology and Biotechnology: A Comprehensive Desk Reference* (Myers ed., 1995); Huston et al., 1993, Cell Biophysics 22:189-224; Plückthun and Skerra, 1989, Meth. Enzymol. 178:497-515; and Day, *Advanced Immunochemistry* (2d ed. 1990). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. Antibodies may be agonistic antibodies or antagonistic antibodies. Antibodies may be neither agonistic nor antagonistic.

An "antigen" is a structure to which an antibody can selectively bind. A target antigen may be a polypeptide, carbohydrate, nucleic acid, lipid, hapten, or other naturally occurring or synthetic compound. In some embodiments, the target antigen is a polypeptide. In certain embodiments, an antigen is associated with a cell, for example, is present on or in a cell.

An "intact" antibody is one comprising an antigen-binding site as well as a CL and at least heavy chain constant regions, CH1, CH2 and CH3. The constant regions may include human constant regions or amino acid sequence variants thereof. In certain embodiments, an intact antibody has one or more effector functions.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of the sFv, see Pluckthun in The Pharmacology of Monoclonal Antibodies, vol. 113, Rosenburg and Moore eds., Springer-Verlag, New York, pp. 269-315 (1994).

The term "heavy chain-only antibody" or "HCAb" refers to a functional antibody, which comprises heavy chains, but lacks the light chains usually found in 4-chain antibodies.Camelid animals (such as camels, llamas, or alpacas) are known to produce HCAbs.

"Single domain antibody" or "sdAb" as used herein refers to a single monomeric variable antibody domain and which is capable of antigen binding (e.g., single domain antibodies that bind to CD20). Single domain antibodies include VHH domains as described herein. Examples of single domain antibodies include, but are not limited to, antibodies naturally devoid of light chains such as those from Camelidae species (e.g., llama), single domain antibodies derived from conventional 4-chain antibodies, engineered antibodies and single domain scaffolds other than those derived from antibodies. Single domain antibodies may be derived from any species including, but not limited to mouse, human, camel, llama, goat, rabbit, and bovine. For example, a single domain antibody can be derived from antibodies raised in Camelidae species, for example in camel, llama, dromedary, alpaca and guanaco, as described herein. Other species besides Camelidae may produce heavy chain antibodies naturally devoid of light chain: VHHs derived from such other species are within the scope of the disclosure. In some embodiments, the single domain antibody (e.g., VHH) provided herein has a structure of FR1-CDR1-FR2-CDR2-FR3-CDR3-FR4. Single domain antibodies may be genetically fused or chemically conjugated to another molecule (e.g., an agent) as described herein. Single domain antibodies may be part of a bigger binding molecule (e.g., a multispecific antibody or a chimeric antigen receptor).

The terms "binds" or "binding" refer to an interaction between molecules including, for example, to form a complex. Interactions can be, for example, non-covalent interactions including hydrogen bonds, ionic bonds, hydrophobic interactions, and/or van der Waals interactions. A complex can also include the binding of two or more molecules held together by covalent or non-covalent bonds, interactions, or forces. The strength of the total non-covalent interactions between a single antigen-binding site on an antibody and a single epitope of a target molecule, such as an antigen, is the affinity of the antibody or functional fragment for that epitope. The ratio of dissociation rate ($k_{off}$) to association rate ($k_{on}$) of a binding molecule (e.g., an antibody) to a monovalent antigen ($k_{off}/k_{on}$) is the dissociation constant $K_D$, which is inversely related to affinity. The lower the $K_D$ value, the higher the affinity of the antibody. The value of $K_D$ varies for different complexes of antibody and antigen and depends on both $k_{on}$ and $k_{off}$. The dissociation constant $K_D$ for an antibody provided herein can be determined using any method provided herein or any other method well known to those skilled in the art. The affinity at one binding site does not always reflect the true strength of the interaction between an antibody and an antigen. When complex antigens containing multiple, repeating antigenic determinants, such as a polyvalent antigen, come in contact with antibodies containing multiple binding sites, the interaction of antibody with antigen at one site will increase the probability of a reaction at a second site. The strength of such multiple interactions between a multivalent antibody and antigen is called the avidity.

In connection with the binding molecules described herein terms such as "bind to," "that specifically bind to," and analogous terms are also used interchangeably herein and refer to binding molecules of antigen binding domains that specifically bind to an antigen, such as a polypeptide. A binding molecule or antigen binding domain that binds to or specifically binds to an antigen can be identified, for example, by immunoassays, Octet®, Biacore®, or other techniques known to those of skill in the art. In some embodiments, a binding molecule or antigen binding domain binds to or specifically binds to an antigen when it binds to an antigen with higher affinity than to any cross-reactive antigen as determined using experimental techniques, such as radioimmunoassay (RIA) and enzyme linked immunosorbent assay (ELISA). Typically, a specific or selective reaction will be at least twice background signal or noise and may be more than 10 times background. See, e.g., *Fundamental Immunology* 332-36 (Paul ed., 2d ed. 1989) for a discussion regarding binding specificity. In certain embodiments, the extent of binding of a binding molecule or antigen binding domain to a "non-target" protein is less than about 10% of the binding of the binding molecule or antigen binding domain to its particular target antigen, for example, as determined by fluorescence activated cell sorting (FACS) analysis or RIA. A binding molecule or antigen binding domain that binds to an antigen includes one that is capable of binding the antigen with sufficient affinity such that the binding molecule is useful, for example, as a therapeutic and/or diagnostic agent in targeting the antigen. In certain embodiments, a binding molecule or antigen binding domain that binds to an antigen has a dissociation constant $(K_D)$ of less than or equal to 1 µM, 800 nM, 600 nM, 550 nM, 500 nM, 300 nM, 250 nM, 100 nM, 50 nM, 10 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, or 0.1 nM. In certain embodiments, a binding molecule or antigen binding domain binds to an epitope of an antigen that is conserved among the antigen from different species.

In certain embodiments, the binding molecules or antigen binding domains can comprise "chimeric" sequences in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., 1984, Proc. Natl. Acad. Sci. USA 81:6851-55). Chimeric sequences may include humanized sequences.

In certain embodiments, the binding molecules or antigen binding domains can comprise portions of "humanized" forms of nonhuman (e.g., camelid, murine, non-human primate) antibodies that include sequences from human immunoglobulins (e.g., recipient antibody) in which the native CDR residues are replaced by residues from the corresponding CDR of a nonhuman species (e.g., donor antibody) such as camelid, mouse, rat, rabbit, or nonhuman primate having the desired specificity, affinity, and capacity. In some instances, one or more FR region residues of the human immunoglobulin sequences are replaced by corresponding nonhuman residues. Furthermore, humanized antibodies can comprise residues that are not found in the recipient antibody or in the donor antibody. These modifications are made to further refine antibody performance. A humanized antibody heavy or light chain can comprise substantially all of at least one or more variable regions, in which all or substantially all of the CDRs correspond to those of a nonhuman immunoglobulin and all or substantially all of the FRs are those of a human immunoglobulin sequence. In certain embodiments, the humanized antibody will comprise at least a portion of an immunoglobulin constant region (Fc), typically that of a human immunoglobulin. For further details, see, Jones et al., Nature 321: 522-25 (1986); Riechmann et al., Nature 332:323-29 (1988); Presta, Curr. Op. Struct. Biol. 2:593-96 (1992); Carter et al., Proc. Natl. Acad. Sci. USA 89:4285-89 (1992); U.S. Pat. Nos. 6,800,738; 6,719,971; 6,639,055; 6,407,213; and 6,054,297.

In certain embodiments, the binding molecules or antigen binding domains can comprise portions of a "fully human antibody" or "human antibody," wherein the terms are used interchangeably herein and refer to an antibody that comprises a human variable region and, for example, a human constant region. The binding molecules may comprise a single domain antibody sequence. In specific embodiments, the terms refer to an antibody that comprises a variable region and constant region of human origin. "Fully human" antibodies, in certain embodiments, can also encompass antibodies which bind polypeptides and are encoded by nucleic acid sequences which are naturally occurring somatic variants of human germline immunoglobulin nucleic acid sequence. The term "fully human antibody" includes antibodies having variable and constant regions corresponding to human germline immunoglobulin sequences as described by Kabat et al. (See Kabat et al. (1991) *Sequences of Proteins of Immunological Interest*, Fifth Edition, U.S. Department of Health and Human Services, NIH Publication No. 91-3242). A "human antibody" is one that possesses an amino acid sequence which corresponds to that of an antibody produced by a human and/or has been made using any of the techniques for making human antibodies. This definition of a human antibody specifically excludes a humanized antibody comprising nonhuman antigen-binding residues. Human antibodies can be produced using various techniques known in the art, including phage-display libraries (Hoogenboom and Winter, J. Mol. Biol. 227:381 (1991); Marks et al., J. Mol. Biol. 222:581 (1991)) and yeast display libraries (Chao et al., Nature Protocols 1: 755-68 (2006)). Also available for the preparation of human monoclonal antibodies are methods described in Cole et al. *Monoclonal Antibodies and Cancer Therapy* 77 (1985); Boemer et al., J. Immunol. 147(1):86-95 (1991); and van Dijk and van de Winkel, Curr. Opin. Pharmacol. 5: 368-74 (2001). Human antibodies can be prepared by administering the antigen to a transgenic animal that has been modified to produce such antibodies in response to antigenic challenge, but whose endogenous loci have been disabled, e.g., mice (see, e.g., Jakobovits, Curr. Opin. Biotechnol. 6(5):561-66 (1995); Brüggemann and Taussing, Curr. Opin. Biotechnol. 8(4):455-58 (1997); and U.S. Pat. Nos. 6,075,181 and 6,150,584 regarding XENO-MOUSE™ technology). See also, for example, Li et al., Proc. Natl. Acad. Sci. USA 103:3557-62 (2006) regarding human antibodies generated via a human B-cell hybridoma technology.

In certain embodiments, the binding molecules or antigen binding domains can comprise portions of a "recombinant human antibody," wherein the phrase includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see. e.g., Taylor. L. D. et al., *Nucl. Acids Res.* 20:6287-6295 (1992)) or antibodies prepared, expressed, created or isolated by any other means that involves splicing of human immunoglobulin gene sequences to other DNA sequences. Such recombinant human antibodies can have variable and constant regions derived from human germline immunoglobulin sequences (See Kabat, E. A. et al. (1991) *Sequences of Proteins of Immunological Interest*. Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

In certain embodiments, the binding molecules or antigen binding domains can comprise a portion of a "monoclonal antibody," wherein the term as used herein refers to an antibody obtained from a population of substantially homogeneous antibodies, e.g., the individual antibodies comprising the population are identical except for possible naturally occurring mutations that may be present in minor amounts or well-known post-translational modifications such as amino acid iomerizatio or deamidation, methionine oxidation or asparagine or glutamine deamidation, each monoclonal antibody will typically recognize a single epitope on the antigen. In specific embodiments, a "monoclonal antibody," as used herein, is an antibody produced by a single hybridoma or other cell. The term "monoclonal" is not limited to any particular method for making the antibody. For example, the monoclonal antibodies useful in the present disclosure may be prepared by the hybridoma methodology first described by Kohler et al., Nature 256:495 (1975), or may be made using recombinant DNA methods in bacterial or eukaryotic animal or plant cells (see, e.g., U.S. Pat. No. 4,816,567). The "monoclonal antibodies" may also be isolated from phage antibody libraries using the techniques described in Clackson et at, Nature 352:624-28 (1991) and Marks et al., J. Mol. Biol. 222:581-97 (1991), for example, Other methods for the preparation of clonal cell lines and of monoclonal antibodies expressed thereby are well known in the art. See. e.g., *Short Protocols in Molecular Biology* (Ausubel et al. eds., 5th ed. 2002).

A typical 4-chain antibody unit is a heterotetrameric glycoprotein composed of two identical light (L) chains and two identical heavy (H) chains. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the α and γ chains and four CH domains for μ and ε isotypes. Each L chain has at the N-terminus, a variable domain (VL) followed by a constant domain (CL) at its other end. The VL is aligned with the VH, and the CL is aligned with the first constant domain of the heavy chain (CH1). Particular amino acid residues are believed to form an interface between the light chain and heavy chain variable domains. The pairing of a VH and VL together forms a single antigen-binding site. For the structure and properties of the different classes of antibodies, see, for example, *Basic and Clinical Immunology* 71 (Stites et al. eds., 8th ed. 1994); and *Immunobiology* (Janeway et al. eds., 5th ed. 2001).

The term "Fab" or "Fab region" refers to an antibody region that binds to antigens. A conventional IgG usually comprises two Fab regions, each residing on one of the two arms of the Y-shaped IgG structure. Each Fab region is typically composed of one variable region and one constant region of each of the heavy and the light chain. More specifically, the variable region and the constant region of the heavy chain in a Fab region are VH and CH1 regions, and the variable region and the constant region of the light chain in a Fab region are VL and CL regions. The VH, CH1, VL, and CL in a Fab region can be arranged in various ways to confer an antigen binding capability according to the present disclosure. For example, VH and CH1 regions can be on one polypeptide, and VL and CL regions can be on a separate polypeptide, similarly to a Fab region of a conventional IgG. Alternatively, VH, CH1, VL and CL regions can all be on the same polypeptide and oriented in different orders as described in more detail the sections below.

The term "variable region," "variable domain," "V region," or "V domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases form part of, the β sheet structure. The hypervariable regions in each chain are held together in close proximity by the FRs and, with the hypervariable regions from the other chain, contribute to the formation of the antigen-binding site of antibodies (see, e.g., Kabat et al., *Sequences of Proteins of Immunological Interest* (5th ed. 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. In specific embodiments, the variable region is a human variable region.

The term "variable region residue numbering according to Kabat" or "amino acid position numbering as in Kabat", and variations thereof, refer to the numbering system used for heavy chain variable regions or light chain variable regions of the compilation of antibodies in Kabat et al., supra. Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Other numbering systems have been described, for example, by AbM, Chothia, Contact, IMGT, and AHon The term "heavy chain" when used in reference to an antibody refers to a polypeptide chain of about 50-70 kDa, wherein the amino-terminal portion includes a variable region of about 120 to 130 or more amino acids, and a carboxy-terminal portion includes a constant region. The constant region can be one of five distinct types, (e.g., isotypes) referred to as alpha (α), delta (δ), epsilon (ε), gamma (γ), and mu (μ), based on the amino acid sequence of the heavy chain constant region. The distinct heavy chains differ in size: α, δ, and γ contain approximately 450 amino acids, while μ and ε contain approximately 550 amino acids. When combined with a light chain, these distinct types of heavy chains give rise to five well known classes (e.g., isotypes) of antibodies, IgA, IgD, IgE, IgG, and IgM, respectively, including four subclasses of IgG, namely IgG1, IgG2, IgG3, and IgG4.

The term "light chain" when used in reference to an antibody refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. There are two distinct types, referred to as kappa (κ) or lambda (λ) based on the amino acid sequence of the constant domains.

As used herein, the terms "hypervariable region," "HVR," "Complementarity Determining Region," and "CDR" are used interchangeably. A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences.

Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see. e.g., Antibody Engineering Vol. 2 (Kontermann and Dübel eds., 2d ed. 2010)). The "contact" hypervariable regions are based on an analysis of the available complex crystal structures. Another universal numbering system that has been developed and widely adopted is ImMunoGeneTics (IMGT) Information System® (Lafranc et al., Dev. Comp. Immunol. 27(1):55-77 (2003)). IMGT is an integrated information system specializing in immunoglobulins (IG), T-cell receptors (TCR), and major histocompatibility complex (MHC) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. An additional numbering system (AHon) has been developed by Honegger and Pluckthun, J. Mol. Biol. 309: 657-70 (2001). Correspondence between the numbering system, including, for example, the Kabat numbering and the IMGT unique numbering system, is well known to one skilled in the art (see. e.g., Kabat, supra; Chothia and Lesk, supra; Martin, supra; Lefranc et al., supra). The residues from each of these hypervariable regions or CDRs are exemplified in Table 1 below.

TABLE 1

Exemplary CDRs According to Various Numbering Systems

| Loop | Kabat | AbM | Chothia | Contact | IMGT |
|---|---|---|---|---|---|
| CDR L1 | L24--L34 | L24--L34 | L26--L32 or L24--L34 | L30-L36 | L27-L38 |
| CDR L2 | L50-L56 | L50-L56 | L50-L52 or L50-L56 | L46-L55 | L56-L65 |
| CDR L3 | L89-L97 | L89-197 | L91--L96 or L89-L97 | L89-L96 | L105-L117 |
| CDR H1 | H31-H35B (Kabat Numbering) | H26--H35B | H26--H32 . . . 34 | H30--H35B | H27-H38 |
| CDR H1 | H31-H35 (Chothia Numbering) | H26--H35 | H26--H32 | H30--H35 | |
| CDR H2 | H50--H65 | H50--H58 | H53--H55 or H52--H56 | H47--H58 | H56-H65 |
| CDR H3 | H95-H102 | H95-H102 | H96-H101 or H95-H102 | H93--H101 | H105-H117 |

CDR regions are well known to those skilled in the art and have been defined by well-known numbering systems. For example, the Kabat Complementarity Determining Regions (CDRs) are based on sequence variability and are the most commonly used (see. e.g., Kabat et al., supra). Chothia refers instead to the location of the structural loops (see, e.g., Chothia and Lesk, J. Mol. Biol. 196:901-17 (1987)). The end of the Chothia CDR-H1 loop when numbered using the The boundaries of a given CDR may vary depending on the scheme used for identification. Thus, unless otherwise specified, the terms "CDR" and "complementary determining region" of a given antibody or region thereof, such as a variable region, as well as individual CDRs (e.g., CDR-H1, CDR-H2) of the antibody or region thereof, should be understood to encompass the complementary determining region as defined by any of the known schemes described herein above. In some instances, the scheme for identification of a particular CDR or CDRs is specified, such as the CDR as defined by the IMGT, Kabat, Chothia, or Contact method. In some instances, one or more positions according to the Kabat numbering may not be occupied in the actual sequence, or the actual sequence may contain more amino acid residues than the number allowed for by the Kabat numbering. See. e.g., Deschacht et al., 2010. J Immunol 184: 5696-704 for an exemplary numbering for VHH domains according to Kabat. In other cases, the particular amino acid sequence of a CDR is given. It should be noted CDR regions may also be defined by a combination of various numbering systems, e.g., a combination of Kabat and Chothia numbering systems, or a combination of Kabat and IMGT numbering systems. Therefore, the term such as "a CDR as set forth in a specific VH or VHH" includes any CDR1 as defined by the exemplary CDR numbering systems described above, but is not limited thereby. Once a variable region (e.g., a VHH, VH or VL) is given, those skilled in the art would understand that CDRs within the region can be defined by different numbering systems or combinations thereof.

Hypervariable regions may comprise "extended hypervariable regions" as follows: 24-36 or 24-34 (L1), 46-56 or 50-56 (L2), and 89-97 or 89-96 (L3) in the VL, and 26-35 or 26-35A (H1), 50-65 or 49-65 (H2), and 93-102, 94-102, or 95-102 (H3) in the VH.

The term "constant region" or "constant domain" refers to a carboxy terminal portion of the light and heavy chain which is not directly involved in binding of the antibody to antigen but exhibits various effector function, such as interaction with the Fc receptor. The term refers to the portion of an immunoglobulin molecule having a more conserved amino acid sequence relative to the other portion of the immunoglobulin, the variable region, which contains the antigen binding site. The constant region may contain the CH1, CH2, and CH3 regions of the heavy chain and the CL region of the light chain.

The term "framework" or "FR" refers to those variable region residues flanking the CDRs. FR residues are present, for example, in chimeric, humanized, human, domain antibodies (e.g., single domain antibodies), diabodies, linear antibodies, and bispecific antibodies. FR residues are those variable domain residues other than the hypervariable region residues or CDR residues.

The term "Fc region" herein is used to define a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. A "functional Fc region" possesses an "effector function" of a native sequence Fc region. Exemplary "effector functions" include Clq binding; CDC; Fc receptor binding; ADCC; phagocytosis; downregulation of cell surface receptors (e.g., B cell receptor), etc. Such effector functions generally require the Fc region to be combined with a binding region or binding domain (e.g., an antibody variable region or domain) and can be assessed using various assays known to those skilled in the art. A "variant Fc region" comprises an amino acid sequence which differs from that of a native sequence Fc region by virtue of at least one amino acid modification (e.g., substituting, addition, or deletion). In certain embodiments, the variant Fc region has at least one amino acid substitution compared to a native sequence Fc region or to the Fc region of a parent polypeptide, for example, from about one to about ten amino acid substitutions, or from about one to about five amino acid substitutions in a native sequence Fc region or in the Fc region of a parent polypeptide. The variant Fc region herein can possess at least about 80% homology with a native sequence Fc region and/or with an Fc region of a parent polypeptide, or at least about 90% homology therewith, for example, at least about 95% homology therewith.

As used herein, an "epitope" is a term in the art and refers to a localized region of an antigen to which a binding molecule (e.g., an antibody comprising a single domain antibody sequence) can specifically bind. An epitope can be a linear epitope or a conformational, non linear, or discontinuous epitope. In the case of a polypeptide antigen, for example, an epitope can be contiguous amino acids of the polypeptide (a "linear" epitope) or an epitope can comprise amino acids from two or more non-contiguous regions of the polypeptide (a "conformational," "non-linear" or "discontinuous" epitope). It will be appreciated by one of skill in the art that, in general, a linear epitope may or may not be dependent on secondary, tertiary, or quaternary structure. For example, in some embodiments, a binding molecule binds to a group of amino acids regardless of whether they are folded in a natural three dimensional protein structure. In other embodiments, a binding molecule requires amino acid residues making up the epitope to exhibit a particular conformation (e.g., bend, twist, turn or fold) in order to recognize and bind the epitope.

A "blocking" antibody or an "antagonist" antibody is one that inhibits or reduces a biological activity of the antigen it binds. In some embodiments, blocking antibodies or antagonist antibodies substantially or completely inhibit the biological activity of the antigen.

An "agonist" or activating antibody is one that enhances or initiates signaling by the antigen to which it binds. In some embodiments, agonist antibodies cause or activate signaling without the presence of the natural ligand.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

The term "specificity" refers to selective recognition of an antigen binding protein (such as a CAR or an sdAb) for a particular epitope of an antigen. Natural antibodies, for example, are monospecific. The term "multispecific" as used herein denotes that an antigen binding protein (such as a CAR or an sdAb) has two or more antigen-binding sites of which at least two bind different antigens. "Bispecific" as used herein denotes that an antigen binding protein (such as a CAR or an sdAb) has two different antigen-binding specificities. The term "monospecific" CARas used herein denotes an antigen binding protein (such as a CAR or an sdAb) that has one or more binding sites each of which bind the same antigen.

The term "valent" as used herein denotes the presence of a specified number of binding sites in an antigen binding protein (such as a CAR or an sdAb). A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein (such as a CAR or an sdAb).

"Chimeric antigen receptor" or "CAR" as used herein refers to genetically engineered receptors, which can be used to graft one or more antigen specificity onto immune effector cells, such as T cells. Some CARs are also known as "artificial T-cell receptors," "chimeric T cell receptors." or "chimeric immune receptors." In some embodiments, the CAR comprises an extracellular antigen binding domain specific for one or more antigens (such as tumor antigens), a transmembrane domain, and an intracellular signaling domain of a T cell and/or other receptors. "CAR-T cell" refers to a T cell that expresses a CAR.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because the polypeptides of this disclosure may be based upon antibodies or other members of the immunoglobulin superfamily, in certain embodiments, a "polypeptide" can occur as a single chain or as two or more associated chains.

"Polynucleotide" or "nucleic acid," as used interchangeably herein, refers to polymers of nucleotides of any length and includes DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. "Oligonucleotide," as used herein, refers to short, generally single-stranded, synthetic polynucleotides that are generally, but not necessarily, fewer than about 200 nucleotides in length. The terms "oligonucleotide" and "polynucleotide" are not mutually exclusive. The description above for polynucleotides is equally and fully applicable to oligonucleotides. A cell that produces a binding molecule of the present disclosure may include a parent hybridoma cell, as well as bacterial and eukaryotic host cells into which nucleic acids encoding the antibodies have been introduced. Unless specified otherwise, the left-hand end of any single-stranded polynucleotide sequence disclosed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences"; sequence regions on the DNA strand having the same sequence as the RNA transcript that are 3' to the 3' end of the RNA transcript are referred to as "downstream sequences."

An "isolated nucleic acid" is a nucleic acid, for example, an RNA, DNA, or a mixed nucleic acids, which is substantially separated from other genome DNA sequences as well as proteins or complexes such as ribosomes and polymerases, which naturally accompany a native sequence. An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, one or more nucleic acid molecules encoding a single domain antibody or an antibody as described herein are isolated or purified. The term embraces nucleic acid sequences that have been removed from their naturally occurring environment, and includes recombinant or cloned DNA isolates and chemically synthesized analogues or analogues biologically synthesized by heterologous systems. A substantially pure molecule may include isolated forms of the molecule. Specifically, an "isolated" nucleic acid molecule encoding a CAR or an sdAb described herein is a nucleic acid molecule that is identified and separated from at least one contaminant nucleic acid molecule with which it is ordinarily associated in the environment in which it was produced.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

As used herein, the term "operatively linked," and similar phrases (e.g., genetically fused), when used in reference to nucleic acids or amino acids, refer to the operational linkage of nucleic acid sequences or amino acid sequence, respectively, placed in functional relationships with each other. For example, an operatively linked promoter, enhancer elements, open reading frame, 5' and 3' UTR, and terminator sequences result in the accurate production of a nucleic acid molecule (e.g., RNA). In some embodiments, operatively linked nucleic acid elements result in the transcription of an open reading frame and ultimately the production of a polypeptide (i.e., expression of the open reading frame). As another example, an operatively linked peptide is one in which the functional domains are placed with appropriate distance from each other to impart the intended function of each domain.

The term "vector" refers to a substance that is used to carts' or include a nucleic acid sequence, including for example, a nucleic acid sequence encoding a binding molecule (e.g., an antibody) as described herein, in order to introduce a nucleic acid sequence into a host cell. Vectors applicable for use include, for example, expression vectors, plasmids, phage vectors, viral vectors, episomes, and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like, which are well known in the art. When two or more nucleic acid molecules are to be co-expressed (e.g., both an antibody heavy and light chain or an antibody VH and VL), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, immunoblotting for expression of gene products, or other suitable analytical methods to test the expression of an introduced nucleic acid sequence or its corresponding gene product. It is understood by those skilled in the art that the nucleic acid molecules are expressed in a sufficient amount to produce a desired product and it is further understood that expression levels can be optimized to obtain sufficient expression using methods well known in the art.

The term "host" as used herein refers to an animal, such as a mammal (e.g., a human).

The term "host cell" as used herein refers to a particular subject cell that may be transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "autologous" is meant to refer to any material derived from the same individual to whom it is later to be re-introduced into the individual.

"Allogeneic" refers to a graft derived from a different individual of the same species.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "pharmaceutically acceptable" as used herein means being approved by a regulatory agency of the Federal or a state government, or listed in *United States Pharmacopeia, European Pharmacopeia*, or other generally recognized Pharmacopeia for use in animals, and more particularly in humans.

"Excipient" means a pharmaceutically-acceptable material, composition, or vehicle, such as a liquid or solid filler, diluent, solvent, or encapsulating material. Excipients include, for example, encapsulating materials or additives such as absorption accelerators, antioxidants, binders, buffers, carriers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof. The term "excipient" can also refer to a diluent, adjuvant (e.g., Freunds' adjuvant (complete or incomplete) or vehicle.

In some embodiments, excipients are pharmaceutically acceptable excipients. Examples of pharmaceutically acceptable excipients include buffers, such as phosphate, citrate, and other organic acids; antioxidants, including ascorbic acid; low molecular weight (e.g., fewer than about 10 amino acid residues) polypeptide; proteins, such as serum albumin, gelatin, or immunoglobulins; hydrophilic polymers, such as polyvinylpyrrolidone; amino acids, such as glycine, glutamine, asparagine, arginine, or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN™, polyethylene glycol (PEG), and PLURONICS™. Other examples of pharmaceutically acceptable excipients are described in Remington and Gennaro, *Remington's Pharmaceutical Sciences* (18th ed. 1990).

In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., Lippincott Williams & Wilkins: Philadelphia, PA, 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, FL, 2009. In some embodiments, pharmaceutically acceptable excipients are nontoxic to the cell or mammal being exposed thereto at the dosages and concentrations employed. In some embodiments, a pharmaceutically acceptable excipient is an aqueous pH buffered solution.

In some embodiments, excipients are sterile liquids, such as water and oils, including those of petroleum, animal, vegetable, or synthetic origin, such as peanut oil, soybean oil, mineral oil, sesame oil, and the like. Water is an exemplary excipient when a composition (e.g., a pharmaceutical composition) is administered intravenously. Saline solutions and aqueous dextrose and glycerol solutions can also be employed as liquid excipients, particularly for injectable solutions. An excipient can also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents. Compositions can take the form of solutions, suspensions, emulsion, tablets, pills, capsules, powders, sustained-release formulations, and the like. Oral compositions, including formulations, can include standard excipients such as pharmaceutical grades of mannitol, lactose, starch, magnesium stearate, sodium saccharine, cellulose, magnesium carbonate, etc.

Compositions, including pharmaceutical compounds, may contain a binding molecule (e.g., an antibody), for example, in isolated or purified form, together with a suitable amount of excipients.

The term "effective amount" or "therapeutically effective amount" as used herein refers to the amount of a single domain antibody or a therapeutic molecule comprising an agent and the single domain antibody or pharmaceutical composition provided herein which is sufficient to result in the desired outcome.

The terms "subject" and "patient" may be used interchangeably. As used herein, in certain embodiments, a subject is a mammal, such as a non-primate or a primate (e.g., human). In specific embodiments, the subject is a human. In one embodiment, the subject is a mammal, e.g., a human, diagnosed with a disease or disorder. In another embodiment, the subject is a mammal, e.g., a human, at risk of developing a disease or disorder.

"Administer" or "administration" refers to the act of injecting or otherwise physically delivering a substance as it exists outside the body into a patient, such as by mucosal, intradermal, intravenous, intramuscular delivery, and/or any other method of physical delivery described herein or known in the art.

As used herein, the terms "treat," "treatment" and "treating" refer to the reduction or amelioration of the progression, severity, and/or duration of a disease or condition resulting from the administration of one or more therapies. Treating may be determined by assessing whether there has been a decrease, alleviation and/or mitigation of one or more symptoms associated with the underlying disorder such that an improvement is observed with the patient, despite that the patient may still be afflicted with the underlying disorder. The term "treating" includes both managing and ameliorating the disease. The terms "manage," "managing," and "management" refer to the beneficial effects that a subject derives from a therapy which does not necessarily result in a cure of the disease.

The terms "prevent," "preventing," and "prevention" refer to reducing the likelihood of the onset (or recurrence) of a disease, disorder, condition, or associated symptom(s) (e.g., diabetes or a cancer).

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

"B cell associated disease or disorder" as used herein refers to a disease or disorder mediated by B cells or conferred by abnormal B cell functions (such as dysregulation of B-cell function). "B cell associated disease or disorder" as used herein includes but not limited to a B cell malignancy such as a B cell leukemia or B cell lymphoma. It also includes marginal zone lymphoma (e.g., splenic marginal zone lymphoma), diffuse large B cell lymphoma (DLBCL), mantle cell lymphoma (MCL), primary central nervous system (CNS) lymphoma, primary mediastinal B cell lymphoma (PMBL), small lymphocytic lymphoma (SLL), B cell prolymphocytic leukemia (B-PLL), follicular lymphoma (FL), burkitt lymphoma, primary intraocular lymphoma, chronic lymphocytic leukemia (CLL), acute lymphoblastic leukemia (ALL), hairy cell leukemia (HCL), precursor B lymphoblastic leukemia, non-hodgkin lymphoma (NHL), high-grade B-cell lymphoma (HGBL), and multiple myelomia (MM). "B cell associated disease or disorder" also includes certain autoimmune and/or inflammatory disease, such as those associated with inappropriate or enhanced B cell numbers and/or activation.

"CD20 associated disease or disorder" as used herein refers to a disease or disorder that comprises a cell or tissue in which CD20 is expressed. In some embodiments. CD20 associated disease or disorder comprises a cell on which CD20 is abnormally expressed. In other embodiments, CD20 associated disease or disorder comprises a cell in or on which CD20 is deficient.

The terms "about" and "approximately" mean within 20%, within 15%, within 10%, within 9%, within 8%, within 7%, within 6%, within 5%, within 4%, within 3%, within 2%, within 1%, or less of a given value or range.

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "between" as used in a phrase as such "between A and B" or "between A-B" refers to a range including both A and B.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

5.2. Single Domain Antibodies

5.2.1. Single Domain Antibodies that Bind to CD20

In one aspect, provided herein are single domain antibodies (e.g., VHH domains) capable of binding to CD20.

In some embodiments, the single domain antibodies (e.g., VHH domains) provided herein bind to human CD20. In some embodiments, the anti-CD20 single domain antibody provided herein modulates one or more CD20 activities. In some embodiments, the anti-CD20 single domain antibody provided herein is an antagonist antibody.

In some embodiments, the anti-CD20 single domain antibody provided herein binds to CD20 (e.g., human CD20) with a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-9}$M to $10^{-13}$M, e.g., from $10^{-9}$M to $10^{-13}$ M). A variety of methods of measuring binding affinity are known in the art, any of which can be used for purposes of the present disclosure, including by RIA, for example, performed with the Fab version of an antibody of interest and its antigen (Chen et al., 1999, J. Mol Biol 293:865-81); by biolayer interferometry (BLI) or surface plasmon resonance (SPR) assays by Octet®, using, for example, an Octet®Red96 system, or by Biacore®, using, for example, a Biacore®TM-2000 or a Biacoreit®TM-3000. An "on-rate" or "rate of association" or "association rate" or "kon" may also be determined with the same biolayer interferometry (BLI) or surface plasmon resonance (SPR) techniques described above using, for example, the Octet®Red96, the Biacore®TM-2000, or the Biacore®TM-3000 system.

In some embodiments, the anti-CD20 single domain antibodies provided herein are VHH domains. Exemplary VHH domains provided herein are generated as described below in Section 6, and these VHH domains are referred to as VHH-273, VHH-283, VHH-313, VHH-440, VHH-466, VHH-496, VHH-653, huVHH-253, huVHH-256, huVHH-260, huVHH-746, huVHH-750, huVHH-753, huVHH-836, huVHH-840, huVHH-843, huVHH-846, 2082H1, 2082H2, 2082H3, 2082H4, 2082H5, 2082H6, VHH-623, VHH-640, and/or VHH-657 as also shown in Table 2 below.

Thus, in some embodiments, the single domain antibody provided herein comprises one or more CDR sequences of any one of VHH-273. VHH-283, VHH-313, VHH-440, VHH-466, VHH-496, VHH-653, huVHH-253, huVHH-256, huVHH-260, huVHH-746, huVHH-750, huVHH-753, huVHH-836, huVHH-840, huVHH-843, huVHH-846, 2082H1, 2082H2, 2082H3, 2082H4, 2082H5, 2082H6, VHH-623, VHH-640, and/or VHH-657. In some embodiments, provided herein is a single domain antibody that binds to CD20 comprising the following structure: FR1-CDR1-FR2-CDR2-FR3-CDR3-FR4, wherein the CDR sequences are selected from those in VHH-273, VHH-283, VHH-313, VHH-440, VHH-466, VHH-496, VHH-653, huVHH-253, huVHH-256, huVHH-260, huVHH-746, huVHH-750, huVHH-753, huVHH-836, huVHH-840, huVHH-843, huVHH-846, 2082H1, 2082H2, 2082H3, 2082H4, 2082H5, 2082H6, VHH-623, VHH-640, and/or VHH-657.

TABLE 2

Exemplary Single Domain Antibodies

| Clone ID | VHH Domain | CDR1 | CDR2 | CDR3 |
|---|---|---|---|---|
| VHH-273 | SEQ ID NO: 41 | SEQ ID NO: 1 or 195 | SEQ ID NO: 2 | SEQ ID NO: 3 |
| | | SEQ ID NO: 4 | SEQ ID NO: 5 | SEQ ID NO: 6 |
| VHH-283 | SEQ ID NO: 42 | SEQ ID NO: 1 or 195 | SEQ ID NO: 7 | SEQ ID NO: 8 |
| | | SEQ ID NO: 4 | SEQ ID NO: 9 | SEQ ID NO: 10 |
| VHH-313 | SEQ ID NO: 43 | SEQ ID NO: 11 or 196 | SEQ ID NO: 12 | SEQ ID NO: 8 |
| | | SEQ ID NO: 13 | SEQ ID NO: 9 | SEQ ID NO: 10 |
| VHH-440 | SEQ ID NO: 44 | SEQ ID NO: 14 or 197 | SEQ ID NO: 15 | SEQ ID NO: 16 |
| | | SEQ ID NO: 17 | SEQ ID NO: 18 | SEQ ID NO: 19 |
| VHH-466 | SEQ ID NO: 45 | SEQ ID NO: 20 or 197 | SEQ ID NO: 21 | SEQ ID NO: 16 |
| | | SEQ ID NO: 22 | SEQ ID NO: 23 | SEQ ID NO: 19 |
| VHH-496 | SEQ ID NO: 46 | SEQ ID NO: 24 or 198 | SEQ ID NO: 25 | SEQ ID NO: 26 |
| | | SEQ ID NO: 27 | SEQ ID NO: 28 | SEQ ID NO: 29 |
| VHH-653 | SEQ ID NO: 47 | SEQ ID NO: 14 or 197 | SEQ ID NO: 30 | SEQ ID NO: 16 |
| | | SEQ ID NO: 17 | SEQ ID NO: 31 | SEQ ID NO: 19 |
| huVHH-253 | SEQ ID NO: 48 | SEQ ID NO: 1 or 195 | SEQ ID NO: 32 | SEQ ID NO: 3 |
| | | SEQ ID NO: 4 | SEQ ID NO: 33 | SEQ ID NO: 6 |
| huVHH-256 | SEQ ID NO: 49 | SEQ ID NO: 1 or 195 | SEQ ID NO: 2 | SEQ ID NO: 3 |
| | | SEQ ID NO: 4 | SEQ ID NO: 33 | SEQ ID NO: 6 |
| huVHH-260 | SEQ ID NO: 50 | SEQ ID NO: 11 or 196 | SEQ ID NO: 12 | SEQ ID NO: 8 |
| | | SEQ ID NO: 13 | SEQ ID NO: 9 | SEQ ID NO: 10 |
| huVHH-746 | SEQ ID NO: 51 | SEQ ID NO: 24 or 198 | SEQ ID NO: 25 | SEQ ID NO: 26 |
| | | SEQ ID NO: 27 | SEQ ID NO: 28 | SEQ ID NO: 29 |
| huVHH-750 | SEQ ID NO: 52 | SEQ ID NO: 24 or 198 | SEQ ID NO: 25 | SEQ ID NO: 26 |
| | | SEQ ID NO: 27 | SEQ ID NO: 28 | SEQ ID NO: 29 |
| huVHH-753 | SEQ ID NO: 53 | SEQ ID NO: 24 or 198 | SEQ ID NO: 25 | SEQ ID NO: 26 |
| | | SEQ ID NO: 27 | SEQ ID NO: 28 | SEQ ID NO: 29 |
| huVHH-836 | SEQ ID NO: 54 | SEQ ID NO: 20 or 197 | SEQ ID NO: 34 | SEQ ID NO: 16 |
| | | SEQ ID NO: 22 | SEQ ID NO: 35 | SEQ ID NO: 19 |
| huVHH-840 | SEQ ID NO: 55 | SEQ ID NO: 20 or 197 | SEQ ID NO: 36 | SEQ ID NO: 16 |
| | | SEQ ID NO: 22 | SEQ ID NO: 23 | SEQ ID NO: 19 |
| huVHH-843 | SEQ ID NO: 56 | SEQ ID NO: 20 or 197 | SEQ ID NO: 37 | SEQ ID NO: 16 |
| | | SEQ ID NO: 22 | SEQ ID NO: 23 | SEQ ID NO: 19 |
| huVHH-846 | SEQ ID NO: 57 | SEQ ID NO: 20 or 197 | SEQ ID NO: 38 | SEQ ID NO: 16 |
| | | SEQ ID NO: 22 | SEQ ID NO: 23 | SEQ ID NO: 19 |
| 2082H1 | SEQ ID NO: 58 | SEQ ID NO: 1 or 195 | SEQ ID NO: 2 | SEQ ID NO: 3 |
| | | SEQ ID NO: 4 | SEQ ID NO: 33 | SEQ ID NO: 6 |
| 2082H2 | SEQ ID NO: 59 | SEQ ID NO: 1 or 195 | SEQ ID NO: 2 | SEQ ID NO: 3 |
| | | SEQ ID NO: 4 | SEQ ID NO: 33 | SEQ ID NO: 39 |
| 2082H3 | SEQ ID NO: 60 | SEQ ID NO: 1 or 195 | SEQ ID NO: 2 | SEQ ID NO: 3 |
| | | SEQ ID NO: 4 | SEQ ID NO: 33 | SEQ ID NO: 6 |
| 2082H4 | SEQ ID NO: 61 | SEQ ID NO: 1 or 195 | SEQ ID NO: 2 | SEQ ID NO: 3 |
| | | SEQ ID NO: 4 | SEQ ID NO: 33 | SEQ ID NO: 40 |
| 2082H5 | SEQ ID NO: 62 | SEQ ID NO: 1 or 195 | SEQ ID NO: 2 | SEQ ID NO: 3 |
| | | SEQ ID NO: 4 | SEQ ID NO: 33 | SEQ ID NO: 39 |
| 2082H6 | SEQ ID NO: 63 | SEQ ID NO: 1 or 195 | SEQ ID NO: 2 | SEQ ID NO: 3 |
| | | SEQ ID NO: 4 | SEQ ID NO: 33 | SEQ ID NO: 6 |
| VHH-623 | SEQ ID NO: 183 | SEQ ID NO: 165 or 199 | SEQ ID NO: 166 | SEQ ID NO: 167 |
| | | SEQ ID NO: 168 | SEQ ID NO: 169 | SEQ ID NO: 170 |
| VHH-640 | SEQ ID NO: 184 | SEQ ID NO: 171 or 200 | SEQ ID NO: 172 | SEQ ID NO: 173 |
| | | SEQ ID NO: 174 | SEQ ID NO: 175 | SEQ ID NO: 176 |
| VHH-657 | SEQ ID NO: 185 | SEQ ID NO: 177 or 197 | SEQ ID NO: 178 | SEQ ID NO: 179 |
| | | SEQ ID NO: 180 | SEQ ID NO: 181 | SEQ ID NO: 182 |

In some embodiments, there is provided an anti-CD20 single domain antibody comprising one, two, or all three CDRs of the amino acid sequence of SEQ ID NO: 41. In some embodiments, there is provided an anti-CD20 single domain antibody comprising one, two, or all three CDRs of the amino acid sequence of SEQ ID NO: 42. In some embodiments, there is provided an anti-CD20 single domain antibody comprising one, two, or all three CDRs of the amino acid sequence of SEQ ID NO: 43. In some embodiments, there is provided an anti-CD20 single domain antibody comprising one, two, or all three CDRs of the amino acid sequence of SEQ ID NO: 44. In some embodiments, there is provided an anti-CD20 single domain antibody comprising one, two, or all three CDRs of the amino acid sequence of SEQ ID NO: 45. In some embodiments, there is provided an anti-CD20 single domain antibody comprising one, two, or all three CDRs of the amino acid sequence of SEQ ID NO: 46. In some embodiments, there is provided an anti-CD20 single domain antibody comprising one, two, or all three CDRs of the amino acid sequence of SEQ ID NO: 47. In some embodiments, there is provided an anti-CD20 single domain antibody comprising one, two, or all three CDRs of the amino acid sequence of SEQ ID NO: 48. In some embodiments, there is provided an anti-CD20 single domain antibody comprising one, two, or all three CDRs of the amino acid sequence of SEQ ID NO: 49. In some embodiments, there is provided an anti-CD20 single domain antibody comprising one, two, or all three CDRs of the amino acid sequence of SEQ ID NO: 50. In some embodiments, there is provided an anti-CD20 single domain antibody comprising one, two, or all three CDRs of the amino acid sequence of SEQ ID NO: 51. In some embodiments, there is provided an anti-CD20 single domain antibody comprising one, two, or all three CDRs of the amino acid sequence of SEQ ID NO: 52. In some embodiments, there is provided an anti-CD20 single domain antibody comprising one, two, or all three CDRs of the amino acid sequence of SEQ ID NO: 53. In some embodiments, there is provided an anti-CD20 single domain antibody comprising one, two, or all three CDRs of the amino acid sequence of SEQ ID NO: 54. In some embodiments, there is provided an anti-CD20 single domain antibody comprising one, two, or all three CDRs of the amino acid sequence of SEQ ID NO: 55. In some embodiments, there is provided an anti-CD20 single domain antibody comprising one, two, or all three CDRs of the amino acid sequence of SEQ ID NO: 56. In some embodiments, there is provided an anti-CD20 single domain antibody comprising one, two, or all three CDRs of the amino acid sequence of SEQ ID NO: 57. In some embodiments, there is provided an anti-CD20 single domain antibody comprising one, two, or all three CDRs of the amino acid sequence of SEQ ID NO: 58. In some embodiments, there is provided an anti-CD20 single domain antibody comprising one, two, or all three CDRs of the amino acid sequence of SEQ ID NO: 59. In some embodiments, there is provided an anti-CD20 single domain antibody comprising one, two, or all three CDRs of the amino acid sequence of SEQ ID NO: 60. In some embodiments, there is provided an anti-CD20 single domain antibody comprising one, two, or all three CDRs of the amino acid sequence of SEQ ID NO: 61. In some embodiments, there is provided an anti-CD20 single domain antibody comprising one, two, or all three CDRs of the amino acid sequence of SEQ ID NO: 62. In some embodiments, there is provided an anti-CD20 single domain antibody comprising one, two, or all three CDRs of the amino acid sequence of SEQ ID NO: 63. In some embodiments, there is provided an anti-CD20 single domain antibody comprising one, two, or all three CDRs of the amino acid sequence of SEQ ID NO: 183. In some embodiments, there is provided an anti-CD20 single domain antibody comprising one, two, or all three CDRs of the amino acid sequence of SEQ ID NO: 184. In some embodiments, there is provided an anti-CD20 single domain antibody comprising one, two, or all three CDRs of the amino acid sequence of SEQ ID NO: 185. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 41. In some embodiments, the single domain antibody has a CDR2 having an amino acid sequence of the CDR2 as set forth in SEQ ID NO: 41. In other embodiments, the single domain antibody has a CDR3 having an amino acid sequence of the CDR3 as set forth in SEQ ID NO: 41 (e.g., SEQ ID NO: 3 or 6). In some embodiments, the single domain antibody has a CDR1 and a CDR2 having amino acid sequences of the CDR1 and the CDR2 as set forth in SEQ ID NO: 41. In some embodiments, the single domain antibody has a CDR1 and a CDR3 having amino acid sequences of the CDR1 and the CDR3 as set forth in SEQ ID NO: 41. In some embodiments, the single domain antibody has a CDR2 and a CDR3 having amino acid sequences of the CDR2 and the CDR3 as set forth in SEQ ID NO: 41. In some embodiments, the single domain antibody has a CDR1, a CDR2, and a CDR3 having amino acid sequences of the CDR1, the CDR2, and the CDR3 as set forth in SEQ ID NO: 41. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 42. In some embodiments, the single domain antibody has a CDR2 having an amino acid sequence of the CDR2 as set forth in SEQ ID NO: 42. In other embodiments, the single domain antibody has a CDR3 having an amino acid sequence of the CDR3 as set forth in SEQ ID NO: 42 (e.g., SEQ ID NO: 8 or 10). In some embodiments, the single domain antibody has a CDR1 and a CDR2 having amino acid sequences of the CDR1 and the CDR2 as set forth in SEQ ID NO: 42. In some embodiments, the single domain antibody has a CDR1 and a CDR3 having amino acid sequences of the CDR1 and the CDR3 as set forth in SEQ ID NO: 42. In some embodiments, the single domain antibody has a CDR2 and a CDR3 having amino acid sequences of the CDR2 and the CDR3 as set forth in SEQ ID NO: 42. In some embodiments, the single domain antibody has a CDR1, a CDR2, and a CDR3 having amino acid sequences of the CDR1, the CDR2, and the CDR3 as set forth in SEQ ID NO: 42. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 43. In some embodiments, the single domain antibody has a CDR2 having an amino acid sequence of the CDR2 as set forth in SEQ ID NO: 43. In other embodiments, the single domain antibody has a CDR3 having an amino acid sequence of the CDR3 as set forth in SEQ ID NO: 43 (e.g., SEQ ID NO: 8 or 10). In some embodiments, the single domain antibody has a CDR1 and a CDR2 having amino acid sequences of the CDR1 and the CDR2 as set forth in SEQ ID NO: 43. In some embodiments, the single domain antibody has a CDR1 and a CDR3 having amino acid sequences of the CDR1 and the CDR3 as set forth in SEQ ID NO: 43. In some embodiments, the single domain antibody has a CDR2 and a CDR3 having amino acid sequences of the CDR2 and the CDR3 as set forth in SEQ ID NO: 43. In some embodiments, the single domain antibody has a CDR1, a CDR2, and a CDR3 having amino acid sequences of the CDR1, the CDR2, and the CDR3 as set forth in SEQ ID NO: 43. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 44. In some embodiments, the single domain antibody has a CDR2 having an amino acid sequence of the CDR2 as set forth in SEQ ID NO: 44. In other embodiments, the single domain antibody has a CDR3 having an amino acid sequence of the CDR3 as set forth in SEQ ID NO: 44 (e.g., SEQ ID NO: 16 or 19). In some embodiments, the single domain antibody has a CDR1 and a CDR2 having amino acid sequences of the CDR1 and the CDR2 as set forth in SEQ ID NO: 44. In some embodiments, the single domain antibody has a CDR1 and a CDR3 having amino acid sequences of the CDR1 and the CDR3 as set forth in SEQ ID NO: 44. In some embodiments, the single domain antibody has a CDR2 and a CDR3 having amino acid sequences of the CDR2 and the CDR3 as set forth in SEQ ID NO: 44. In some embodiments, the single domain antibody has a CDR1, a CDR2, and a CDR3 having amino acid sequences of the CDR1, the CDR2, and the CDR3 as set forth in SEQ ID NO: 44. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 45. In some embodiments, the single domain antibody has a CDR2 having an amino acid sequence of the CDR2 as set forth in SEQ ID NO: 45. In other embodiments, the single domain antibody has a CDR3 having an amino acid sequence of the CDR3 as set forth in SEQ ID NO: 45 (e.g., SEQ ID NO: 16 or 19). In some embodiments, the single domain antibody has a CDR1 and a CDR2 having amino acid sequences of the CDR1 and the CDR2 as set forth in SEQ ID NO: 45. In some embodiments, the single domain antibody has a CDR1 and a CDR3 having amino acid sequences of the CDR1 and the CDR3 as set forth in SEQ ID NO: 45. In some embodiments, the single domain antibody has a CDR2 and a CDR3 having amino acid sequences of the CDR2 and the CDR3 as set forth in SEQ ID NO: 45. In some embodiments, the single domain antibody has a CDR1, a CDR2, and a CDR3 having amino acid sequences of the CDR1, the CDR2, and the CDR3 as set forth in SEQ ID NO: 45. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 46. In some embodiments, the single domain antibody has a CDR2 having an amino acid sequence of the CDR2 as set forth in SEQ ID NO: 46. In other embodiments, the single domain antibody has a CDR3 having an amino acid sequence of the CDR3 as set forth in SEQ ID NO: 46 (e.g., SEQ ID NO: 26 or 29). In some embodiments, the single domain antibody has a CDR1 and a CDR2 having amino acid sequences of the CDR1 and the CDR2 as set forth in SEQ ID NO: 46. In some embodiments, the single domain antibody has a CDR1 and a CDR3 having amino acid sequences of the CDR1 and the CDR3 as set forth in SEQ ID NO: 46. In some embodiments, the single domain antibody has a CDR2 and a CDR3 having amino acid sequences of the CDR2 and the CDR3 as set forth in SEQ ID NO: 46. In some embodiments, the single domain antibody has a CDR1, a CDR2, and a CDR3 having amino acid sequences of the CDR1, the CDR2, and the CDR3 as set forth in SEQ ID NO: 46. CDR sequences can be determined according to well-known numbering systems. In some embodiments, the CDRs are according to IMGT numbering.

In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 47. In some embodiments, the single domain antibody has a CDR2 having an amino acid sequence of the CDR2 as set forth in SEQ ID NO: 47. In other embodiments, the single domain antibody has a CDR3 having an amino acid sequence of the CDR3 as set forth in SEQ ID NO: 47 (e.g., SEQ ID NO: 16 or 19). In some embodiments, the single domain antibody has a CDR1 and a CDR2 having amino acid sequences of the CDR1 and the CDR2 as set forth in SEQ ID NO: 47. In some embodiments, the single domain antibody has a CDR1 and a CDR3 having amino acid sequences of the CDR1 and the CDR3 as set forth in SEQ ID NO: 47. In some embodiments, the single domain antibody has a CDR2 and a CDR3 having amino acid sequences of the CDR2 and the CDR3 as set forth in SEQ ID NO: 47. In some embodiments, the single domain antibody has a CDR1, a CDR2, and a CDR3 having amino acid sequences of the CDR1, the CDR2, and the CDR3 as set forth in SEQ ID NO: 47. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 48. In some embodiments, the single domain antibody has a CDR2 having an amino acid sequence of the CDR2 as set forth in SEQ ID NO: 48. In other embodiments, the single domain antibody has a CDR3 having an amino acid sequence of the CDR3 as set forth in SEQ ID NO: 48 (e.g., SEQ ID NO: 3 or 6). In some embodiments, the single domain antibody has a CDR1 and a CDR2 having amino acid sequences of the CDR1 and the CDR2 as set forth in SEQ ID NO: 48. In some embodiments, the single domain antibody has a CDR1 and a CDR3 having amino acid sequences of the CDR1 and the CDR3 as set forth in SEQ ID NO: 48. In some embodiments, the single domain antibody has a CDR2 and a CDR3 having amino acid sequences of the CDR2 and the CDR3 as set forth in SEQ ID NO: 48. In some embodiments, the single domain antibody has a CDR1, a CDR2, and a CDR3 having amino acid sequences of the CDR1, the CDR2, and the CDR3 as set forth in SEQ ID NO: 48. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 49. In some embodiments, the single domain antibody has a CDR2 having an amino acid sequence of the CDR2 as set forth in SEQ ID NO: 49. In other embodiments, the single domain antibody has a CDR3 having an amino acid sequence of the CDR3 as set forth in SEQ ID NO: 49 (e.g., SEQ ID NO: 3 or 6). In some embodiments, the single domain antibody has a CDR1 and a CDR2 having amino acid sequences of the CDR1 and the CDR2 as set forth in SEQ ID NO: 49. In some embodiments, the single domain antibody has a CDR1 and a CDR3 having amino acid sequences of the CDR1 and the CDR3 as set forth in SEQ ID NO: 49. In some embodiments, the single domain antibody has a CDR2 and a CDR3 having amino acid sequences of the CDR2 and the CDR3 as set forth in SEQ ID NO: 49. In some embodiments, the single domain antibody has a CDR1, a CDR2, and a CDR3 having amino acid sequences of the CDR1, the CDR2, and the CDR3 as set forth in SEQ ID NO: 49. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 50. In some embodiments, the single domain antibody has a CDR2 having an amino acid sequence of the CDR2 as set forth in SEQ 1D NO: 50. In other embodiments, the single domain antibody has a CDR3 having an amino acid sequence of the CDR3 as set forth in SEQ ID NO: 50 (e.g., SEQ ID NO: 8 or 10). In some embodiments, the single domain antibody has a CDR1 and a CDR2 having amino acid sequences of the CDR1 and the CDR2 as set forth in SEQ ID NO: 50. In some embodiments, the single domain antibody has a CDR1 and a CDR3 having amino acid sequences of the CDR1 and the CDR3 as set forth in SEQ ID NO: 50. In some embodiments, the single domain antibody has a CDR2 and a CDR3 having amino acid sequences of the CDR2 and the CDR3 as set forth in SEQ ID NO: 50. In some embodiments, the single domain antibody has a CDR1, a CDR2, and a CDR3 having amino acid sequences of the CDR1, the CDR2, and the CDR3 as set forth in SEQ ID NO: 50. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 51. In some embodiments, the single domain antibody has a CDR2 having an amino acid sequence of the CDR2 as set forth in SEQ ID NO: 51. In other embodiments, the single domain antibody has a CDR3 having an amino acid sequence of the CDR3 as set forth in SEQ ID NO: 51 (e.g., SEQ ID NO: 26 or 29). In some embodiments, the single domain antibody has a CDR1 and a CDR2 having amino acid sequences of the CDR1 and the CDR2 as set forth in SEQ ID NO: 51. In some embodiments, the single domain antibody has a CDR1 and a CDR3 having amino acid sequences of the CDR1 and the CDR3 as set forth in SEQ ID NO: 51. In some embodiments, the single domain antibody has a CDR2 and a CDR3 having amino acid sequences of the CDR2 and the CDR3 as set forth in SEQ ID NO: 51. In some embodiments, the single domain antibody has a CDR1, a CDR2, and a CDR3 having amino acid sequences of the CDR1, the CDR2, and the CDR3 as set forth in SEQ ID NO: 51. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 52. In some embodiments, the single domain antibody has a CDR2 having an amino acid sequence of the CDR2 as set forth in SEQ ID NO: 52. In other embodiments, the single domain antibody has a CDR3 having an amino acid sequence of the CDR3 as set forth in SEQ ID NO: 52 (e.g., SEQ ID NO: 26 or 29). In some embodiments, the single domain antibody has a CDR1 and a CDR2 having amino acid sequences of the CDR1 and the CDR2 as set forth in SEQ ID NO: 52. In some embodiments, the single domain antibody has a CDR1 and a CDR3 having amino acid sequences of the CDR1 and the CDR3 as set forth in SEQ ID NO: 52. In some embodiments, the single domain antibody has a CDR2 and a CDR3 having amino acid sequences of the CDR2 and the CDR3 as set forth in SEQ ID NO: 52. In some embodiments, the single domain antibody has a CDR1, a CDR2, and a CDR3 having amino acid sequences of the CDR1, the CDR2, and the CDR3 as set forth in SEQ ID NO: 52. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 53. In some embodiments, the single domain antibody has a CDR2 having an amino acid sequence of the CDR2 as set forth in SEQ ID NO: 53. In other embodiments, the single domain antibody has a CDR3 having an amino acid sequence of the CDR3 as set forth in SEQ ID NO: 53 (e.g., SEQ ID NO: 26 or 29). In some embodiments, the single domain antibody has a CDR1 and a CDR2 having amino acid sequences of the CDR1 and the CDR2 as set forth in SEQ ID NO: 53. In some embodiments, the single domain antibody has a CDR1 and a CDR3 having amino acid sequences of the CDR1 and the CDR3 as set forth in SEQ ID NO: 53. In some embodiments, the single domain antibody has a CDR2 and a CDR3 having amino acid sequences of the CDR2 and the CDR3 as set forth in SEQ ID NO: 53. In some embodiments, the single domain antibody has a CDR1, a CDR2, and a CDR3 having amino acid sequences of the CDR1, the CDR2, and the CDR3 as set forth in SEQ ID NO: 53. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 54. In some embodiments, the single domain antibody has a CDR2 having an amino acid sequence of the CDR2 as set forth in SEQ ID NO: 54. In other embodiments, the single domain antibody has a CDR3 having an amino acid sequence of the CDR3 as set forth in SEQ ID NO: 54 (e.g., SEQ ID NO: 16 or 19). In some embodiments, the single domain antibody has a CDR1 and a CDR2 having amino acid sequences of the CDR1 and the CDR2 as set forth in SEQ ID NO: 54. In some embodiments, the single domain antibody has a CDR1 and a CDR3 having amino acid sequences of the CDR1 and the CDR3 as set forth in SEQ ID NO: 54. In some embodiments, the single domain antibody has a CDR2 and a CDR3 having amino acid sequences of the CDR2 and the CDR3 as set forth in SEQ ID NO: 54. In some embodiments, the single domain antibody has a CDR1, a CDR2, and a CDR3 having amino acid sequences of the CDR1, the CDR2, and the CDR3 as set forth in SEQ ID NO: 54. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 55. In some embodiments, the single domain antibody has a CDR2 having an amino acid sequence of the CDR2 as set forth in SEQ ID NO: 55. In other embodiments, the single domain antibody has a CDR3 having an amino acid sequence of the CDR3 as set forth in SEQ ID NO: 55 (e.g., SEQ ID NO: 16 or 19). In some embodiments, the single domain antibody has a CDR1 and a CDR2 having amino acid sequences of the CDR1 and the CDR2 as set forth in SEQ ID NO: 55. In some embodiments, the single domain antibody has a CDR1 and a CDR3 having amino acid sequences of the CDR1 and the CDR3 as set forth in SEQ ID NO: 55. In some embodiments, the single domain antibody has a CDR2 and a CDR3 having amino acid sequences of the CDR2 and the CDR3 as set forth in SEQ ID NO: 55. In some embodiments, the single domain antibody has a CDR1, a CDR2, and a CDR3 having amino acid sequences of the CDR1, the CDR2, and the CDR3 as set forth in SEQ ID NO: 55. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 56. In some embodiments, the single domain antibody has a CDR2 having an amino acid sequence of the CDR2 as set forth in SEQ ID NO: 56. In other embodiments, the single domain antibody has a CDR3 having an amino acid sequence of the CDR3 as set forth in SEQ ID NO: 56 (e.g., SEQ ID NO: 16 or 19). In some embodiments, the single domain antibody has a CDR1 and a CDR2 having amino acid sequences of the CDR1 and the CDR2 as set forth in SEQ ID NO: 56. In some embodiments, the single domain antibody has a CDR1 and a CDR3 having amino acid sequences of the CDR1 and the CDR3 as set forth in SEQ ID NO: 56. In some embodiments, the single domain antibody has a CDR2 and a CDR3 having amino acid sequences of the CDR2 and the CDR3 as set forth in SEQ ID NO: 56. In some embodiments, the single domain antibody has a CDR1, a CDR2, and a CDR3 having amino acid sequences of the CDR1, the CDR2, and the CDR3 as set forth in SEQ ID NO: 56. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 57. In some embodiments, the single domain antibody has a CDR2 having an amino acid sequence of the CDR2 as set forth in SEQ ID NO: 57. In other embodiments, the single domain antibody has a CDR3 having an amino acid sequence of the CDR3 as set forth in SEQ ID NO: 57 (e.g., SEQ ID NO: 16 or 19). In some embodiments, the single domain antibody has a CDR1 and a CDR2 having amino acid sequences of the CDR1 and the CDR2 as set forth in SEQ ID NO: 57. In some embodiments, the single domain antibody has a CDR1 and a CDR3 having amino acid sequences of the CDR1 and the CDR3 as set forth in SEQ ID NO: 57. In some embodiments, the single domain antibody has a CDR2 and a CDR3 having amino acid sequences of the CDR2 and the CDR3 as set forth in SEQ ID NO: 57. In some embodiments, the single domain antibody has a CDR1, a CDR2, and a CDR3 having amino acid sequences of the CDR1, the CDR2, and the CDR3 as set forth in SEQ ID NO: 57. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 58. In some embodiments, the single domain antibody has a CDR2 having an amino acid sequence of the CDR2 as set forth in SEQ ID NO: 58. In other embodiments, the single domain antibody has a CDR3 having an amino acid sequence of the CDR3 as set forth in SEQ ID NO: 58 (e.g., SEQ ID NO: 3 or 6). In some embodiments, the single domain antibody has a CDR1 and a CDR2 having amino acid sequences of the CDR1 and the CDR2 as set forth in SEQ ID NO: 58. In some embodiments, the single domain antibody has a CDR1 and a CDR3 having amino acid sequences of the CDR1 and the CDR3 as set forth in SEQ ID NO: 58. In some embodiments, the single domain antibody has a CDR2 and a CDR3 having amino acid sequences of the CDR2 and the CDR3 as set forth in SEQ ID NO: 58. In some embodiments, the single domain antibody has a CDR1, a CDR2, and a CDR3 having amino acid sequences of the CDR1, the CDR2, and the CDR3 as set forth in SEQ ID NO: 58. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 59. In some embodiments, the single domain antibody has a CDR2 having an amino acid sequence of the CDR2 as set forth in SEQ ID NO: 59. In other embodiments, the single domain antibody has a CDR3 having an amino acid sequence of the CDR3 as set forth in SEQ ID NO: 59 (e.g., SEQ ID NO: 3 or 39). In some embodiments, the single domain antibody has a CDR1 and a CDR2 having amino acid sequences of the CDR1 and the CDR2 as set forth in SEQ ID NO: 59. In some embodiments, the single domain antibody has a CDR1 and a CDR3 having amino acid sequences of the CDR1 and the CDR3 as set forth in SEQ ID NO: 59. In some embodiments, the single domain antibody has a CDR2 and a CDR3 having amino acid sequences of the CDR2 and the CDR3 as set forth in SEQ ID NO: 59. In some embodiments, the single domain antibody has a CDR1, a CDR2, and a CDR3 having amino acid sequences of the CDR1, the CDR2, and the CDR3 as set forth in SEQ ID NO: 59. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 60. In some embodiments, the single domain antibody has a CDR2 having an amino acid sequence of the CDR2 as set forth in SEQ ID NO: 60. In other embodiments, the single domain antibody has a CDR3 having an amino acid sequence of the CDR3 as set forth in SEQ ID NO: 60 (e.g., SEQ ID NO: 3 or 6). In some embodiments, the single domain antibody has a CDR1 and a CDR2 having amino acid sequences of the CDR1 and the CDR2 as set forth in SEQ ID NO: 60. In some embodiments, the single domain antibody has a CDR1 and a CDR3 having amino acid sequences of the CDR1 and the CDR3 as set forth in SEQ ID NO: 60. In some embodiments, the single domain antibody has a CDR2 and a CDR3 having amino acid sequences of the CDR2 and the CDR3 as set forth in SEQ ID NO: 60. In some embodiments, the single domain antibody has a CDR1, a CDR2, and a CDR3 having amino acid sequences of the CDR1, the CDR2, and the CDR3 as set forth in SEQ ID NO: 60. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 61. In some embodiments, the single domain antibody has a CDR2 having an amino acid sequence of the CDR2 as set forth in SEQ ID NO: 61. In other embodiments, the single domain antibody has a CDR3 having an amino acid sequence of the CDR3 as set forth in SEQ ID NO: 61 (e.g., SEQ ID NO: 3 or 40). In some embodiments, the single domain antibody has a CDR1 and a CDR2 having amino acid sequences of the CDR1 and the CDR2 as set forth in SEQ ID NO: 61. In some embodiments, the single domain antibody has a CDR1 and a CDR3 having amino acid sequences of the CDR1 and the CDR3 as set forth in SEQ ID NO: 61. In some embodiments, the single domain antibody has a CDR2 and a CDR3 having amino acid sequences of the CDR2 and the CDR3 as set forth in SEQ ID NO: 61. In some embodiments, the single domain antibody has a CDR1, a CDR2, and a CDR3 having amino acid sequences of the CDR1, the CDR2, and the CDR3 as set forth in SEQ ID NO: 61. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 62. In some embodiments, the single domain antibody has a CDR2 having an amino acid sequence of the CDR2 as set forth in SEQ ID NO: 62. In other embodiments, the single domain antibody has a CDR3 having an amino acid sequence of the CDR3 as set forth in SEQ ID NO: 62 (e.g., SEQ ID NO: 3 or 39). In some embodiments, the single domain antibody has a CDR1 and a CDR2 having amino acid sequences of the CDR1 and the CDR2 as set forth in SEQ ID NO: 62. In some embodiments, the single domain antibody has a CDR1 and a CDR3 having amino acid sequences of the CDR1 and the CDR3 as set forth in SEQ ID NO: 62. In some embodiments, the single domain antibody has a CDR2 and a CDR3 having amino acid sequences of the CDR2 and the CDR3 as set forth in SEQ ID NO: 62. In some embodiments, the single domain antibody has a CDR1, a CDR2, and a CDR3 having amino acid sequences of the CDR1, the CDR2, and the CDR3 as set forth in SEQ ID NO: 62. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 63. In some embodiments, the single domain antibody has a CDR2 having an amino acid sequence of the CDR2 as set forth in SEQ ID NO: 63. In other embodiments, the single domain antibody has a CDR3 having an amino acid sequence of the CDR3 as set forth in SEQ ID NO: 63 (e.g., SEQ ID NO: 3 or 6). In some embodiments, the single domain antibody has a CDR1 and a CDR2 having amino acid sequences of the CDR1 and the CDR2 as set forth in SEQ ID NO: 63. In some embodiments, the single domain antibody has a CDR1 and a CDR3 having amino acid sequences of the CDR1 and the CDR3 as set forth in SEQ ID NO: 63. In some embodiments, the single domain antibody has a CDR2 and a CDR3 having amino acid sequences of the CDR2 and the CDR3 as set forth in SEQ ID NO: 63. In some embodiments, the single domain antibody has a CDR1, a CDR2, and a CDR3 having amino acid sequences of the CDR1, the CDR2, and the CDR3 as set forth in SEQ ID NO: 63. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 183. In some embodiments, the single domain antibody has a CDR2 having an amino acid sequence of the CDR2 as set forth in SEQ ID NO: 183. In other embodiments, the single domain antibody has a CDR3 having an amino acid sequence of the CDR3 as set forth in SEQ ID NO: 183 (e.g., SEQ ID NO: 167 or 170). In some embodiments, the single domain antibody has a CDR1 and a CDR2 having amino acid sequences of the CDR1 and the CDR2 as set forth in SEQ ID NO: 183. In some embodiments, the single domain antibody has a CDR1 and a CDR3 having amino acid sequences of the CDR1 and the CDR3 as set forth in SEQ ID NO: 183. In some embodiments, the single domain antibody has a CDR2 and a CDR3 having amino acid sequences of the CDR2 and the CDR3 as set forth in SEQ ID NO: 183. In some embodiments, the single domain antibody has a CDR1, a CDR2, and a CDR3 having amino acid sequences of the CDR1, the CDR2, and the CDR3 as set forth in SEQ ID NO: 183. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 184. In some embodiments, the single domain antibody has a CDR2 having an amino acid sequence of the CDR2 as set forth in SEQ ID NO: 184. In other embodiments, the single domain antibody has a CDR3 having an amino acid sequence of the CDR3 as set forth in SEQ ID NO: 184 (e.g., SEQ ID NO: 173 or 176). In some embodiments, the single domain antibody has a CDR1 and a CDR2 having amino acid sequences of the CDR1 and the CDR2 as set forth in SEQ ID NO: 184. In some embodiments, the single domain antibody has a CDR1 and a CDR3 having amino acid sequences of the CDR1 and the CDR3 as set forth in SEQ ID NO: 184. In some embodiments, the single domain antibody has a CDR2 and a CDR3 having amino acid sequences of the CDR2 and the CDR3 as set forth in SEQ ID NO: 184. In some embodiments, the single domain antibody has a CDR1, a CDR2, and a CDR3 having amino acid sequences of the CDR1, the CDR2, and the CDR3 as set forth in SEQ ID NO: 184. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody has a CDR1 having an amino acid sequence of the CDR1 as set forth in SEQ ID NO: 185. In some embodiments, the single domain antibody has a CDR2 having an amino acid sequence of the CDR2 as set forth in SEQ ID NO: 185. In other embodiments, the single domain antibody has a CDR3 having an amino acid sequence of the CDR3 as set forth in SEQ ID NO: 185 (e.g., SEQ ID NO: 179 or 182). In some embodiments, the single domain antibody has a CDR1 and a CDR2 having amino acid sequences of the CDR1 and the CDR2 as set forth in SEQ ID NO: 185. In some embodiments, the single domain antibody has a CDR1 and a CDR3 having amino acid sequences of the CDR1 and the CDR3 as set forth in SEQ ID NO: 185. In some embodiments, the single domain antibody has a CDR2 and a CDR3 having amino acid sequences of the CDR2 and the CDR3 as set forth in SEQ ID NO: 185. In some embodiments, the single domain antibody has a CDR1, a CDR2, and a CDR3 having amino acid sequences of the CDR1, the CDR2, and the CDR3 as set forth in SEQ ID NO: 185. CDR sequences can be determined according to well-known numbering systems. In some embodiments, the CDRs are according to IMGT numbering. In some embodiments, the CDRs are according to Kabat numbering. In some embodiments, the CDRs are according to AbM numbering. In other embodiments, the CDRs are according to Chothia numbering. In other embodiments, the CDRs are according to Contact numbering. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is a single domain antibody that binds to CD20 comprising the following structure: FR1-CDR1-FR2-CDR2-FR3-CDR3-FR4, wherein (i) the CDR1 comprises an amino acid sequence of SEQ ID NO: 1 or 195, SEQ ID NO: 4, SEQ ID NO: 11 or 1%, SEQ ID NO: 13, SEQ ID NO: 14 or 197, SEQ ID NO: 17, SEQ ID NO: 20 or 197, SEQ ID NO: 22, SEQ ID NO: 24 or 198, SEQ ID NO: 27; SEQ ID NO: 165 or 199, SEQ ID NO: 168, SEQ ID NO: 171 or 200, SEQ ID NO: 174, SEQ ID NO: 177 or 197, or SEQ ID NO: 180; (ii) the CDR2 comprises an amino acid sequence of SEQ ID NO: 2, SEQ ID NO: 5, SEQ ID NO: 7, SEQ ID NO: 9, SEQ ID NO: 12, SEQ ID NO: 15, SEQ ID NO: 18, SEQ ID NO: 21, SEQ ID NO: 23, SEQ ID NO: 25, SEQ ID NO: 28, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 166, SEQ ID NO: 169, SEQ ID NO: 172, SEQ ID NO: 175, SEQ ID NO: 178, or SEQ ID NO: 181; and/or (iii) the CDR3 comprises an amino acid sequence of SEQ ID NO: 3, SEQ ID NO: 6, SEQ ID NO: 8, SEQ ID NO: 10, SEQ ID NO: 16, SEQ ID NO: 19, SEQ ID NO: 26, SEQ ID NO: 29, SEQ ID NO: 39, SEQ ID NO: 40, SEQ ID NO: 167, SEQ ID NO: 170, SEQ ID NO: 173, SEQ ID NO: 176, SEQ ID NO: 179 or SEQ ID NO: 182. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In other embodiments, provided herein is a single domain antibody that binds to CD20 comprising the following structure: FR1-CDR1-FR2-CDR2-FR3-CDR3-FR4, wherein (i) the CDR1 comprises an amino acid sequence having at least 75%, 80%, 85%, 86%, 87%, 88%, 89%, 90%, 91%, 92%, 93%, 94%, 95%, 96%, 97%, 98%, or 99% sequence identity to SEQ ID NO: 1 or 195, SEQ ID NO: 4, SEQ ID NO: 11 or 196, SEQ ID NO: 13, SEQ ID NO: 14 or 197, SEQ ID NO: 17, SEQ ID NO: 20 or 197, SEQ ID NO: 22, SEQ ID NO: 24 or 198, SEQ ID NO: 27, SEQ ID NO: 165 or 199, SEQ ID NO: 168, SEQ ID NO: 171 or 200, SEQ ID NO: 174, SEQ ID NO: 177 or 197, or SEQ ID NO: 180; (ii) the CDR2 comprises an amino acid sequence having at least 75%, 80%, 85%, 86%, 87%, 88%, 89% 90%, 91%, 92%, 93%, 94%, 95%, 96% 97%, 98%, or 99% sequence identity to SEQ ID NO: 2, SEQ ID NO: 5, SEQ ID NO: 7, SEQ ID NO: 9, SEQ ID NO: 12, SEQ ID NO: 15, SEQ ID NO: 18, SEQ ID NO: 21, SEQ ID NO: 23, SEQ ID NO: 25, SEQ ID NO: 28, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 166, SEQ ID NO: 169, SEQ ID NO: 172, SEQ ID NO: 175, SEQ ID NO: 178, or SEQ ID NO: 181; and/or (iii) the CDR3 comprises an amino acid sequence having at least 75%, 80%, 85%, 86%, 87%, 88%, 89%, 90%, 91%, 92%, 93%, 94%, 95%, 96%, 97%, 98%, or 99% sequence identity to SEQ ID NO: 3, SEQ ID NO: 6, SEQ ID NO: 8, SEQ ID NO: 10, SEQ ID NO: 16, SEQ ID NO: 19, SEQ ID NO: 26, SEQ ID NO: 29, SEQ ID NO: 39, SEQ ID NO: 40, SEQ ID NO: 167, SEQ ID NO: 170, SEQ ID NO: 173, SEQ ID NO: 176, SEQ ID NO: 179 or SEQ ID NO: 182. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 1 or 195; a CDR2 comprising the amino acid sequence of SEQ ID NO: 2; and a CDR3 comprising the amino acid sequence of SEQ ID NO: 3. In some embodiments, provided herein is an anti-CD20 single domain antibody (sdAb) comprising a CDR1 comprising the amino acid sequence of SEQ ID NO: 1; a CDR2 comprising the amino acid sequence of SEQ ID NO: 2; and a CDR3 comprising the amino acid sequence of SEQ ID NO: 3. In some embodiments, provided herein is an anti-CD20 single domain antibody (sdAb) comprising a CDR1 comprising the amino acid sequence of SEQ ID NO: 195; a CDR2 comprising the amino acid sequence of SEQ ID NO: 2; and a CDR3 comprising the amino acid sequence of SEQ ID NO: 3. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 4; a CDR2 comprising the amino acid sequence of SEQ ID NO: 5; and a CDR3 comprising the amino acid sequence of SEQ ID NO: 6. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 1 or 195; a CDR2 comprising the amino acid sequence of SEQ ID NO: 7; and a CDR3 comprising the amino acid sequence of SEQ ID NO: 8. In some embodiments, provided herein is an anti-CD20 single domain antibody (sdAb) comprising a CDR1 comprising the amino acid sequence of SEQ ID NO: 1; a CDR2 comprising the amino acid sequence of SEQ ID NO: 7; and a CDR3 comprising the amino acid sequence of SEQ ID NO: 8. In some embodiments, provided herein is an anti-CD20 single domain antibody (sdAb) comprising a CDR1 comprising the amino acid sequence of SEQ ID NO: 195; a CDR2 comprising the amino acid sequence of SEQ ID NO: 7; and a CDR3 comprising the amino acid sequence of SEQ ID NO: 8. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 4; a CDR2 comprising the amino acid sequence of SEQ ID NO: 9; and a CDR3 comprising the amino acid sequence of SEQ ID NO: 10. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 11 or 196; a CDR2 comprising the amino acid sequence of SEQ ID NO: 12; and a CDR3 comprising the amino acid sequence of SEQ ID NO: 8. In some embodiments, provided herein is an anti-CD20 single domain antibody (sdAb) comprising a CDR1 comprising the amino acid sequence of SEQ ID NO: 11; a CDR2 comprising the amino acid sequence of SEQ ID NO: 12; and a CDR3 comprising the amino acid sequence of SEQ ID NO: 8. In some embodiments, provided herein is an anti-CD20 single domain antibody (sdAb) comprising a CDR1 comprising the amino acid sequence of SEQ ID NO: 196; a CDR2 comprising the amino acid sequence of SEQ ID NO: 12; and a CDR3 comprising the amino acid sequence of SEQ ID NO: 8. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 13; a CDR2 comprising the amino acid sequence of SEQ ID NO: 9; and a CDR3 comprising the amino acid sequence of SEQ ID NO: 10. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 14 or 197; a CDR2 comprising the amino acid sequence of SEQ ID NO: 15; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 14; a CDR2 comprising the amino acid sequence of SEQ ID NO: 15; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 197; a CDR2 comprising the amino acid sequence of SEQ ID NO: 15; and a CDR3 comprising the amino acid sequence of SEQ ID NO: 16. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 17; a CDR2 comprising the amino acid sequence of SEQ ID NO: 18; and a CDR3 comprising the amino acid sequence of SEQ ID NO: 19. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 20 or 197; a CDR2 comprising the amino acid sequence of SEQ ID NO: 21; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 20; a CDR2 comprising the amino acid sequence of SEQ ID NO: 21; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 197; a CDR2 comprising the amino acid sequence of SEQ ID NO: 21; and a CDR3 comprising the amino acid sequence of SEQ ID NO: 16. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 22; a CDR2 comprising the amino acid sequence of SEQ ID NO: 23; and a CDR3 comprising the amino acid sequence of SEQ ID NO: 19. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 24 or 198; a CDR2 comprising the amino acid sequence of SEQ ID NO: 25; and a CDR3 comprising the amino acid sequence of SEQ ID NO: 26. In some embodiments, provided herein is an anti-CD20 single domain antibody (sdAb) comprising a CDR1 comprising the amino acid sequence of SEQ ID NO: 24; a CDR2 comprising the amino acid sequence of SEQ ID NO: 25; and a CDR3 comprising the amino acid sequence of SEQ ID NO: 26. In some embodiments, provided herein is an anti-CD20 single domain antibody (sdAb) comprising a CDR1 comprising the amino acid sequence of SEQ ID NO: 198; a CDR2 comprising the amino acid sequence of SEQ ID NO: 25; and a CDR3 comprising the amino acid sequence of SEQ ID NO: 26. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 27; a CDR2 comprising the amino acid sequence of SEQ ID NO: 28; and a CDR3 comprising the amino acid sequence of SEQ ID NO: 29. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 14 or 197; a CDR2 comprising the amino acid sequence of SEQ ID NO: 30; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 14; a CDR2 comprising the amino acid sequence of SEQ ID NO: 30; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 197; a CDR2 comprising the amino acid sequence of SEQ ID NO: 30; and a CDR3 comprising the amino acid sequence of SEQ ID NO: 16. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 17; a CDR2 comprising the amino acid sequence of SEQ ID NO: 31; and a CDR3 comprising the amino acid sequence of SEQ ID NO: 19. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 1 or 195; a CDR2 comprising the amino acid sequence of SEQ ID NO: 32; and a CDR3 comprising the amino acid sequence of SEQ ID NO: 3. In some embodiments, provided herein is an anti-CD20 single domain antibody (sdAb) comprising a CDR1 comprising the amino acid sequence of SEQ ID NO: 1; a CDR2 comprising the amino acid sequence of SEQ ID NO: 32; and a CDR3 comprising the amino acid sequence of SEQ ID NO: 3. In some embodiments, provided herein is an anti-CD20 single domain antibody (sdAb) comprising a CDR1 comprising the amino acid sequence of SEQ ID NO: 195; a CDR2 comprising the amino acid sequence of SEQ ID NO: 32; and a CDR3 comprising the amino acid sequence of SEQ ID NO: 3. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 4; a CDR2 comprising the amino acid sequence of SEQ ID NO: 33; and a CDR3 comprising the amino acid sequence of SEQ ID NO: 6. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 20 or 197; a CDR2 comprising the amino acid sequence of SEQ ID NO: 34; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 20; a CDR2 comprising the amino acid sequence of SEQ ID NO: 34; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 197; a CDR2 comprising the amino acid sequence of SEQ ID NO: 34; and a CDR3 comprising the amino acid sequence of SEQ ID NO: 16. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 22; a CDR2 comprising the amino acid sequence of SEQ ID NO: 35; and a CDR3 comprising the amino acid sequence of SEQ ID NO: 19. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 20 or 197; a CDR2 comprising the amino acid sequence of SEQ ID NO: 36; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 20; a CDR2 comprising the amino acid sequence of SEQ ID NO: 36; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 197; a CDR2 comprising the amino acid sequence of SEQ ID NO: 36; and a CDR3 comprising the amino acid sequence of SEQ ID NO: 16. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 20 or 197; a CDR2 comprising the amino acid sequence of SEQ ID NO: 37; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 20; a CDR2 comprising the amino acid sequence of SEQ ID NO: 37; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 197; a CDR2 comprising the amino acid sequence of SEQ ID NO: 37: and a CDR3 comprising the amino acid sequence of SEQ ID NO: 16. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 20 or 197; a CDR2 comprising the amino acid sequence of SEQ ID NO: 38; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 20; a CDR2 comprising the amino acid sequence of SEQ ID NO: 38; and a CDR3 comprising the amino acid sequence of SEQ ID NO: 16. In some embodiments, provided herein is an anti-CD20 single domain antibody (sdAb) comprising a CDR1 comprising the amino acid sequence of SEQ ID NO: 197; a CDR2 comprising the amino acid sequence of SEQ ID NO: 38: and a CDR3 comprising the amino acid sequence of SEQ ID NO: 16. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 4; a CDR2 comprising the amino acid sequence of SEQ ID NO: 33; and a CDR3 comprising the amino acid sequence of SEQ ID NO: 39. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 4; a CDR2 comprising the amino acid sequence of SEQ ID NO: 33; and a CDR3 comprising the amino acid sequence of SEQ ID NO: 40. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 165 or 199; a CDR2 comprising the amino acid sequence of SEQ ID NO: 166; and a CDR3 comprising the amino acid sequence of SEQ ID NO: 167. In some embodiments, provided herein is an anti-CD20 single domain antibody (sdAb) comprising a CDR1 comprising the amino acid sequence of SEQ ID NO: 165; a CDR2 comprising the amino acid sequence of SEQ ID NO: 166; and a CDR3 comprising the amino acid sequence of SEQ ID NO: 167. In some embodiments, provided herein is an anti-CD20 single domain antibody (sdAb) comprising a CDR1 comprising the amino acid sequence of SEQ ID NO: 199; a CDR2 comprising the amino acid sequence of SEQ ID NO: 166; and a CDR3 comprising the amino acid sequence of SEQ ID NO: 167. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 168; a CDR2 comprising the amino acid sequence of SEQ ID NO: 169; and a CDR3 comprising the amino acid sequence of SEQ ID NO: 170. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 171 or 200; a CDR2 comprising the amino acid sequence of SEQ ID NO: 172; and a CDR3 comprising the amino acid sequence of SEQ ID NO: 173. In some embodiments, provided herein is an anti-CD20 single domain antibody (sdAb) comprising a CDR1 comprising the amino acid sequence of SEQ ID NO: 171; a CDR2 comprising the amino acid sequence of SEQ ID NO: 172; and a CDR3 comprising the amino acid sequence of SEQ ID NO: 173. In some embodiments, provided herein is an anti-CD20 single domain antibody (sdAb) comprising a CDR1 comprising the amino acid sequence of SEQ ID NO: 200; a CDR2 comprising the amino acid sequence of SEQ ID NO: 172; and a CDR3 comprising the amino acid sequence of SEQ ID NO: 173. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 174; a CDR2 comprising the amino acid sequence of SEQ ID NO: 175; and a CDR3 comprising the amino acid sequence of SEQ ID NO: 176. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 177 or 197; a CDR2 comprising the amino acid sequence of SEQ ID NO: 178; and a CDR3 comprising the amino acid sequence of SEQ ID NO: 179. In some embodiments, provided herein is an anti-CD20 single domain antibody (sdAb) comprising a CDR1 comprising the amino acid sequence of SEQ ID NO: 177; a CDR2 comprising the amino acid sequence of SEQ ID NO: 178; and a CDR3 comprising the amino acid sequence of SEQ ID NO: 179. In some embodiments, provided herein is an anti-CD20 single domain antibody (sdAb) comprising a CDR1 comprising the amino acid sequence of SEQ ID NO: 197; a CDR2 comprising the amino acid sequence of SEQ ID NO: 178; and a CDR3 comprising the amino acid sequence of SEQ ID NO: 179. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, provided herein is an anti-CD20 single domain antibody (sdAb) comprising a CDR1 comprising the amino acid sequence of SEQ ID NO: 180; a CDR2 comprising the amino acid sequence of SEQ ID NO: 181; and a CDR3 comprising the amino acid sequence of SEQ ID NO: 182. In some embodiments, the anti-CD20 single domain antibody is camelid. In some embodiments, the anti-CD20 single domain antibody is humanized. In some embodiments, the anti-CD20 single domain antibody comprises an acceptor human framework, e.g., a human immunoglobulin framework or a human consensus framework.

In some embodiments, the single domain antibody further comprises one or more framework region(s) of VHH-273, VHH-283, VHH-313, VHH-440, VHH-466, VHH-496, VHH-653, huVHH-253, huVHH-256, huVHH-260, huVHH-746, huVHH-750, huVHH-753, huVHH-836, huVHH-840, huVHH-843, huVHH-846, 2082H1, 2082H2, 2082H3, 2082H4, 2082H5, 2082H6, VHH-623, VHH-640, and/or VHH-657. In some embodiments, the single domain antibody comprises one or more framework(s) derived from a VHH domain comprising the sequence of SEQ ID NO: 41. In some embodiments, the single domain antibody comprises one or more framework(s) derived from a VHH domain comprising the sequence of SEQ ID NO: 42. In some embodiments, the single domain antibody comprises one or more framework(s) derived from a VHH domain comprising the sequence of SEQ ID NO: 43. In some embodiments, the single domain antibody comprises one or more framework(s) derived from a VHH domain comprising the sequence of SEQ ID NO: 44. In some embodiments, the single domain antibody comprises one or more framework(s) derived from a VHH domain comprising the sequence of SEQ ID NO: 45. In some embodiments, the single domain antibody comprises one or more framework(s) derived from a VHH domain comprising the sequence of SEQ ID NO: 46. In some embodiments, the single domain antibody comprises one or more framework(s) derived from a VHH domain comprising the sequence of SEQ ID NO: 47. In some embodiments, the single domain antibody comprises one or more framework(s) derived from a VHH domain comprising the sequence of SEQ ID NO: 48. In some embodiments, the single domain antibody comprises one or more framework(s) derived from a VHH domain comprising the sequence of SEQ ID NO: 49. In some embodiments, the single domain antibody comprises one or more framework(s) derived from a VHH domain comprising the sequence of SEQ ID NO: 50. In some embodiments, the single domain antibody comprises one or more framework(s) derived from a VHH domain comprising the sequence of SEQ ID NO: 51. In some embodiments, the single domain antibody comprises one or more framework(s) derived from a VHH domain comprising the sequence of SEQ ID NO: 52. In some embodiments, the single domain antibody comprises one or more framework(s) derived from a VHH domain comprising the sequence of SEQ ID NO: 53. In some embodiments, the single domain antibody comprises one or more framework(s) derived from a VHH domain comprising the sequence of SEQ ID NO: 54. In some embodiments, the single domain antibody comprises one or more framework(s) derived from a VHH domain comprising the sequence of SEQ ID NO: 55. In some embodiments, the single domain antibody comprises one or more framework(s) derived from a VHH domain comprising the sequence of SEQ ID NO: 56. In some embodiments, the single domain antibody comprises one or more framework(s) derived from a VHH domain comprising the sequence of SEQ ID NO: 57. In some embodiments, the single domain antibody comprises one or more framework(s) derived from a VHH domain comprising the sequence of SEQ ID NO: 58. In some embodiments, the single domain antibody comprises one or more framework(s) derived from a VHH domain comprising the sequence of SEQ ID NO: 59. In some embodiments, the single domain antibody comprises one or more framework(s) derived from a VHH domain comprising the sequence of SEQ ID NO: 60. In some embodiments, the single domain antibody comprises one or more framework(s) derived from a VHH domain comprising the sequence of SEQ ID NO: 61. In some embodiments, the single domain antibody comprises one or more framework(s) derived from a VHH domain comprising the sequence of SEQ ID NO: 62. In some embodiments, the single domain antibody comprises one or more framework(s) derived from a VHH domain comprising the sequence of SEQ ID NO: 63. In some embodiments, the single domain antibody comprises one or more framework(s) derived from a VHH domain comprising the sequence of SEQ ID NO: 183. In some embodiments, the single domain antibody comprises one or more framework(s) derived from a VHH domain comprising the sequence of SEQ ID NO: 184. In some embodiments, the single domain antibody comprises one or more framework(s) derived from a VHH domain comprising the sequence of SEQ ID NO: 185.

In some embodiments, the single domain antibody provided herein is a humanized single domain antibody. In some embodiments, humanized single domain antibodies can be generated using the method exemplified in the Section 6 below or the methods described in the section below.

Framework regions described herein are determined based upon the boundaries of the CDR numbering system. In other words, if the CDRs are determined by, e.g., Kabat, IMGT, or Chothia, then the framework regions are the amino acid residues surrounding the CDRs in the variable region in the format, from the N-terminus to C-terminus: FR1-CDR1-FR2-CDR2-FR3-CDR3-FR4. For example, FR1 is defined as the amino acid residues N-terminal to the CDR1 amino acid residues as defined by, e.g., the Kabat numbering system, the IMGT numbering system, or the Chothia numbering system, FR2 is defined as the amino acid residues between CDR1 and CDR2 amino acid residues as defined by, e.g., the Kabat numbering system, the IMGT numbering system, or the Chothia numbering system, FR3 is defined as the amino acid residues between CDR2 and CDR3 amino acid residues as defined by, e.g., the Kabat numbering system, the IMGT numbering system, or the Chothia numbering system, and FR4 is defined as the amino acid residues C-terminal to the CDR3 amino acid residues as defined by, e.g., the Kabat numbering system, the IMGT numbering system, or the Chothia numbering system.

In some embodiments, there is provided an isolated anti-CD20 single domain antibody comprising a VHH domain having the amino acid sequence of SEQ ID NO: 41. In some embodiments, there is provided a poi peptide comprising the amino acid sequence of SEQ ID NO: 41 In some embodiments, there is provided an isolated anti-CD20 single domain antibody comprising a VHH domain having the amino acid sequence of SEQ ID NO: 42. In some embodiments, there is provided a polypeptide comprising the amino acid sequence of SEQ ID NO: 42. In some embodiments, there is provided an isolated anti-CD20 single domain antibody comprising a VHH domain having the amino acid sequence of SEQ ID NO: 43. In some embodiments, there is provided a polypeptide comprising the amino acid sequence of SEQ II) NO: 43. In some embodiments, there is provided an isolated anti-CD20 single domain antibody comprising a VHH domain having the amino acid sequence of SEQ ID NO: 44. In some embodiments, there is provided a polypeptide comprising the amino acid sequence of SEQ ID NO: 44 In some embodiments, there is provided an isolated anti-CD20 single domain antibody comprising a VIM domain having the amino acid sequence of SEQ ID NO: 45. In some embodiments, there is provided a poly-peptide comprising the amino acid sequence of SEQ ID NO: 45. In some embodiments, there is provided an isolated anti-CD20 single domain antibody comprising a VHH domain having the amino acid sequence of SEQ ID NO: 46. In some embodiments, there is provided a polypeptide comprising the amino acid sequence of SEQ ID NO: 46. In some embodiments, there is provided an isolated anti-CD20 single domain antibody comprising a VHH domain having the amino acid sequence of SEQ ID NO: 47. In some embodiments, there is provided a polypeptide comprising the amino acid sequence of SEQ ID NO: 47. In some embodiments, there is provided an isolated anti-CD20 single domain antibody comprising a VHH domain having the amino acid sequence of SEQ ID NO: 4:3 In some embodiments, there is provided a polypeptide comprising the amino acid sequence of SEQ ID NO: 48. In some embodiments, there is provided an isolated anti-CD20 single domain antibody comprising a VHH domain having the amino acid sequence of SEQ ID NO: 49. In some embodiments, there is provided a polypeptide comprising the amino acid sequence of SEQ ID NO: 49. In some embodiments, there is provided an isolated anti-CD20 single domain antibody comprising a VHH domain having the amino acid sequence of SEQ ID NO: 50. In some embodiments, there is provided a poly-peptide comprising the amino acid sequence of SEQ ID NO: 50. In some embodiments, there is provided an isolated anti-CD20 single domain antibody comprising a VHH domain having the amino acid sequence of SEQ ID NO: 51. In some embodiments, there is provided a polypeptide comprising the amino acid sequence of SEQ ID NO: 51 In some embodiments, there is provided an isolated anti-CD20 single domain antibody comprising a VHH domain having the amino acid sequence of SEQ ID NO: 52. In some embodiments, there is provided a polypeptide comprising the amino acid sequence of SEQ ID NO: 52. In some embodiments, there is provided an isolated anti-CD20 single domain antibody comprising a VHH domain having the amino acid sequence of SEQ ID NO: 53. In some embodiments, there is provided a polypeptide comprising the amino acid sequence of SEQ ID NO: 53. In some embodiments, there is provided an isolated anti-CD20 single domain antibody comprising a VHH domain having the amino acid sequence of SEQ ID NO: 54. In some embodiments, there is provided a polypeptide comprising the amino acid sequence of SEQ ID NO: 54. In some embodiments, there is provided an isolated anti-CD20 single domain antibody comprising a VHH domain having the amino acid sequence of SEQ ID NO: 55. In some embodiments, there is provided a poly-peptide comprising the amino acid sequence of SEQ II) NO: 55. In some embodiments, there is provided an isolated anti-CD20 single domain antibody comprising a VHH domain having the amino acid sequence of SEQ ID NO: 56. In some embodiments, there is provided a polypeptide comprising the amino acid sequence of SEQ ID NO: 56 In some embodiments, there is provided an isolated anti-CD20 single domain antibody comprising a VHH domain having the amino acid sequence of SEQ ID NO: 57. In some embodiments, there is provided a polypeptide comprising the amino acid sequence of SEQ ID NO: 57. In some embodiments, there is provided an isolated anti-CD20 single domain antibody comprising a VHH domain having the amino acid sequence of SEQ ID NO: 58. In some embodiments, there is provided a polypeptide comprising the amino acid sequence of SEQ ID NO: 58. In some embodiments, there is provided an isolated anti-CD20 single domain antibody comprising a VHH domain having the amino acid sequence of SEQ ID NO: 59. In some embodiments, there is provided a polypeptide comprising the amino acid sequence of SEQ ID NO: 59. In some embodiments, there is provided an isolated anti-CD20 single domain antibody comprising a VHH domain having the amino acid sequence of SEQ ID NO: 60 In some embodiments, there is provided a polypep-tide comprising the amino acid sequence of SEQ ID NO: 60. In some embodiments, there is provided an isolated anti-CD20 single domain antibody comprising a VHH domain having the amino acid sequence of SEQ ID NO: 61. In some embodiments, there is provided a polypeptide comprising the amino acid sequence of SEQ ID NO: 61. In some embodiments, there is provided an isolated anti-CD20 single domain antibody comprising a VHH domain having the amino acid sequence of SEQ ID NO: 62. In some embodi-ments, there is provided a polypeptide comprising the amino acid sequence of SEQ ID NO: 62. In some embodiments, there is provided an isolated anti-CD20 single domain antibody comprising a VHH domain having the amino acid sequence of SEQ ID NO: 63. In some embodiments, there is provided a polypeptide comprising the amino acid sequence of SEQ ID NO: 63 In some embodiments, there is provided an isolated anti-CD20 single domain antibody comprising a VHH domain having the amino acid sequence of SEQ ID NO: 183. In some embodiments, there is provided a poly-peptide comprising the amino acid sequence of SEQ ID NO: 183. In some embodiments, there is provided an isolated anti-CD20 single domain antibody comprising a VHH domain having the amino acid sequence of SEQ ID NO: 184. In some embodiments, there is provided a polypeptide comprising the amino acid sequence of SEQ ID NO: 184. In some embodiments, there is provided an isolated anti-CD20 single domain antibody comprising a VHH domain having the amino acid sequence of SEQ ID NO: 185. In some embodiments, there is provided a polypeptide comprising the amino acid sequence of SEQ II) NO: 185.

In certain embodiments, an antibody described herein or an antigen-binding fragment thereof comprises amino acid sequences with certain percent identity relative to any one of antibodies VHH-273, VHH-283, VHH-313, VHH-440, VHH-466, VHH-496, VHH-653, huVHH-253, huVHH-256, huVHH-260, huVHH-746, huVHH-750, huVHH-753, huVHH-836, huVHH-840, huVHH-843, huVHH-846, 2082H1, 2082H2, 2082H3, 2082H4, 2082H5, 2082H6, VHH-623, VHH-640, and VHH-657.

The determination of percent identity between two sequences (e.g., amino acid sequences or nucleic acid sequences) can be accomplished using a mathematical algorithm. A non-limiting example of a mathematical algorithm utilized for the comparison of two sequences is the algorithm of Karlin and Altschul, Proc. Natl. Acad. Sci. U.S.A. 87:2264 2268 (1990), modified as in Karlin and Altschul, Proc. Natl. Acad. Sci. U.S.A. 90:5873 5877 (1993). Such an algorithm is incorporated into the NBLAST and XBLAST programs of Altschul et at, J. Mol. Biol. 215:403 (1990). BLAST nucleotide searches can be performed with the NBLAST nucleotide program parameters set, e.g., for score=100, word length=12 to obtain nucleotide sequences homologous to a nucleic acid molecules described herein. BLAST protein searches can be performed with the XBLAST program parameters set, e.g., to score 50, word length=3 to obtain amino acid sequences homologous to a protein molecule described herein. To obtain gapped alignments for comparison purposes, Gapped BLAST can be utilized as described in Altschul et al., Nucleic Acids Res. 25:3389 3402 (1997). Alternatively, PSI BLAST can be used to perform an iterated search which detects distant relationships between molecules (Id). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another non-limiting example of a mathematical algorithm utilized for the comparison of sequences is the algorithm of Myers and Miller, CABIOS 4:11-17 (1998). Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. The percent identity between two sequences can be determined using techniques similar to those described above, with or without allowing gaps. In calculating percent identity, typically only exact matches are counted.

In some embodiments, there is provided an anti-CD20 single domain antibody comprising a VHH domain having at least about any one of 75%, 80%, 85%, 86%, 87%, 88%, 89%, 90%, 91%, 92%, 93%, 94%, 95%, 96%, 97%, 98%, 99%, or 100% sequence identity to an amino acid sequence selected from SEQ ID NOs: 41-63 and 183-185. In some embodiments, a VHH sequence having at least about any one of 75%, 80%, 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-CD20 single domain antibody comprising that sequence retains the ability to bind to CD20. In some embodiments, a total of 1 to 10 amino acids have been substituted, inserted and/or deleted in an amino acid sequence selected from SEQ ID NOs: 41-63 and 183-185. In some embodiments, substitutions, insertions, or deletions occur in regions outside the CDRs (i.e., in the ERs). Optionally, the anti-CD20 single domain antibody comprises an amino acid sequence selected from SEQ ID NOs: 41-63 and 183-185, including post-translational modifications of that sequence.

In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 41, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 42, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 43, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 44, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 45, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 46, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 47, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 48, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 49, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 50, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 51, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 52, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 53, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 54, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 55, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 56, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 57, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 58, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 59, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 60, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 61, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97°/o, at least 98%, or at least 99% sequence identity to the amino acid sequence of SEQ ID NO: 62, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 63, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 183, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 184, wherein the single domain antibody binds to CD20. In certain embodiments, the single domain antibody described herein comprises a VHH domain having at least 75%, at least 80%, at least 85%, at least 90%, at least 91%, at least 92%, at least 93%, at least 94%, at least 95%, at least 96%, at least 97%, at least 98%, or at least 99% sequence identity to the amino acid sequence of SEQ ID NO: 185, wherein the single domain antibody binds to CD20.

In some embodiments, functional epitopes can be mapped, e.g., by combinatorial alanine scanning, to identify amino acids in the CD20 protein that are necessary for interaction with anti-CD20 single domain antibodies provided herein. In some embodiments, conformational and crystal structure of anti-CD20 single domain antibody bound to CD20 may be employed to identify the epitopes. In some embodiments, the present disclosure provides an antibody that specifically binds to the same epitope as any of the anti-CD20 single domain antibodies provided herein. For example, in some embodiments, an antibody is provided that binds to the same epitope as an anti-CD20 single domain antibody comprising the amino acid sequence of SEQ ID NO: 41. In some embodiments, an antibody is provided that binds to the same epitope as an anti-CD20 single domain antibody comprising the amino acid sequence of SEQ ID NO: 42. In some embodiments, an antibody is provided that binds to the same epitope as an anti-CD20 single domain antibody comprising the amino acid sequence of SEQ ID NO: 43. In some embodiments, an antibody is provided that binds to the same epitope as an anti-CD20 single domain antibody comprising the amino acid sequence of SEQ ID NO: 44. In some embodiments, an antibody is provided that binds to the same epitope as an anti-CD20 single domain antibody comprising the amino acid sequence of SEQ ID NO: 45. In some embodiments, an antibody is provided that binds to the same epitope as an anti-CD20 single domain antibody comprising the amino acid sequence of SEQ ID NO: 46. In some embodiments, an antibody is provided that binds to the same epitope as an anti-CD20 single domain antibody comprising the amino acid sequence of SEQ ID NO: 47. In some embodiments, an antibody is provided that binds to the same epitope as an anti-CD20 single domain antibody comprising the amino acid sequence of SEQ ID NO: 48. In some embodiments, an antibody is provided that binds to the same epitope as an anti-CD20 single domain antibody comprising the amino acid sequence of SEQ ID NO: 49. In some embodiments, an antibody is provided that binds to the same epitope as an anti-CD20 single domain antibody comprising the amino acid sequence of SEQ ID NO: 50. In some embodiments, an antibody is provided that binds to the same epitope as an anti-CD20 single domain antibody comprising the amino acid sequence of SEQ ID NO: 51. In some embodiments, an antibody is provided that binds to the same epitope as an anti-CD20 single domain antibody comprising the amino acid sequence of SEQ ID NO: 52. In some embodiments, an antibody is provided that binds to the same epitope as an anti-CD20 single domain antibody comprising the amino acid sequence of SEQ ID NO: 53. In some embodiments, an antibody is provided that binds to the same epitope as an anti-CD20 single domain antibody comprising the amino acid sequence of SEQ ID NO: 54. In some embodiments, an antibody is provided that binds to the same epitope as an anti-CD20 single domain antibody comprising the amino acid sequence of SEQ ID NO: 55. In some embodiments, an antibody is provided that binds to the same epitope as an anti-CD20 single domain antibody comprising the amino acid sequence of SEQ ID NO: 56. In some embodiments, an antibody is provided that binds to the same epitope as an anti-CD20 single domain antibody comprising the amino acid sequence of SEQ ID NO: 57. In some embodiments, an antibody is provided that binds to the same epitope as an anti-CD20 single domain antibody comprising the amino acid sequence of SEQ ID NO: 58. In some embodiments, an antibody is provided that binds to the same epitope as an anti-CD20 single domain antibody comprising the amino acid sequence of SEQ ID NO: 59. In some embodiments, an antibody is provided that binds to the same epitope as an anti-CD20 single domain antibody comprising the amino acid sequence of SEQ ID NO: 60. In some embodiments, an antibody is provided that binds to the same epitope as an anti-CD20 single domain antibody comprising the amino acid sequence of SEQ ID NO: 61. In some embodiments, an antibody is provided that binds to the same epitope as an anti-CD20 single domain antibody comprising the amino acid sequence of SEQ ID NO: 62. In some embodiments, an antibody is provided that binds to the same epitope as an anti-CD20 single domain antibody comprising the amino acid sequence of SEQ ID NO: 63. In some embodiments, an antibody is provided that binds to the same epitope as an anti-CD20 single domain antibody comprising the amino acid sequence of SEQ ID NO: 183. In some embodiments, an antibody is provided that binds to the same epitope as an anti-CD20 single domain antibody comprising the amino acid sequence of SEQ ID NO: 184. In some embodiments, an antibody is provided that binds to the same epitope as an anti-CD20 single domain antibody comprising the amino acid sequence of SEQ ID NO: 185.

In some embodiments, provided herein is an anti-CD20 antibody, or antigen binding fragment thereof, that specifically binds to CD20 competitively with any one of the anti-CD20 single domain antibodies described herein. In some embodiments, competitive binding may be determined using an ELISA assay. For example, in some embodiments, an antibody is provided that specifically binds to CD20 competitively with an anti-CD20 single domain antibody comprising the amino acid sequence of SEQ ID NO: 41. In some embodiments, an antibody is provided that specifically binds to CD20 competitively with an anti-CD20 single domain antibody comprising the amino acid sequence of SEQ ID NO: 42. In some embodiments, an antibody is provided that specifically binds to CD20 competitively with an anti-CD20 single domain antibody comprising the amino acid sequence of SEQ ID NO: 43. In some embodiments, an antibody is provided that specifically binds to CD20 competitively with an anti-CD20 single domain antibody comprising the amino acid sequence of SEQ ID NO: 44. In some embodiments, an antibody is provided that specifically binds to CD20 competitively with an anti-CD20 single domain antibody comprising the amino acid sequence of SEQ ID NO: 45. In some embodiments, an antibody is provided that specifically binds to CD20 competitively with an anti-CD20 single domain antibody comprising the amino acid sequence of SEQ ID NO: 46. In some embodiments, an antibody is provided that specifically binds to CD20 competitively with an anti-CD20 single domain antibody comprising the amino acid sequence of SEQ ID NO: 47. In some embodiments, an antibody is provided that specifically binds to CD20 competitively with an anti-CD20 single domain antibody comprising the amino acid sequence of SEQ ID NO: 48. In some embodiments, an antibody is provided that specifically binds to CD20 competitively with an anti-CD20 single domain antibody comprising the amino acid sequence of SEQ ID NO: 49. In some embodiments, an antibody is provided that specifically binds to CD20 competitively with an anti-CD20 single domain antibody comprising the amino acid sequence of SEQ ID NO: 50. In some embodiments, an antibody is provided that specifically binds to CD20 competitively with an anti-CD20 single domain antibody comprising the amino acid sequence of SEQ ID NO: 51. In some embodiments, an antibody is provided that specifically binds to CD20 competitively with an anti-CD20 single domain antibody comprising the amino acid sequence of SEQ ID NO: 52. In some embodiments, an antibody is provided that specifically binds to CD20 competitively with an anti-CD20 single domain antibody comprising the amino acid sequence of SEQ ID NO: 53. In some embodiments, an antibody is provided that specifically binds to CD20 competitively with an anti-CD20 single domain antibody comprising the amino acid sequence of SEQ ID NO: 54. In some embodiments, an antibody is provided that specifically binds to CD20 competitively with an anti-CD20 single domain antibody comprising the amino acid sequence of SEQ ID NO: 55. In some embodiments, an antibody is provided that specifically binds to CD20 competitively with an anti-CD20 single domain antibody comprising the amino acid sequence of SEQ ID NO: 56. In some embodiments, an antibody is provided that specifically binds to CD20 competitively with an anti-CD20 single domain antibody comprising the amino acid sequence of SEQ ID NO: 57. In some embodiments, an antibody is provided that specifically binds to CD20 competitively with an anti-CD20 single domain antibody comprising the amino acid sequence of SEQ ID NO: 58. In some embodiments, an antibody is provided that specifically binds to CD20 competitively with an anti-CD20 single domain antibody comprising the amino acid sequence of SEQ ID NO: 59. In some embodiments, an antibody is provided that specifically binds to CD20 competitively with an anti-CD20 single domain antibody comprising the amino acid sequence of SEQ ID NO: 60. In some embodiments, an antibody is provided that specifically binds to CD20 competitively with an anti-CD20 single domain antibody comprising the amino acid sequence of SEQ ID NO: 61. In some embodiments, an antibody is provided that specifically binds to CD20 competitively with an anti-CD20 single domain antibody comprising the amino acid sequence of SEQ ID NO: 62. In some embodiments, an antibody is provided that specifically binds to CD20 competitively with an anti-CD20 single domain antibody comprising the amino acid sequence of SEQ ID NO: 63. In some embodiments, an antibody is provided that specifically binds to CD20 competitively with an anti-CD20 single domain antibody comprising the amino acid sequence of SEQ ID NO: 183. In some embodiments, an antibody is provided that specifically binds to CD20 competitively with an anti-CD20 single domain antibody comprising the amino acid sequence of SEQ ID NO: 184. In some embodiments, an antibody is provided that specifically binds to CD20 competitively with an anti-CD20 single domain antibody comprising the amino acid sequence of SEQ ID NO: 185.

In some embodiments, provided herein is a CD20 binding protein comprising any one of the anti-CD20 single domain antibodies described above. In some embodiments, the CD20 binding protein is a monoclonal antibody, including a camelid, chimeric, humanized or human antibody. In some embodiments, the anti-CD20 antibody is an antibody fragment, e.g., a VHH fragment. In some embodiments, the anti-CD20 antibody is a full-length heavy-chain only antibody comprising an Fc region of any antibody class or isotype, such as IgG1 or IgG4. In some embodiments, the Fc region has reduced or minimized effector function. In some embodiments, the CD20 binding protein is a fusion protein comprising the anti-CD20 single domain antibody provided herein. In other embodiments, the CD20 binding protein is a multispecific antibody comprising the anti-CD20 single domain antibody provided herein. Other exemplary CD20 binding molecules are described in more detail in the following sections.

In some embodiments, the anti-CD20 antibody (such as anti-CD20 single domain antibody) or antigen binding protein according to any of the above embodiments may incorporate any of the features, singly or in combination, as described in Sections 5.2.2 to 5.2.7 below.

5.2.2. Humanized Single Domain Antibodies

The single domain antibodies described herein include humanized single domain antibodies. General strategies to humanize single domain antibodies from Camelidae species have been described (see, e.g., Vincke et al., J. Biol. Chem., 284(5):3273-3284 (2009)) and may be useful for producing humanized VHH domains as disclosed herein. The design of humanized single domain antibodies from Camelidae species may include the hallmark residues in the VHH, such as residues 11, 37, 44, 45 and 47 (residue numbering according to Kabat) (Muyldermans, Reviews Mol Biotech 74:277-302 (2001).

Humanized antibodies, such as the humanized single domain antibodies disclosed herein can also be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, Molecular Immunology 28(4/5): 489-498 (1991); Studnicka et al., Protein Engineering 7(6): 805-814 (1994); and Roguska et al., PNAS 91:969-973 (1994)), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (19%), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), each of which is incorporated by reference herein in its entirety.

In some embodiments, single domain antibodies provided herein can be humanized single domain antibodies that bind to CD20, including human CD20. For example, humanized single chain antibodies of the present disclosure may comprise one or more CDRs set forth in SEQ ID NOs: 41-63 and 183-185. Various methods for humanizing non-human antibodies are known in the art. For example, a humanized antibody can have one or more amino acid residues introduced into it from a source that is non-human. These non-human amino acid residues are often referred to as "import" residues, which are typically taken from an "import" variable domain. Humanization may be performed, for example, following the method of Jones et al., Nature 321:522-25 (1986): Riechmann et al., Nature 332:323-27 (1988); and Verhoeyen et al., Science 239:1534-36 (1988)), by substituting hypervariable region sequences for the corresponding sequences of a human antibody. In a specific embodiment, humanization of the single domain antibody provided herein is performed as described in Section 6 below.

In some cases, the humanized antibodies are constructed by CDR grafting, in which the amino acid sequences of the CDRs of the parent non-human antibody are grafted onto a human antibody framework. For example, Padlan et al. determined that only about one third of the residues in the CDRs actually contact the antigen, and termed these the "specificity determining residues," or SDRs (Padlan et al., FASEB J. 9:133-39 (1995)). In the technique of SDR grafting, only the SDR residues are grafted onto the human antibody framework (see, e.g., Kashmiri et al., Methods 36:25-34 (2005)).

The choice of human variable domains to be used in making the humanized antibodies can be important to reduce antigenicity. For example, according to the so-called "best-fit" method, the sequence of the variable domain of a non-human antibody is screened against the entire library of known human variable-domain sequences. The human sequence that is closest to that of the non-human antibody may be selected as the human framework for the humanized antibody (Sims et al., J. Immunol. 151:2296-308 (1993); and Chothia et al., J. Mol. Biol. 196:901-17 (1987)). Another method uses a particular framework derived from the consensus sequence of all human antibodies of a particular subgroup of light or heavy chains. The same framework may be used for several different humanized antibodies (Carter et al., Proc. Natl. Acad. Sci. USA 89:4285-89 (1992); and Presta et al., J. Immunol. 151:2623-32 (1993)). In some cases, the framework is derived from the consensus sequences of the most abundant human subclasses, $V_L6$ subgroup I ($V_L6I$) and $V_H$ subgroup III ($V_HIII$). In another method, human germline genes are used as the source of the framework regions.

In an alternative paradigm based on comparison of CDRs, called superhumanization, FR homology is irrelevant. The method consists of comparison of the non-human sequence with the functional human germline gene repertoire. Those genes encoding the same or closely related canonical structures to the murine sequences are then selected. Next, within the genes sharing the canonical structures with the non-human antibody, those with highest homology within the CDRs are chosen as FR donors. Finally, the non-human CDRs are grafted onto these FRs (see, e.g., Tan et al., J. Immunol. 169:1119-25 (2002)).

It is further generally desirable that antibodies be humanized with retention of their affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. These include, for example, WAM (Whitelegg and Rees, Protein Eng. 13:819-24 (2002)), Modeller (Sali and Blundell, J. Mol. Biol. 234:779-815 (1993)), and Swiss PDB Viewer (Guex and Peitsch, Electrophoresis 18:2714-23 (1997)). Inspection of these displays permits analysis of the likely role of the residues in the functioning of the candidate immunoglobulin sequence, e.g., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Another method for antibody humanization is based on a metric of antibody humanness termed Human String Content (HSC). This method compares the mouse sequence with the repertoire of human germline genes, and the differences are scored as HSC. The target sequence is then humanized by maximizing its HSC rather than using a global identity measure to generate multiple diverse humanized variants (Lazar et al., Mol. Immunol. 44:1986-98 (2007)).

In addition to the methods described above, empirical methods may be used to generate and select humanized antibodies. These methods include those that are based upon the generation of large libraries of humanized variants and selection of the best clones using enrichment technologies or high throughput screening techniques. Antibody variants may be isolated from phage, ribosome, and yeast display libraries as well as by bacterial colony screening (see. e.g., Hoogenboom, Nat. Biotechnol. 23:1105-16 (2005); Dufner et al., Trends Biotechnol. 24:523-29 (2006); Feldhaus et al., Nat. Biotechnol. 21:163-70 (2003); and Schlapschy et al., Protein Eng. Des. Sel. 17:847-60 (2004)).

In the FR library approach, a collection of residue variants are introduced at specific positions in the FR followed by screening of the library to select the FR that best supports the grafted CDR. The residues to be substituted may include some or all of the "Vernier" residues identified as potentially contributing to CDR structure (see, e.g., Foote and Winter, J. Mol. Biol. 224:487-99 (1992)), or from the more limited set of target residues identified by Baca et al. J. Biol. Chem. 272:10678-84 (1997).

In FR shuffling, whole FRs are combined with the non-human CDRs instead of creating combinatorial libraries of selected residue variants (see, e.g., Dall'Acqua et al., Methods 36:43 60 (2005)). A one-step FR shuffling process may be used. Such a process has been shown to be efficient, as the resulting antibodies exhibited improved biochemical and physicochemical properties including enhanced expression, increased affinity, and thermal stability (see, e.g., Damschroder et al., Mol. Immunol. 44:3049-60 (2007)).

The "humaneering" method is based on experimental identification of essential minimum specificity determinants (MSDs) and is based on sequential replacement of non-human fragments into libraries of human FRs and assessment of binding. This methodology typically results in epitope retention and identification of antibodies from multiple subclasses with distinct human V-segment CDRs.

The "human engineering" method involves altering a non-human antibody or antibody fragment by making specific changes to the amino acid sequence of the antibody so as to produce a modified antibody with reduced immunogenicity in a human that nonetheless retains the desirable binding properties of the original non-human antibodies. Generally, the technique involves classifying amino acid residues of a non-human antibody as "low risk," "moderate risk," or "high risk" residues. The classification is performed using a global risk/reward calculation that evaluates the predicted benefits of making particular substitution (e.g., for immunogenicity in humans) against the risk that the substitution will affect the resulting antibody's folding. The particular human amino acid residue to be substituted at a given position (e.g., low or moderate risk) of a non-human antibody sequence can be selected by aligning an amino acid sequence from the non-human antibody's variable regions with the corresponding region of a specific or consensus human antibody sequence. The amino acid residues at low or moderate risk positions in the non-human sequence can be substituted for the corresponding residues in the human antibody sequence according to the alignment. Techniques for making human engineered proteins are described in greater detail in Studnicka et al., Protein Engineering 7:805-14 (1994); U.S. Pat. Nos. 5,766,886; 5,770,196; 5,821,123; and 5,869,619; and PCT Publication WO 93/11794.

A composite human antibody can be generated using, for example, Composite Human Antibody™ (technology (Antitope Ltd., Cambridge, United Kingdom). To generate composite human antibodies, variable region sequences are designed from fragments of multiple human antibody variable region sequences in a manner that avoids T cell epitopes, thereby minimizing the immunogenicity of the resulting antibody.

A deimmunized antibody is an antibody in which T-cell epitopes have been removed. Methods for making deimmunized antibodies have been described. See, e.g., Jones et al., Methods Mol Biol. 525:405-23 (2009), xiv, and De Groot et al., Cell. Immunol. 244:148 153(2006)). Deimmunized antibodies comprise T-cell epitope-depleted variable regions and human constant regions. Briefly, variable regions of an antibody are cloned and T-cell epitopes are subsequently identified by testing overlapping peptides derived from the variable regions of the antibody in a T cell proliferation assay. T cell epitopes are identified via in silico methods to identify peptide binding to human MHC class II. Mutations are introduced in the variable regions to abrogate binding to human MHC class II. Mutated variable regions are then utilized to generate the deimmunized antibody.

5.2.3. Single Domain Antibody Variants

In some embodiments, amino acid sequence modification(s) of the single domain antibodies that bind to CD20 described herein are contemplated. For example, it may be desirable to optimize the binding affinity and/or other biological properties of the antibody, including but not limited to specificity, thermostability, expression level, effector functions, glycosylation, reduced immunogenicity, or solubility. Thus, in addition to the single domain antibodies that bind to CD20 described herein, it is contemplated that variants of the single domain antibodies that bind to CD20 described herein can be prepared. For example, single domain antibody variants can be prepared by introducing appropriate nucleotide changes into the encoding DNA, and/or by synthesis of the desired antibody or polypeptide. Those skilled in the art who appreciate that amino acid changes may alter post-translational processes of the single domain antibody.

Chemical Modifications

In some embodiments, the single domain antibodies provided herein are chemically modified, for example, by the covalent attachment of any type of molecule to the single domain antibody. The antibody derivatives may include antibodies that have been chemically modified, for example, by glycosylation, acetylation, pegylation, phosphorylation, amidation, derivatization by known protecting/blocking groups, proteolytic cleavage, linkage to a cellular ligand or other protein, or conjugation to one or more immunoglobulin domains (e.g., Fc or a portion of an Fc). Any of numerous chemical modifications may be carried out by known techniques, including, but not limited to, specific chemical cleavage, acetylation, formulation, metabolic synthesis of tunicamycin, etc. Additionally, the antibody may contain one or more non-classical amino acids.

In some embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

When the single domain antibody provided herein is fused to an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See. e.g., Wright et al. TIBTECH 15:26 32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the binding molecules provided herein may be made in order to create variants with certain improved properties.

In other embodiments, when the single domain antibody provided herein is fused to an Fc region, antibody variants provided herein may have a carbohydrate structure that lacks fucose attached (directly or indirectly) to said Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g., complex, hybrid and high mannose structures) as measured by MALDI-TOF mass spectrometry, as described in WO 2008/077546, for example, Asn297 refers to the asparagine residue located at about position 297 in the Fc region (EU numbering of Fc region residues): however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 and US 2004/0093621. Examples of publications related to "defucosylated" or "fucose-deficient" antibody variants include: US 2003/

0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249:533-545 (1986); US Patent Application No. US 2003/0157108; and WO 2004/056312, especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda. Y. et al., Biotechnol. Bioeng., 94(4):680-688 (2006); and WO2003/085107).

The binding molecules comprising a single domain antibody provided herein are further provided with bisected oligosaccharides, e.g., in which a biantennary oligosaccharide attached to the Fc region is bisected by GlcNAc. Such variants may have reduced fucosylation and/or improved ADCC function. Examples of such variants are described, e.g., in WO 2003/011878 (Jean-Mairet et al.): U.S. Pat. No. 6,602,684 (Umana et al.); and US 2005/0123546 (Umana el al.). Variants with at least one galactose residue in the oligosaccharide attached to the Fc region are also provided. Such variants may have improved CDC function. Such variants are described, e.g., in WO 1997/30087; WO 1998/58964; and WO 1999/22764.

In molecules that comprise the present single domain antibody and an Fc region, one or more amino acid modifications may be introduced into the Fc region, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In some embodiments, the present application contemplates variants that possesses some but not all effector functions, which make it a desirable candidate for applications in which the half life of the binding molecule in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the binding molecule lacks FcγR binding (hence likely lacking ADCC activity), but retains FcRn binding ability. Non-limiting examples of in vitro assays to assess ADCC activity of a molecule of interest is described in U.S. Pat. No. 5,500,362 (see. e.g. Hellstrom, I. et al. Proc. Nat'l Acad. Sci. USA 84:7059-7063 (1986)) and Hellstrom, I et al., Proc. Nat'l Acad. Sci. LISA 82:1499-1502 (1985); 5,821,337 (see Bruggemann, M. et al., J. Exp. Med 166:1351-1361 (1987)). Alternatively, non radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). Clq binding assays may also be carried out to confirm that the antibody is unable to bind C1q and hence lacks CDC activity. See. e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., Blood 101:1045-1052 (2003); and Cragg, M. S. and M. J. Glennie, *Blood* 103: 2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Binding molecules with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain variants with improved or diminished binding to FcRs are described. (See, e.g., U.S. Pat. No. 6,737,056; WO 2004/056312, and Shields et al. *J. Biol. Chem.* 9(2): 6591-6604 (2001).)

In some embodiments, a variant comprises an Fc region with one or more amino acid substitutions which improve ADCC, e.g., substitutions at positions 298, 333, and/or 334 of the Fc region (EU numbering of residues). In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Binding molecules with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those molecules comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, Nature 322:738-40 (1988); U.S. Pat. Nos. 5,648,260; 5,624,821; and WO 94/29351 concerning other examples of Fc region variants.

In some embodiments, it may be desirable to create cysteine engineered antibodies, in which one or more residues of an antibody are substituted with cysteine residues. In some embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein.

Substitutions, Deletions, or Insertions

Variations may be a substitution, deletion, or insertion of one or more codons encoding the single domain antibody or polypeptide that results in a change in the amino acid sequence as compared with the original antibody or polypeptide. Sites of interest for substitutional mutagenesis include the CDRs and FRs.

Amino acid substitutions can be the result of replacing one amino acid with another amino acid having similar structural and/or chemical properties, such as the replacement of a leucine with a serine, e.g., conservative amino acid replacements. Standard techniques known to those of skill in the art can be used to introduce mutations in the nucleotide sequence encoding a molecule provided herein, including, for example, site-directed mutagenesis and PCR-mediated mutagenesis which results in amino acid substitutions. Insertions or deletions may optionally be in the range of about 1 to 5 amino acids. In certain embodiments, the substitution, deletion, or insertion includes fewer than 25 amino acid substitutions, fewer than 20 amino acid substitutions, fewer than 15 amino acid substitutions, fewer than 10 amino acid substitutions, fewer than 5 amino acid substitutions, fewer than 4 amino acid substitutions, fewer than 3 amino acid substitutions, or fewer than 2 amino acid substitutions relative to the original molecule. In a specific embodiment, the substitution is a conservative amino acid substitution made at one or more predicted non-essential amino acid residues. The variation allowed may be determined by systematically making insertions, deletions, or substitutions of amino acids in the sequence and testing the resulting variants for activity exhibited by the parental antibodies.

Amino acid sequence insertions include amino- and/or carboxyl-terminal fusions ranging in length from one residue to polypeptides containing multiple residues, as well as intrasequence insertions of single or multiple amino acid residues. Examples of terminal insertions include an antibody with an N-terminal methionyl residue.

Single domain antibodies generated by conservative amino acid substitutions are included in the present disclosure. In a conservative amino acid substitution, an amino acid residue is replaced with an amino acid residue having a side chain with a similar charge. As described above, families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined. Conservative (e.g., within an amino acid group with similar properties and/or side chains) substitutions may be made, so as to maintain or not significantly change the properties. Exemplary substitutions are shown in Table 3 below.

TABLE 3

| Amino Acid Substitutions | |
| --- | --- |
| Original Residue | Exemplary Substitutions |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |

TABLE 3-continued

| Amino Acid Substitutions | |
| --- | --- |
| Original Residue | Exemplary Substitutions |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to similarities in the properties of their side chains (see, e.g., Lehninger, *Biochemistry* 73-75 (2d ed. 1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); and (4) basic: Lys (K), Arg (R), His(H). Alternatively, naturally occurring residues may be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; and (6) aromatic: Trp, Tyr, Phe. For example, any cysteine residue not involved in maintaining the proper conformation of the single domain antibody also may be substituted, for example, with another amino acid, such as alanine or serine, to improve the oxidative stability of the molecule and to prevent aberrant crosslinking. Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more CDR residues are mutated and the variant antibodies displayed on phage and screened for a particular biological activity (e.g binding affinity).

Alterations (e.g., substitutions) may be made in CDRs, e.g., to improve antibody affinity. Such alterations may be made in CDR "hotspots," i.e., residues encoded by codons that undergo mutation at high frequency during the somatic maturation process (see, e.g., Chowdhury, *Methods Mol. Biol.* 207:179-1% (2008)), and/or SDRs (a-CDRs), with the resulting variant antibody or fragment thereof being tested for binding affinity. Affinity maturation by constructing and reselecting from secondary libraries has been described, e.g., in Hoogenboom et al, in *Methods in Molecular Biology* 178:1-37 (O'Brien et al., ed., Human Press, Totowa, NJ, (2001)) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. More detailed description regarding affinity maturation is provided in the section below.

In some embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In some embodiments of the variant VHH sequences provided herein, each CDR either is unaltered, or contains no more than one, two or three amino acid substitutions.

A useful method for identification of residues or regions of an antibody that may be targeted for mutagenesis is called "alanine scanning mutagenesis" as described by Cunningham and Wells, *Science,* 244:1081-1085 (1989). In this method, a residue or group of target residues (e.g., charged residues such as Mg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

The variations can be made using methods known in the art such as oligonucleotide-mediated (site-directed) mutagenesis, alanine scanning, and PCR mutagenesis. Site-directed mutagenesis (see, e.g., Carter, Biochem J. 237:1-7 (1986); and Zoller et al., *Nucl. Acids Res.* 10:6487-500 (1982)), cassette mutagenesis (see. e.g., Wells et al., Gene 34:315-23 (1985)), or other known techniques can be performed on the cloned DNA to produce the single domain antibody variant DNA.

5.2.4. In vitro Affinity Maturation

In some embodiments, antibody variants having an improved property such as affinity, stability, or expression level as compared to a parent antibody may be prepared by in vitro affinity maturation. Like the natural prototype, in vitro affinity maturation is based on the principles of mutation and selection. Libraries of antibodies are displayed on the surface of an organism (e.g., phage, bacteria, yeast, or mammalian cell) or in association (e.g., covalently or noncovalently) with their encoding mRNA or DNA. Affinity selection of the displayed antibodies allows isolation of organisms or complexes carrying the genetic information encoding the antibodies. Two or three rounds of mutation and selection using display methods such as phage display usually results in antibody fragments with affinities in the low nanomolar range. Affinity matured antibodies can have nanomolar or even picomolar affinities for the target antigen.

Phage display is a widespread method for display and selection of antibodies. The antibodies are displayed on the surface of Fd or M13 bacteriophages as fusions to the bacteriophage coat protein. Selection involves exposure to antigen to allow phage-displayed antibodies to bind their targets, a process referred to as "panning." Phage bound to antigen are recovered and used to infect bacteria to produce phage for further rounds of selection. For review, see, for example, Hoogenboom, Methods. Mol. Biol. 178:1-37 (2002); and Bradbury and Marks. J. Immunol. Methods 290:29-49 (2004).

In a yeast display system (see, e.g., Boder et al., Nat. Biotech. 15:553-57 (1997); and Chao et al., Nat. Protocols 1:755-68 (2006)), the antibody may be fused to the adhesion subunit of the yeast agglutinin protein Aga2p, which attaches to the yeast cell wall through disulfide bonds to Aga1p. Display of a protein via Aga2p projects the protein away from the cell surface, minimizing potential interactions with other molecules on the yeast cell wall. Magnetic separation and flow cytometry are used to screen the library to select for antibodies with improved affinity or stability. Binding to a soluble antigen of interest is determined by labeling of yeast with biotinylated antigen and a secondary reagent such as streptavidin conjugated to a fluorophore. Variations in surface expression of the antibody can be measured through immunofluorescence labeling of either the hem agglutinin or c-Myc epitope tag flanking the single chain antibody (e.g., scFv). Expression has been shown to correlate with the stability of the displayed protein, and thus antibodies can be selected for improved stability as well as affinity (see, e.g., Shusta et al., J. Mol. Biol. 292:949-56 (1999)). An additional advantage of yeast display is that displayed proteins are folded in the endoplasmic reticulum of the eukaryotic yeast cells, taking advantage of endoplasmic reticulum chaperones and quality-control machinery. Once maturation is complete, antibody affinity can be conveniently "titrated" while displayed on the surface of the yeast, eliminating the need for expression and purification of each clone. A theoretical limitation of yeast surface display is the potentially smaller functional library size than that of other display methods; however, a recent approach uses the yeast cells' mating system to create combinatorial diversity estimated to be $10^{14}$ in size (see, e.g., U.S. Pat. Publication 2003/0186374; and Blaise et al., Gene 342:211-18 (2004)).

In ribosome display, antibody-ribosome-mRNA (ARM) complexes are generated for selection in a cell-free system. The DNA library coding for a particular library of antibodies is genetically fused to a spacer sequence lacking a stop codon. This spacer sequence, when translated, is still attached to the peptidyl tRNA and occupies the ribosomal tunnel, and thus allows the protein of interest to protrude out of the ribosome and fold. The resulting complex of mRNA, ribosome, and protein can bind to surface-bound ligand, allowing simultaneous isolation of the antibody and its encoding mRNA through affinity capture with the ligand. The ribosome-bound mRNA is then reverse transcribed back into cDNA, which can then undergo mutagenesis and be used in the next round of selection (see. e.g., Fukuda et al., Nucleic Acids Res. 34: e127 (2006)). In mRNA display, a covalent bond between antibody and mRNA is established using puromycin as an adaptor molecule (Wilson et al., Proc. Natl. Acad. Sci. USA 98:3750-55 (2001)).

As these methods are performed entirely in vitro, they provide two main advantages over other selection technologies. First, the diversity of the library is not limited by the transformation efficiency of bacterial cells, but only by the number of ribosomes and different mRNA molecules present in the test tube. Second, random mutations can be introduced easily after each selection round, for example, by non-proofreading polymerises, as no library must be transformed after any diversification step.

In some embodiments, mammalian display systems may be used.

Diversity may also be introduced into the CDRs of the antibody libraries in a targeted manner or via random introduction. The former approach includes sequentially targeting all the CDRs of an antibody via a high or low level of mutagenesis or targeting isolated hot spots of somatic hypermutations (see. e.g., Ho et al., J. Biol. Chem. 280:607-17 (2005)) or residues suspected of affecting affinity on experimental basis or structural reasons. Diversity may also be introduced by replacement of regions that are naturally diverse via DNA shuffling or similar techniques (see. e.g., Lu et al., J. Biol. Chem. 278:43496-507 (2003); U.S. Pat. Nos. 5,565,332 and 6,989,250). Alternative techniques target hypervariable loops extending into framework-region residues (see. e.g., Bond et al., J. Mol. Biol. 348:699-709 (2005)) employ loop deletions and insertions in CDRs or use hybridization-based diversification (see, e.g., U.S. Pat. Publication No. 2004/0005709). Additional methods of generating diversity in CDRs are disclosed, for example, in U.S. Pat. No. 7,985,840. Further methods that can be used to generate antibody libraries and/or antibody affinity maturation are disclosed, e.g., in U.S. Pat. Nos. 8,685,897 and 8,603,930, and U.S. Publ. Nos. 2014/0170705, 2014/0094392, 2012/0028301, 2011/0183855, and 2009/0075378, each of which are incorporated herein by reference.

Screening of the libraries can be accomplished by various techniques known in the art. For example, single domain antibodies can be immobilized onto solid supports, columns, pins, or cellulose/poly (vinylidene fluoride) membranes/other filters, expressed on host cells affixed to adsorption plates or used in cell sorting, or conjugated to biotin for capture with streptavidin-coated beads or used in any other method for panning display libraries.

For review of in vitro affinity maturation methods, see, e.g., Hoogenboom, Nature Biotechnology 23:1105-16 (2005); Quiroz and Sinclair, Revista Ingeneria Biomedia 4:39-51 (2010); and references therein.

5.2.5. Modifications of Single Domain Antibodies

Covalent modifications of single domain antibodies are included within the scope of the present disclosure. Covalent modifications include reacting targeted amino acid residues of a single domain antibody with an organic derivatizing agent that is capable of reacting with selected side chains or the N- or C-terminal residues of the single domain antibody. Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains (see. e.g., Creighton, *Proteins: Structure and Molecular Properties* 79-86 (1983)), acetylation of the N-terminal amine, and amidation of any C-terminal carboxyl group.

Other types of covalent modification of the single domain antibody included within the scope of this present disclosure include altering the native glycosylation pattern of the antibody or polypeptide as described above (see, e.g., Beck et al., Curr. Pharm. Biotechnol. 9:482-501 (2008); and Walsh, Drug Discov. Today 15:773-80 (2010)), and linking the antibody to one of a variety of nonproteinaceous polymers, e.g., polyethylene glycol (PEG), polypropylene glycol, or polyoxyallylenes, in the manner set forth, for example, in U.S. Pat. Nos. 4,640,835; 4,496,689; 4,301,144; 4,670,417; 4,791,192; or 4,179,337. The single domain antibody that binds to CD20 of the disclosure may also be genetically fused or conjugated to one or more immunoglobulin constant regions or portions thereof (e.g., Fc) to extend half-life and/or to impart known Fc-mediated effector functions.

The single chain antibody that binds to CD20 of the present disclosure may also be modified to form chimeric molecules comprising the single chain antibody that binds to CD20 fused to another, heterologous polypeptide or amino acid sequence, for example, an epitope tag (see, e.g., Terpe, Appl. Microbiol. Biotechnol. 60:523-33 (2003)) or the Fc region of an IgG molecule (see. e.g., Aruffo, *Antibody Fusion Proteins* 221-42 (Chamow and Ashkenazi eds., 1999)). The single chain antibody that binds to CD20 may also be used to generate CD20 binding chimeric antigen receptor (CAR), as described in more detail below.

Also provided herein are fusion proteins comprising the single chain antibody that binds to CD20 of the disclosure and a heterologous polypeptide. In some embodiments, the heterologous polypeptide to which the antibody is genetically fused or chemically conjugated is useful for targeting the antibody to cells having cell surface-expressed CD20.

Also provided herein are panels of antibodies that bind to a CD20 antigen. In specific embodiments, the panels of antibodies have different association rates, different dissociation rates, different affinities for a CD20 antigen, and/or different specificities for a CD20 antigen. In some embodiments, the panels comprise or consist of about 10 to about 1000 antibodies or more. Panels of antibodies can be used, for example, in 96-well or 384-well plates, for assays such as ELISAs.

5.2.6. Preparation of Single Domain Antibodies

Methods of preparing single domain antibodies have been described. See, e.g., Els Pardon et al, *Nature Protocol,* 9(3): 674 (2014). Single domain antibodies (such as VHHs) may be obtained using methods known in the art such as by immunizing a Camelid species (such as camel or llama) and obtaining hybridomas therefrom, or by cloning a library of single domain antibodies using molecular biology techniques known in the art and subsequent selection by ELISA with individual clones of unselected libraries or by using phage display.

Single domain antibodies provided herein may be produced by culturing cells transformed or transfected with a vector containing a single domain antibody-encoding nucleic acids. Polynucleotide sequences encoding polypeptide components of the antibody of the present disclosure can be obtained using standard recombinant techniques. Desired polynucleotide sequences may be isolated and sequenced from antibody producing cells such as hybridomas cells or B cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in host cells. Many vectors that are available and known in the art can be used for the purpose of the present disclosure. Selection of an appropriate vector will depend mainly on the size of the nucleic acids to be inserted into the vector and the particular host cell to be transformed with the vector. Host cells suitable for expressing antibodies of the present disclosure include prokaryotes such as Archaebacteria and Eubacteria, including Gram-negative or Gram-positive organisms, eukaryotic microbes such as filamentous fungi or yeast, invertebrate cells such as insect or plant cells, and vertebrate cells such as mammalian host cell lines. Host cells are transformed with the above-described expression vectors and cultured in conventional nutrient media modified as appropriate for inducing promoters, selecting transformants, or amplifying the genes encoding the desired sequences. Antibodies produced by the host cells are purified using standard protein purification methods as known in the art.

Methods for antibody production including vector construction, expression, and purification are further described in Plückthun et al., *Antibody Engineering: Producing antibodies in Escherichia coli: From PCR to fermentation* 203-52 (McCafferty et al. eds., 1996); Kwong and Rader, *E. coli Expression and Purification of F ab Antibody Fragments, in Current Protocols in Protein Science* (2009): Tachibana and Takekoshi, *Production of Antibody Fab Fragments in Escherichia coli,* in Antibody Expression and Production (Al-Rubeai ed., 2011); and *Therapeutic Monoclonal Antibodies: From Bench to Clinic* (An ed., 2009).

It is, of course, contemplated that alternative methods, which are well known in the art, may be employed to prepare anti-CD20 single domain antibodies. For instance, the appropriate amino acid sequence, or portions thereof, may be produced by direct peptide synthesis using solid-phase techniques (see. e.g., Stewart et al., *Solid-Phase Peptide Synthesis* (1969); and Merrifield, J. Am. Chem. Soc. 85:2149-54 (1963)). In vitro protein synthesis may be performed using manual techniques or by automation. Various portions of the anti-CD20 antibody may be chemically synthesized separately and combined using chemical or enzymatic methods to produce the desired anti-CD20 antibody. Alternatively, antibodies may be purified from cells or bodily fluids, such as milk, of a transgenic animal engineered to express the antibody, as disclosed, for example, in U.S. Pat. Nos. 5,545,807 and 5,827,690.

Specifically, the single domain antibodies, or other CD20 binders provided herein, can be generated by immunizing llamas, performing single B-cell sorting, undertaking V-gene extraction, cloning the CD20 binders, such as VHH-Fc fusions, and then performing small scale expression and purification. Additional screening of the single domain antibodies and other molecules that bind to CD20 can be performed, including one or more of selecting for ELISA-positive, BLI-positive, and $K_D$ less than 100 nM. These selection criteria can be combined as described in Section 6 below. Additionally, individual VHH binders (and other molecules that bind to CD20) can be assayed for their ability to bind to cells expressing CD20. Such assay can be performed using FACS analysis with cells expressing CD20, and measuring the mean fluorescence intensity (MFI) of fluorescently-labeled VHH molecules. Various aspects mentioned above are described in more details below.

Polyclonal Antibodies

Polyclonal antibodies are generally raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

For example, the animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response.

Monoclonal Antibodies

Monoclonal antibodies are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature. 256:495 (1975), or may be made by recombinant DNA methods (U.S. Pat. No. 4,816,567).

In the hybridoma method, an appropriate host animal is immunized to elicit lymphocytes that produce or are capable of producing antibodies that will specifically bind the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press. 1986).

The immunizing agent will typically include the antigenic protein or a fusion variant thereof. Goding, *Monoclonal Antibodies: Principles and Practice*, Academic Press (1986), pp. 59-103. Immortalized cell lines are usually transformed mammalian cells. The hybridoma cells thus prepared are seeded and grown in a suitable culture medium that preferably contains one or more substances that inhibit the growth or survival of the unfused, parental myeloma cells. Preferred immortalized myeloma cells are those that fuse efficiently, support stable high-level production of antibody by the selected antibody-producing cells, and are sensitive to a medium such as HAT medium.

Culture medium in which hybridoma cells are growing is assayed for production of monoclonal antibodies directed against the antigen. The culture medium in which the hybridoma cells are cultured can be assayed for the presence of monoclonal antibodies directed against the desired antigen. Such techniques and assays are known in the in art. For example, binding affinity may be determined by the Scatchard analysis of Munson et al. *Anal. Biochem.* 107:220 (1980).

After hybridoma cells are identified that produce antibodies of the desired specificity, affinity, and/or activity, the clones may be subcloned by limiting dilution procedures and grown by standard methods (Coding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

Monoclonal antibodies may also be made by recombinant DNA methods, such as those described in U.S. Pat. No. 4,816,567, and as described above. DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et at, *Curr. Opinion in Immunol.* 5:256-262 (1993) and Plückthun, *Immunol. Revs.* 130:151-188 (1992).

In a further embodiment, antibodies can be isolated from antibody phage libraries generated using the techniques described in McCafferty et al., Nature, 348:552-554 (1990). Clackson et al., Nature. 352:624-628 (1991) and Marks et al., J. Mol. Biol., 222:581-597 (1991). Subsequent publications describe the production of high affinity (nM range) human antibodies by chain shuffling (Marks et al., *Bio/Technoloy.* 10:779-783 (1992)), as well as combinatorial infection and in vivo recombination as a strategy for constructing very large phage libraries (Waterhouse et al., *Nucl. Acids Res.,* 21:2265-2266 (1993)). Thus, these techniques are viable alternatives to traditional monoclonal antibody hybridoma techniques for isolation of monoclonal antibodies.

The DNA also may be modified, for example, by substituting the coding sequence (U.S. Pat. No. 4,816,567; Morrison, et al., *Proc. Nat Acad Sci. USA.* 81:6851 (1984)), or by covalently joining to the coding sequence all or part of the coding sequence for a non-immunoglobulin polypeptide. Such non-immunoglobulin polypeptides can be substituted to create a chimeric bivalent antibody comprising one antigen-combining site having specificity for an antigen and another antigen-combining site having specificity for a different antigen.

Chimeric or hybrid antibodies also may be prepared in Nitro using known methods in synthetic protein chemistry, including those invoking crosslinking agents. For example, immunotoxins may be constructed using a disulfide-exchange reaction or by forming a thioether bond. Examples of suitable reagents for this purpose include iminothiolate and methyl-4-mercaptobutyrimidate.

Recombinant Production in Prokaryotic Cells

Polynucleic acid sequences encoding the antibodies of the present disclosure can be obtained using standard recombinant techniques. Desired polynucleic acid sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present disclosure. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to, an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as GEM™-11 may be utilized in making a recombinant vector which can be used to transform susceptible host cells such as *E. coli* LE392.

The expression vector of the present application may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the present antibody by removing the promoter from the source DNA via restriction enzyme digestion and inserting the isolated promoter sequence into the vector of the present application. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the -galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleic acid sequences have been published, thereby enabling a skilled worker operably to ligate them to cistrons encoding the target peptide (Siebenlist et al. *Cell* 20: 269 (1980)) using linkers or adaptors to supply any required restriction sites.

In one aspect, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence can be substituted by a prokaryotic signal sequence selected, for example, from the group consisting of the alkaline phosphatase, penicillinase, 1pp, or heat-stable enterotoxin II (STII) leaders, LamB, PhoE, PelB, OmpA and MBP.

In some embodiments, the production of the antibodies according to the present disclosure can occur in the cytoplasm of the host cell, and therefore does not require the presence of secretion signal sequences within each cistron. Certain host strains (e.g., the *E. coli* trxB⁻ strains) provide cytoplasm conditions that are favorable for disulfide bond formation, thereby permitting proper folding and assembly of expressed protein subunits.

Prokaryotic host cells suitable for expressing the antibodies of the present disclosure include Archaebacteria and Eubacteria, such as Gram-negative or Gram-positive organisms. Examples of useful bacteria include *Escherichia* (e.g., *E. coli*), *Bacilli* (e.g., *B. subtilis*), Enterobacteria, *Pseudomonas* species (e.g., *P. aeruginosa*), *Salmonella typhimurium*. *Serratia marcescans*. *Klebsiella, Proteus, Shigella, Rhizobia, Vitreoscilla*, or *Paracoccus*. In some embodiments, gram-negative cells are used. In one embodiment, *E. coli* cells are used as hosts. Examples of *E. coli* strains include strain W3110 (Bachmann, *Cellular and Molecular Biology*, vol. 2 (Washington, D.C.: American Society for Microbiology, 1987), pp. 1190-1219: ATCC Deposit No. 27,325) and derivatives thereof, including strain 33D3 having genotype W3110 AfhuA (AtonA) ptr3 lac Iq lacL8 AompT A(nmpc-fepE) degP41 kan$^R$(U.S. Pat. No. 5,639,635). Other strains and derivatives thereof, such as *E. coli* 294 (ATCC 31,446). *E. coli* B, *E. coli* 1776 (ATCC 31,537) and *E. coli* RV 308 (ATCC 31,608) are also suitable. These examples are illustrative rather than limiting. Methods for constructing derivatives of any of the above-mentioned bacteria having defined genotypes are known in the art and described in, for example, Bass et al., *Proteins*, 8:309-314 (1990). It is generally necessary to select the appropriate bacteria taking into consideration replicability of the replicon in the cells of a bacterium. For example, *E. coli*, Serrano, or *Salmonella* species can be suitably used as the host when well known plasmids such as pBR322, pBR325, pACYC 177, or pKN410 are used to supply the replicon.

Typically the host cell should secrete minimal amounts of proteolytic enzymes, and additional protease inhibitors may desirably be incorporated in the cell culture.

Host cells are transformed with the above-described expression vectors and cultured in conventional nutrient media modified as appropriate for inducing promoters, selecting transformants, or amplifying the genes encoding the desired sequences. Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol DMSO. Yet another technique used is electroporation.

Prokaryotic cells used to produce the antibodies of the present application are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol. The prokaryotic host cells are cultured at suitable temperatures and pHs.

If an inducible promoter is used in the expression vector of the present application, protein expression is induced under conditions suitable for the activation of the promoter. In one aspect of the present application. PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* 263:133-147 (2002)). A variety of other inducers may be used, according to the vector construct employed, as is known in the art.

The expressed antibodies of the present disclosure are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

Alternatively, protein production is conducted in large quantity by a fermentation process. Various large-scale fed-batch fermentation procedures are available for production of recombinant proteins. To improve the production yield and quality of the antibodies of the present disclosure, various fermentation conditions can be modified. For example, the chaperone proteins have been demonstrated to facilitate the proper folding and solubility of heterologous proteins produced in bacterial host cells. Chen et al. *J Bio Chem* 274:19601-19605 (1999); U.S. Pat. Nos. 6,083,715; 6,027,888; Bothmann and Pluckthun. *J. Biol. Chem.* 275: 17100-17105 (200)); Ramm and Pluckthun, J. Biol. Chem. 275:17106-17113 (2000); Arie et Microbiol. 39:199-210 (2001).

To minimize proteolysis of expressed heterologous proteins (especially those that are proteolytically sensitive), certain host strains deficient for proteolytic enzymes can be used for the present invention, as described in, for example, U.S. Pat. Nos. 5,264,365; 5,508,192; Hara et al., Microbial Drug Resistance. 2:63-72 (1996). *E. coli* strains deficient for proteolytic enzymes and transformed with plasmids over-expressing one or more chaperone proteins may be used as host cells in the expression system encoding the antibodies of the present application.

The antibodies produced herein can be further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75. Protein A immobilized on a solid phase for example can be used in some embodiments for immunoaffinity purification of binding molecules of the present disclosure. The solid phase to which Protein A is immobilized is preferably a column comprising a glass or silica surface, more preferably a controlled pore glass column or a silicic acid column. In some embodiments, the column has been coated with a reagent, such as glycerol, in an attempt to prevent nonspecific adherence of contaminants. The solid phase is then washed to remove contaminants non-specifically bound to the solid phase. Finally the antibodies of interest is recovered from the solid phase by elution.

Recombinant Production in Eukaryotic Cells

For eukaryotic expression, the vector components generally include, but are not limited to, one or more of the following, a signal sequence, an origin of replication, one or more marker genes, and enhancer element, a promoter, and a transcription termination sequence.

A vector for use in a eukaryotic host may also an insert that encodes a signal sequence or other polypeptide having a specific cleavage site at the N-terminus of the mature protein or polypeptide. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region can be ligated in reading frame to DNA encoding the antibodies of the present application.

Generally, the origin of replication component is not needed for mammalian expression vectors (the SV40 origin may typically be used only because it contains the early promoter).

Expression and cloning vectors may contain a selection gene, also termed a selectable marker. Selection genes may encode proteins that confer resistance to antibiotics or other toxins, e.g., ampicillin, neomycin, methotrexate, or tetracycline; complement auxotrophic deficiencies; or supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up nucleic acid encoding the antibodies of the present application. For example, cells transformed with the DHFR selection gene are first identified by culturing all of the transformants in a culture medium that contains methotrexate (Mtx), a competitive antagonist of DHFR. An exemplary appropriate host cell when wild-type DHFR is employed is the Chinese hamster ovary (CHO) cell line deficient in DHFR activity. Alternatively, host cells (particularly wild-type hosts that contain endogenous DHFR) transformed or co-transformed with the polypeptide encoding-DNA sequences, wild-type DHFR protein, and another selectable marker such as aminoglycoside 3'-phosphotransferase (APH) can be selected by cell growth in medium containing a selection agent for the selectable marker such as an aminoglycosidic antibiotic.

Expression and cloning vectors usually contain a promoter that is recognized by the host organism and is operably linked to the nucleic acid encoding the desired polypeptide sequences. Eukaryotic genes have an AT-rich region located approximately 25 to 30 based upstream from the site where transcription is initiated. Another sequence found 70 to 80 bases upstream from the start of the transcription of many genes may be included. The 3' end of most eukaryotic may be the signal for addition of the poly A tail to the 3' end of the coding sequence. All of these sequences may be inserted into eukaryotic expression vectors.

Polypeptide transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

Transcription of a DNA encoding the antibodies of the present disclosure by higher eukaryotes is often increased by inserting an enhancer sequence into the vector. Many enhancer sequences are now known from mammalian genes (globin, elastase, albumin. α-fetoprotein, and insulin). Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the polypeptide encoding sequence, but is preferably located at a site 5' from the promoter.

Expression vectors used in eukaryotic host cells (yeast, fungi, insect, plant, animal, human, or nucleated cells from other multicellular organisms) also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the polypeptide-encoding mRNA. One useful transcription termination component is the bovine growth hormone polyadenylation region.

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells can be transformed with the above-described expression or cloning vectors for antibodies production and cultured in conventional nutrient media modified as appropriate for inducing promoters, selecting transformants, or amplifying the genes encoding the desired sequences.

The host cells used to produce the antibodies of the present application may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMY-CIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibodies can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The protein composition prepared from the cells can be purified using, for example, hydroxylapatite chromatography, gel electrophoresis, dialysis, and affinity chromatography, with affinity chromatography being the preferred purification technique. The matrix to which the affinity ligand is attached is most often agarose, but other matrices are available. Mechanically stable matrices such as controlled pore glass or poly (styrene-divinyl) benzene allow for faster flow rates and shorter processing times than can be achieved with agarose. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered. Following any preliminary purification step(s), the mixture comprising the antibody of interest and contaminants may be subjected to low pH hydrophobic interaction chromatography.

5.2.7. Binding Molecules Comprising the Single Domain Antibodies

In another aspect, provided herein is a binding molecule comprising a single domain antibody (e.g., a VHH domain against CD20) provided herein. In addition to chimeric antigen receptors (CARs) provided herein as described in Section 5.3 below, in some embodiments, a single domain antibody against CD20 provided herein is part of other binding molecules. Exemplary binding molecules of the present disclosure are described herein.

Fusion Protein

In various embodiments, the single domain antibody provided herein can be genetically fused or chemically conjugated to another agent, for example, protein-based entities. The single domain antibody may be chemically-conjugated to the agent, or otherwise non-covalently conjugated to the agent. The agent can be a peptide or antibody (or a fragment thereof).

Thus, in some embodiments, provided herein are single domain antibodies (e.g., VHH domains) that are recombinantly fused or chemically conjugated (covalent or non-covalent conjugations) to a heterologous protein or polypeptide (or fragment thereof, for example, to a polypeptide of about 10, about 20, about 30, about 40, about 50, about 60, about 70, about 80, about 90, about 100, about 150, about 200, about 250, about 300, about 350, about 400, about 450 or about 500 amino acids, or over 500 amino acids) to generate fusion proteins, as well as uses thereof. In particular, provided herein are fusion proteins comprising an antigen-binding fragment of the single domain antibody provided herein (e.g., CDR1, CDR2, and/or CDR3) and a heterologous protein, polypeptide, or peptide.

Moreover, antibodies provided herein can be fused to marker or "tag" sequences, such as a peptide, to facilitate purification. In specific embodiments, the marker or tag amino acid sequence is a hexa-histidine peptide, hemagglutinin ("HA") tag, and "FLAG" tag.

Methods for fusing or conjugating moieties (including polypeptides) to antibodies are known (see, e.g., Amon et al., Monoclonal Antibodies for Immunotargeting of Drugs in Cancer Therapy, in Monoclonal Antibodies and Cancer Therapy 243-56 (Reisfeld et al. eds., 1985); Hellstrom et al., Antibodies for Drug Delivery, in Controlled Drug Delivery 623-53 (Robinson et al. eds., 2d ed. 1987); Thorpe, Antibody Carriers of Cytotoxic Agents in Cancer Therapy: A Review, in Monoclonal Antibodies: Biological and Clinical Applications 475-506 (Pinchera et al. eds., 1985); Analysis, Results, and Future Prospective of the Therapeutic Use of Radiolabeled Antibody in Cancer Therapy, in Monoclonal Antibodies for Cancer Detection and Therapy 303-16 (Baldwin et al. eds., 1985); Thorpe et al., Immunol. Rev. 62:119-58 (1982); U.S. Pat. Nos. 5,336,603; 5,622,929; 5,359,046; 5,349,053; 5,447,851; 5,723,125; 5,783,181; 5,908,626; 5,844,095; and 5,112,946; EP 307,434; EP 367,166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-39 (1991); Traunecker et al., Nature, 331:84-86 (1988); Zheng et al., J. Immunol. 154:5590-600 (1995); and Vil et al., Proc. Natl. Acad. Sci. USA 89:11337-41 (1992)).

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of the single domain antibodies as provided herein, including, for example, antibodies with higher affinities and lower dissociation rates (see, e.g., U.S. Pat. Nos. 5,605,793; 5,811,238; 5,830,721; 5,834,252; and 5,837,458; Patten et al., Curr. Opinion Biotechnol. 8:724-33 (1997); Harayama, Trends Biotechnol. 16(2):76-82 (1998); Hansson et al., J. Mol. Biol. 287:265-76 (1999); and Lorenzo and Blasco, Biotechniques 24(2):308-13 (1998)). Antibodies, or the encoded antibodies, may be altered by being subjected to random mutagenesis by error-prone PCR, random nucleotide insertion, or other methods prior to recombination. A polynucleotide encoding an antibody provided herein may be recombined with one or more components, motifs, sections, parts, domains, fragments, etc. of one or more heterologous molecules.

In some embodiments, a single domain antibody provided herein (e.g., VHH domain) is conjugated to a second antibody to form an antibody heteroconjugate.

In various embodiments, the single domain antibody is genetically fused to the agent. Genetic fusion may be accomplished by placing a linker (e.g., a polypeptide) between the single domain antibody and the agent. The linker may be a flexible linker.

In various embodiments, the single domain antibody is genetically conjugated to a therapeutic molecule, with a hinge region linking the single domain antibody to the therapeutic molecule.

Also provided herein are methods for making the various fusion proteins provided herein. The various methods described in Section 5.2.6 above may also be utilized to make the fusion proteins provided herein.

In a specific embodiment, the fusion protein provided herein is recombinantly expressed. Recombinant expression of a fusion protein provided herein may require construction of an expression vector containing a polynucleotide that encodes the protein or a fragment thereof. Once a polynucleotide encoding a protein provided herein or a fragment thereof has been obtained, the vector for the production of the molecule may be produced by recombinant DNA technology using techniques well-known in the art. Thus, methods for preparing a protein by expressing a polynucleotide containing an encoding nucleotide sequence are described herein. Methods which are well known to those skilled in the art can be used to construct expression vectors containing coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding a fusion protein provided herein, or a fragment thereof, or a CDR, operably linked to a promoter.

The expression vector can be transferred to a host cell by conventional techniques and the transfected cells are then cultured by conventional techniques to produce a fusion protein provided herein. Thus, also provided herein are host cells containing a polynucleotide encoding a fusion protein provided herein or fragments thereof operably linked to a heterologous promoter.

A variety of host-expression vector systems may be utilized to express the fusion protein provided herein. Such host-expression systems represent vehicles by which the coding sequences of interest may be produced and subsequently purified, but also represent cells which may, when transformed or transfected with the appropriate nucleotide coding sequences, express a fusion protein provided herein in situ. These include but are not limited to microorganisms such as bacteria (e.g., *E. coli* and *B. subtilis*) transformed with recombinant bacteriophage DNA, plasmid DNA or cosmid DNA expression vectors containing coding sequences; yeast (e.g., *Saccharomyces Pichia*) transformed with recombinant yeast expression vectors containing coding sequences; insect cell systems infected with recombinant virus expression vectors (e.g., baculovirus) containing coding sequences; plant cell systems infected with recombinant virus expression vectors (e.g., cauliflower mosaic virus, CaMV, tobacco mosaic virus, TMV) or transformed with recombinant plasmid expression vectors (e.g., Ti plasmid) containing coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, or, eukaryotic cells, especially for the expression of whole recombinant antibody molecule, can be used for the expression of a recombinant fusion protein. For example, mammalian cells such as Chinese hamster ovary cells (CHO), in conjunction with a vector such as the major intermediate early gene promoter element from human cytomegalovirus is an effective expression system for antibodies or variants thereof. In a specific embodiment, the expression of nucleotide sequences encoding the fusion proteins provided herein is regulated by a constitutive promoter, inducible promoter or tissue specific promoter.

In bacterial systems, a number of expression vectors may be advantageously selected depending upon the use intended for the fusion protein being expressed. For example, when a large quantity of such a fusion protein is to be produced, for the generation of pharmaceutical compositions of a fusion protein, vectors which direct the expression of high levels of fusion protein products that are readily purified may be desirable. Such vectors include, but are not limited to, the *E. coli* expression vector pUR278 (Ruther et al., EMBO 12:1791 (1983)), in which the coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fusion protein in infected hosts (e.g., see Logan & Shenk, Proc. Natl. Acad. Sci. USA 8 1:355-359 (1984)). Specific initiation signals may also be required for efficient translation of inserted coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., Methods in Envy mol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant proteins, stable expression can be utilized. For example, cell lines which stably express the fusion proteins may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the fusion protein. Such engineered cell lines may be particularly useful in screening and evaluation of compositions that interact directly or indirectly with the binding molecule.

A number of selection systems may be used, including but not limited to, the herpes simplex virus thymidine kinase (Wigler et at, Cell 11:223 (1977)), hypoxanthineguanine phosphoribosyltransferase (Szybalska & Szvbalski, Proc. Natl. Acad. Sci. USA 48:202 (1992)), and adenine phosphoribosyltransferase (Lowy et al., Cell 22:8-17 (1980)) genes can be employed in tk-, hgprt- or aprt-cells, respectively. Also, antimetabolite resistance can be used as the basis of selection for the following genes; dhfr, which confers resistance to methotrexate (Wigler et al., Natl. Acad. Sci. USA 77:357 (1980); O'Hare et at, Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 (Wu and Wu. Biotherapy 3:87-95 (1991); Tolstoshev, Ann. Rev. Pharmacol. Toxicol. 32:573-5% (1993): Mulligan. Science 260:926-932 (1993); and Morgan and Anderson, Ann. Rev. Biochem. 62:191-217 (1993); May, TIB TECH 11(5):155-2 15 (1993)); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, *Gene Transfer and Expression*, A Laboratory Manual, Stockton Press, NY (1990); and in Chapters 12 and 13, Dracopoli et al. (eds.), *Current Protocols in Human Genetics*. John Wiley & Sons, NY (1994); Colberre-Garapin et al., *J. Mol. Biol.* 150:1 (1981), which are incorporated by reference herein in their entireties.

The expression level of a fusion protein can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing a fusion protein is amplifiable, increase in the level of inhibitor present in culture of host cell will increase the number of copies of the marker gene. Since the amplified region is associated with the fusion protein gene, production of the fusion protein will also increase (Crouse et al., Mol. Cell. Biol. 3:257 (1983)).

The host cell may be co-transfected with multiple expression vectors provided herein. The vectors may contain identical selectable markers which enable equal expression of respective encoding polypeptides. Alternatively, a single vector may be used which encodes, and is capable of expressing multiple polypeptides. The coding sequences may comprise cDNA or genomic DNA.

Once a fusion protein provided herein has been produced by recombinant expression, it may be purified by any method known in the art for purification of a polypeptide (e.g., an immunoglobulin molecule), for example, by chromatography (e.g., ion exchange, affinity, particularly by affinity for the specific antigen after Protein A, sizing column chromatography, and Kappa select affinity chromatography), centrifugation, differential solubility, or by any other standard technique for the purification of proteins. Further, the fusion protein molecules provided herein can be fused to heterologous polypeptide sequences described herein or otherwise known in the art to facilitate purification.

Immunoconjugates

In some embodiments, the present disclosure also provides immunoconjugates comprising any of the antibodies (such as anti-CD20 single domain antibodies) described herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some embodiments, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 11477-523 (2006); Jeffrey et al. *Bioorganic & Med Chem. Letters* 16158-362 (2006); Torgov et al., *Bioconj. Chem.* 16:717-721 (2005); Nagy et al., *Proc. Natl. Acad Sci. USA* 97:829-834 (2000); Dubowchik et al., *Bioorg. & Med. Chem. Letters* 12:1529-1532 (2002); King et al., *J. Med Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC 1065.

In some embodiments, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins. *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

The linker may be a "cleavable linker" facilitating release of the conjugated agent in the cell, but non-cleavable linkers are also contemplated herein. Linkers for use in the conjugates of the present disclosure include, without limitation, acid labile linkers (e.g., hydrazone linkers), disulfide-containing linkers, peptidase-sensitive linkers (e.g., peptide linkers comprising amino acids, for example, valine and/or citrulline such as citrulline-valine or phenylalanine-lysine), photolabile linkers, dimethyl linkers, thioether linkers, or hydrophilic linkers designed to evade multidrug transporter-mediated resistance.

The immunuoconjugates or ADCs herein contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)ben-zoate) which are commercially available (e.g., from Pierce Biotechnology, Inc., Rockford, IL., U.S.A).

In other embodiments, antibodies provided herein are conjugated or recombinantly fused, e.g., to a diagnostic molecule. Such diagnosis and detection can be accom-plished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin or avidin/biotin; fluorescent materials, such as, but not limited to, umbelliferone, fluorescein, fluorescein isothio-cynate, rhodamine, dichlorotriazinylamine fluorescein, dan-syl chloride, or phycoerythrin; luminescent materials, such as, but not limited to, luminol; bioluminescent materials, such as, but not limited to, luciferase, luciferin, or aequorin; chemiluminescent material, such as, 225Acγ-emitting, Auger-emitting, β-emitting, an alpha-emitting or positron-emitting radioactive isotope.

5.3. Chimeric Antigen Receptors

In another aspect, provided herein is a chimeric antigen receptor (CAR) comprising an extracellular antigen binding domain comprising at least one single domain antibody (e.g., VHH) provided herein that binds to CD20. Exemplary CARs comprising the present VHH domains (i.e., VHH-based CARs) are illustrated and compared with conventional CARS comprising scFvs (i.e., scFv-based CARs) as described in Section 6 below.

In some embodiments, the chimeric antigen receptor (CAR) provided herein comprises a polypeptide comprising: (a) an extracellular antigen binding domain comprising at least one single domain antibody (sdAb) specifically binding to CD20 as provided herein, and optionally one or more additional binding domain(s); (b) a transmembrane domain; and (c) an intracellular signaling domain. Each components and additional regions are described in more detail below.

5.3.1. Extracellular Antigen Binding Domain

The extracellular antigen binding domain of the CARS described herein comprises one or more (such as any one of 1, 2, 3, 4, 5, 6 or more) single domain antibodies. The single domain antibodies can be fused to each other directly via peptide bonds, or via peptide linkers.

Single Domain Antibodies

The CARs of the present disclosure comprise an extra-cellular antigen binding domain comprising one or more single domain antibodies. The sdAbs may be of the same or different origins, and of the same or different sizes. Exem-plary sdAbs include, but are not limited to, heavy chain variable domains from heavy-chain only antibodies (e.g., VHH or $V_{NAR}$), binding molecules naturally devoid of light chains, single domains (such as $V_H$ or $V_L$) derived from conventional 4-chain antibodies, humanized heavy-chain only antibodies, human single domain antibodies produced by transgenic mice or rats expressing human heavy chain segments, and engineered domains and single domain scaffolds other than those derived from antibodies. Any sdAbs known in the art or developed by the present disclosure, including the single domain antibodies described above in the present disclosure, may be used to construct the CARs described herein. The sdAbs may be derived from any species including, but not limited to mouse, rat, human, camel, llama, lamprey, fish, shark, goat, rabbit, and bovine. Single domain antibodies contemplated herein also include naturally occurring single domain antibody molecules from species other than Camelidae and sharks.

In some embodiments, the sdAb is derived from a natu-rally occurring single domain antigen binding molecule known as heavy chain antibody devoid of light chains (also referred herein as "heave chain only antibodies"). Such single domain molecules are disclosed in WO 94/04678 and Hamers-Casterman, C. et al., *Nature* 363:446-448 (1993), for example, For clarity reasons, the variable domain derived from a heavy chain molecule naturally devoid of light chain is known herein as a VHH to distinguish it from the conventional $V_H$ of four chain immunoglobulins. Such a VHH molecule can be derived from antibodies raised in Camelidae species, for example, camel, llama, vicuna, dromedary, alpaca and guanaco. Other species besides Cam-elidae may produce heavy chain molecules naturally devoid of light chain, and such VHHs are within the scope of the present disclosure. In addition, humanized versions of VHHs as well as other modifications and variants are also contemplated and within the scope of the present disclosure.

VHH molecules from Camelids are about 10 times smaller than IgG molecules. They are single polypeptides and can be very stable, resisting extreme pH and temperature conditions. Moreover, they can be resistant to the action of proteases which is not the case for conventional 4-chain antibodies. Furthermore, in vitro expression of VHHs pro-duces high yield, properly folded functional VHHs. In addition, antibodies generated in Camelids can recognize epitopes other than those recognized by antibodies generated in vitro through the use of antibody libraries or via immu-nization of mammals other than Camelids (see, for example, WO9749805). As such, multispecific or multivalent CARs comprising one or more VHH domains may interact more efficiently with targets than multispecific or multivalent CARs comprising antigen binding fragments derived from conventional 4-chain antibodies. Since VHHs are known to bind into "unusual" epitopes such as cavities or grooves, the affinity of CARs comprising such VHHs may be more suitable for therapeutic treatment than conventional multi-specific polypeptides.

In some embodiments, the sdAb is derived from a variable region of the immunoglobulin found in cartilaginous fish. For example, the sdAb can be derived from the immuno-globulin isotype known as Novel Antigen Receptor (NAR) found in the serum of shark. Methods of producing single domain molecules derived from a variable region of NAR ("IgNARs") are described in WO 03/014161 and Streltsov, *Protein Sci.* 14:2901-2909 (2005).

In some embodiments, the sdAb is recombinant, CDR-grafted, humanized, camelized, de-immunized and/or in vitro generated (e.g., selected by phage display). In some embodiments, the amino acid sequence of the framework regions may be altered by "camelization" of specific amino acid residues in the framework regions. Camelization refers to the replacing or substitution of one or more amino acid residues in the amino acid sequence of a (naturally occur-ring) $V_H$ domain from a conventional 4-chain antibody by one or more of the amino acid residues that occur at the corresponding position(s) in a VHH domain of a heavy chain antibody. This can be performed in a manner known in the field, which will be clear to the skilled person. Such "camelizing" substitutions are preferably inserted at amino acid positions that form and/or are present at the $V_H$-$V_L$ interface, and/or at the so-called Camelidae hallmark residues, as defined herein (see for example WO 94/04678, Davies and Riechmann FEBS Letters 339: 285-290 (1994): Davies and Riechmann, Protein Engineering 9 (6): 531-537 (1996); Riechmann, J. Mol. Biol. 259: 957-969 (1996); and Riechmann and Muyldermans. J. Immunol. Meth. 231: 25-38 (1999)).

In some embodiments, the sdAb is a human single domain antibody produced by transgenic mice or rats expressing human heavy chain segments. See, e.g., US20090307787. U.S. Pat. No. 8,754,287, US20150289489, US20100122358, and WO2004049794. In some embodiments, the sdAb is affinity matured.

In some embodiments, naturally occurring VHH domains against a particular antigen or target, can be obtained from (naïve or immune) libraries of Camelid VHH sequences. Such methods may or may not involve screening such a library using said antigen or target, or at least one part, fragment, antigenic determinant or epitope thereof using one or more screening techniques known in the field. Such libraries and techniques are for example described in WO 99/37681, WO 01/90190, WO 03/025020 and WO 03/035694. Alternatively, improved synthetic or semi-synthetic libraries derived from (naïve or immune) VHH libraries may be used, such as VHH libraries obtained from (naïve or immune) VHH libraries by techniques such as random mutagenesis and/or CDR shuffling, as for example described in WO 00/43507.

In some embodiments, the single domain antibodies are generated from conventional four-chain antibodies. See, for example, EP 0 368 684; Ward et al., Nature, 341 (6242): 544-6 (1989); Holt et al., Trends Biotechnol., 21(11):484-490 (2003); WO 06/030220; and WO 06/003388.

In some embodiments, the extracellular antigen binding domain provided herein comprises at least one binding domain, and the at least one binding domain comprises a single domain antibody that binds to CD20 as provided herein, e.g., the anti-CD20 single domain antibodies described in Section 5.2 above.

In some embodiments, provided herein is a CAR comprising a polypeptide comprising: (a) an extracellular antigen binding domain comprising an anti-CD20 sdAb; (b) a transmembrane domain; and (c) an intracellular signaling domain, wherein the anti-CD20 sdAb is an anti-CD20 sdAb as described in Section 5.2 above, including, e.g., the VHH domains in Table 2 and those having one, two or all three CDRs in any of those VHH domains in Table 2. In some embodiments, the anti-CD20 sdAb is camelid, chimeric, human, or humanized.

In some embodiments, provided herein is a CAR comprising a polypeptide comprising: (a) an extracellular antigen binding domain comprising an anti-CD20 sdAb; (b) a transmembrane domain; and (c) an intracellular signaling domain, wherein the anti-CD20 sdAb comprises the amino acid sequence of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184, or SEQ ID NO: 185. In other embodiments, provided herein is a CAR comprising a polypeptide comprising: (a) an extracellular antigen binding domain comprising an anti-CD20 sdAb; (b) a transmembrane domain; and (c) an intracellular signaling domain, wherein the anti-CD20 sdAb comprises an amino acid sequence having at least 75%, 80%, 85%, 86%, 87%, 88%, 89%, 90%, 91%, 92%, 93%, 94%, 95%, 96%, 97%, 98%, 99%, or 100% sequence identify to the amino acid sequence of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184, or SEQ ID NO: 185.

In other embodiments, the extracellular antigen binding domain comprises two or more antigen binding domains. Among these two or more antigen binding domains, at least one is a VHH that binds to CD20 as provided herein. In some embodiments, the one or more additional binding domain(s) is/are also VHH(s) that bind(s) to CD20. In other embodiments, the one or more additional binding domain(s) bind(s) to one or more additional different antigen(s), e.g., 1, 2, 3, 4 or more additional single domain antibody binding regions (sdAbs) targeting one or more additional different antigen(s).

In some embodiments, provided herein is a multivalent (such as bivalent and trivalent) CAR comprising a polypeptide comprising: (a) an extracellular antigen binding domain comprising two or more single domain antibodies (sdAbs) specifically binding to CD20; (b) a transmembrane domain; and (c) an intracellular signaling domain. In some embodiments, the extracellular antigen binding domain comprises two single domain antibodies (sdAbs) specifically binding to CD20 provided herein. In other embodiments, the extracellular antigen binding domain comprises three single domain antibodies (sdAbs) specifically binding to CD20 provided herein. In some embodiments, the two or more anti-CD20 sdAbs are selected from those anti-CD20 sdAbs described in Section 5.2 above, including, e.g., the VHH domains in Table 2 and those having one, two or all three CDRs in any of those VHH domains in Table 2. In some embodiments, the anti-CD20 sdAb is camelid, chimeric, human, or humanized. In some embodiments, the two or more anti-CD20 sdAbs are each independently selected from anti-CD20 sdAbs comprising an amino acid sequence having at least 75%, 80%, 85%, 86%, 87%, 88%, 89%, 90%, 91%, 92%, 93%, 94%, 95%, 96%, 97%, 98%, 99%, or 100% sequence identify to the amino acid sequence of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184, and SEQ ID NO: 185.

In other embodiments, provided herein is a multispecific (such as bispecific and trispecific) CAR comprising a polypeptide comprising: (a) an extracellular antigen binding domain comprising a first single domain antibody (sdAb) specifically binding to CD20; (b) a transmembrane domain; and (c) an intracellular signaling domain. In some embodiments, the CAR further comprises a second single domain antibody (sdAb) specifically binding to a second antigen (such as a second tumor antigen). In some embodiments, the CAR further comprises a second single domain antibody (sdAb) specifically binding to a second antigen (such as a second tumor antigen); and a third single domain antibody (sdAb) specifically binding to a third antigen (such as a third tumor antigen).

In some embodiments, the additional antigen(s) targeted by the CARs of the present disclosure are cell surface molecules. The single domain antibodies may be chosen to recognize an antigen that acts as a cell surface marker on target cells associated with a special disease state. In some embodiments, the antigen is a tumor antigen. In some embodiments, the tumor antigen is associated with a B cell malignancy. Tumors express a number of proteins that can serve as a target antigen for an immune response, particularly T cell mediated immune responses. The antigens targeted by the CAR may be antigens on a single diseased cell or antigens that are expressed on different cells that each contribute to the disease. The antigens targeted by the CAR may be directly or indirectly involved in the diseases.

Tumor antigens are proteins that are produced by tumor cells that can elicit an immune response, particularly T-cell mediated immune responses. The selection of the additional targeted antigen of the present disclosure will depend on the particular type of cancer to be treated. Exemplary tumor antigens include, but not limited to, a glioma-associated antigen, carcinoembryonic antigen (CEA), β-human chorionic gonadotropin, alphafetoprotein (AFP), lectin-reactive AFP, thyroglobulin, RAGE-1, MN-CAIX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-la, p53, prostein, PSMA, HER2/neu, survivin and telomerase, prostate-carcinoma tumor antigen-1 (PCTA-1), MAGE, ELF2M, neutrophil elastase, ephrinB2. CD19, insulin growth factor (IGF)-I, IGF-II, IGF-I receptor and mesothelin.

In some embodiments, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and gp100 in melanoma and prostatic acid phosphatase (PAP) and prostate-specific antigen (PSA) in prostate cancer. Other target molecules belong to the group of transformation-related molecules such as the oncogene HER2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. In addition to CD20, B-cell differentiation antigens such as CD22 and CD37 are other candidates for target antigens in B-cell lymphoma.

In some embodiments, the tumor antigen is a tumor-specific antigen (TSA) or a tumor-associated antigen (TAA). A TSA is unique to tumor cells and does not occur on other cells in the body. A TAA associated antigen is not unique to a tumor cell, and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development, when the immune system is immature, and unable to respond or they may be antigens that are normally present at extremely low levels on normal cells, but which are expressed at much higher levels on tumor cells.

Non-limiting examples of TSA or TAA antigens include: differentiation antigens such as MART-1/MelanA (MART-I), gp 100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7.

Other large, protein-based antigens include TSP-180, MAGE-4, MAGE-5, MAGE-6, RAGE, NY-ESO, p185erbB2, p180erbB-3, c-met, nm-23HI, PSA, TAG-72, CA 19-9, CA 72-4, CAM 17.1, NuMa, K-ras, beta-Catenin, CDK4, Mum-1, p15, p16, 43-9F, 5T4, 791Tgp72, alpha-fetoprotein, beta-HCG, BCA225, BTAA, CA 125, CA 15-3CA 27.291BCAA, CA 195, CA 242, CA-50, CAM43, CD68P1, CO-029, FGF-5, G250, Ga733EpCAM, HTgp-175, M344, MA-50, MG7-Ag, MOV18, NB/70K, NY-CO-1, RCAS 1, SDCCAG16, TA-90Mac-2 binding protein/cyclophilin C-associated protein, TAAL6, TAG72, TLP, and TPS.

In some more specific embodiments, the one or more additional antigen(s) is selected from a group consisting of CD20, CD19, CD33, CD38, BCMA, CS1, ROR1, GPC3, CD123, IL-13R, CD138, c-Met, EGFRvIII, GD-2, NY-ESO-1, MAGE A3, and glycolipid F77.

In a specific embodiment, the CAR provided herein comprises a VHH that binds to CD20 and a VHH that binds to CD19. In another specific embodiment, the CAR provided herein comprises a VHH that binds to CD20 and a VHH that binds to CD22. In some embodiments, the sdAb provided herein is camelid, chimeric, human, or humanized.

In addition to the one or more antigen binding domain(s) provided herein, the CAR provided herein may further comprise one or more of the following: a linker (e.g., a peptide linker), a transmembrane domain, a hinge region, a signal peptide, an intracellular signaling domain, a co-stimulatory signaling domain, each of which is described in more detail below.

For example, in some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the co-stimulatory signaling domain is derived from CD137. In some embodiments, the CD20 CAR further comprises a hinge domain (such as a CD8α hinge domain) located between the C-terminus of the extracellular antigen binding domain and the N-terminus of the transmembrane domain. In some embodiments, the CD20 CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen-binding domain, a CD8α hinge domain, a CD8α transmembrane domain, a co-stimulatory signaling domain derived from CD137, and a primary intracellular signaling domain derived from CD3ζ. In some embodiments, the CD20 CAR is monospecific. In some embodiments, the CD20 CAR is monovalent. In other embodiments, the CD20 CAR is multivalent.

Peptide Linkers

The various single domain antibodies in the multispecific or multivalent CARS described herein may be fused to each other via peptide linkers. In some embodiments, the single domain antibodies are directly fused to each other without any peptide linkers. The peptide linkers connecting different single domain antibodies (e.g., VHH) may be the same or different. Different domains of the CARS may also be fused to each other via peptide linkers.

Each peptide linker in a CAR may have the same or different length and/or sequence depending on the structural and/or functional features of the single domain antibodies and/or the various domains. Each peptide linker may be selected and optimized independently. The length, the degree of flexibility and/or other properties of the peptide linker(s) used in the CARS may have some influence on properties, including but not limited to the affinity, specificity or avidity for one or more particular antigens or epitopes. For example, longer peptide linkers may be selected to ensure that two adjacent domains do not sterically interfere with one another. In some embodiments, a short peptide linker may be disposed between the transmembrane domain and the intracellular signaling domain of a CAR. In some embodiment, a peptide linker comprises flexible residues (such as glycine and serine) so that the adjacent domains are free to move relative to each other. For example, a glycine-serine doublet can be a suitable peptide linker.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acids to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a flexible linker. Exemplary flexible linkers include but not limited to glycine polymers $(G)_n$, glycine-serine polymers (including, for example, $(GS)_n$, $(GSGGS)_n$, $(GGGS)_n$, and $(GGGGS)_n$, where n is an integer of at least one), glycine-alanine polymers, alanine-serine polymers, and other flexible linkers known in the art. Exemplary peptide linkers are listed in the table below. In a specific embodiment, the peptide linker that connects two or more anti-CD20 VHH domains provided herein is $(GGGGS)_n$ (SEQ ID NO: 138), wherein n is optionally 1, 2, 3, 4, or 5.

TABLE 4

Exemplary Peptide Linkers

| Sequences | SEQ ID NO |
|---|---|
| $(GS)_n$, n is an integer including, e.g., 1, 2, 3, 4, 5, and 6. | SEQ ID NO: 134 |
| $(GSGGS)_n$, n is an integer including, e.g., 1, 2, 3, 4, 5, and 6. | SEQ ID NO: 135 |
| $(GGGS)_n$, n is an integer including, e.g., 1, 2, 3, 4, 5, and 6. | SEQ ID NO: 136 |
| GGGGSGGGGSGGGGGSGSGGGGSGGGGSGGGGS | SEQ ID NO: 137 |
| $(GGGGS)_n$, n is an integer including, e.g., 1, 2, 3, 4, 5, and 6. | SEQ ID NO: 138 |
| DGGGS | SEQ ID NO: 139 |
| TGEKP | SEQ ID NO: 140 |
| GGRR | SEQ ID NO: 141 |
| GGGGSGGGGSGGGGGSGSGGGGS | SEQ ID NO: 142 |
| EGKSSGSGSESKVD | SEQ ID NO: 143 |
| KESGSVSSEQLAQFRS | SEQ ID NO: 144 |
| GGRRGGGS | SEQ ID NO: 145 |
| LRQRDGERP | SEQ ID NO: 146 |
| LRQKDGGGSERP | SEQ ID NO: 147 |
| LRQKDGGGSGGGSERP | SEQ ID NO: 148 |
| GSTSGSGKPGSGEGST | SEQ ID NO: 149 |
| GSTSGSGKSSEGKG | SEQ ID NO: 150 |
| KESGSVSSEQLAQFRSLD | SEQ ID NO: 151 |

Other linkers known in the art, for example, as described in WO2016014789, WO2015158671, WO2016102965, US20150299317, WO2018067992, U.S. Pat. No. 7,741,465, Colcher et al., *J. Nat. Cancer Inst.* 82:1191-1197 (1990), and Bird et al. *Science* 242:423-426 (1988) may also be included in the CARs provided herein, the disclosure of each of which is incorporated herein by reference.

5.3.2. Transmembrane Domain

The CARs of the present disclosure comprise a transmembrane domain that can be directly or indirectly fused to the extracellular antigen binding domain. The transmembrane domain may be derived either from a natural or from a synthetic source. As used herein, a "transmembrane domain" refers to any protein structure that is thermodynamically stable in a cell membrane, preferably an eukaryotic cell membrane. Transmembrane domains compatible for use in the CARs described herein may be obtained from a naturally occurring protein. Alternatively, it can be a synthetic, non-naturally occurring protein segment, e.g., a hydrophobic protein segment that is thermodynamically stable in a cell membrane.

Transmembrane domains are classified based on the three dimensional structure of the transmembrane domain. For example, transmembrane domains may form an alpha helix, a complex of more than one alpha helix, a beta-barrel, or any other stable structure capable of spanning the phospholipid bilayer of a cell. Furthermore, transmembrane domains may also or alternatively be classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 2, 3, 4, 5, 6, 7 or more times). Membrane proteins may be defined as Type I, Type II or Type III depending upon the topology of their termini and membrane-passing segment(s) relative to the inside and outside of the cell. Type I membrane proteins have a single membrane-spanning region and are oriented such that the N-terminus of the protein is present on the extracellular side of the lipid bilayer of the cell and the C-terminus of the protein is present on the cytoplasmic side. Type II membrane proteins also have a single membrane-spanning region but are oriented such that the C-terminus of the protein is present on the extracellular side of the lipid bilayer of the cell and the N-terminus of the protein is present on the cytoplasmic side. Type III membrane proteins have multiple membrane-spanning segments and may be further sub-classified based on the number of transmembrane segments and the location of N- and C-termini.

In some embodiments, the transmembrane domain of the CAR described herein is derived from a Type I single-pass membrane protein. In some embodiments, transmembrane domains from multi-pass membrane proteins may also be compatible for use in the CARs described herein. Multi-pass membrane proteins may comprise a complex (at least 2, 3, 4, 5, 6, 7 or more) alpha helices or a beta sheet structure. In some embodiments, the N-terminus and the C-terminus of a multi-pass membrane protein are present on opposing sides of the lipid bilayer, e.g., the N-terminus of the protein is present on the cytoplasmic side of the lipid bilayer and the C-terminus of the protein is present on the extracellular side.

In some embodiments, the transmembrane domain of the CAR comprises a transmembrane domain chosen from the transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIRDS2, OX40, CD2, CD27, LFA-1 (CD1 la, CD18), ICOS (CD278), 4-1BB (CD137), GITR, CD40, BAFFR, HVEM (LIGHTR), SLAMF7, NKp80 (KLRF1), CD160, CD19, IL-2R beta, IL-2R gamma, IL-7R a, ITGA1, VLA 1, CD49a, ITGA4, IA4, CD49D, ITGA6, VLA-6, CD49f, ITGAD, CD1 ld, ITGAE, CD103, 1TGAL, CD1 la, LFA-1, ITGAM, CD1 lb, ITGAX, CD1 lc, ITGB1, CD29, ITGB2, CD18, LFA-1, ITGB7, TNFR2, DNAM1 (CD226), SLAMF4 (CD244, 2B4), CD84, CD % (Tactile), CEACAM1, CRT AM, Ly9 (CD229), CD160 (BY55), PSGL1, CDIOO (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C. In some embodiments, the transmembrane domain is derived from a molecule selected from the group consisting of CD8α, CD4, CD28, CD137, CD80, CD86, CD152 and PD1.

In some specific embodiments, the transmembrane domain is derived from CD8α. In some embodiments, the transmembrane domain is a transmembrane domain of CD8α comprising the amino acid sequence of SEQ ID NO: 154.

Transmembrane domains for use in the CARS described herein can also comprise at least a portion of a synthetic, non-naturally occurring protein segment. In some embodiments, the transmembrane domain is a synthetic, non-naturally occurring alpha helix or beta sheet. In some embodiments, the protein segment is at least approximately 20 amino acids, e.g., at least 18, 19, 20, 21, 22, 23, 24, 25, 26, 27, 28, 29, 30, or more amino acids. Examples of synthetic transmembrane domains are known in the art, for example in U.S. Pat. No. 7,052,906 and PCT Publication No. WO 2000/032776, the relevant disclosures of which are incorporated by reference herein.

The transmembrane domain provided herein may comprise a transmembrane region and a cytoplasmic region located at the C-terminal side of the transmembrane domain. The cytoplasmic region of the transmembrane domain may comprise three or more amino acids and, in some embodiments, helps to orient the transmembrane domain in the lipid bilayer. In some embodiments, one or more cysteine residues are present in the transmembrane region of the transmembrane domain. In some embodiments, one or more cysteine residues are present in the cytoplasmic region of the transmembrane domain. In some embodiments, the cytoplasmic region of the transmembrane domain comprises positively charged amino acids. In some embodiments, the cytoplasmic region of the transmembrane domain comprises the amino acids arginine, serine, and lysine.

In some embodiments, the transmembrane region of the transmembrane domain comprises hydrophobic amino acid residues. In some embodiments, the transmembrane domain of the CAR provided herein comprises an artificial hydrophobic sequence. For example, a triplet of phenylalanine, tryptophan and valine may be present at the C terminus of the transmembrane domain. In some embodiments, the transmembrane region comprises mostly hydrophobic amino acid residues, such as alanine, leucine, isoleucine, methionine, phenylalanine, tryptophan, or valine. In some embodiments, the transmembrane region is hydrophobic. In some embodiments, the transmembrane region comprises a poly-leucine-alanine sequence. The hydropathy, or hydrophobic or hydrophilic characteristics of a protein or protein segment, can be assessed by any method known in the art, for example the Kyte and Doolittle hydropathy analysis.

5.3.3. Intracellular Signaling Domain

The CARs of the present disclosure comprise an intracellular signaling domain. The intracellular signaling domain is responsible for activation of at least one of the normal effector functions of the immune effector cell expressing the CARs. The term "effector function" refers to a specialized function of a cell. Effector function of a T cell, for example, may be cytolytic activity or helper activity including the secretion of cytokines. Thus the term "cytoplasmic signaling domain" refers to the portion of a protein which transduces the effector function signal and directs the cell to perform a specialized function. While usually the entire cytoplasmic signaling domain can be employed, in many cases it is not necessary to use the entire chain. To the extent that a truncated portion of the cytoplasmic signaling domain is used, such truncated portion may be used in place of the intact chain as long as it transduces the effector function signal. The term cytoplasmic signaling domain is thus meant to include any truncated portion of the cytoplasmic signaling domain sufficient to transduce the effector function signal.

In some embodiments, the intracellular signaling domain comprises a primary intracellular signaling domain of an immune effector cell. In some embodiments, the CAR comprises an intracellular signaling domain consisting essentially of a primary intracellular signaling domain of an immune effector cell. "Primary intracellular signaling domain" refers to cytoplasmic signaling sequence that acts in a stimulatory manner to induce immune effector functions. In some embodiments, the primary intracellular signaling domain contains a signaling motif known as immunoreceptor tyrosine-based activation motif, or ITAM. An "ITAM," as used herein, is a conserved protein motif that is generally present in the tail portion of signaling molecules expressed in many immune cells. The motif may comprises two repeats of the amino acid sequence YxxL/I separated by 6-8 amino acids, wherein each x is independently any amino acid, producing the conserved motif YxxL/Ix(6-8)YxxL/I. ITAMs within signaling molecules are important for signal transduction within the cell, which is mediated at least in part by phosphorylation of tyrosine residues in the ITAM following activation of the signaling molecule. ITAMs may also function as docking sites for other proteins involved in signaling pathways. Exemplary ITAM-containing primary cytoplasmic signaling sequences include those derived from CD3ζ, FcR gamma (FCER1G), FcR beta (Fc Epsilon Rib), CD3 gamma, CD3 delta, CD3 epsilon, CD5. CD22, CD79a, CD79b, and CD66d.

In some embodiments, the primary intracellular signaling domain is derived from CD3ζ. In some embodiments, the intracellular signaling domain consists of the cytoplasmic signaling domain of CD3ζ. In some embodiments, the primary intracellular signaling domain is a cytoplasmic signaling domain of wild-type CD3ζ. In some embodiments, the primary intracellular signaling domain of CD3ζ comprises the amino acid sequence of SEQ ID NO: 156. In some embodiments, the primary intracellular signaling domain of wild-type CD34. In some embodiments, the primary intracellular signaling domain is a functional mutant of the cytoplasmic signaling domain of CD3ζ containing one or more mutations, such as Q65K.

5.3.4. Co-Stimulatory Signaling Domain

Many immune effector cells require co-stimulation, in addition to stimulation of an antigen-specific signal, to promote cell proliferation, differentiation and survival, as well as to activate effector functions of the cell. In some embodiments, the CAR comprises at least one co-stimulatory signaling domain. The term "co-stimulatory signaling domain," as used herein, refers to at least a portion of a protein that mediates signal transduction within a cell to induce an immune response such as an effector function. The co-stimulatory signaling domain of the chimeric receptor described herein can be a cytoplasmic signaling domain from a co-stimulatory protein, which transduces a signal and modulates responses mediated by immune cells, such as T cells. NK cells, macrophages, neutrophils, or eosinophils. "Co-stimulatory signaling domain" can be the cytoplasmic portion of a co-stimulatory molecule. The term "co-stimulatory molecule" refers to a cognate binding partner on an immune cell (such as T cell) that specifically binds with a co-stimulatory ligand, thereby mediating a co-stimulatory response by the immune cell, such as, but not limited to, proliferation and survival.

In some embodiments, the intracellular signaling domain comprises a single co-stimulatory signaling domain. In some embodiments, the intracellular signaling domain comprises two or more (such as about any of 2, 3, 4, or more) co-stimulatory signaling domains. In some embodiments, the intracellular signaling domain comprises two or more of the same co-stimulatory signaling domains. In some embodiments, the intracellular signaling domain comprises two or more co-stimulatory signaling domains from different co-stimulatory proteins, such as any two or more co-stimulatory proteins described herein. In some embodiments, the intracellular signaling domain comprises a primary intracellular signaling domain (such as cytoplasmic signaling domain of CD3ζ) and one or more co-stimulatory signaling domains. In some embodiments, the one or more co-stimulatory signaling domains and the primary intracellular signaling domain (such as cytoplasmic signaling domain of CD3ζ) are fused to each other via optional peptide linkers. The primary intracellular signaling domain, and the one or more co-stimulatory signaling domains may be arranged in any suitable order. In some embodiments, the one or more co-stimulatory signaling domains are located between the transmembrane domain and the primary intracellular signaling domain (such as cytoplasmic signaling domain of CD3ζ). Multiple co-stimulatory signaling domains may provide additive or synergistic stimulatory effects.

Activation of a co-stimulatory signaling domain in a host cell (e.g., an immune cell) may induce the cell to increase or decrease the production and secretion of cytokines, phagocytic properties, proliferation, differentiation, survival, and/or cytotoxicity. The co-stimulatory signaling domain of any co-stimulatory molecule may be compatible for use in the CARs described herein. The type(s) of co-stimulatory signaling domain is selected based on factors such as the type of the immune effector cells in which the effector molecules would be expressed (e.g., T cells, NK cells, macrophages, neutrophils, or eosinophils) and the desired immune effector function (e.g., ADCC effect). Examples of co-stimulatory signaling domains for use in the CARs can be the cytoplasmic signaling domain of co-stimulatory proteins, including, without limitation, members of the B7/CD28 family (e.g., B7-1/CD80, B7-2/CD86, B7-HI/PD-L1, B7-H2, B7-H3, B7-H4, B7-H6, B7-H7, BTLA/CD272, CD28, CTLA-4, Gi24/VISTAB7-H5, ICOS/CD278, PD-1, PD-L2/B7-DC, and PDCD6); members of the TNF superfamily (e.g., 4-1 BB/TNFSF9/CD137, 4-1 BB Ligand/TNFSF9, BAFF/LyS/TNFSF13B, BAFF R/TNFRSF13C, CD27/TNFRSF7, CD27 Ligand-TNFSF7, CD30/TNFRSF8, CD30 Ligand/TNFSF8, CD40; TNFRSF5, CD40/TNFSF5, CD40 Ligand/TNFSF5, DR3/TNFRSF25, GITR/TNFRSF18, GITR Ligand/TNFSF18, HVEM/TNFRSF14, LIGHT/TNFSF14, Lymphotoxin-alpha/TNF-beta, OX40/TNFRSF4, OX40 Ligand-TNFSF4, RELT/TNFRSF19L, TACI/TNFRSF13B, TL1A/TNFSF15, TNF-alpha, and TNF RII/TNFRSF1B); members of the SLAM family (e.g., 2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLAMF6, and SLAM/CD150); and any other co-stimulatory molecules, such as CD2, CD7, CD53, CD82/Kai-1, CD90/Thy1, CD96, CD160, CD200, CD300a/LMIR1, HLA Class I, HLA-DR, Ikaros, Integrin alpha 4/CD49d, Integrin alpha 4 beta 1, Integrin alpha 4 beta 7/LPAM-1, LAG-3, TCL1A, TCL1B, CRTAM, DAP 12, Dectin-1/CLEC7A, DPPIV/CD26, EphB6, TIM-1/KIM-1/HAVCR, TIM-4, TSLP, TSLP R, lymphocyte function associated antigen-1 (LFA-1), and NKG2C.

In some embodiments, the one or more co-stimulatory signaling domains are selected from the group consisting of CD27, CD28, CD137, OX40, CD30, CD40, CD3, lymphocyte function-associated antigen-1(LFA-1), CD2, CD7, LIGHT, NKG2C, B7-H3 and ligands that specially bind to CD83.

In some embodiments, the intracellular signaling domain in the CAR of the present disclosure comprises a co-stimulatory signaling domain derived from CD137 (i.e., 4-1BB). In some embodiments, the intracellular signaling domain comprises a cytoplasmic signaling domain of CD3ζ and a co-stimulatory signaling domain of CD137. In some embodiments, the intracellular signaling domain comprises a co-stimulatory signaling domain of CD137 comprising the amino acid sequence of SEQ ID NO: 155.

Also within the scope of the present disclosure are variants of any of the co-stimulatory signaling domains described herein, such that the co-stimulatory signaling domain is capable of modulating the immune response of the immune cell. In some embodiments, the co-stimulatory signaling domains comprises up to 10 amino acid residue variations (e.g., 1, 2, 3, 4, 5, or 8) as compared to a wild-type counterpart. Such co-stimulatory signaling domains comprising one or more amino acid variations may be referred to as variants. Mutation of amino acid residues of the co-stimulatory signaling domain may result in an increase in signaling transduction and enhanced stimulation of immune responses relative to co-stimulatory signaling domains that do not comprise the mutation. Mutation of amino acid residues of the co-stimulatory signaling domain may result in a decrease in signaling transduction and reduced stimulation of immune responses relative to co-stimulatory signaling domains that do not comprise the mutation.

5.3.5. Hinge Region

The CARs of the present disclosure may comprise a hinge domain that is located between the extracellular antigen binding domain and the transmembrane domain. A hinge domain is an amino acid segment that is generally found between two domains of a protein and may allow for flexibility of the protein and movement of one or both of the domains relative to one another. Any amino acid sequence that provides such flexibility and movement of the extracellular antigen binding domain relative to the transmembrane domain of the effector molecule can be used.

The hinge domain may contain about 10-100 amino acids, e.g., about any one of 15-75 amino acids, 20-50 amino acids, or 30-60 amino acids. In some embodiments, the hinge domain may be at least about any one of 10, 11, 12, 13, 14, 15, 16, 17, 18, 19, 20, 21, 22, 23, 24, 25, 26, 27, 28, 29, 30, 35, 40, 45, 50, 55, 60, 65, 70, or 75 amino acids in length.

In some embodiments, the hinge domain is a hinge domain of a naturally occurring protein. Hinge domains of any protein known in the art to comprise a hinge domain are compatible for use in the chimeric receptors described herein. In some embodiments, the hinge domain is at least a portion of a hinge domain of a naturally occurring protein and confers flexibility to the chimeric receptor. In some embodiments, the hinge domain is derived from CD8α. In some embodiments, the hinge domain is a portion of the hinge domain of CD8α, e.g., a fragment containing at least 15 (e.g., 20, 25, 30, 35, or 40) consecutive amino acids of the hinge domain of CD8α. In some embodiments, the hinge domain of CD8α comprises the amino acid sequence of SEQ ID NO: 153.

Hinge domains of antibodies, such as an IgG, IgA, IgM, IgE, or IgD antibodies, are also compatible for use in the pH-dependent chimeric receptor systems described herein. In some embodiments, the hinge domain is the hinge domain that joins the constant domains CH1 and CH2 of an antibody. In some embodiments, the hinge domain is of an antibody and comprises the hinge domain of the antibody and one or more constant regions of the antibody, in some embodiments, the hinge domain comprises the hinge domain of an antibody and the CH3 constant region of the antibody. In some embodiments, the hinge domain comprises the hinge domain of an antibody and the CH2 and CH3 constant regions of the antibody. In some embodiments, the antibody is an IgG, IgA, IgM, IgE, or IgD antibody. In some embodiments, the antibody is an IgG antibody. In some embodiments, the antibody is an IgG1, IgG2, IgG3, or IgG4 antibody. In some embodiments, the hinge region comprises the hinge region and the CH2 and CH3 constant regions of an IgG1 antibody. In some embodiments, the hinge region comprises the hinge region and the CH3 constant region of an IgG1 antibody.

Non-naturally occurring peptides may also be used as hinge domains for the chimeric receptors described herein. In some embodiments, the hinge domain between the C-terminus of the extracellular ligand-binding domain of an Fc receptor and the N-terminus of the transmembrane domain is a peptide linker, such as a (GxS)n linker, wherein x and n, independently can be an integer between 3 and 12, including 3, 4, 5, 6, 7, 8, 9, 10, 11, 12, or more.

5.3.6. Signal Peptide

The CARs of the present disclosure may comprise a signal peptide (also known as a signal sequence) at the N-terminus of the polypeptide. In general, signal peptides are peptide sequences that target a polypeptide to the desired site in a cell. In some embodiments, the signal peptide targets the effector molecule to the secretory pathway of the cell and will allow for integration and anchoring of the effector molecule into the lipid bilayer. Signal peptides including signal sequences of naturally occurring proteins or synthetic, non-naturally occurring signal sequences, which are compatible for use in the CARs described herein will be evident to one of skill in the art. In some embodiments, the signal peptide is derived from a molecule selected from the group consisting of CD8α. GM-CSF receptor a, and IgG1 heavy chain. In some embodiments, the signal peptide is derived from CD8α. In some embodiments, the signal peptide of CD8α comprises the amino acid sequence of SEQ ID NO: 152.

5.3.7. Exemplary CARs

Exemplary monovalent CARS are generated as shown in Section 6 below, such as VHH-273 CAR VHH-283 CAR VHH-313 CAR VHH-440 CAR VHH-466 CAR VHH-496 CAR. VHH-653 CAR, huVHH-253 CAR, huVHH-256 CAR, huVHH-260 CAR, huVHH-746 CAR, huVHH-750 CAR, huVHH-753 CAR, huVHH-836 CAR, huVHH-840 CAR, huVHH-843 CAR, huVHH-846 CAR, and VHH-623 CAR, VHH-640 CAR, and/or VHH-657 CAR In addition, exemplary multivalent CARS, such as bivalent and trivalent CARS, are generated as shown in Section 6, including Bi-VHH1 CAR. Bi-VHH2 CAR, Bi-VHH3 CAR, Bi-VHH4 (G4S)$_1$ CAR. Bi-VHH4 (G4S)$_2$ CAR, Bi-VHH4 (G4S)$_3$ CAR, Bi-VHH4 (G4S)$_4$ CAR, Bi-VHH4 (G4S)$_5$ CAR, and Tri-VHH CAR.

In some embodiments, provided herein is a CAR comprising or consisting of the amino acid sequence of SEQ ID NO: 81. In some embodiments, provided herein is a CAR comprising or consisting of the amino acid sequence of SEQ ID NO: 82. In some embodiments, provided herein is a CAR comprising or consisting of the amino acid sequence of SEQ ID NO: 83. In some embodiments, provided herein is a CAR comprising or consisting of the amino acid sequence of SEQ ID NO: 84. In some embodiments, provided herein is a CAR comprising or consisting of the amino acid sequence of SEQ ID NO: 85. In some embodiments, provided herein is a CAR comprising or consisting of the amino acid sequence of SEQ ID NO: 86. In some embodiments, provided herein is a CAR comprising or consisting of the amino acid sequence of SEQ ID NO: 87. In some embodiments, provided herein is a CAR comprising or consisting of the amino acid sequence of SEQ ID NO: 88. In some embodiments, provided herein is a CAR comprising or consisting of the amino acid sequence of SEQ ID NO: 89. In some embodiments, provided herein is a CAR comprising or consisting of the amino acid sequence of SEQ ID NO: 90. In some embodiments, provided herein is a CAR comprising or consisting of the amino acid sequence of SEQ ID NO: 91. In some embodiments, provided herein is a CAR comprising or consisting of the amino acid sequence of SEQ ID NO: 92. In some embodiments, provided herein is a CAR comprising or consisting of the amino acid sequence of SEQ ID NO: 93. In some embodiments, provided herein is a CAR comprising or consisting of the amino acid sequence of SEQ ID NO: 94. In some embodiments, provided herein is a CAR comprising or consisting of the amino acid sequence of SEQ ID NO: 95. In some embodiments, provided herein is a CAR comprising or consisting of the amino acid sequence of SEQ ID NO: 96. In some embodiments, provided herein is a CAR comprising or consisting of the amino acid sequence of SEQ ID NO: 97. In some embodiments, provided herein is a CAR comprising or consisting of the amino acid sequence of SEQ ID NO: 98. In some embodiments, provided herein is a CAR comprising or consisting of the amino acid sequence of SEQ ID NO: 99. In some embodiments, provided herein is a CAR comprising or consisting of the amino acid sequence of SEQ ID NO: 100. In some embodiments, provided herein is a CAR comprising or consisting of the amino acid sequence of SEQ ID NO: 101. In some embodiments, provided herein is a CAR comprising or consisting of the amino acid sequence of SEQ ID NO: 102. In some embodiments, provided herein is a CAR comprising or consisting of the amino acid sequence of SEQ ID NO: 103. In some embodiments, provided herein is a CAR comprising or consisting of the amino acid sequence of SEQ ID NO: 104. In some embodiments, provided herein is a CAR comprising or consisting of the amino acid sequence of SEQ ID NO: 105. In some embodiments, provided herein is a CAR comprising or consisting of the amino acid sequence of SEQ ID NO: 106. In some embodiments, provided herein is a CAR comprising or consisting of the amino acid sequence of SEQ ID NO: 189. In some embodiments, provided herein is a CAR comprising or consisting of the amino acid sequence of SEQ ID NO: 190. In some embodiments, provided herein is a CAR comprising or consisting of the amino acid sequence of SEQ ID NO: 191.

In certain embodiments, the CAR provided herein comprises amino acid sequences with certain percent identity relative to any one of the CARs exemplified in the Section 6 below.

In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 81. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 82. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 83. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 84. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 85. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 86. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 87. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98% 99%, or 100% sequence identity to the amino acid sequence of SEQ ID NO: 88. In some embodiments, provided herein is a CD20 CAR comprising a polypeptide having at least 75%, 80%, 85%, 86%, 87%, 88% 89%, 90%, 91%, 92%, 93%, 94%, 95%, 96%, 97%, 98%, 99%, or 100% sequence identity to the amino acid sequence of SEQ ID NO: 89. In some embodiments, provided herein is a CD20 CAR comprising a polypeptide having at least 75%, 80%, 85%, 86%, 87%, 88%, 89%, 90%, 91%%, 92%, 93%, 94%, 95%, 96%, 97%, 98%, 99%, or 100% sequence identity to the amino acid sequence of SEQ ID NO: 90. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 91. In some embodiments, provided herein is a CD20 CAR comprising a polypeptide having at least 75%, 80%, 85%%, 86%, 87%, 88%, 89%, 90%, 91%, 92%, 93%, 94%, 95%, 96%, 97%, 98%, 99%, or 100% sequence identity to the amino acid sequence of SEQ ID NO: 92. In some embodiments, provided herein is a CD20 CAR comprising a polypeptide having at least 75%, 80%, 85%, 86%, 87%, 88%, 89%%, 90%, 91%, 92%, 93%%, 94%, 95%, 96%, 97%, 98%, 99%, or 100% sequence identity to the amino acid sequence of SEQ ID NO: 93. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 94. In some embodiments, provided herein is a CD20 CAR comprising a polypeptide having at least 75%, 80%, 85%, 86%, 87%, 88%%, 89%, 90%, 91%, 92%, 93%, 94%, 95%, 96%, 97%, 98%, 99%, or 100% sequence identity to the amino acid sequence of SEQ ID NO: 95. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 96. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 97. In some embodiments, provided herein is a CD20 CAR comprising a poly-peptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 98. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 99. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 100. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 101. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 102. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 103. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 104. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 105. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 106. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 189. In some embodiments, provided herein is a CD20 CAR comprising a polypeptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 190. In some embodiments, provided herein is a CD20 CAR comprising a poly peptide having at least 75%, 80%, 85%, 86%, 87%, 88%, 89%, 90%, 91%, 92%, 93%, 94%, 95%, 96%, 97%, 98%, 99%, or 100% sequence identity to the amino acid sequence of SEQ ID NO: 191.

In some embodiments, provided herein is an isolated nucleic acid encoding any of the CD20 CARS provided herein. More detailed description regarding nucleic acid sequences and vectors are provided below.

5.4. Engineered Immune Effector Cells

In yet another aspect, provided herein are host cells (such as immune effector cells) comprising any one of the CARS described herein.

Thus, in some embodiments, provided herein is an engineered immune effector cell (such as T cell) comprising a CAR which comprises a polypeptide comprising: (a) an extracellular antigen binding domain comprising one or more anti-CD20 sdAb(s); (b) a transmembrane domain; and (c) an intracellular signaling domain, wherein the anti-CD20 sdAb is an anti-CD20 sdAb as described in Section 5.2 above, including, e.g., the VHH domains in Table 2 and those having one, two or all three CDRs in any of those VHH domains in Table 2. In some embodiments, the anti-CD20 sdAb is camelid, chimeric, human, or humanized. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the CAR further comprises a hinge domain (such as a CD8α hinge domain) located between the C-terminus of the extracellular antigen binding domain and the N-terminus of the transmembrane domain. In some embodiments, the CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3;

In some embodiments, provided herein is an engineered immune effector cell (such as T cell) comprising a CAR which comprises a polypeptide comprising: (a) an extracellular antigen binding domain comprising one or more anti-CD20 sdAb(s); (b) a transmembrane domain; and (c) an intracellular signaling domain, wherein the anti-CD20 sdAb comprises the amino acid sequence of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184, or SEQ ID NO: 185. In some embodiments, provided herein is an engineered immune effector cell (such as T cell) comprising a CAR which comprises a polypeptide comprising: (a) an extracellular antigen binding domain comprising one or more anti-CD20 sdAb(s); (b) a transmembrane domain; and (c) an intracellular signaling domain, wherein the anti-CD20 sdAb comprises an amino acid sequence having at least 75%, 80%, 85%, 86%, 87%, 88%, 89%, 90%, 91%, 92%, 93%, 94%, 95%, 96%, 97%, 98%, 99%, or 100% sequence identify to the amino acid sequence of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184, or SEQ ID NO: 185. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C, B7-H3, ligands of CD83 and combinations thereof. In some embodiments, the CAR further comprises a hinge domain (such as a CD8α hinge domain) located between the C-terminus of the extracellular antigen binding domain and the N-terminus of the transmembrane domain. In some embodiments, the CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ.

In some embodiments, provided herein is an engineered immune effector cell (such as T cell) comprising a CAR which comprises an amino acid sequence selected from the group consisting of SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 189, SEQ ID NO: 190, and SEQ ID NO: 191. In some embodiments, provided herein is an engineered immune effector cell (such as T cell) comprising a CAR which comprises a polypeptide having at least 75%, 80%, 85%, 86%, 87%, 88%, 89%, 90%, 91%, 92%, 93%, 94%, 95%, 96%, 97%, 98%, 99%, or 100% sequence identity to an amino acid sequence selected from the group consisting of SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 189, SEQ ID NO: 190, and SEQ ID NO: 191.

In other embodiments, there is provided an engineered immune effector cell (such as T cell) comprising a multispecific (such as bispecific or trispecific) chimeric antigen receptor (CAR) comprising a polypeptide comprising: (a) an extracellular antigen binding domain comprising a first single domain antibody (sdAb) specifically binding to CD20 and one or more additional antigen binding domain(s); (b) a transmembrane domain; and (c) an intracellular signaling domain. In some embodiments, the additional antigen binding domain binds to an antigen selected from the group consisting of CD22, CD19, CD33, CD38, BCMA, CS1, ROR1, GPC3, CD123, IL-13R, CD138, c-Met, EGFRvIII, GD-2, NY-ESO-1, MAGE A3, and glycolipid F77. In some embodiments, the first sdAb and/or the additional sdAb is camelid, chimeric, human, or humanized. In some embodiments, the first single domain antibody and the additional single domain antibody are fused to each other via a peptide bond or a peptide linker. In some embodiments, the peptide linker is no more than about 50 (such as no more than about any one of 35, 25, 20, 15, 10, or 5) amino acids long. In some embodiments, the transmembrane domain is selected from the group consisting of CD8α, CD4, CD28, CD137, CD80, CD86, CD152 and PD1. In some embodiments, the intracellular signaling domain comprises a primary intracellular signaling domain of an immune effector cell (such as T cell). In some embodiments, the primary intracellular signaling domain is derived from CD3ζ. In some embodiments, the intracellular signaling domain comprises a co-stimulatory signaling domain. In some embodiments, the co-stimulatory signaling domain is derived from a co-stimulatory molecule selected from the group consisting of CD27, CD28, CD137, OX40, CD30, CD40, CD3, LFA-1, CD2, CD7, LIGHT, NKG2C. B7-H3, ligands of CD83 and combinations thereof. In some embodiments, the multispecific CAR further comprises a hinge domain (such as a CD8α hinge domain) located between the C-terminus of the extracellular antigen binding domain and the N-terminus of the transmembrane domain. In some embodiments, the multispecific CAR further comprises a signal peptide (such as a CD8α signal peptide) located at the N-terminus of the polypeptide. In some embodiments, the polypeptide comprises from the N-terminus to the C-terminus: a CD8α signal peptide, the extracellular antigen binding domain, a CD8α hinge domain, a CD8α transmembrane domain, a co-stimulatory signaling domain derived from CD137, and a primary intracellular signaling domain derived from CD3ζ.

In some embodiments, the engineered immune effector cell is a T cell, an NK cell, a peripheral blood mononuclear cell (PBMC), a hematopoietic stem cell, a pluripotent stem cell, or an embryonic stem cell. In some embodiments, the engineered immune effector cell is autologous. In some embodiments, the engineered immune effector cell is allogenic.

Also provided are engineered immune effector cells comprising (or expressing) two or more different CARs. Any two or more of the CARs described herein may be expressed in combination. The CARS may target different antigens, thereby providing synergistic or additive effects. The two or more CARs may be encoded on the same vector or different vectors.

The engineered immune effector cell may further express one or more therapeutic proteins and/or immunomodulators, such as immune checkpoint inhibitors. See, e.g., International Patent Application NOs. PCT/CN2016/073489 and PCT/CN2016/087855, which are incorporated herein by reference in their entirety.

5.4.1. Vectors

The present disclosure provides vectors for cloning and expressing any one of the CARS described herein. In some embodiments, the vector is suitable for replication and integration in eukaryotic cells, such as mammalian cells. In some embodiments, the vector is a viral vector. Examples of viral vectors include, but are not limited to, adenoviral vectors, adeno-associated virus vectors, lentiviral vector, retroviral vectors, vaccinia vector, herpes simplex viral vector, and derivatives thereof. Viral vector technology is well known in the art and is described, for example, in Sambrook et al. (2001, Molecular Cloning: A Laboratory Manual. Cold Spring Harbor Laboratory, New York), and in other virology and molecular biology manuals.

A number of viral based systems have been developed for gene transfer into mammalian cells. For example, retroviruses provide a convenient platform for gene delivery systems. The heterologous nucleic acid can be inserted into a vector and packaged in retroviral particles using techniques known in the art. The recombinant virus can then be isolated and delivered to the engineered mammalian cell in vitro or ex viva. A number of retroviral systems are known in the art. In some embodiments, adenovirus vectors are used. A number of adenovirus vectors are known in the art. In some embodiments, lentivirus vectors are used. In some embodiments, self-inactivating lentiviral vectors are used. For example, self-inactivating lentiviral vectors carrying the immunomodulator (such as immune checkpoint inhibitor) coding sequence and/or self-inactivating lentiviral vectors carrying chimeric antigen receptors can be packaged with protocols known in the art. The resulting lentiviral vectors can be used to transduce a mammalian cell (such as primary human T cells) using methods known in the art. Vectors derived from retroviruses such as lentivirus are suitable tools to achieve long-term gene transfer, because they allow long-term, stable integration of a transgene and its propagation in progeny cells. Lentiviral vectors also have low immunogenicity, and can transduce non-proliferating cells.

In some embodiments, the vector comprises any one of the nucleic acids encoding a CAR described herein. The nucleic acid can be cloned into the vector using any known molecular cloning methods in the art, including, for example, using restriction endonuclease sites and one or more selectable markers. In some embodiments, the nucleic acid is operably linked to a promoter. Varieties of promoters have been explored for gene expression in mammalian cells, and any of the promoters known in the art may be used in the present disclosure. Promoters may be roughly categorized as constitutive promoters or regulated promoters, such as inducible promoters.

In some embodiments, the nucleic acid encoding the CAR is operably linked to a constitutive promoter. Constitutive promoters allow heterologous genes (also referred to as transgenes) to be expressed constitutively in the host cells. Exemplary constitutive promoters contemplated herein include, but are not limited to, Cytomegalovirus (CMV) promoters, human elongation factors-1 alpha (hEF1α), ubiquitin C promoter (UbiC), phosphoglycerokinase promoter (PGK), simian virus 40 early promoter (SV40), and chicken β-Actin promoter coupled with CMV early enhancer (CAGG). The efficiencies of such constitutive promoters on driving transgene expression have been widely compared in a huge number of studies. For example, Michael C. Milone et al compared the efficiencies of CMV, hEF1α, UbiC and PGK to drive chimeric antigen receptor expression in primary human T cells, and concluded that hEF1α promoter not only induced the highest level of transgene expression, but was also optimally maintained in the CD4 and CD8 human T cells (Molecular Therapy, 17(8): 1453-1464 (2009)). In some embodiments, the nucleic acid encoding the CAR is operably linked to a hEF1α promoter.

In some embodiments, the nucleic acid encoding the CAR is operably linked to an inducible promoter. Inducible promoters belong to the category of regulated promoters. The inducible promoter can be induced by one or more conditions, such as a physical condition, microenvironment of the engineered immune effector cell, or the physiological state of the engineered immune effector cell, an inducer (i.e., an inducing agent), or a combination thereof.

In some embodiments, the inducing condition does not induce the expression of endogenous genes in the engineered mammalian cell, and/or in the subject that receives the pharmaceutical composition. In some embodiments, the inducing condition is selected from the group consisting of; inducer, irradiation (such as ionizing radiation, light), temperature (such as heat), redox state, tumor environment, and the activation state of the engineered mammalian cell.

In some embodiments, the vector also contains a selectable marker gene or a reporter gene to select cells expressing the CAR from the population of host cells transfected through lentiviral vectors. Both selectable markers and reporter genes may be flanked by appropriate regulatory sequences to enable expression in the host cells. For example, the vector may contain transcription and translation terminators, initiation sequences, and promoters useful for regulation of the expression of the nucleic acid sequences.

In some embodiments, the vector comprises more than one nucleic acid encoding CARs. In some embodiments, the vector comprises a nucleic acid comprising a first nucleic acid sequence encoding a first CAR and a second nucleic acid sequence encoding a second CAR, wherein the first nucleic acid is operably linked to the second nucleic acid via a third nucleic acid sequence encoding a self-cleaving peptide. In some embodiments, the self-cleaving peptide is selected from the group consisting of T2A, P2A and F2A.

5.4.2. Immune Effector Cells

"Immune effector cells" are immune cells that can perform immune effector functions. In some embodiments, the immune effector cells express at least FcγRIII and perform ADCC effector function. Examples of immune effector cells which mediate ADCC include peripheral blood mononuclear cells (PBMC), natural killer (NK) cells, monocytes, cytotoxic T cells, neutrophils, and eosinophils.

In some embodiments, the immune effector cells are T cells. In some embodiments, the T cells are CD4+/CD8−, CD4−/CD8+, CD4+/CD8+. CD4−/CD8−, or combinations thereof. In some embodiments, the T cells produce IL-2, TFN, and/or TNF upon expressing the CAR and binding to the target cells, such as CD20+ tumor cells. In some embodiments, the CD8+ T cells lyse antigen-specific target cells upon expressing the CAR and binding to the target cells.

In some embodiments, the immune effector cells are NK cells. In other embodiments, the immune effector cells can be established cell lines, for example, NK-92 cells.

In some embodiments, the immune effector cells are differentiated from a stem cell, such as a hematopoietic stem cell, a pluripotent stem cell, an iPS, or an embryonic stem cell.

The engineered immune effector cells are prepared by introducing the CARs into the immune effector cells, such as T cells. In some embodiments, the CAR is introduced to the immune effector cells by transfecting any one of the isolated nucleic acids or any one of the vectors described above. In some embodiments, the CAR is introduced to the immune effector cells by inserting proteins into the cell membrane while passing cells through a microfluidic system, such as CELL SQUEEZE™ (see, e.g., U.S. Patent Application Publication No. 20140287509).

Methods of introducing vectors or isolated nucleic acids into a mammalian cell are known in the art. The vectors described can be transferred into an immune effector cell by physical, chemical, or biological methods.

Physical methods for introducing the vector into an immune effector cell include calcium phosphate precipitation, lipofection, particle bombardment, microinjection, electroporation, and the like. Methods for producing cells comprising vectors and/or exogenous nucleic acids are well-known in the art. See, e.g., Sambrook et al. (2001) Molecular Cloning: A Laboratory Manual. Cold Spring Harbor Laboratory, New York. In some embodiments, the vector is introduced into the cell by electroporation.

Biological methods for introducing the vector into an immune effector cell include the use of DNA and RNA vectors. Viral vectors have become the most widely used method for inserting genes into mammalian, e.g., human cells.

Chemical means for introducing the vector into an immune effector cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro is a liposome (e.g., an artificial membrane vesicle).

In some embodiments, RNA molecules encoding any of the CARs described herein may be prepared by a conventional method (e.g., in vitro transcription) and then introduced into the immune effector cells via known methods such as mRNA electroporation. See, e.g., Rabinovich et al., Human Gene Therapy 17:1027-1035 (2006).

In some embodiments, the transduced or transfected immune effector cell is propagated ex vivo after introduction of the vector or isolated nucleic acid. In some embodiments, the transduced or transfected immune effector cell is cultured to propagate for at least about any of 1 day, 2 days, 3 days, 4 days, 5 days, 6 days, 7 days, 10 days, 12 days, or 14 days. In some embodiments, the transduced or transfected immune effector cell is further evaluated or screened to select the engineered mammalian cell.

Reporter genes may be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al. FEBS Letters 479: 79-82 (2000)). Suitable expression systems are well known and may be prepared using known techniques or obtained commercially. Other methods to confirm the presence of the nucleic acid encoding the CARS in the engineered immune effector cell, include, for example, molecular biological assays well known to those of skill in the art, such as Southern and Northern blotting, RT-PCR and PCR; biochemical assays, such as detecting the presence or absence of a particular peptide, e.g., by immunological methods (such as ELISAs and Western blots).

5.4.3. Sources of T Cells

In some embodiments, prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments, any number of T cell lines available in the art, may be used. In some embodiments, T cells can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. Initial activation steps in the absence of calcium may lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as CD3+, CD28+, CD4+, CD8+, CD45RA+, and CD45RO+ T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In a further embodiment, the time period ranges from 30 minutes to 36 hours or longer and all integer values there between. In a further embodiment, the time period is at least 1, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, in some embodiments, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used. In some embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR and CD8. In certain embodiments, it may be desirable to enrich for or positively select for regulatory T cells which typically express CD4+, CD25+, CD62Lhi, GITR+, and FoxP3+. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations may result in increased cell yield, cell activation, and cell expansion. Further, use of high cell concentrations may allow more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. In some embodiments, using high concentration of cells allows more efficient selection of CD8+ T cells that normally have weaker CD28 expression.

In some embodiments, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In some embodiments, the concentration of cells used is $5\times10^6$/ml. In some embodiments, the concentration used can be from about $1\times10^5$/ml to $1\times10^6$/ml, and any integer value in between.

In some embodiments, the cells may be incubated on a rotator for varying lengths of time at varying speeds at either 2-10° C., or at room temperature.

T cells for stimulation can also be frozen after a washing step. Without being bound by theory, the freeze and subsequent thaw step may provide a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% dextran 40 and 5% dextrose, 20% human serum albumin and 7.5% DMSO, or 31.25% plasmalyte-A, 31.25% dextrose 5%, 0.45% NaCl, 10% dextran 40 and 5% dextrose, 20% human serum albumin, and 7.5% DMSO or other suitable cell freezing media containing for example, Hespan and PlasmaLyte A. The cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In some embodiments, cryopreserved cells are thawed and washed as described herein and allowed to rest for one hour at room temperature prior to activation.

Also contemplated in the present disclosure is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment, a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAM-PATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815 (1991); Henderson et al., Immun 73:316-321 (1991); Bierer et al., Curr. Opin. Immun. 5:763-773 (1993)). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rittman.

In some embodiments, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present disclosure to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

5.4.4. Activation and Expansion of T Cells

In some embodiments, prior to or after genetic modification of the T cells with the CARS described herein, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, T cells can be expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., biyostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. Examples of an anti-CD3 antibody include UCHT1, OKT3, HIT3a (BioLegend. San Diego, US) can be used as can other methods commonly known in the art (Graves J, et al., J. Immunol. 146:2102 (1991); Li B, et al., Immunology 116:487 (2005); Rivollier A, et al., Blood 104:4029 (2004)). Examples of an anti-CD28 antibody include 9.3, B-T3, XR-CD28 (Diaclone, Besancon, France) can be used as can other methods commonly known in the art (Berg et al., Transplant Proc. 30(8):3975-3977 (1998); Haanen et al., J. Exp. Med. 190 (9):13191328 (1999); Garland et al., J. Immunol Meth. 227(1-2):53-63 (1999)).

In some embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in certain embodiments in the present disclosure.

In some embodiments, the T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment, the cells (for example, $10^4$ to $4\times10^8$ T cells) and beads (for example, anti-CD 3/CD28 MACSiBead particlesa at a recommended titer of 1:100) are combined in a buffer, preferably PBS (without divalent cations such as, calcium and magnesium). Those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present disclosure. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/mL is used. In another embodiment, greater than 100 million cells/mL is used. In a further embodiment, a concentration of cells of 10, 15, 20, 25, 30, 35, 40, 45, or 50 million cells/mL is used. In yet another embodiment, a concentration of cells from 75, 80, 85, 90, 95, or 100 million cells/mL is used. In further embodiments, concentrations of 125 or 150 million cells/mL can be used. Using high concentrations may result in increased cell yield, cell activation, and cell expansion. Further, use of high cell concentrations may allow more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In some embodiments, the mixture may be cultured for several hours (about 3 hours) to about 14 days or any hourly integer value in between. In another embodiment, the mixture may be cultured for 21 days. In one embodiment, the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), inter-leukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$). T cells that have been exposed to varied stimulation times may exhibit different characteristics. For example, typical blood or apheresed peripheral blood mononuclear cell products have a helper T cell population (TH, CD4+) that is greater than the cytotoxic or suppressor T cell population (TC, CD8). Ex vivo expansion of T cells by stimulating CD3 and CD28 receptors produces a population of T cells that prior to about days 8-9 consists predominately of TH cells, while after about days 8-9, the population of T cells comprises an increasingly greater population of TC cells. Accordingly, depending on the purpose of treatment, infusing a subject with a T cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

5.5. Polynucleotides

In certain embodiments, the disclosure provides polynucleotides that encode the single domain antibodies that bind to CD20 and fusion proteins comprising the single domain antibodies that bind to CD20 described herein. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand. In some embodiments, the polynucleotide is in the form of cDNA. In some embodiments, the polynucleotide is a synthetic polynucleotide. In exemplary embodiments, the nucleic acid molecule provided herein comprises a sequence that encodes the single domain antibody having the sequence of SEQ ID NO: 41, such as a nucleic acid having SEQ ID NO: 64. In exemplary embodiments, the nucleic acid molecule provided herein comprises a sequence that encodes the single domain antibody having the sequence of SEQ ID NO: 42, such as a nucleic acid having SEQ ID NO: 65. In exemplary embodiments, the nucleic acid molecule provided herein comprises a sequence that encodes the single domain antibody having the sequence of SEQ ID NO: 43, such as a nucleic acid having SEQ ID NO: 66. In exemplar), embodiments, the nucleic acid molecule provided herein comprises a sequence that encodes the single domain antibody having the sequence of SEQ ID NO: 44, such as a nucleic acid having SEQ ID NO: 67. In exemplary embodiments, the nucleic acid molecule provided herein comprises a sequence that encodes the single domain antibody having the sequence of SEQ ID NO: 45, such as a nucleic acid having SEQ ID NO: 68. In exemplary embodiments, the nucleic acid molecule provided herein comprises a sequence that encodes the single domain antibody having the sequence of SEQ ID NO: 46, such as a nucleic acid having SEQ ID NO: 69. In exemplary embodiments, the nucleic acid molecule provided herein comprises a sequence that encodes the single domain antibody having the sequence of SEQ ID NO: 47, such as a nucleic acid having SEQ ID NO: 70. In exemplary embodiments, the nucleic acid molecule provided herein comprises a sequence that encodes the single domain antibody having the sequence of SEQ ID NO: 48, such as a nucleic acid having SEQ ID NO: 71. In exemplary embodiments, the nucleic acid molecule provided herein comprises a sequence that encodes the single domain antibody having the sequence of SEQ ID NO: 49, such as a nucleic acid having SEQ ID NO: 72. In exemplary embodiments, the nucleic acid molecule provided herein comprises a sequence that encodes the single domain antibody having the sequence of SEQ ID NO: 50, such as a nucleic acid having SEQ ID NO: 73. In exemplary embodiments, the nucleic acid molecule provided herein comprises a sequence that encodes the single domain antibody having the sequence of SEQ ID NO: 51, such as a nucleic acid having SEQ ID NO: 74. In exemplary embodiments, the nucleic acid molecule provided herein comprises a sequence that encodes the single domain antibody having the sequence of SEQ ID NO: 52, such as a nucleic acid having SEQ ID NO: 75. In exemplary embodiments, the nucleic acid molecule provided herein comprises a sequence that encodes the single domain antibody having the sequence of SEQ ID NO: 53, such as a nucleic acid having SEQ ID NO: 76. In exemplary embodiments, the nucleic acid molecule provided herein comprises a sequence that encodes the single domain antibody having the sequence of SEQ ID NO: 54, such as a nucleic acid having SEQ ID NO: 77. In exemplary embodiments, the nucleic acid molecule provided herein comprises a sequence that encodes the single domain antibody having the sequence of SEQ ID NO: 55, such as a nucleic acid having SEQ ID NO: 78. In exemplary embodiments, the nucleic acid molecule provided herein comprises a sequence that encodes the single domain antibody having the sequence of SEQ ID NO: 56, such as a nucleic acid having SEQ ID NO: 79. In exemplary embodiments, the nucleic acid molecule provided herein comprises a sequence that encodes the single domain antibody having the sequence of SEQ ID NO: 57, such as a nucleic acid having SEQ ID NO: 80. In exemplary embodiments, the nucleic acid molecule provided herein comprises a sequence that encodes the single domain antibody having the sequence of SEQ ID NO: 58. In exemplary embodiments, the nucleic acid molecule provided herein comprises a sequence that encodes the single domain antibody having the sequence of SEQ ID NO: 59. In exemplary embodiments, the nucleic acid molecule provided herein comprises a sequence that encodes the single domain antibody having the sequence of SEQ ID NO: 60. In exemplary embodiments, the nucleic acid molecule provided herein comprises a sequence that encodes the single domain antibody having the sequence of SEQ ID NO: 61. In exemplary embodiments, the nucleic acid molecule provided herein comprises a sequence that encodes the single domain antibody having the sequence of SEQ ID NO: 62. In exemplary embodiments, the nucleic acid molecule provided herein comprises a sequence that encodes the single domain antibody having the sequence of SEQ ID NO: 63. In exemplary embodiments, the nucleic acid molecule provided herein comprises a sequence that encodes the single domain antibody having the sequence of SEQ ID NO: 183, such as a nucleic acid having SEQ ID NO: 186. In exemplary embodiments, the nucleic acid molecule provided herein comprises a sequence that encodes the single domain antibody having the sequence of SEQ ID NO: 184, such as a nucleic acid having SEQ ID NO: 187. In exemplary embodiments, the nucleic acid molecule provided herein comprises a sequence that encodes the single domain antibody having the sequence of SEQ ID NO: 185, such as a nucleic acid having SEQ ID NO: 188.

In certain embodiments, the disclosure provides polynucleotides that encode the CD20 CAR provided herein. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand. In some embodiments, the polynucleotide is in the form of cDNA. In some embodiments, the polynucleotide is a synthetic polynucleotide. In exemplary embodiments, the nucleic acid molecule provided herein comprises a sequence that encodes the CAR having the sequence of SEQ ID NO: 81, such as a nucleic acid having SEQ ID NO: 108. In exemplary embodiments, the nucleic acid molecule provided herein comprises a sequence that encodes the CAR having the sequence of SEQ ID NO: 82, such as a nucleic acid having SEQ ID NO: 109. In exemplary embodiments, the nucleic acid molecule provided herein comprises a sequence that encodes the CAR having the sequence of SEQ ID NO: 83, such as a nucleic acid having SEQ ID NO: 110. In exemplary embodiments, the nucleic acid molecule provided herein comprises a sequence that encodes the CAR having the sequence of SEQ ID NO: 84, such as a nucleic acid having SEQ ID NO: 111. In exemplary embodiments, the nucleic acid molecule provided herein comprises a sequence that encodes the CAR having the sequence of SEQ ID NO: 85, such as a nucleic acid having SEQ ID NO: 112. In exemplary embodiments, the nucleic acid molecule provided herein comprises a sequence that encodes the CAR having the sequence of SEQ ID NO: 86, such as a nucleic acid having SEQ ID NO: 113. In exemplary embodiments, the nucleic acid molecule provided herein comprises a sequence that encodes the CAR having the sequence of SEQ ID NO: 87, such as a nucleic acid having SEQ ID NO: 114. In exemplary embodiments, the nucleic acid molecule provided herein comprises a sequence that encodes the CAR having the sequence of SEQ ID NO: 88, such as a nucleic acid having SEQ ID NO: 115. In exemplary embodiments, the nucleic acid molecule provided herein comprises a sequence that encodes the CAR having the sequence of SEQ ID NO: 89, such as a nucleic acid having SEQ ID NO: 116. In exemplary embodiments, the nucleic acid molecule provided herein comprises a sequence that encodes the CAR having the sequence of SEQ ID NO: 90, such as a nucleic acid having SEQ ID NO: 117. In exemplary embodiments, the nucleic acid molecule provided herein comprises a sequence that encodes the CAR having the sequence of SEQ ID NO: 91, such as a nucleic acid having SEQ ID NO: 118. In exemplary embodiments, the nucleic acid molecule provided herein comprises a sequence that encodes the CAR having the sequence of SEQ ID NO: 92, such as a nucleic acid having SEQ ID NO: 119. In exemplary embodiments, the nucleic acid molecule provided herein comprises a sequence that encodes the CAR having the sequence of SEQ ID NO: 93, such as a nucleic acid having SEQ ID NO: 120. In exemplary embodiments, the nucleic acid molecule provided herein comprises a sequence that encodes the CAR having the sequence of SEQ ID NO: 94, such as a nucleic acid having SEQ ID NO: 121. In exemplary embodiments, the nucleic acid molecule provided herein comprises a sequence that encodes the CAR having the sequence of SEQ ID NO: 95, such as a nucleic acid having SEQ ID NO: 122. In exemplary embodiments, the nucleic acid molecule provided herein comprises a sequence that encodes the CAR having the sequence of SEQ ID NO: 96, such as a nucleic acid having SEQ ID NO: 123. In exemplary embodiments, the nucleic acid molecule provided herein comprises a sequence that encodes the CAR having the sequence of SEQ ID NO: 97, such as a nucleic acid having SEQ ID NO: 124. In exemplary embodiments, the nucleic acid molecule provided herein comprises a sequence that encodes the CAR having the sequence of SEQ ID NO: 98, such as a nucleic acid having SEQ ID NO: 125. In exemplary embodiments, the nucleic acid molecule provided herein comprises a sequence that encodes the CAR having the sequence of SEQ ID NO: 99, such as a nucleic acid having SEQ ID NO: 126. In exemplary embodiments, the nucleic acid molecule provided herein comprises a sequence that encodes the CAR having the sequence of SEQ ID NO: 100, such as a nucleic acid having SEQ ID NO: 127. In exemplary embodiments, the nucleic acid molecule provided herein comprises a sequence that encodes the CAR having the sequence of SEQ ID NO: 101, such as a nucleic acid having SEQ ID NO: 128. In exemplary embodiments, the nucleic acid molecule provided herein comprises a sequence that encodes the CAR having the sequence of SEQ ID NO: 102, such as a nucleic acid having SEQ ID NO: 129. In exemplary embodiments, the nucleic acid molecule provided herein comprises a sequence that encodes the CAR having the sequence of SEQ ID NO: 103, such as a nucleic acid having SEQ ID NO: 130. In exemplary embodiments, the nucleic acid molecule provided herein comprises a sequence that encodes the CAR having the sequence of SEQ ID NO: 104, such as a nucleic acid having SEQ ID NO: 131. In exemplary embodiments, the nucleic acid molecule provided herein comprises a sequence that encodes the CAR having the sequence of SEQ ID NO: 105, such as a nucleic acid having SEQ ID NO: 132. In exemplary embodiments, the nucleic acid molecule provided herein comprises a sequence that encodes the CAR having the sequence of SEQ ID NO: 106, such as a nucleic acid having SEQ ID NO: 133. In exemplary embodiments, the nucleic acid molecule provided herein comprises a sequence that encodes the CAR having the sequence of SEQ ID NO: 189, such as a nucleic acid having SEQ ID NO: 192. In exemplary embodiments, the nucleic acid molecule provided herein comprises a sequence that encodes the CAR having the sequence of SEQ ID NO: 190, such as a nucleic acid having SEQ ID NO: 193. In exemplary embodiments, the nucleic acid molecule provided herein comprises a sequence that encodes the CAR having the sequence of SEQ ID NO: 191, such as a nucleic acid having SEQ ID NO: 194.

The present disclosure further relates to variants of the polynucleotides described herein, wherein the variant encodes, for example, fragments, analogs, and/or derivatives of the single domain antibody or CAR that binds CD20 of the disclosure. In certain embodiments, the present disclosure provides a polynucleotide comprising a polynucleotide having a nucleotide sequence at least about 75% identical, at least about 80% identical, at least about 85% identical, at least about 90% identical, at least about 95% identical, and in some embodiments, at least about 96%, 97%, 98% or 99% identical to a polynucleotide encoding the single domain antibody or CAR that binds CD20 of the disclosure. As used herein, the phrase "a polynucleotide having a nucleotide sequence at least, for example, 95% "identical" to a reference nucleotide sequence" is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as E. coli). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

Also provided are vectors comprising the nucleic acid molecules described herein. In an embodiment, the nucleic acid molecules can be incorporated into a recombinant expression vector. The present disclosure provides recombinant expression vectors comprising any of the nucleic acids of the disclosure. As used herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors described herein are not naturally-occurring as a whole; however, parts of the vectors can be naturally-occurring. The described recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. The non-naturally occurring or altered nucleotides or internucleotide linkages do not hinder the transcription or replication of the vector.

In an embodiment, the recombinant expression vector of the disclosure can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λEMBL4, and λNM1149, λZapII (Stratagene) can be used. Examples of plant expression vectors include pBI01, pBI01.2, pBI121, pBI101.3, and pBIN19 (Clontech). Examples of animal expression vectors include pEUK-C1, pMAM, and pMAM-neo (Clontech). The recombinant expression vector may be a viral vector, e.g., a retroviral vector, e.g., a gamma retroviral vector.

In an embodiment, the recombinant expression vectors are prepared using standard recombinant DNA techniques described in, for example, Sambrook et al., supra, and Ausubel et al., supra Constructs of expression vectors, which are circular or linear, can be prepared to contain a replication system functional in a prokaryotic or eukaryotic host cell. Replication systems can be derived, e.g., from ColE1, SV40, 2μ plasmid, λ, bovine papilloma virus, and the like.

The recombinant expression vector may comprise regulatory sequences, such as transcription and translation initiation and termination codons, which are specific to the type of host (e.g., bacterium, plant, fungus, or animal) into which the vector is to be introduced, as appropriate, and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the described expression vectors include, for instance, neomycin/G418 resistance genes, histidinol x resistance genes, histidinol resistance genes, tetracycline resistance genes, and ampicillin resistance genes.

The recombinant expression vector can comprise a native or normative promoter operably linked to the nucleotide sequence of the disclosure. The selection of promoters, e.g., strong, weak, tissue-specific, inducible and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an RSV promoter, an SV40 promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art and include, for example, the Herpes Simplex Virus (HSV) thymidine kinase (TK) gene, cytosine deaminase, purine nucleoside phosphorylase, and nitroreductase.

In certain embodiments, a polynucleotide is isolated. In certain embodiments, a polynucleotide is substantially pure.

Also provided are host cells comprising the nucleic acid molecules described herein. The host cell may be any cell that contains a heterologous nucleic acid. The heterologous nucleic acid can be a vector (e.g., an expression vector). For example, a host cell can be a cell from any organism that is selected, modified, transformed, grown, used or manipulated in any way, for the production of a substance by the cell, for example the expression by the cell of a gene, a DNA or RNA sequence, a protein or an enzyme. An appropriate host may be determined. For example, the host cell may be selected based on the vector backbone and the desired result. By way of example, a plasmid or cosmid can be introduced into a prokaryote host cell for replication of several types of vectors. Bacterial cells such as, but not limited to DH5α, JM109, and KCB, SURE® Competent Cells, and SOLO-PACK Gold Cells, can be used as host cells for vector replication and/or expression. Additionally, bacterial cells such as *E. coli* LE392 could be used as host cells for phage viruses. Eukaryotic cells that can be used as host cells include, but are not limited to yeast (e.g., YPH499, YPH500 and YPH501), insects and mammals. Examples of mammalian eukaryotic host cells for replication and/or expression of a vector include, but are not limited to. HeLa, NIH3T3, Jurkat, 293, COS, Saos, PC 12, SP2/0 (American Type Culture Collection (ATCC). Manassas, VA, CRL-1581), NS0 (European Collection of Cell Cultures (ECACC), Salisbury, Wiltshire, UK, ECACC No. 85110503), FO (ATCC CRL-1646) and Ag653 (ATCC CRL-1580) murine cell lines. An exemplary human myeloma cell line is U266 (ATCC CRL-TIB-196). Other useful cell lines include those derived from Chinese Hamster Ovary (CHO) cells such as CHO-K1 SV (Lonza Biologics, Walkersville, MD), CHO-K1 (ATCC CRL-61) or DG44.

5.6. Pharmaceutical Compositions

In one aspect, the present disclosure further provides pharmaceutical compositions comprising a single domain antibody, a binding molecule or therapeutic molecule comprising a single domain antibody, or an engineered immune effector cell of the present disclosure. In some embodiments, a pharmaceutical composition comprises a therapeutically effective amount of the single domain antibody, the binding molecule or therapeutic molecule comprising the single domain antibody, or the engineered immune effector cell of the present disclosure and a pharmaceutically acceptable excipient.

In some embodiments, provided herein is a pharmaceutical composition comprising a therapeutically effective amount of the single domain antibody provided herein and a pharmaceutically acceptable excipient.

In some embodiments, provided herein is a pharmaceutical composition comprising a therapeutically effective amount of the therapeutic molecule (such as a fusion protein, immunoconjugate, and a multispecific binding molecule) comprising the single domain antibody provided herein and a pharmaceutically acceptable excipient.

In other embodiments, provided herein is a pharmaceutical composition comprising a therapeutically effective amount of CAR comprising the single domain antibody provided herein and a pharmaceutically acceptable excipient.

In other embodiments, provided herein is a pharmaceutical composition comprising a therapeutically effective amount of engineered immune effector cells provided herein and a pharmaceutically acceptable excipient.

In other embodiments, provided herein is a pharmaceutical composition comprising a therapeutically effective amount of a nucleic acid provided herein, e.g., in a vector, and a pharmaceutically acceptable excipient, e.g., suitable for gene therapy.

In a specific embodiment, the term "excipient" can also refer to a diluent, adjuvant (e.g., Freunds' adjuvant (complete or incomplete), carrier or vehicle. Pharmaceutical excipients can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid excipients. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical excipients are described in *Remington's Pharmaceutical Sciences* (1990) Mack Publishing Co., Easton, PA Such compositions will contain a prophylactically or therapeutically effective amount of the active ingredient provided herein, such as in purified form, together with a suitable amount of excipient so as to provide the form for proper administration to the patient. The formulation should suit the mode of administration.

In some embodiments, the choice of excipient is determined in part by the particular cell, binding molecule, and/or antibody, and/or by the method of administration. Accordingly, there are a variety of suitable formulations.

Typically, acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

Buffers may be used to control the pH in a range which optimizes the therapeutic effectiveness, especially if stability is pH dependent. Suitable buffering agents for use with the present disclosure include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives may be added to retard microbial growth. Suitable preservatives for use with the present disclosure include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" can be present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Exemplary tonicity agents include polyhydric sugar alcohols, trihydric or higher sugar alcohols, such as glycerin, erythritol, arabitol, xylitol, sorbitol and mannitol.

Additional exemplary excipients include: (1) bulking agents, (2) solubility enhancers, (3) stabilizers and (4) agents preventing denaturation or adherence to the container wall. Such excipients include: polyhydric sugar alcohols (enumerated above); amino acids such as alanine, glycine, glutamine, asparagine, histidine, arginine, lysine, omithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") may be present to help solubilize the therapeutic agent as well as to protect the therapeutic protein against agitation-induced aggregation, which also permits the formulation to be exposed to shear surface stress without causing denaturation of the active therapeutic protein or antibody. Suitable non-ionic surfactants include, e.g., polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they are preferably sterile. The pharmaceutical composition may be rendered sterile by filtration through sterile filtration membranes. The pharmaceutical compositions herein generally can be placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

In another embodiment, a pharmaceutical composition can be provided as a controlled release or sustained release system. In one embodiment, a pump may be used to achieve controlled or sustained release (see. e.g., Sefton, Crit. Ref. Biomed. Eng. 14:201-40 (1987); Buchwald et at, Surgery 88:507-16 (1980); and Saudek et at, N. Engl. J. Med. 321:569-74 (1989)). In another embodiment, polymeric materials can be used to achieve controlled or sustained release of a prophylactic or therapeutic agent (e.g., a fusion protein as described herein) or a composition provided herein (see, e.g., *Medical Applications of Controlled Release* (Langer and Wise eds., 1974); *Controlled Drug Bioavailability. Drug Product Design and Performance* (Smolen and Ball eds., 1984); Ranger and Peppas, J. Macromol. Sci. Rev. Macromol. Chem. 23:61-126 (1983); Levy et at, *Science* 228:190-92 (1985); During et al., Ann. Neurol. 25:351-56 (1989); Howard et al., J. Neurosurg. 71:105-12 (1989); U.S. Pat. Nos. 5,679,377; 5,916,597; 5,912,015; 5,989,463; and 5,128,326; PCT Publication Nos. WO 99/15154 and WO 99/20253). Examples of polymers used in sustained release formulations include, but are not limited to, poly(2-hydroxy ethyl methacrylate), poly(methyl methacrylate), poly (acrylic acid), poly(ethylene-co-vinyl acetate), poly(methacrylic acid), polyglycolides (PLG), polyanhydrides, poly (N-vinyl pyrrolidone), poly(vinyl alcohol), polyacrylamide, poly(ethylene glycol), polylactides (PLA), poly(lactide-co-glycolides) (PLGA), and polyorthoesters. In one embodiment, the polymer used in a sustained release formulation is inert, free of leachable impurities, stable on storage, sterile, and biodegradable. In yet another embodiment, a controlled or sustained release system can be placed in proximity of a particular target tissue, for example, the nasal passages or lungs, thus requiring only a fraction of the systemic dose (see, e.g., Goodson, *Medical Applications of Controlled Release* Vol. 2, 115-38 (1984)). Controlled release systems are discussed, for example, by Langer, Science 249:1527-33 (1990). Any technique known to one of skill in the art can be used to produce sustained release formulations comprising one or more agents as described herein (see, e.g., U.S. Pat. No. 4,526,938, PCT publication Nos. WO 91/05548 and WO 96/20698, Ning et al., Radiotherapy & Oncology 39:179-89 (1996); Song et al., PDA J. of Pharma Sci. & Tech. 50:372-97 (1995); Cleek et al., Pro. Int'l. Symp. Control. Rel. Bioact. Mater. 24:853-54 (1997); and Lam et al., Proc. Int'l. Symp. Control Rel. Bioact. Mater. 24:759-60 (1997)).

The pharmaceutical compositions described herein may also contain more than one active compound or agent as necessary for the particular indication being treated. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coascervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 18th edition.

Various compositions and delivery systems are known and can be used with the therapeutic agents provided herein, including, but not limited to, encapsulation in liposomes, microparticles, microcapsules, recombinant cells capable of expressing the single domain antibody or therapeutic molecule provided herein, construction of a nucleic acid as part of a retroviral or other vector, etc.

In some embodiments, the pharmaceutical composition provided herein contains the binding molecules and/or cells in amounts effective to treat or prevent the disease or disorder, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined.

5.7. Methods and Uses

In another aspect, provided herein are methods for using and uses of the CD20 binding molecules provided herein, including the anti-CD20 VHH, chimeric antigen receptors (CARs), and/or engineered cells expressing the recombinant receptors.

5.7.1. Therapeutic Methods and Uses

Such methods and uses include therapeutic methods and uses, for example, involving administration of the molecules, cells, or compositions containing the same, to a subject having a disease, condition, or disorder expressing or associated with CD20 expression, and/or in which cells or tissues express CD20. In some embodiments, the molecule, cell, and/or composition is administered in an effective amount to effect treatment of the disease or disorder. Uses include uses of the antibodies and cells in such methods and treatments, and in the preparation of a medicament in order to carry out such therapeutic methods. In some embodiments, the methods are carried out by administering the antibodies or cells, or compositions comprising the same, to the subject having or suspected of having the disease or condition. In some embodiments, the methods thereby treat the disease or disorder in the subject.

In some embodiments, the treatment provided herein cause complete or partial amelioration or reduction of a disease or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms include, but do not imply, complete curing of a disease or complete elimination of any symptom or effect(s) on all symptoms or outcomes.

As used herein, in some embodiments, the treatment provided herein delay development of a disease or disorder, e.g., defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease or disorder. For example, a late stage cancer, such as development of metastasis, may be delayed. In other embodiments, the method or the use provided herein prevents a disease or disorder.

In some embodiments, the disease or disorder is a CD20 associated disease or disorder. In some embodiments, the disease or disorder is a B cell associated disease or disorder. In some embodiments, the disease or disorder is a B cell malignancy. In some embodiments, the B cell malignancy is a B cell leukemia or B cell lymphoma. In a specific embodiment, the disease or disorder is marginal zone lymphoma (e.g., splenic marginal zone lymphoma). In a specific embodiment, the disease or disorder is diffuse large B cell lymphoma (DLBCL). In another specific embodiment, the disease or disorder is mantle cell lymphoma (MCL). In another specific embodiment, the disease or disorder is primary central nervous system (CNS) lymphoma. In another specific embodiment, the disease or disorder is primary mediastinal B cell lymphoma (PMBL). In another specific embodiment, the disease or disorder is small lymphocytic lymphoma (SLL). In another specific embodiment, the disease or disorder is B cell prolymphocytic leukemia (B-PLL). In another specific embodiment, the disease or disorder is follicular lymphoma (FL). In another specific embodiment, the disease or disorder is burkitt lymphoma. In another specific embodiment, the disease or disorder is primary intraocular lymphoma. In another specific embodiment, the disease or disorder is chronic lymphocytic leukemia (CLL). In another specific embodiment, the disease or disorder is acute lymphoblastic leukemia (ALL). In another specific embodiment, the disease or disorder is hairy cell leukemia (HCL). In another specific embodiment, the disease or disorder is precursor B lymphoblastic leukemia. In another specific embodiment, the disease or disorder is non-hodgkin lymphoma (NHL). In another specific embodiment, the disease or disorder is high-grade B-cell lymphoma (HGBL). In another specific embodiment, the disease or disorder is multiple myelomia (MM). In other embodiments, the disease or disorder is a relapsed or refractory B cell malignancy, such as relapsed or refractory ALL (R/R ALL).

In other embodiments, the disease or disorder is an autoimmune and inflammatory disease, including, e.g., those associated with inappropriate or enhanced B cell numbers and/or activation.

In some embodiments, the methods include adoptive cell therapy, whereby genetically engineered cells expressing the provided CD20-targeted CARS are administered to a subject. Such administration can promote activation of the cells (e.g., T cell activation) in a CD20-targeted manner, such that the cells of the disease or disorder are targeted for destruction.

In some embodiments, the methods include administration of the cells or a composition containing the cells to a subject, tissue, or cell, such as one having, at risk for, or suspected of having the disease or disorder. In some embodiments, the cells, populations, and compositions are administered to a subject having the particular disease or disorder to be treated, e.g., via adoptive cell therapy, such as adoptive T cell therapy. In some embodiments, the cells or compositions are administered to the subject, such as a subject having or at risk for the disease or disorder. In some embodiments, the methods thereby treat, e.g., ameliorate one or more symptom of the disease or disorder, such as by lessening tumor burden in a CD20-expressing cancer.

Methods for administration of cells for adoptive cell therapy are known, as described. e.g., in US Patent Application Publication No. 2003/0170238; U.S. Pat. No. 4,690, 915; Rosenberg, *Nat Rev Clin Oncol.* 8 (10):577-85 (2011); Themeli et al., Nat Biotechnol. 31(10): 928-933 (2013); Tsukahara et al., Biochem Biophys Res Commun 438(1): 84-9 (2013); and Davila et al., PLoS ONE 8(4): e61338 (2013). These methods may be used in connection with the methods and compositions provided herein.

In some embodiments, the cell therapy (e.g., adoptive T cell therapy) is carried out by autologous transfer, in which the cells are isolated and/or otherwise prepared from the subject who is to receive the cell therapy, or from a sample derived from such a subject. Thus, in some aspects, the cells are derived from a subject in need of a treatment and the cells, following isolation and processing are administered to the same subject. In other embodiments, the cell therapy (e.g., adoptive T cell therapy) is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject, to whom the cells, cell populations, or compositions are administered is a primate, such as a human. The subject can be male or female and can be any suitable age, including infant, juvenile, adolescent, adult, and geriatric subjects. In some examples, the subject is a validated animal model for disease, adoptive cell therapy, and/or for assessing toxic outcomes.

The CD20-binding molecules, such as VHHs and chimeric receptors containing the VHHs and cells expressing the same, can be administered by any suitable means, for example, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration.

The amount of a prophylactic or therapeutic agent provided herein that will be effective in the prevention and/or treatment of a disease or condition can be determined by standard clinical techniques. Effective doses may be extrapolated from dose-response curves derived from in vitro or animal model test systems. For the prevention or treatment of disease, the appropriate dosage of the binding molecule or cell may depend on the type of disease or disorder to be treated, the type of binding molecule, the severity and course of the disease or disorder, whether the therapeutic agent is administered for preventive or therapeutic purposes, previous therapy, the patient's clinical history and response to the agent, and the discretion of the attending physician. The compositions, molecules and cells are in some embodiments suitably administered to the patient at one time or over a series of treatments.

For example, depending on the type and severity of the disease, dosages of antibodies may include about 10 ug/kg to 100 mg/kg or more. Multiple doses may be administered intermittently. An initial higher loading dose, followed by one or more lower doses may be administered. In some embodiments, wherein the pharmaceutical composition comprises any one of the single domain antibodies described herein, the pharmaceutical composition is administered at a dosage of about 10 ng/kg up to about 100 mg/kg of body weight of the individual or more per day, for example, at about 1 mg/kg/day to 10 mg/kg/day, depending upon the route of administration. Guidance as to particular dosages and methods of delivery is provided in the literature (see, e.g., U.S. Pat. Nos. 4,657,760; 5,206,344; and 5,225,212).

In the context of genetically engineered cells containing the binding molecules, in some embodiments, a subject may be administered the range of about one million to about 100 billion cells and/or that amount of cells per kilogram of body weight. In some embodiments, wherein the pharmaceutical composition comprises any one of the engineered immune cells described herein, the pharmaceutical composition is administered at a dosage of at least about any of $10^4$, $10^5$, $10^6$, $10^7$, $10^8$, or $10^9$ cells/kg of body weight of the individual. Dosages may vary depending on attributes particular to the disease or disorder and/or patient and/or other treatments.

In some embodiments, the pharmaceutical composition is administered for a single time. In some embodiments, the pharmaceutical composition is administered for multiple times (such as any of 2, 3, 4, 5, 6, or more times). In some embodiments, the pharmaceutical composition is administered once or multiple times during a dosing cycle. A dosing cycle can be, e.g., 1, 2, 3, 4, 5 or more week(s), or 1, 2, 3, 4, 5, or more month(s). The optimal dosage and treatment regime for a particular patient can be determined by one skilled in the art of medicine by monitoring the patient for signs of disease and adjusting the treatment accordingly.

In some embodiments, the cells or antibodies are administered as part of a combination treatment, such as simultaneously with or sequentially with, in any order, another therapeutic intervention, such as another antibody or engineered cell or receptor or agent, such as a cytotoxic or therapeutic agent.

In some embodiments, the cells or antibodies are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells or antibodies are administered prior to the one or more additional therapeutic agents. In some embodiments, the cells or antibodies are administered after to the one or more additional therapeutic agents.

In certain embodiments, once the cells are administered to a mammal (e.g., a human), the biological activity of the engineered cell populations and/or antibodies is measured by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285 (1): 25-40 (2004). In certain embodiments, the biological activity of the cells also can be measured by assaying expression and/or secretion of certain cytokines, such as CD107a, IFNγ, IL-2, and TNF. In some aspects the biological activity is measured by assessing clinical outcome, such as reduction in tumor burden or load.

In some specific embodiments, provided herein is a method for treating a disease or disorder in a subject comprising administering to the subject a binding molecule comprising a single domain antibody that binds to CD20 as described in Section 5.2 above, including, e.g., those with CDRs in Table 2, those comprising the amino acid sequence of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184 or SEQ ID NO: 185; and those comprising an amino acid sequence having at least 75%, 80%, 85%, 90%, 91%, 92%, 93%, 94%, 95%, 96%, 97%, 98%, or 99% sequence identify to SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184, or SEQ ID NO: 185. In some embodiments, the disease or disorder is a CD20 associated disease or disorder. In some embodiments, the disease or disorder is a B cell associated disease or disorder. In some embodiments, the disease or disorder is a B cell malignancy. In some embodiments, the B cell malignancy is a B cell leukemia or B cell lymphoma. In a specific embodiment, the disease or disorder is marginal zone lymphoma (e.g., splenic marginal zone lymphoma). In a specific embodiment, the disease or disorder is diffuse large B cell lymphoma (DLBCL). In another specific embodiment, the disease or disorder is mantle cell lymphoma (MCL). In another specific embodiment, the disease or disorder is primary central nervous system (CNS) lymphoma. In another specific embodiment, the disease or disorder is primary mediastinal B cell lymphoma (PMBL). In another specific embodiment, the disease or disorder is small lymphocytic lymphoma (SLL). In another specific embodiment, the disease or disorder is B cell prolymphocytic leukemia (B-PLL). In another specific embodiment, the disease or disorder is follicular lymphoma (FL). In another specific embodiment, the disease or disorder is burkitt lymphoma. In another specific embodiment, the disease or disorder is primary intraocular lymphoma. In another specific embodiment, disease or disorder is chronic lymphocytic leukemia (CLL). In another specific embodiment, the disease or disorder is acute lymphoblastic leukemia (ALL). In another specific embodiment, the disease or disorder is hairy cell leukemia (HCL). In another specific embodiment, the disease or disorder is precursor B lymphoblastic leukemia, in another specific embodiment, the disease or disorder is non-hodgkin lymphoma (NHL). In another specific embodiment, the disease or disorder is high-grade B-cell lymphoma (HGBL). In another specific embodiment, the disease or disorder is multiple myelomia (MM). In other embodiments, the disease or disorder is a relapsed or refractory B cell malignancy, such as relapsed or refractory ALL (R/R ALL), in other embodiments, the disease or disorder is an autoimmune and inflammatory disease, including, e.g., those associated with inappropriate or enhanced B cell numbers and/or activation.

In other embodiments, provided herein is a method for treating a disease or disorder comprising administering to the subject an engineered immune effector cell (such as T cell) as provided in Section 5.4, including, e.g., the cells comprising a CAR provided in Section 5.3. In some embodiments, the engineered immune cell administered to the subject comprises a CAR comprising a polypeptide comprising: (a) an extracellular antigen binding domain comprising one or more anti-CD20 sdAb(s); (b) a transmembrane domain; and (c) an intracellular signaling domain, wherein the anti-CD20 sdAb is as described in Section 5.2 above, including e.g., those with CDRs in Table 2, those comprising the amino acid sequence of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184 or SEQ ID NO: 185; and those comprising an amino acid sequence having at least 75%, 80%, 85%, 90%, 91%, 92%, 93%, 94%, 95%, 96%, 97%, 98%, or 99% sequence identify to SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184 or SEQ ID NO: 185. In some embodiments, the engineered immune cell administered to the subject comprises a CAR comprising an amino acid sequence selected from the group consisting of SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 189, SEQ ID NO: 190, and SEQ ID NO: 191: or comprising a polypeptide having at least 75%, 80%, 85%, 86%, 87%, 88%, 89%, 90%, 91%, 92%, 93%, 94%, 95%, 96%, 97%, 98%, or 99% sequence identity to an amino acid sequence selected from the group consisting of SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 189, SEQ ID NO: 190, and SEQ ID NO: 191. In some embodiments, the disease or disorder is a CD20 associated disease or disorder. In some embodiments, the disease or disorder is a B cell associated disease or disorder. In some embodiments, the disease or disorder is a B cell malignancy. In some embodiments, the B cell malignancy is a B cell leukemia or B cell lymphoma. In a specific embodiment, the disease or disorder is marginal zone lymphoma (e.g., splenic marginal zone lymphoma). In a specific embodiment, the disease or disorder is diffuse large B cell lymphoma (DLBCL). In another specific embodiment, the disease or disorder is mantle cell lymphoma (MCL). In another specific embodiment, the disease or disorder is primary central nervous system (CNS) lymphoma. In another specific embodiment, the disease or disorder is primary mediastinal B cell lymphoma (PMBL). In another specific embodiment, the disease or disorder is small lymphocytic lymphoma (SLL). In another specific embodiment, the disease or disorder is B cell prolymphocytic leukemia (B-PLL). In another specific embodiment, the disease or disorder is follicular lymphoma (FL). In another specific embodiment, the disease or disorder is burkitt lymphoma. In another specific embodiment, the disease or disorder is primary intraocular lymphoma. In another specific embodiment, the disease or disorder is chronic lymphocytic leukemia (CLL). In another specific embodiment, the disease or disorder is acute lymphoblastic leukemia (ALL). In another specific embodiment, the disease or disorder is hairy cell leukemia (HCL). In another specific embodiment, the disease or disorder is precursor B lymphoblastic leukemia. In another specific embodiment, the disease or disorder is non-hodgkin lymphoma (NHL). In another specific embodiment, the disease or disorder is high-grade B-cell lymphoma (HGBL). In another specific embodiment, the disease or disorder is multiple myelomia (MM). In other embodiments, the disease or disorder is a relapsed or refractory B cell malignancy, such as relapsed or refractory ALL (R/R ALL). In other embodiments, the disease or disorder is an autoimmune and inflammatory disease, including, e.g., those associated with inappropriate or enhanced B cell numbers and/or activation.

5.7.2. Diagnostic and Detection Methods and Uses

In another aspect, provided herein are methods involving use of the binding molecules provided herein, e.g., VHHs that binds CD20 and molecules (such as conjugates and complexes) containing such VHHs, for detection, prognosis, diagnosis, staging, determining binding of a particular treatment to one or more tissues or cell types, and/or informing treatment decisions in a subject, such as by the detection of CD20 and/or the presence of an epitope thereof recognized by the antibody.

In some embodiments, an anti-CD20 antibody (such as any one of the anti-CD20 single domain antibodies described herein) for use in a method of diagnosis or detection is provided. In a further aspect, a method of detecting the presence of CD20 in a biological sample is provided. In certain embodiments, the method comprises detecting the presence of CD20 protein in a biological sample. In certain embodiments, CD20 is human CD20. In some embodiments, the methods are diagnostic and/or prognostic methods in association with a CD20-expressing disease or disorder. The methods in some embodiments include incubating and/or probing a biological sample with the antibody and/or administering the antibody to a subject. In certain embodiments, a biological sample includes a cell or tissue or portion thereof, such as tumor or cancer tissue or biopsy or section thereof. In certain embodiments, the contacting is under conditions permissive for binding of the anti-CD20 antibody to CD20 present in the sample. In some embodiments, the methods further include detecting whether a complex is formed between the anti-CD20 antibody and CD20 in the sample, such as detecting the presence or absence or level of such binding. Such a method may be an in vitro or in vivo method. In one embodiment, an anti-CD20 antibody is used to select subjects eligible for therapy with an anti-CD20 antibody or engineered antigen receptor, e.g., where CD20 is a biomarker for selection of patients.

In some embodiments, a sample, such as a cell, tissue sample, lysate, composition, or other sample derived therefrom is contacted with the anti-CD20 antibody and binding or formation of a complex between the antibody and the sample (e.g., CD20 in the sample) is determined or detected. When binding in the test sample is demonstrated or detected as compared to a reference cell of the same tissue type, it may indicate the presence of an associated disease or disorder, and/or that a therapeutic containing the antibody will specifically bind to a tissue or cell that is the same as or is of the same type as the tissue or cell or other biological material from which the sample is derived. In some embodiments, the sample is from human tissues and may be from diseased and/or normal tissue, e.g., from a subject having the disease or disorder to be treated and/or from a subject of the same species as such subject but that does not have the disease or disorder to be treated. In some cases, the normal tissue or cell is from a subject having the disease or disorder to be treated but is not itself a diseased cell or tissue, such as a normal tissue from the same or a different organ than a cancer that is present in a given subject.

Various methods known in the art for detecting specific antibody-antigen binding can be used. Exemplary immunoassays include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (MA). An indicator moiety, or label group, can be used so as to meet the needs of various uses of the method which are often dictated by the availability of assay equipment and compatible immunoassay procedures.

Exemplary labels include radionuclides (e.g. $^{125}$I, $^{131}$I, $^{35}$S, $^3$H, or $^{32}$P and/or chromium ($^{51}$Cr), cobalt ($^{57}$Co), fluorine ($^{18}$F), gadolinium ($^{153}$Gd, $^{159}$Gd), germanium ($^{68}$Ge), holmium ($^{166}$Ho), indium ($^{115}$In, $^{113}$In, $^{112}$In, $^{111}$In), iodine ($^{125}$I, $^{123}$I, $^{121}$I), lanthanum ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium (186Re, 188Re), rhodium (105Rh), rutheroium (97Ru), samarium ($^{153}$Sm), scandium ($^{47}$Sc), selenium ($^{75}$Se), ($^{85}$Sr), sulphur ($^{35}$S), technetium ($^{99}$Tc), thallium ($^{201}$Ti) tin ($^{113}$Sn, $^{117}$Sn), tritium (3H), xenon ($^{133}$Xe), ytterbium ($^{169}$Yb, $^{175}$Yb), yttrium ($^{90}$Y),), enzymes (e.g., alkaline phosphatase, horseradish peroxidase, luciferase, or β-glactosidase), fluorescent moieties or proteins (e.g., fluorescein, rhodamine, phycoerythrin, GFP, or BFP), or luminescent moieties (e.g., Qdot™ nanoparticles supplied by the Quantum Dot Corporation, Palo Alto, Calif.). Various general techniques to be used in performing the various immunoassays noted above are known.

In certain embodiments, labeled antibodies (such as anti-CD20 single domain antibodies) are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. In other embodiments, antibodies are not labeled, and the presence thereof can be detected using a labeled antibody which binds to any of the antibodies.

5.8. Kits and Articles of Manufacture

Further provided are kits, unit dosages, and articles of manufacture comprising any of the single domain antibodies, the chimeric antigen receptors, or the engineered immune effector cells described herein. In some embodiments, a kit is provided which contains any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder (such as cancer) described herein, and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical composition and instructions for use, packaged in quantities sufficient for storage and use in pharmacies, for example, hospital pharmacies and compounding pharmacies.

For the sake of conciseness, certain abbreviations are used herein. One example is the single letter abbreviation to represent amino acid residues. The amino acids and their corresponding three letter and single letter abbreviations are as follows:

| Amino acid | Three letter | One letter |
|---|---|---|
| alanine | Ala | (A) |
| arginine | Arg | (R) |
| asparagine | Asn | (N) |
| aspartic acid | Asp | (D) |
| cysteine | Cys | (C) |
| glutamic acid | Glu | (E) |
| glutamine | Gln | (Q) |
| glycine | Gly | (G) |
| histidine | His | (H) |
| isoleucine | Ile | (I) |
| leucine | Leu | (L) |
| lysine | Lys | (K) |
| methionine | Met | (M) |
| phenylalanine | Phe | (F) |
| proline | Pro | (P) |
| serine | Ser | (S) |
| threonine | Thr | (T) |
| tryptophan | Trp | (W) |
| tyrosine | Tyr | (Y) |
| valine | Val | (V) |

The disclosure is generally disclosed herein using affirmative language to describe the numerous embodiments. The disclosure also specifically includes embodiments in which particular subject matter is excluded, in full or in part, such as substances or materials, method steps and conditions, protocols, procedures, assays or analysis. Thus, even though the disclosure is generally not expressed herein in terms of what the disclosure does not include, aspects that are not expressly included in the disclosure are nevertheless disclosed herein.

A number of embodiments of the disclosure have been described. Nevertheless, it will be understood that various modifications may be made without departing from the spirit and scope of the disclosure. Accordingly, the following examples are intended to illustrate but not limit the scope of disclosure described in the claims.

6. EXAMPLES

The following is a description of various methods and materials used in the studies, and are put forth so as to provide those of ordinary skill in the art with a complete disclosure and description of how to make and use the present disclosure, and are not intended to limit the scope of what the inventors regard as their disclosure nor are they intended to represent that the experiments below were performed and are all of the experiments that may be performed. It is to be understood that exemplary descriptions written in the present tense were not necessarily performed, but rather that the descriptions can be performed to generate the data and the like associated with the teachings of the present disclosure. Efforts have been made to ensure accuracy with respect to numbers used (e.g., amounts, percentages, etc.), but some experimental errors and deviations should be accounted for.

6.1. Example 1—Preparation of Anti-CD20 VHH

To develop VHH with high binding affinity to CD20 antigen, camels were immunized with human CD20 protein. A phage-display library was then constructed to screen VHH leads. Unique clones were picked based on specific binding and were ranked according to the VHH complementarity determining region (CDR), especially CDR3 which enlarges antigen recognition repertoire and binding.

6.1.1. Cell Line Construction

Human membrane spanning 4-domains A1 (MS4A1) encoding cDNA (NM_021950.3) was synthesized into plasmid PLVX-puro (Clontech, #632164) by GenScript and the plasmid was named as PLVX-CD20. High-titer recombinant lentiviruses were produced in virus packaging system and were transduced to K562 cells (ATCC, #CRL-24), CHO cells (ATCC, #CCL-61) and Dubca cells (ATCC, #CRL2276). After 3 rounds of selection with puromycin-containing cell culture medium, the surface expression of human CD20 on the transduced cell lines was validated by flow cytometry using PE conjugated anti-human CD20 specific monoclonal antibody (MILTENYI, #130098084). Briefly, $2 \times 10^5$ of transduced cells or parental cells were incubated with PE conjugated anti-human CD20 antibody at 4° C. for 30 mins, followed by three time washes, and were re-suspended in 200 µL of DPBS with 0.5% FBS for FACS analysis on Attune NXT flow cytometry (Thermo Fisher) to detect the expression level of human CD20 antigen. The mean fluorescence intensity (MFI) of CHO-CD20 was 1067.44 folds higher than that of un-transduced CHO cells, and the mean fluorescence intensity (MFI) of Dubca-CD20 was 1621.21 folds higher than that of un-transduced Dubca cells.

6.1.2. Animal Immunization and Immune Response Testing

One adult male alpaca (*Vicugna pacos*) was immunized five times (days 1, 21, 35, 49, and 63) subcutaneously with human CD20 protein. Complete Freund's adjuvant, incomplete Freund's adjuvant and no adjuvant were used for the first, the second to the forth, and the fifth immunization, respectively. A pre-immune 10 mL serum sample and serum sample during the vaccination procedure were collected to monitor the antigen specific humoral response. Binding of alpaca immunoglobulins presented in the diluted pre-immune samples (Pre) and the final immune serum sample (TB) was scored for differential staining of CD20 transfected versus non-transfected cells via flow cytometry. MC conjugated anti-llama IgG heavy and light chain antibody (BETHYL, #A160100F) was used as the detection antibody. The antibody in the final Test-bleeding serum (TB) showed significant increase of binding to CHO-CD20 cells, starting from 0.16% binding in pre-immunization to 86.8% binding in TB. The data suggested the animal immunization was successful.

At the same time, one adult male camel (*Camelus bactrian*) was immunized subcutaneously with human CD20 protein for five times with two week intervals. Blood was collected on the pre-immune day (Pre) and final immunization day (TB). Immune response of the camel was evaluated by ELISA, in which the serum samples were tested for binding to immobilized antigen. A series of diluted sera were added to the plate. HRP-conjugated anti-llama IgG secondary antibody (BETHYL, #A1601 OOP) was added as the second antibody for detection. The ELISA results suggested that a robust immune response was induced upon CD20 antigen injection to the animal, with the serum titer reached >1:729 k, indicting the animal immunization was also successful.

Three to five days after the final immunization, 100 mL of blood was collected from the jugular vein as production bleed. Peripheral blood lymphocytes (PBLs) were isolated from the blood according to the procedure of lymphoprep.

6.1.3. Antibody Phage Library Construction

Total RNAs were extracted from the isolated lymphocytes according to the manual of TRlzol® Reagent (Thermofisher, #15596026). After quality testing, total RNAs were reverse transcribed into cDNA using oligo(dT)$_{20}$ primer according to the manual of PrimeScript™ 1st Strand cDNA Synthesis Kit (Takara, #6110A). Nested PCR primers (as described in CN105555310B) were designed for the amplification of VHH fragments, with two SfiI restriction sites introduced. The VHH fragments were amplified using a two-step polymerase chain reaction (PCR), and the PCR products were digested with SfiI and gel purified, and then inserted into phagemid vector-pFL249, which were electro-transferred into *E. coli* cells to generate the phage display VHH immune library.

A small portion of the transformed cells were diluted and streaked on 2×YT plates supplemented with 100 μg/mL ampicillin. The colonies were counted to calculate the library size. Positive clones were randomly picked and sequenced to assess the quality of the library. The rest of the transformed cells were streaked onto 245-mm square 2×YT-agar dishes supplemented with 100 μg/mL ampicillin and 2% glucose. Lawns of colonies were scraped off the dishes. A small aliquot of the cells were used for library plasmids isolation. The rest were supplemented with glycerol and stored at −80° C. as stock.

6.1.4. Phage-Display Panning

After infection with helper phage, recombinant phage particles which display VHH doamins on the surface as gene ITT fusion proteins were produced. Phage particles were prepared according to standard methods and stored after filter sterilization at 4° C. for further research. Before each round of panning, VHH-displaying phage particles were rescued and amplified by adding helper phage.

Phage libraries were used with different panning strategies. Based on protein level, in the first and second rounds, biotinylated human CD20 (biotinylating in house according to manufacturer instructions using Sulfo-NHS-LC-Biotin Kit) was incubated with the phage libraries and subsequently captured on Streptavidin Dynabeads (Invitogen). Followed by extensive washing, bound phages were eluted with triethylamine.

Based on cellular level, in the first selection. CHO-CD20 cells, Dubca-CD20 cells or Raji cells (ATCC, #CCL-86) expressing human CD20 antigen were incubated with the phage libraries. After extensive washing, bound phages were eluted from the cells by resuspension in 1 mg/mL trypsin. In a second selection, phage libraries were incubated with CHO-CD20 cells. After extensive washing, bound phages were eluted as previously described.

6.1.5. ELISA Screening

Individual library clones were inoculated and induced for expression in 96-deep-well plates. ELISA screening was performed to isolate VHH clones which recognize human CD20 antigen specifically.

Single clones were randomly picked from the output library, and cultured in a 96-deep-well plate. When the OD600 of bacteria culture reached as 0.60.8, IPTG was added to induce the expression for overnight. The bacteria were collected by centrifugation and seeded in a microwell plate.

Exemplary anti-CD20 VHH domains of the disclosure (i.e., VHH-273, VHH-283, VHH-313, VHH-440, VHH-466, VHH-496, VHH-653, VHH-623, VHH-640 and VHH-657) were selected and sequenced. The CDR (e.g., as defined by Kabat or IMGT numbering scheme) and VHH sequences are summarized in Table 2 and the Sequence Listing provided herein.

6.2. Example 2—Constructions and Immune Cells Expression of VHH Chimeric Receptor Polypeptides 6.2.1. Construction of CD20 VHH CARs A nucleic acid sequence encoding a CAR backbone polypeptide comprising from the N-terminus to the C-terminus: a CD8α hinge domain, a CD8α transmembrane domain, a CD137 cytoplasmic domain, and a CD3ζ cytoplasmic domain was chemically synthesized and cloned into a pre-modified lentiviral vector downstream and operably linked to a hEF1α promoter. Multi-cloning sites (MCS) in the vector allowed insertion of a nucleic acid sequence comprising a Kozak sequence (GCCGCCACC (SEQ ID NO: 160)) operably linked to a nucleic acid sequence encoding a CD8α signal peptide fused to the N-terminus of VHH fragment(s), and the upstream was operably linked to the CAR backbone sequence.

To construct a monovalent VHH-based CAR using the CAR backbone vector, the nucleic acid sequence encoding the VHH domain was operably linked to the 3' of the nucleic acid sequence encoding the CD8α signal peptide. The fusion nucleic acid sequence was chemically synthesized and cloned into the CAR backbone via the EcoRI (5'-GAATTC-3' (SEQ ID NO: 161)) and SpeI (5'-ACTAGT-3' (SEQ ID NO: 162)) restriction sites by molecular cloning techniques known in the art. Exemplary monospecific and monovalent CD20 VHH CAR constructs are listed in Table 5. Anti-CD20 scFv (Leu16 scFv) (SEQ ID NO: 157) construct was also cloned into the CAR backbone to serve as a positive control and is listed in Table 5 too.

TABLE 5

| | | | Exemplary Monospecific and Monovalent CD20 CAR Constructs | | | |
|---|---|---|---|---|---|---|
| Exemplary CAR Code | Amino Acid Sequence | Signal Peptide | Extracellular antigen binding domain | Hinge & TM | Co-stimulatory signaling domain | Primary intracellular signaling domain |
| VHH-273 CAR | SEQ ID NO: 81 | CD8α | VHH-273 | CD8α | CD137 | CD3ζ |
| VHH-283 CAR | SEQ ID NO: 82 | CD8α | VHH-283 | CD8α | CD137 | CD3ζ |
| VHH-313 CAR | SEQ ID NO: 83 | CD8α | VHH-313 | CD8α | CD137 | CD3ζ |
| VHH-440 CAR | SEQ ID NO: 84 | CD8α | VHH-440 | CD8α | CD137 | CD3ζ |
| VHH-466 CAR | SEQ ID NO: 85 | CD8α | VHH-466 | CD8α | CD137 | CD3ζ |
| VHH-496 CAR | SEQ ID NO: 86 | CD8α | VHH-496 | CD8α | CD137 | CD3ζ |
| VHH-653 CAR | SEQ ID NO: 87 | CD8α | VHH-653 | CD8α | CD137 | CD3ζ |
| CD20 scFv CAR | SEQ ID NO: 107 | CD8α | Leu16 scFv | CD8α | CD137 | CD3ζ |
| VHH-623 CAR | SEQ ID NO: 189 | CD8α | VHH-623 | CD8α | CD137 | CD3ζ |
| VHH-640 CAR | SEQ ID NO: 190 | CD8α | VHH-640 | CD8α | CD137 | CD3ζ |
| VHH-657 CAR | SEQ ID NO: 191 | CD8α | VHH-657 | CD8α | CD137 | CD3ζ |

To construct a multivalent VHH-based CAR, a nucleic acid sequence encoding multiple copies of a VHH, or multiple different VHHs fused to each other via peptide linkers was cloned into the CAR backbone vector. These constructs were prepared by fusing two or three anti-CD20 VHH domains with a series of Glycine-Serine peptide linkers followed by directly synthesizing this fusion sequence in combination with a Kozak-CD8α signal peptide nucleic acid sequence and cloning into the CAR backbone via EcoRI and SpeI restriction sites. Exemplary monospecific and multivalent CD20 VHH CAR constructs are listed in Table 6.

NO: 152, SEQ ID NO: 153, SEQ ID NO: 154, SEQ ID NO: 155, and SEQ ID NO: 156, respectively.

6.2.2. Packaging of Lentivirus Vector

The lentivirus packaging plasmids mixture containing pMDLg.pRRE (Addgene, #12251), pRSV-REV (Addgene, #12253) and pMD2.G (Addgene, #12259) was pre-mixed with the vectors expressing CAR constructs at a pre-optimized ratio with polyetherimide (PEI). The transfection mixture was then added dropwise to the HEK293T cells and mixed gently, followed by medium replacement post 6-8 hours. The virus-containing supernatants were collected at

TABLE 6

| | | | Exemplary Monospecific and Multivalent CD20 CAR Constructs | | | | | | | |
|---|---|---|---|---|---|---|---|---|---|---|
| | | | Extracellular antigen binding domain | | | | | | | |
| Exemplary CAR Code | Amino Acid | Signal Peptide | VHH #1 | linker #1[1] | VHH #2 | linker #2[1] | VHH #3 | Hinge & TM | CT SD[2] | PI SD[3] |
| Bi-VHH1 CAR | SEQ ID NO: 98 | CD8α | VHH-273 | X2 | VHH-496 | NA | NA | CD8α | CD137 | CD3ζ |
| Bi-VHH2 CAR | SEQ ID NO: 99 | CD8α | VHH-283 | X2 | VHH-496 | NA | NA | CD8α | CD137 | CD3ζ |
| Bi-VHH3 CAR | SEQ ID NO: 100 | CD8α | VHH-313 | X2 | VHH-440 | NA | NA | CD8α | CD137 | CD3ζ |
| Bi-VHH4 (G4S)$_1$ CAR | SEQ ID NO: 101 | CD8α | VHH-273 | X1 | VHH-653 | NA | NA | CD8α | CD137 | CD3ζ |
| Bi-VHH4 (G4S)$_2$ CAR | SEQ ID NO: 102 | CD8α | VHH-273 | X2 | VHH-653 | NA | NA | CD8α | CD137 | CD3ζ |
| Bi-VHH4 (G4S)$_3$ CAR | SEQ ID NO: 103 | CD8α | VHH-273 | X3 | VHH-653 | NA | NA | CD8α | CD137 | CD3ζ |
| Bi-VHH4 (G4S)$_4$ CAR | SEQ ID NO: 104 | CD8α | VHH-273 | X4 | VHH-653 | NA | NA | CD8α | CD137 | CD3ζ |
| Bi-VHH4 (G4S)$_5$ CAR | SEQ ID NO: 105 | CD8α | VHH-273 | X5 | VHH-653 | NA | NA | CD8α | CD137 | CD3ζ |
| Tri-VHH CAR | SEQ ID NO: 106 | CD8α | VHH-273 | X2 | VHH-496 | X2 | VHH-440 | CD8α | CD137 | CD3ζ |

Note:
[1]The linker used in the constructs in Table 6 is (GGGGS)$_n$, n is an integer including, e.g., 1, 2, 3, 4, 5, and 6 (SEQ ID NO: 138), wherein in linker X1, n = 1; in linker X2, n = 2; in linker X3, n = 3; in linker X4, n = 4; and in linker X5, n = 5.
[2]CT SD represents co-stimulatory signaling domain.
[3]PI SD represents primary intracellular signaling domain.

The nucleic acid sequences of monovalent and multivalent CD20 VHH CARS described above are shown in SEQ ID NOs: 108-133 and 192-194 in the Sequence Listing. In these exemplary CAR constructs, the sequences of the CD8α signal peptide, the CD8α hinge domain, the CD8α transmembrane domain, the CD137 cytoplasmic domain, and the CD3ζ cytoplasmic domain are shown in SEQ ID 48 hours and 72 hours, then centrifuged at 3000 g for 10 mins at 4° C. Post lentivirus concentration, the supernatants were carefully discarded and the virus pellets were re-suspended with D10 medium (DMEM, 10% FBS, 1 mM Sodium Pyruvate and 2 mM L-Glutamine). The harvested virus was aliquoted and stored at −80° C. immediately. The virus titer was assessed and determined by CHO mammalian cells transduction efficiency. The LV titers of CD20 mono-/bi-/tri-VHH-based CAR reached within a range of $1\times10^8\sim4.5\times10^8$.

6.2.3. T Cell Isolation and Activation

Human PBMCs were collected from healthy donors. Human T cells were purified from PBMCs using Miltenyi Pan T cell isolation kit (Cat. #130-096-535), according to manufacturer's protocol as described below. The cell number was counted and the cell suspension was centrifuged at 300 g for 10 mins at 4° C. The supernatant was then aspirated off and the cell pellets were re-suspended in 40 μL of the buffer per $10^7$ total cells. 10 μL of Pan T Cell Biotin-Antibody Cocktail was added per $10^7$ total cells, mixed thoroughly and incubated for 5 mins at 4° C. 30 μL of the buffer was then added per $10^7$ total cells. 20 μL of Pan T Cell MicroBead Cocktail was added per $10^7$ cells. The cell suspension mixture was mixed thoroughly and incubated for an additional 10 mins at 4° C. A minimum volume (vol.) of 500 μL was required for magnetic separation. In magnetic separation, an LS column was placed in the magnetic field of a suitable MACS Separator. The LS column was rinsed with 3 mL of buffer. The cell suspension was then applied onto the column, and flow-through was collected containing the unlabeled cells which represented the enriched T cell fractions. Additional T cells were collected by washing the column with 3 mL of buffer and collecting unlabeled cells that passed through. These unlabeled cells again represented the enriched T cells and were combined with the flow-through from the previous step. The pooled enriched T cells were then centrifuged and re-suspended with T cell culture medium (RPMI1640, 10% heat-inactivated fetal bovine serum (FBS) and 300 IU/mL of IL-2).

The isolated T cells were subsequently pre-activated for 48 hours with human T Cell TransAct™ (Miltenvi, Cat. #130-111-160) according to manufacturer's protocol. The freshly isolated T cells were activated by the addition of anti-CD3/CD28 MACSiBead particles (Miltenyi, Cat. #130-111-160) in T cell culture medium according to manufacturer's protocol.

6.2.4. Generation of CD20 VHH CAR-T Cells

Based on the preliminary results of CD20 CAR-T cells generated by RNA electroporation and screened by in vitro assays, mono-, bi- and tri-VHH CAR-T cells were selected, designed and generated by lentivirus transduction for the efficacy analysis in human primary T cells. Additionally, CD20 scFv CAR-T cells were generated as the positive control. Activated T cells were cultured at $0.5\times10^6$ cells in 0.5 mL medium per well of a 24-well plate. After 24 hours, when T cells were blasting, 0.5 mL of non-concentrated, or smaller volumes of concentrated viral supernatant was added. T cells were transduced at a multiplicity of infection (MOI) of 10 by centrifugation at 1200 g for 1.5 hours at 32° C. The transduced cells were then transferred to the cell culture incubator for transgene expression under suitable conditions. T cells began to divide in a logarithmic growth pattern, which was monitored by measuring the cell number (viable cells/per mL) and viability (%). The T cell culture was replenished with fresh medium every two days. As the T cells began to rest down after approximately 6-7 days, they were ready to be harvested and cryopreserved for later analysis.

Before cryopreserving, the percentages of cells transduced (expressing VHH domain or scFv domain on T cell surface) were determined by flow cytometric analysis. The T cells were stained with LIVE/DEAD™ Fixable Dead Cell Stain Kits (Invitrogen, Cat. #L34976), VHH-based CAR-T cells were stained with Goat anti-Llama IgG FITC Conjugate (Bethyl, Cat. #A160-100F), and scFv-based CAR-T cells were stained with FITC-labeled Recombinant Protein L (Acro, Cat. #RPL-PF141) at 4° C. for 30 mins, followed by three-time washes, and were re suspended in 200 μL of DPBS with 0.5% FBS for FACS analysis on a NovoCyte Flow Cytometer (ACEA Biosciences).

The transduced T cells showed different CAR expression levels with mono-, bi- and tri-VHH domains, indicating the transduction efficiency (percent cells transduced) was related with the size and structure of CAR. Mono-VHH CAR-T cells showed significantly higher transduction efficiency than bi- or tri-VHH CAR-T cells, and were comparable to scFv CAR-T cells. CD20 VHH CAR-T cells expanded about 20-30 folds in a week. The cell counts and viability (82%~96%) of the CD20 VHH CAR-T cell cultures indicated that there was no detectable negative effect of the VHH(s) on the T cells ability to proliferate and expand when compared to the un-transduced T cells (UnT), as shown in Table 7.

TABLE 7

| Viability and Expansion of CD20 CAR-T Cells | | | |
|---|---|---|---|
| Exemplary CAR-T cell Code | CAR Positive Ratio (CAR+ %) | Cell Culture (Day 7) | |
| | | Viability (%) | Expansion fFold |
| VHH-273 CAR-T cells | 47.1 | 82.3 | 17.7 |
| VHH-313 CAR-T cells | 44.7 | 81.9 | 20.6 |
| VHH-466 CAR-T cells | 29.8 | 86.6 | 32.8 |
| VHH-496 CAR-T cells | 42.4 | 82.6 | 16.7 |
| Bi-VHH1 CAR-T cells | 24.4 | 95.5 | 33.3 |
| Bi-VHH2 CAR-T cells | 23.3 | 90.4 | 28.9 |
| Bi-VHH3 CAR-T cells | 26.2 | 93.9 | 29.9 |
| Tri-VHH CAR-T cells | 6.9 | 87.1 | 19.5 |
| CD20 scFv CAR-T cells | 41.8 | 81.7 | 25.4 |
| UnT | 0 | 83.4 | 32.7 |

6.3. Example 3—Characterization of Immune Cells Expressing Chimeric Receptor Polypeptides In Vitro 6.3.1. Expression of CD19, CD20 and CD22 Antigens on Target Cell Surface To evaluate the expression levels of CD19, CD20 and CD22 on the assessed target cell surface, $5\times10^5$ of cells per well were incubated with PE-labeled anti-CD19, anti-CD20 and anti-CD 22 mAbs, respectively (BioLegend, Cat. #302208, Cat. #302306 & Cat. #302506, respectively), and assessed by flow cytometry with QUANTI-BRITE PE beads (BD Bioscience, Cat. #340495). The assays and data analysis were performed in accordance with the manufacturer's instructions. "Receptor Number per Cell" indicates the approximate absolute number of molecules per cell on each of the indicated cell lines and is shown in Table 8.

TABLE 8

| CD19, CD20 and CD22 Receptor Number per Target Cell | | | |
|---|---|---|---|
| Cell line | CD19 receptor number per cell | CD20 receptor number per cell | CD22 receptor number per cell |
| K562.Luc | <10 | <10 | <50 |
| K562-CD19.Luc | 189789 | NA | NA |
| K562-CD20.Luc | <10 | 28303 | NA |
| K562-CD22.Luc | <10 | NA | 93339 |

TABLE 8-continued

| CD19, CD20 and CD22 Receptor Number per Target Cell | | | |
| Cell line | CD19 receptor number per cell | CD20 receptor number per cell | CD22 receptor number per cell |
| --- | --- | --- | --- |
| Raji.Luc | 77641 | 132614 | 34854 |
| Daudi.Luc | 49158 | 247729 | 39586 |
| Nalm.6.Luc | 32773 | <10 | 10441 |

6.3.2. Efficacy Evaluation of CD20 VHH CAR-T Cells

To assess the cytotoxicity of CD20 VHH CAR-T cells against tumor cells, the cells generated as described above were counted and co-cultured with antigen specific cancer cells to read out the killing potency. The control CD20 scFv CAR-T cells were used in all assays to compare assay variation and/or act as an internal control. The un-transduced T cells (UnT) were used as the non-targeting T cells control. CAR-T cell killing assays were conducted towards CD20 positive cell lines—human lymphoma cell line Raji (ATCC, #CCL-86) and K562-CD20: and CD20 negative cell lines—K562-CD19 and K562 (ATCC, #CCL-243). All cell lines were engineered in-house to express firefly luciferase as a reporter for cell viability/killing. The transduced cells were selected with puromycin and refreshed by the selection culture medium (Eagle's Minimum Essential Medium supplemented with 10% FBS and 2 µg/mL puromycin) in every 2-3 days. Post three rounds of selections, the selected cell clones were harvested and preserved for further use. The cytotoxicity of CD20 VHH CAR-T cells was measured at the effector to target cell ratio (E:T) of 15:1, 10:1 or 5:1 for 24 hours. Assays were initiated by mixing the respective number of T cells with a constant number of target cells. The remaining luciferase activity per well was assessed by ONE-Glo luciferase assay (Promega, Cat. #E6110), to quantify the remaining viable target cells per well.

Figure 1A:
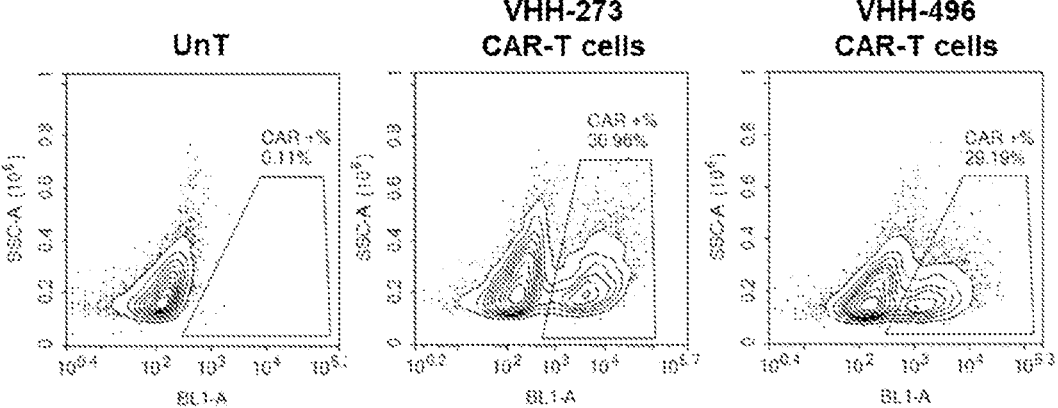
FIGS. 1A-1B show the exemplary transduction efficiency of VHH-based CAR-T cells (FIG. 1A) and scFv-based CAR-T cells (FIG. 1B). UnT refers to T cells un-transduced with CAR.
Figure 1B:
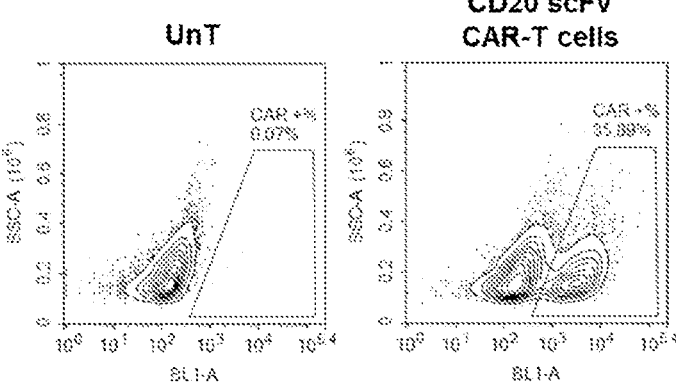
Figures 2A, 2B:
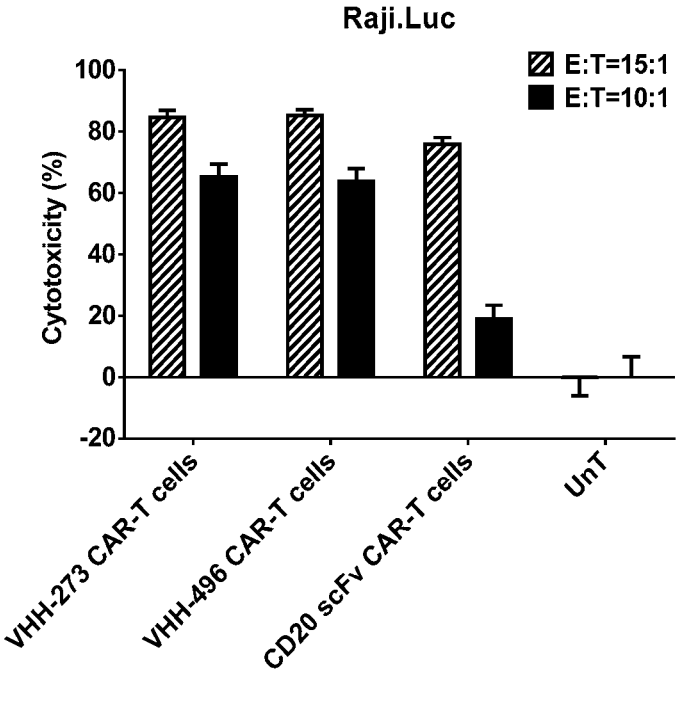
FIGS. 2A-2F show in vitro cytotoxicity of VHH-based CAR-T cells compared to that of scFv-based CAR-T cells against CD20 positive cell lines (FIGS. 2A-2B and FIGS. 2E-2F) or CD20 negative cell lines (FIGS. 2C-2D).
Figure 2C:
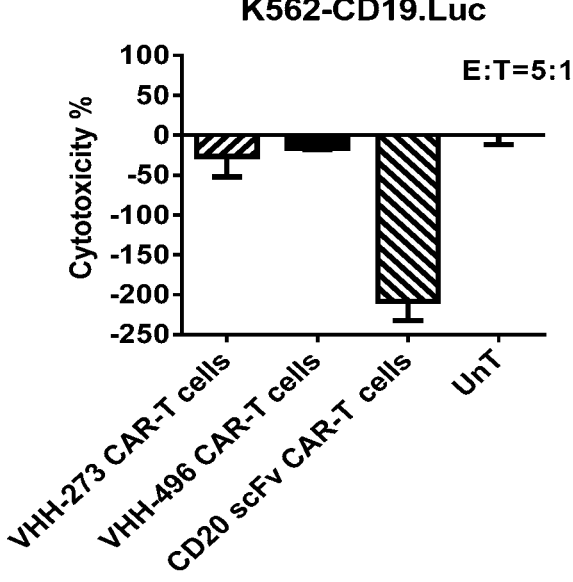
Figure 2D:
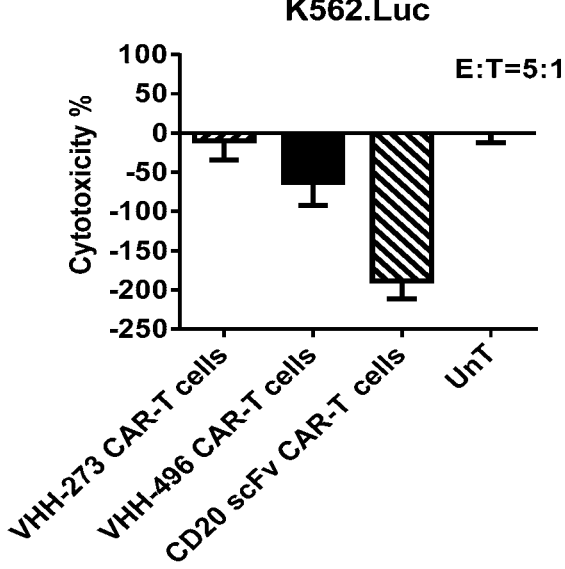
Figure 2E:
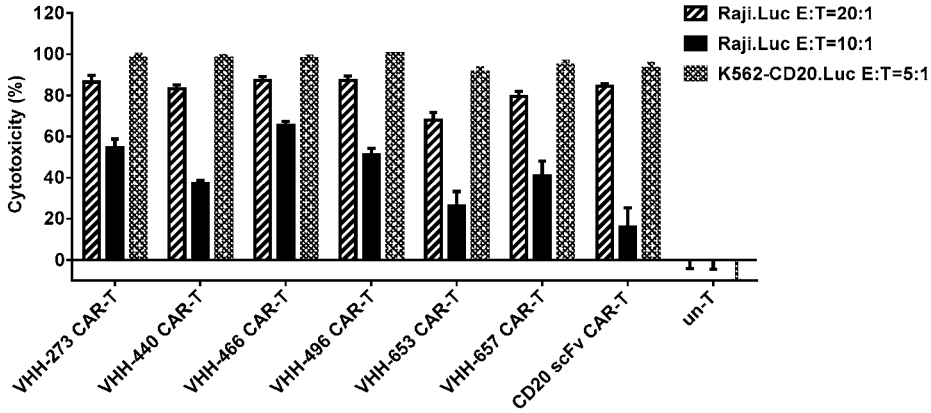
Figure 2F:
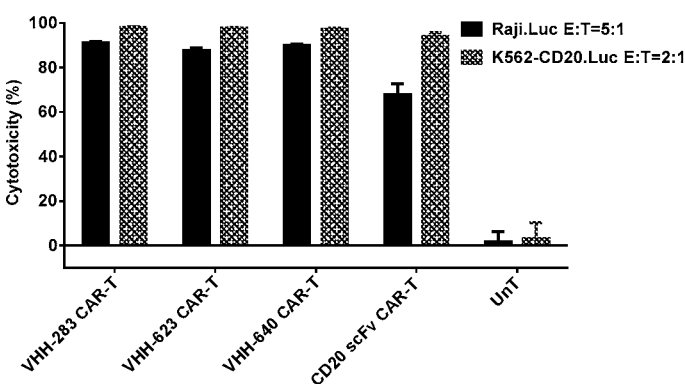

Hundreds of monovalent VHH CAR-T cells targeting CD20 were constructed and screened by in vitro cytotoxicity assay. Exemplary data are shown in FIGS. 1A-1B and FIGS. 2A-2F. The T cells were stained with LIVE/DEADT™ Fixable Dead Cell Stain Kits (Invitrogen, Cat. #L34976), VHH-based CAR-T cells were stained with Goat anti-Llama IgG FITC Conjugate (Bethyl, Cat. #A160-100F), and scFv-based CAR-T cells were stained with FITC-labeled Recombinant Protein L (Acro, Cat. #RPL-PF141). CAR+ expression level (%) of the exemplary VHH CAR-T cells reached around 30% at the harvest day (FIG. 1A). All of the exemplary CD20 VHH CAR-T cells exhibited higher cytotoxicity than positive control (i.e., CD20 scFv CAR-T cells) against Raji.Luc cells (E:T=10:1) (FIG. 2A, and FIGS. 2E-2F), and were comparable to CD20 scFv CAR-T cells against K562-CD20.Luc cells (FIG. 2B, and FIGS. 2E-2F). No significant cytotoxicity effect was detected against CD20 negative cell lines by the CD20 VHH CAR-T cells as compared to UnT control (FIGS. 2C-2D).

Figure 3A:
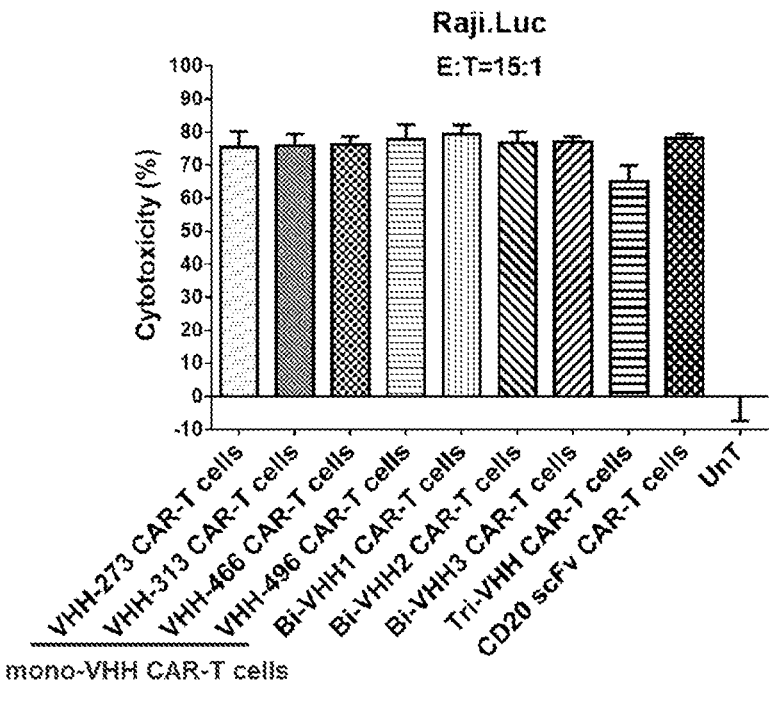
FIGS. 3A-3D show in vitro cytotoxicity of mono-, bi- and tri-VHH CAR-T cells compared to that of CD20 scFv CAR-T cells against CD20 positive cell lines (FIGS. 3A-3B) or CD20 negative cell lines (FIGS. 3C-3D).
Figure 3B:
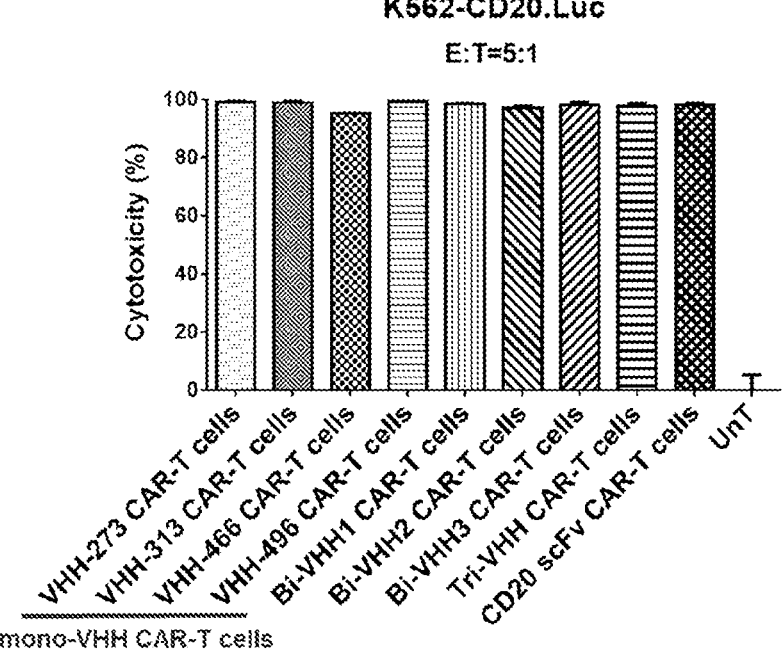
Figure 3C:
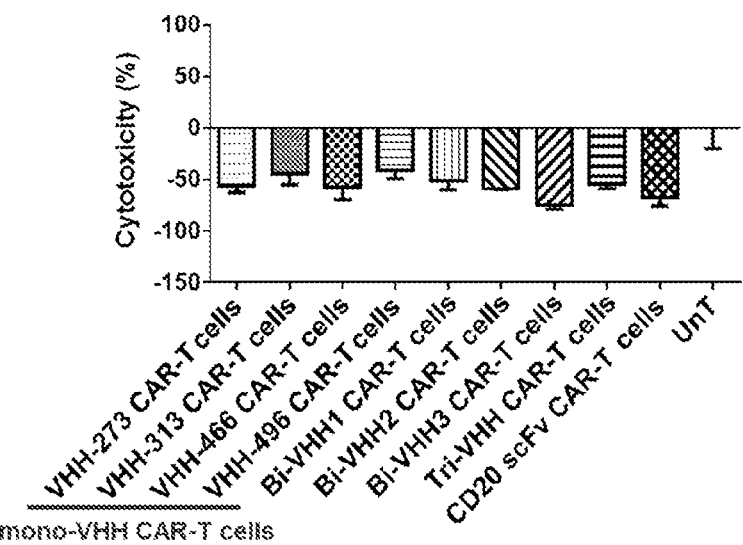
Figure 3D:
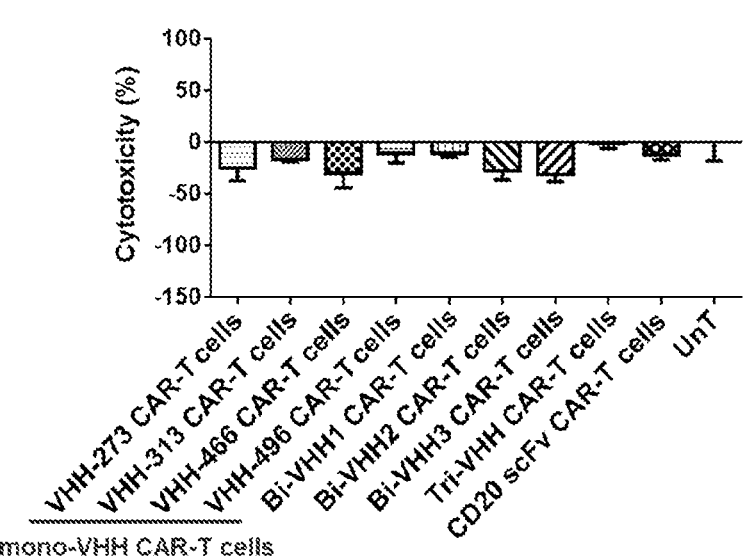

To assess the potency of multivalent VHH CAR-T cells, mono-, bi- and tri-VHH CAR T cells were constructed and generated, and the CAR-T cells' cytotoxicity were assessed. The exemplary data showed that multivalent CD20 VHH CAR-T cells exhibit different levels of cytotoxicity against Raji.Luc and K562-CD20.Luc cells (FIGS. 3A-3B). In the 24 hours of in vitro killing assay, mono-VHH CAR-T cells and bi-VHH CAR-T cells showed higher killing than Tri-VHH CAR-T cells against Raji.Luc cells. None of the CD20 VHH CAR-T cells showed cytotoxicity effect against CD20-negative cell lines, as compared to UnT control (FIGS. 3C-3D).

Figure 4A:
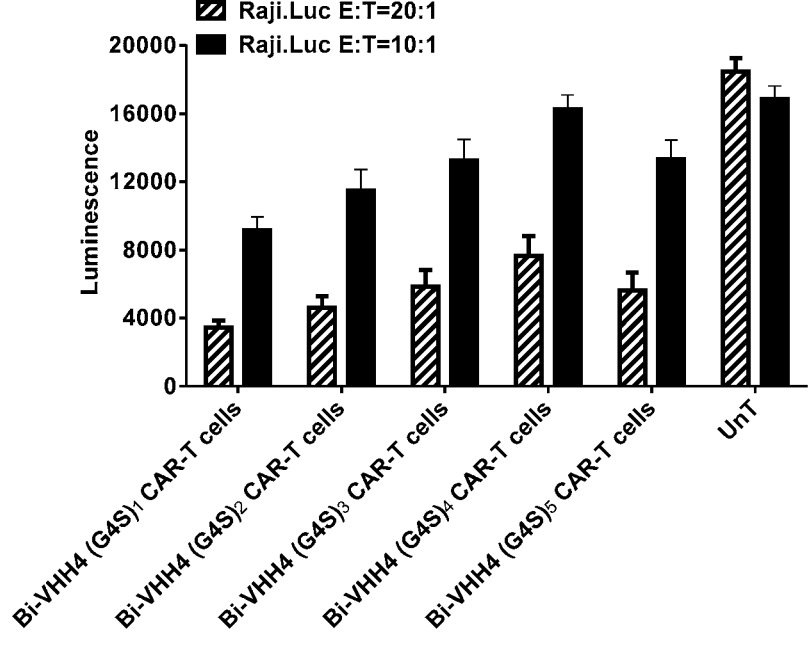
FIGS. 4A-4B show in vitro cytotoxicity of bi-VHH CAR-T cells with different length of peptide linkers against Raji.Luc cells.
Figure 4B:
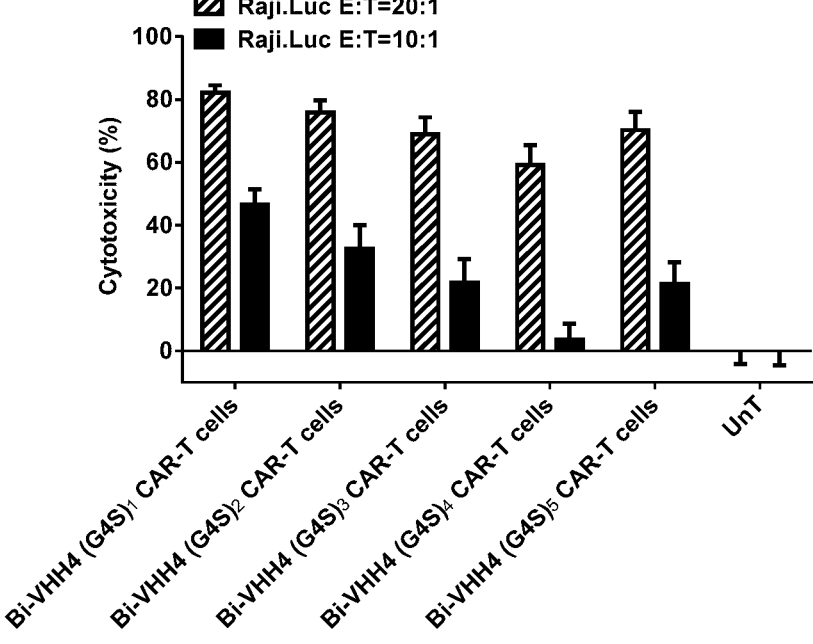

To assess the effect of (G4S) linker(s) between the VHHs, two exemplary VHHs linked with (G4S)$_n$ (n=1~5) (SEQ ID NO: 138) peptides were constructed and five of the Bi-VHH4 CAR-T cells were generated (Table 6). The exemplary data showed that the shorter the (G4S) linker between two VHH domains, the more potent the bi-VHH CAR-T cells were in killing target cells-Raji.Luc cells, and the bi-VHH CAR-T cells with the linker as (G4S)$_1$ showed the highest cytotoxicity against Raji.Luc at E:T ratios of 20:1 and 10:1 (FIGS. 4A-4B).

The observation above indicates that the CD20 VHH CARs provided herein induce T cell activation via specific recognizing CD20 receptor expressing cells, activate T cell endogenous signaling pathway, induce activation of cytotoxic T lymphocytes (CTL) and enhance anti-tumor responses.

6.3.3. IFN-γ Release Evaluation of CD20 VHH CAR-T Cells

To measure cytokine production of CD20 VHH CAR-T cells in response to CD20-expressing cells, CAR-T cells were co-cultured with the CD20 positive cell lines—Raji.Luc or K562-CD20.Luc and CD20 negative cell line—K562.Luc at an E:T ratio of 15:1, 10:1 or 5:1 for 24 hours, after which the media was harvested for the cytokine analysis using the human IFN-γ kit (Cisbio, Cat. #62HIFNGPEG) for cytokine quantification, and the absorbance of each well (triplicate per teste article) was read by a multimode microplate reader (Tecan Spark).

Figure 5A:
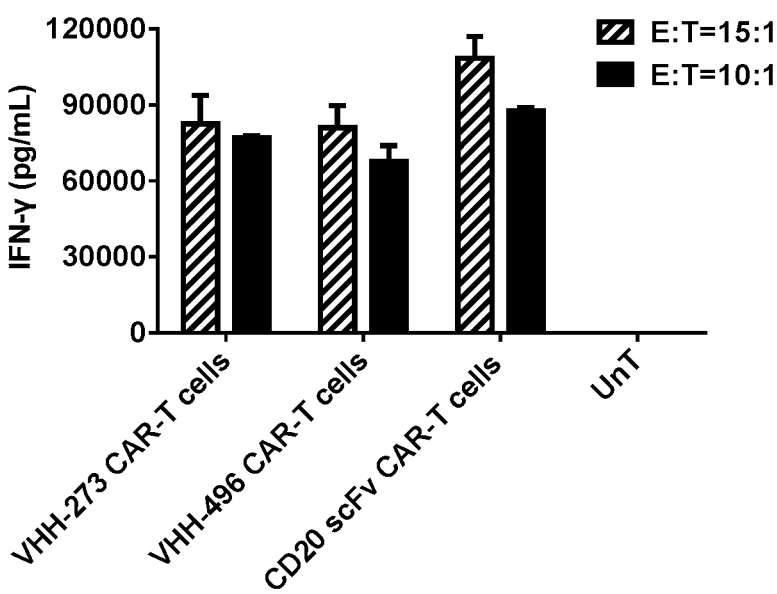
FIGS. 5A-5B show IFN-γ release level of VHH-based CAR-T cells compared to that of scFv-based CAR-T cells after co-culture with Raji.Luc or K562-CD20.Luc cells at different E:T ratios for 24 hours.
Figure 5B:
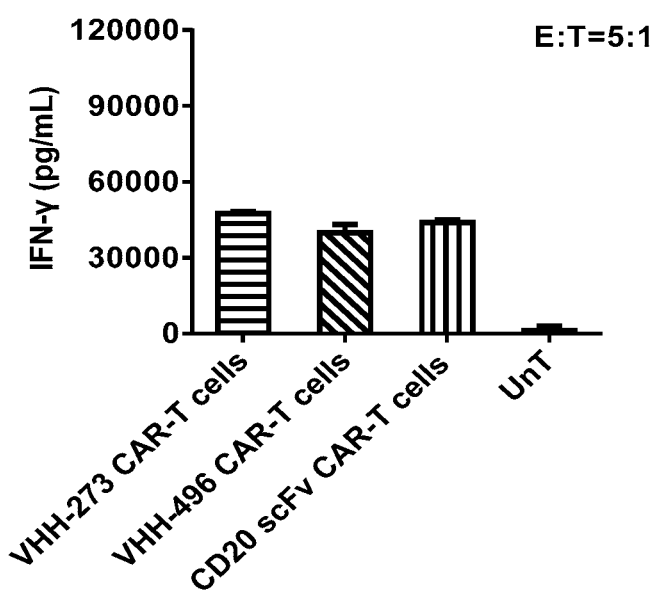
Figure 6:
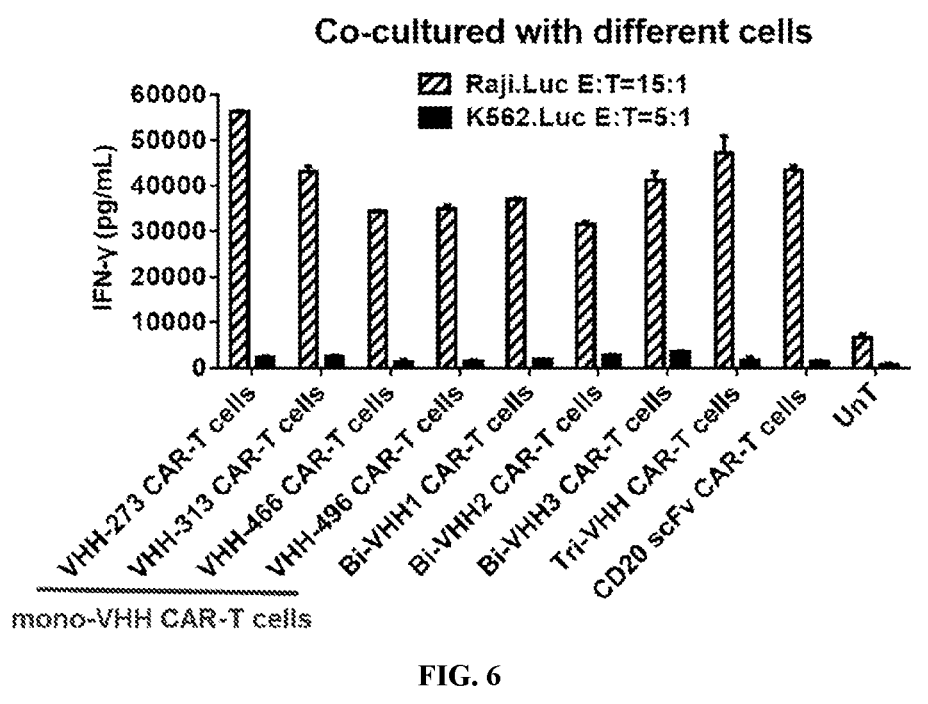

The data showed that the exemplary cells VHH-273 CAR-T cells and VHH-496 CAR-T cells produced less IFN-γ than CD20 scFv CAR-T cells when co-cultured with Raji.Luc cells (FIG. 5A), and produced comparable IFN-γ to CD20 scFv CAR-T cells when co-cultured with K562-CD20.Luc cells (FIG. 5B). Mono-VHH CAR-T cells, bi-VHH CAR-T cells and tri-VHH CAR-T cells showed different levels of IFN-γ release against Raji.Luc cells (FIG. 6). In contrast, IFN-γ release was not detectable or extremely low in cultures containing either un-transduced T cells or negative control cells—K562.Luc, confirming that CD20-specificity of the CAR-T cells was required for reactivity to CD20 expressing cells (FIG. 6).

6.3.4. CD20 VHH CAR-T Cells Proliferation Capacity

To assess the proliferation capacity of CD20 VHH CAR-T cells, T cells were stimulated with irradiated K562-CD20 cells or K562 cells at an E:T ratio of 2:1 and co-cultured for 40 days (triplicates per test article). In even four days, T cells were counted and stained with LIVE/DEAD™ Fixable Dead Cell Stain Kit (Invitrogen, Cat. #L34976), CD3+ and CAR+ were assessed by FACS. CD3 receptors were stained with FITC-anti-human CD3 (Biolegend, Cat. #300306). VHH-based CAR-T cells were stained with Goat anti-Llama IgG FITC Conjugate (Bethyl, Cat. #A160-100F), and scFv-based CAR-T cells were stained with FITC-labeled Recombinant Protein L (ACRO, Cat. #RPL-PF141) at 4° C., for 30 mins, followed by three-time washes, and were re-suspended in 200 ELL of DPBS with 0.5% FBS for FACS analysis on a NovoCyte Flow Cytometer (ACEA Biosciences). The FACS data was analyzed by Novoexpress software.

Figure 7A:
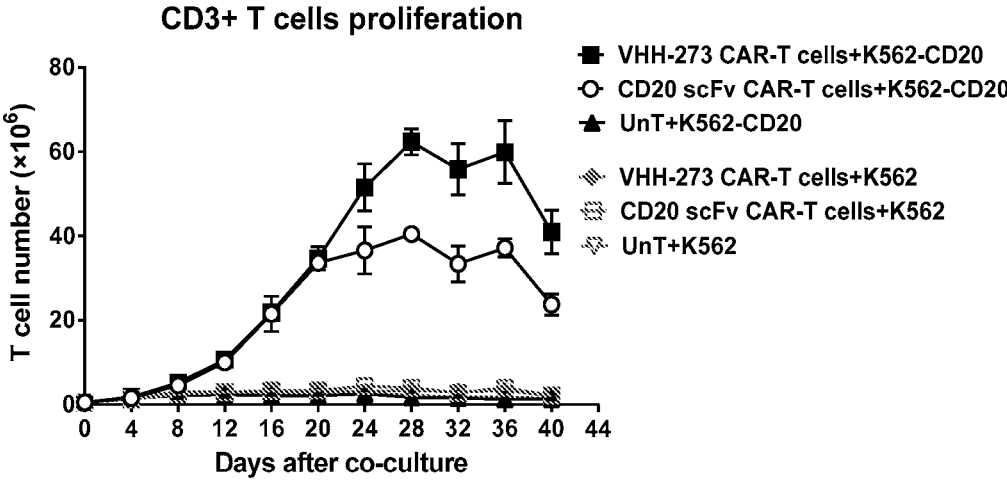
FIGS. 7A-7D show the proliferation capacity and CAR positive ratio of the exemplary CD20 VHH CAR-T cells compared to that of CD20 scFv CAR-T cells with or without antigen specific stimulation.
Figure 7B:
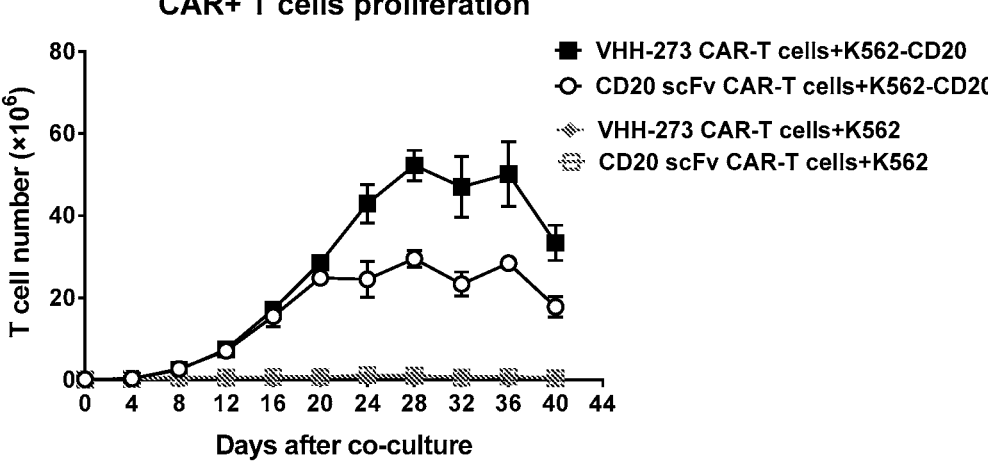
Figure 7C:
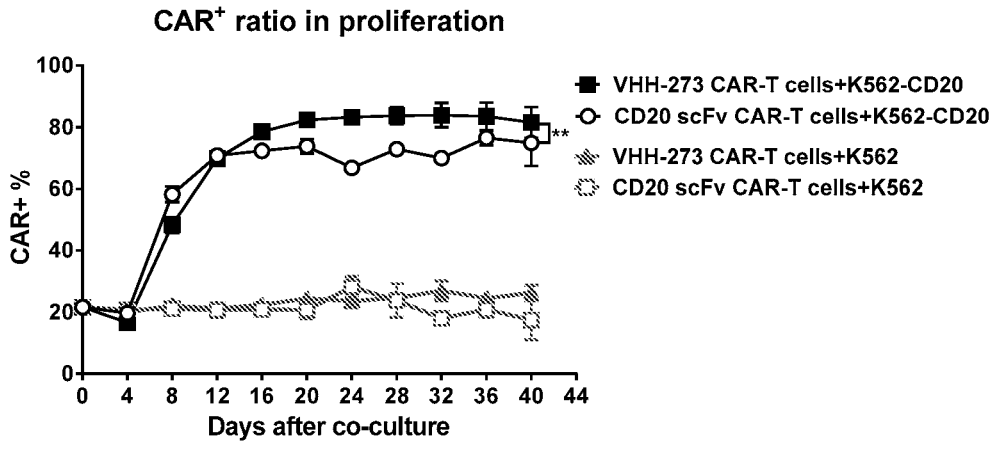
Figure 7D:
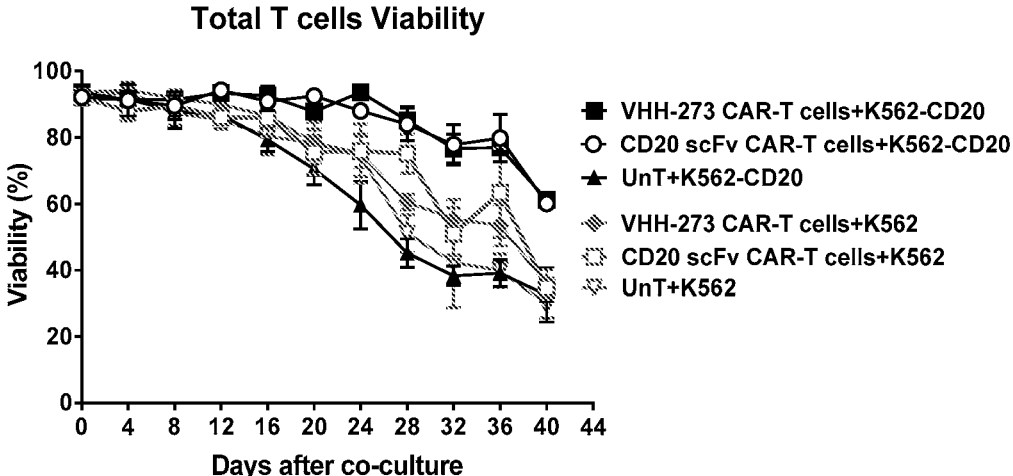

In the expansion stimulated by CD20 specific antigen (co-cultured with K562-CD20 cells), VHH-273 CAR-T cells showed dramatically enhanced CD3+ T cells and CAR+ T cells proliferation, compared to CD20 scFv CAR-T cells from Day 20 to Day 40, and showed around 1.6~2 folds higher than CD20 scFv CAR-T cells in CD3+ or CAR+ T cells proliferation from Day 28 to Day 40 (FIGS. 7A-7B). Enhanced CD3+ T cells or CAR+ T cells proliferation was not observed in co-cultures containing negative control cells—K562 (FIGS. 7A-7B). Both of CD20 VHH CAR-T cells and CD20 scFv CAR-T cells demonstrated that the percentages of CAR+ expression were increased in a time-dependent manner in the first 20 days and plateaued post 20 days (FIG. 7C). In addition, CD20 VHH CAR-T cells exhibited significantly higher percentage of CAR+ expression than CD20 scFv CAR-T cells (FIG. 7C). CD20 antigen stimulated CD20 VHH CAR-T cells or CD20 scFv CAR-T cells maintained significantly higher viability in 40-days proliferation assay than the respective non-stimulated CD20 VHH CAR-T cells or CD20 scFv CAR-T cells (FIG. 7D). The data indicates that CD20 VHH CAR-T cells induce robust and persistent T cells activation and proliferation in a tumor associated antigen dependent manner.

6.3.5. CD20 VHH CAR-T Cells Exhaustion Markers and Memory Markers Assessment

To assess the exhaustion markers and memory markers of CD20 VHH CAR-T cells, T cells were stimulated with irradiated K562-CD20 cells at an E:T ratio of 2:1 and co-cultured for 28 days (triplicates per test article). In every four days, T cells were counted with a live/dead staining, and CAR+, T cell exhaustion markers and T cell memory markers were assessed by a multi-color FACS staining. T cell exhaustion markers were co-stained with fluorochrome conjugated anti-human CD279 (PD-1), anti-human CD223 (LAG-3) and anti-human CD366 (Tim-3). T cell memory markers were co-stained with fluorochrome conjugated anti-human CD45RA and anti-human CD197 (CCR7). FACS analysis was ran with a BD LSRFortessa Flow Cytometer (BD Biosciences).

Figure 8:
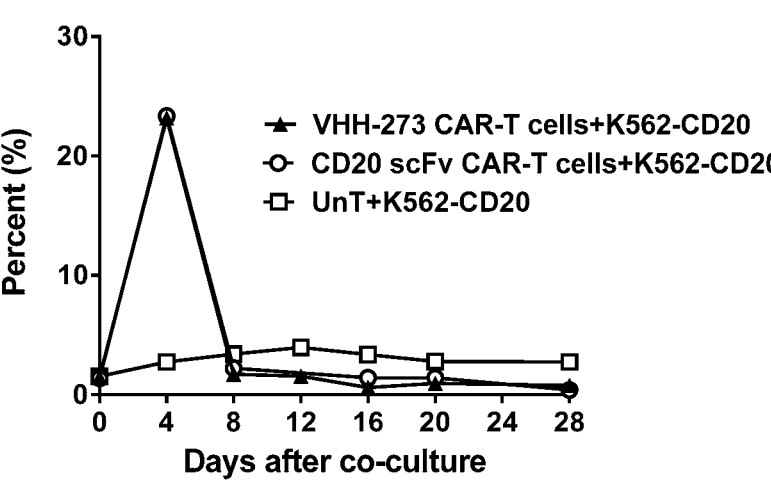
FIG. 8 shows the results of exhaustion markers assessment of exemplary CD20 VHH CAR-T cells and CD20 scFv CAR-T cells.

The FACS data of exhaustion markers assessment showed that the exhaustion markers of both VHH-273 CAR-T cells and CD20 scFv CAR-T cells were peaked at Day 4 post antigen specific stimulation and dropped dramatically afterward. Post Day 8, the expression levels of exhaustion markers of both CD20 VHH CAR-T cells and CD20 scFv CAR-T cells were kept low till Day 28 (FIG. 8). The data suggests that T cell exhaustion is driven by strong T cell activation only at early stage when exposed to tumor associated antigen and normally the expression returns to baseline after activation.

Figure 9A:
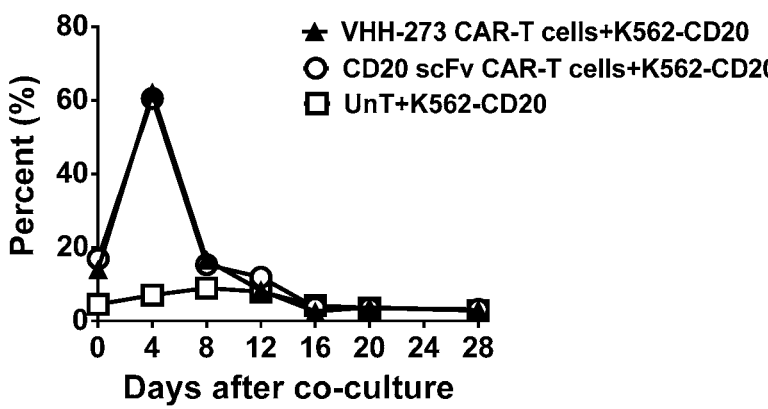
FIGS. 9A-9D show the results of memory markers assessment of exemplary CD20 VHH CAR-T cells and CD20 scFv CAR-T cells.
Figure 9B:
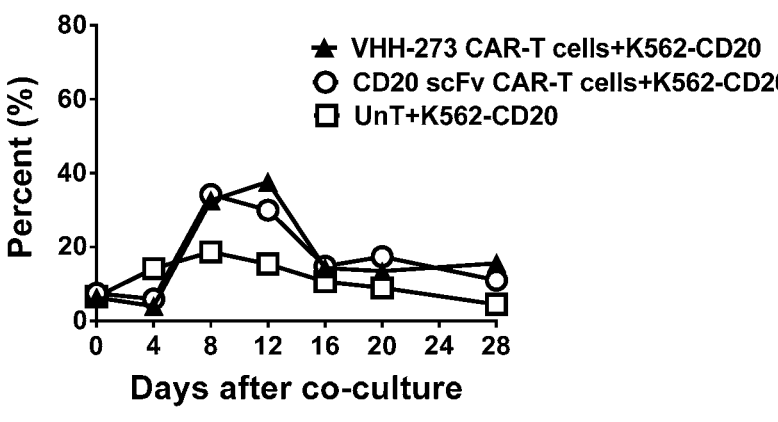
Figures 9C, 9D:
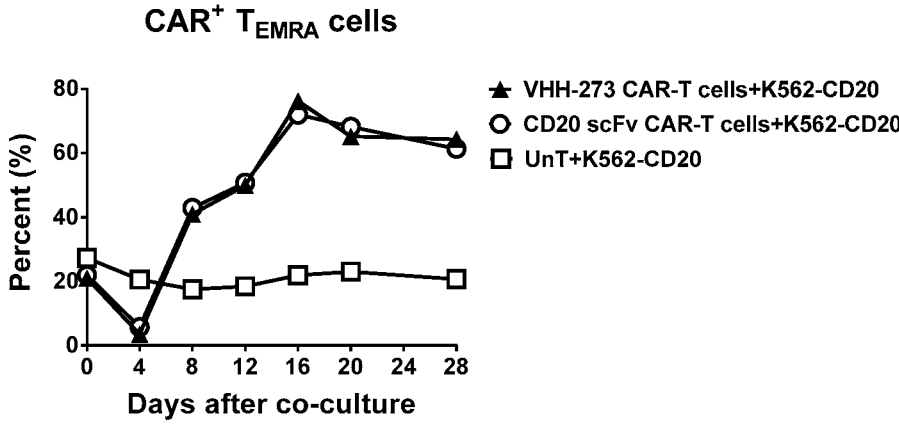

The FACS data of memory markers assessment showed that VHH-273 CAR-T cells and CD20 scFv CAR-T cells demonstrated similar time-dependent pattern of central memory T cells ($T_{CM}$) and effector memory T cells ($T_{EM}$) post antigen-specific stimulation. In addition, CAR-T cells initially differentiated into $T_{CM}$, which peaked at Day 4, then gradually differentiated to $T_{EM}$ or $T_{EMRA}$, which peaked at Day 8 or Day 16 respectively (FIGS. 9A-9C). $T_{CM}$ and $T_{EMRA}$ of UnT were maintained at the baseline (FIGS. 9A-9C). The engineered second generation CAR-T cells direct T cells to their fates by balancing effector and memory programs.

6.4. Example 4—In Vin Efficacy of CD20 VHH CAR-T Cells in Tumor Xenograft Mice

Anti-tumor activity of CD20 VHH CAR-T cells was assessed in vivo in a Raji xenograft NCG mouse model and CD20 scFv CAR-T cells and un-transduced cells (UnT) were evaluated as either positive or negative control.

Cell line: Raji (ATCC #CCL-86) is the lymphoblast-like cell line, established by Pulvertaft in 1963 from a Burkitt's lymphoma of the 11-year-old male. Raji cells were grown in RMPI medium containing 10% fetal bovine serum. This cell line grows in suspension in tissue culture flasks. This cell line persists and expands in mice when implanted intravenously. The Raji cells had been modified to express luciferase, so that tumor cell growth could also be monitored by imaging the mice. The Raji model endogenously expresses high levels of CD19, CD20 and CD22 and thus, can be used to test the in vivo efficacy of CD20-directed engineered T cells.

Mice: 5-6 weeks old NCG (NOD-Prkdcem26Cd52I12rgem26Cd22/Nju) female mice were received from Model Animal Research Center of Nanjing University, with similar weight (around 20 g). Animals were allowed to acclimate in the animal facility for 7 days prior to experimentation. Animals were handled in accordance with ACUC regulations and guidelines.

6.4.1. CD20 Mono-VHH CAR-T Cells Efficacy and Re-challenging In Vivo Tests 6.4.1.1. CD20 Mono-VHH CAR-T Cells Efficacy In Vivo Test To create the tumor xenograft, NCG Mice were injected intravenously with Raji.Luc. The mice were treated with the T cells post 4 days with Raji.Luc tumor cell implantation. The mice were injected intravenously via the tail vein with 400 µL of the T cells for a dose of $1\times10^6$ T cells per mouse. The four mice per group were treated with either CD20 mono-VHH CAR-T cells (VHH-273 CAR-T cells or VHH-496 CAR-T cells) or CD20 scFv CAR-T cells, and 400 µL of HBSS alone and un-transduced T cells (UnT) were used as controls. All the T cells were prepared from the same donor in parallel. Animal health status was monitored twice per week, including body weight measurement. Tumors were monitored weekly by bioluminescence imaging (BLI) until animals achieved endpoint.

The mean bioluminescence for all treatment groups is plotted in FIGS. 10A-10F. The HBSS treatment group (vehicle), which did not receive any T cells, demonstrated baseline Raji tumor growth kinetics in intravenously injected NCG mice. The UnT treatment group received non-transduced T cells as negative control for the engineered T cells. Both the HBSS and the UnT treatment groups demonstrated continuous aggressive tumor progression throughout this study and were euthanized on Day 16. CD20 mono-VHH CAR-T cells significantly inhibited tumor growth when compared to UnT treatment and showed complete tumor inhibition during the 35 days of the in vivo efficacy study, as indicated from the mean bioluminescence and the image of bioluminescence (FIGS. 10A-10B). In addition, the twice per week monitored mice health status was normal and the body weights were increased in CD20 mono-VHH CAR-T cells treatment groups throughout the 35 days of in vivo study (FIG. 10C).

6.4.1.2. PK Study—Detection Copies of CARs in Mouse Peripheral Blood

To assess pharmacokinetics of CD20 VHH CAR-T cells and to monitor circulating CAR-T cells proliferation and persistence in mouse, the genomic DNA of mouse peripheral blood was extracted with QIAamp-DNA-mini Blood Kit (Qiagen, Cat. #51106) and the concentration was measured by Nanodrop One (ThermoFisher, Cat. #ND-ONE-W). The genomic DNA (of 3 mice per group) was diluted at the concentration of 50 ng/µL with ddH$_2$O and mixed with PCR reaction reagents, including forward and reverse primer sets binding onto CAR backbone. The mixture was then assessed with digital PCR and ran on the QX200 Droplet Reader (Bio Rad, Cat. #1864003). The copies/ng genomic DNA of VHH-273 CAR was 2 folds higher than that of CD20 scFv CAR observed at peak level (Day 14) (FIG. 10D).

6.4.1.3. Raji.Luc Tumor Cells Re-challenging In Vivo Study

To investigate CAR-T cells efficacy on those at least 5 weeks tumor-free mice under the additional tumor burdens, those mice with undetectable CAR copy number (copies/ng of genomic DNA) in PBMC were selected for re-challenging assay. The selected mice were injected intravenously with half amount of Raji.Luc tumor cells. Animal health status was monitored twice per week, including body weight measurement. The Raji tumors were monitored weekly by bioluminescence imaging (BLI) until animals achieved endpoint.

The naïve mice (not implanted with Raji.Luc cells or treated with CAR-T cells previously) injected with Raji.Luc as control demonstrated continuous aggressive tumor progression and were euthanized on Day 19. VHH-273 CAR-T cells showed complete tumor inhibition for 28 days post re-challenging. Both CD20 VHH CAR-T cells and CD20 scFv CAR T cells treatment groups relapsed around Day 12, as indicated from the mean bioluminescence (FIG. 10E). In addition, the twice per week monitored mice health status and body weight under VHH-273 CAR-T cells treatment were normal throughout the 28 days re-challenging in vivo study (FIG. 10F).

6.4.2. CD20 Mono-VHH, Bi-VHH and Tri-VHH CAR-T Cells Efficacy and Re-challenging In Vivo Tests 6.4.2.1. CD20 Mono-VHH, Bi-VHH and Tri-VHH CAR-T Cells Efficacy In Vivo Test To create the tumor xenograft, NCG Mice were injected intravenously with Raji.Luc. The mice were treated with the T cells post 4 days with Raji.Luc tumor cell implantation. The mice were injected intravenously via the tail vein with 400 μL of the T cells for a dose of $1 \times 10^6$ T cells per mouse. The six mice per group were treated with CD20 mono-VHH CAR-T cells (VHH-313 CAR-T cells), bi-VHH CAR-T cells (Bi-VHH3 CAR-T cells) or Tri-VHH CAR-T cells, and CD20 scFv CAR-T cells, 400 μL of HBSS alone and un-transduced T cells (UnT) were used as the controls. All the T cells were prepared from the same donor in parallel. Animal health status was monitored twice per week, including body weight measurement. Tumors were monitored weekly by bioluminescence imaging (BLI) until animals achieved endpoint.

The HBSS treatment group (vehicle), which did not receive any T cells, demonstrated baseline Raji tumor growth kinetics in intravenously injected NCG mice. The UnT treatment group received non-transduced T cells as negative control for the engineered T cells. Both the HBSS and the UnT treatment groups demonstrated continuous aggressive tumor progression throughout this study and were euthanized on Day 14. VHH-313 CAR-T cells, Bi-VHH3 CAR-T cells and Tri-VHH CAR-T cells all significantly inhibited tumor growth when compared to UnT treatment and showed complete tumor inhibition during 42 days of the in vivo efficacy study, as indicated from the mean bioluminescence and the image of bioluminescence (FIGS. 11A-11B). Tri-VHH CAR-T cells were slightly more efficacious than mono-VHH CAR-T cells and bi-VHH CAR-T cells in Raji tumor inhibition. CD20 scFv CAR-T cells treatment group relapsed at Day 28 (FIGS. 11A-11B). In addition, the twice per week monitored mice health status was normal and body weights were increased in CD20 mono-VHH, bi-VHH and tri-VHH CAR-T cells treatment groups throughout the in vivo study (FIG. 11C).

6.4.2.2. PK Study—Detection Copies of CARs in Mouse Peripheral Blood

To assess pharmacokinetics of CD20 mono-VHH, bi-VHH and tri-VHH CAR-T cells and to monitor circulating CAR-T cells proliferation and persistence in mouse, the genomic DNA of mouse peripheral blood was extracted with QIAamp-DNA-mini Blood Kit (Qiagen, Cat. #51106) and the concentration was measured by Nanodrop One (ThermoFisher. Cat. #ND-ONE-W). The genomic DNA (of 3 mice per group) was diluted at the concentration of 50 ng/μL with ddH$_2$O and mixed with PCR reaction reagents, including forward and reverse primer sets binding onto CAR backbone. The mixture was then assessed with digital PCR and ran on the QX200 Droplet Reader (Bio Rad, Cat. #1864003). Both VHH-313 CAR copies and Bi-VHH3 CAR copies peaked at Day 7 and CD20 scFv CAR copies peaked at Day 21 (FIG. 11D, which is adopted from FIG. 11E and the scale of Y-axis is adjusted to enhance the resolution of copies/ng genomic DNA). In addition, the Tri-VHH CAR-T cells demonstrated higher expansion capability and peaked at Day 21, and then gradually dropped till the endpoint (Day 35) (FIG. 11E).

6.4.2.3. Raji.Luc Tumor Cells Re-challenging In Vivo Study

To investigate CD20 mono-VHH, bi-VHH and tri-VHH CAR-T cells efficacy on those at least 6 weeks tumor-free mice under the additional tumor burdens, the mice were selected for re-challenging assay. The selected mice were injected intravenously with half amount of Raji.Luc cells. Animal health status was monitored weekly, including body weight measurement. The Raji tumors were monitored weekly by bioluminescence imaging (BLI) until animals achieved endpoint.

CD20 scFv CAR-T cells treatment group showed continued remissions and relapses, VHH-313 CAR-T cells or Bi-VHH3 CAR-T cells treated mice relapsed around Day 11 to Day 18, and Tri-VHH CAR-T cells treated mice showed significant tumor inhibition for 32 days post Raji.Luc cells re-challenging, as indicated by the mean bioluminescence (FIG. 11F).

6.5. Example 5—Characterization of Anti-CD20 VHH-huIgG1Fc Monoclonal Antibody (mAb) Binding and On-/off-target Activity In Vitro 6.5.1. Anti-CD20 VHH-huIgG1Fc mAb On-Target Binding to CD20 Receptor Expressing Cells and EC$_{50}$ Each of three exemplary of anti-CD20 VHH sequences (clone ID: VHH-273, VHH-466 and VHH-496) with human IgG1 Fc fragment sequence (SEQ ID NO: 159) were cloned into a mammalian expression vector—pcDNA3.4, to facilitate the recombinant protein expression. The DNA codons were further optimized for optimal expression in mammalian host cell—Expi293F. The antibodies were harvested from the supernatant of cell culture, one-step purified by MabSelect SuRe LX and sterilized via a 0.2 μm filter. The purified antibody concentrations were determined by A280 and reached 2-6 mg/mL with ~90% purity. Anti-CD20 scFv-huIgG1Fc mAb with amino acid sequence of Rituximab (C2B8) scFv shown in SEQ ID NO: 158 and anti-CD20 Fab-huIgG1Fc mAb with amino acid sequences of Leu16 V$_H$-CH1 and V$_L$-CL shown in SEQ ID NO: 163 and SEQ ID NO: 164 were used as positive controls for the cell surface binding assay. CD20 positive cell lines—Raji, K562-CD20 and negative cell line—K562 were re-suspended in complete culture medium, cells concentration was diluted to $1 \times 10^6$ cells/mL and the staining was performed in $2 \times 10^5$ cells per well. The mAbs were serially diluted from maximal concentration of 2000 nM (3-fold reduction, 12 pts) and added according to the experimental plan and protocol. The mAbs and cells were co-incubated for 1 hour at 4° C. Then, the cells were washed with 200 μL of DPBS+0.5% FBS and spun at 300 g for 5 mins, 4° C. The cells were stained with the detection antibody—PE-conjugated mouse anti-human IgG1 Fc (BioLegend, Cat. #409304, 1:100) for 40 mins at 4° C. The cells were then washed again and re-suspended with 200 μL of DPBS+0.5% FBS for flow cytometric analysis on a NovoCyte Flow Cytometer (ACEA Biosciences). The FACS data was analyzed by Novoexpress software, and the MFI (median fluorescent intensity) was analyzed by GraphPad PRISM version 6.0.

Figure 12A:
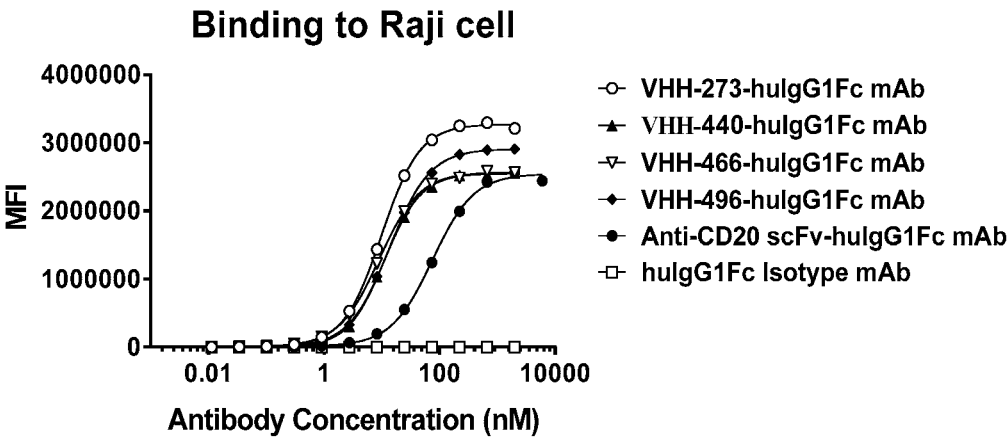
Figure 12B:
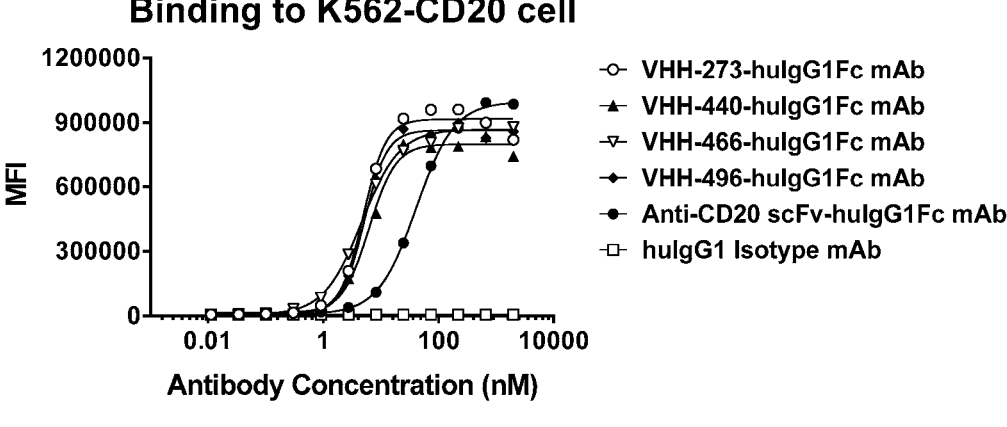
Figure 12C:
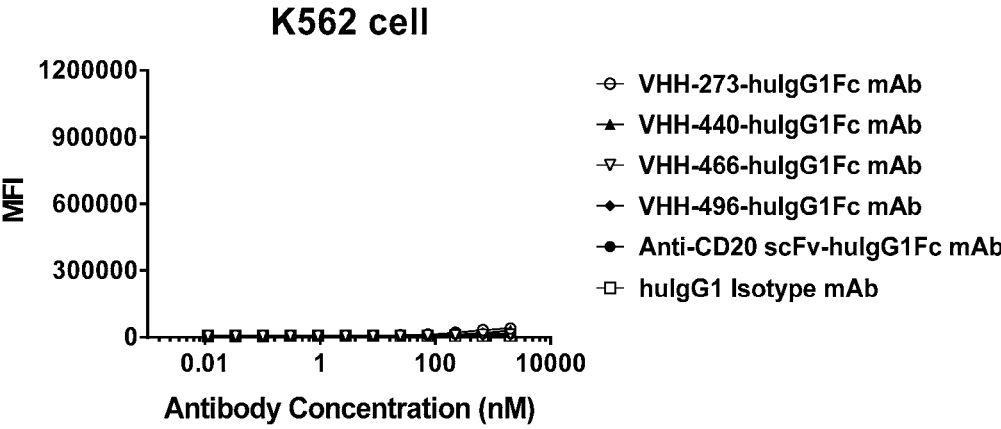
Figure 12D:
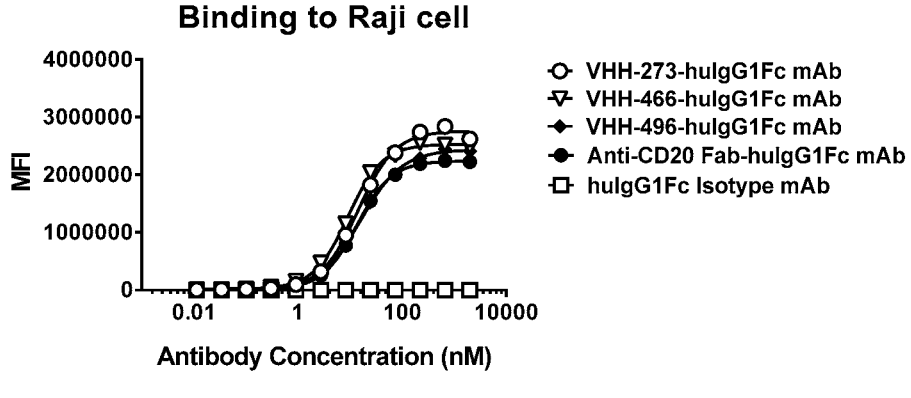
Figure 12E:
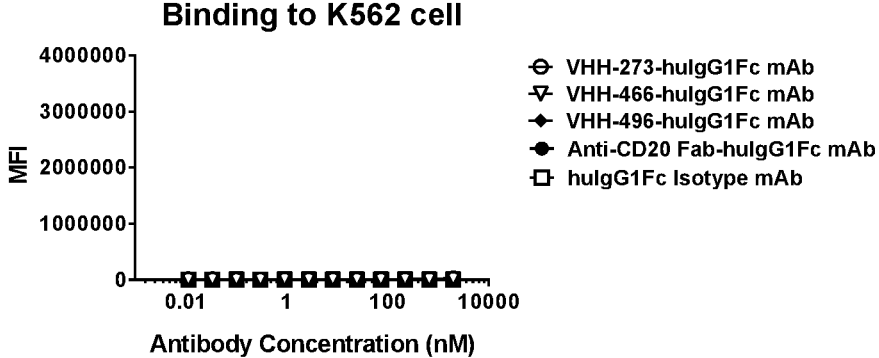

The cell surface binding data showed that anti-CD20 VHH-huIgG1Fc mAbs specifically bound to CD20 positive cells—Raji cells and K562-CD20 cells in a dose-dependent manner, and significantly stronger binding than anti-CD20 scFv-huIgG1Fc mAb on both target cells (FIGS. 12A-12B). Anti-CD20 VHH-huIgG1 Fc mAbs showed a comparable binding to anti-CD20 Fab-huIgG1Fc mAb on target cells and stronger binding to Raji at higher mAb concentration (FIG. 12D). None of the antibodies showed significant binding to CD20 negative cell line—K562 (FIG. 12C and FIG. 12E). $EC_{50}$ of anti-CD20 VHH-huIgG1Fc mAbs vs. positive control mAbs are shown in Table 9 and Table 10. The term "EC50", also known as half maximal effective concentration, refers to the concentration of an antibody which induces a response halfway between the baseline and maximum after a specified exposure time.

TABLE 9

$EC_{50}$ of Anti-CD20 VHH-huIgG1Fc mAbs and
Anti-CD20 scFv-huIgG1Fc mAb
Binding with Raji or K562-CD20 Cells

| mAb | $EC_{50}$ (nM) On-target Raji cells | $EC_{50}$ (nM) On-target K562-CD20 cells |
| --- | --- | --- |
| VHH-273-huIgG1Fc mAb | 9.8 | 4.9 |
| VHH-466-huIgG1Fc mAb | 8.9 | 4.7 |
| VHH-496-huIgG1Fc mAb | 13.5 | 5.1 |
| VHH-440-huIgG1Fc mAb | 11.12 | 6.24 |
| Anti-CD20 scFv-huIgG1Fc mAb | 75.3 | 41.1 |

TABLE 10

$EC_{50}$ of Anti-CD20 VHH-huIgG1Fc mAbs and
Anti-CD20 Fab-huIgG1Fc mAb
Binding with Raji Cells

| mAb | $EC_{50}$ (nM) On-target Raji cells |
| --- | --- |
| VHH-273-huIgG1Fc mAb | 14.28 |
| VHH-466-huIgG1Fc mAb | 9.12 |
| VHH-496-huIgG1Fc mAb | 16.00 |
| Anti-CD20 Fab-huIgG1Fc mAb | 13.51 |

6.5.2. Anti-CD20 VHH-huIgG1Fc mAb of Target Binding Assessment

To validate off-target binding, anti-CD20 VHH-huIgG1Fc mAbs were assessed with various human cell lines. The exemplary tested cell lines are listed in Table 11. The mAbs were incubated with $1\times10^5$ cells per well for 1 hour at 4° C. Then, the cells were washed with 200 μL of DPBS and 0.5% FBS and spun at 300 g for 5 mins at 4° C. The cells were stained with the detection antibody—PE-conjugated mouse anti-human IgG1 Fc (BioLegend, Cat. #409304, 1:100) for 30 mins at 4° C. The cells were then washed again and re-suspended with 200 μL of DPBS+0.5% FBS for flow cytometric analysis on a NovoCyte Flow Cytometer (ACEA Biosciences) and the FACS histogram data was analyzed with Novoexpress software. As for the above three exemplary anti-CD20 VHH-huIgG1Fc mAbs (VHH clone ID: VHH-273, VHH-466 and VHH-496), non-specific binding to off-target cells was not observed of at the concentration yielding maximum binding to Raji cell (Table 11).

TABLE 11

| Anti-CD20 VHH-huIgG1Fc mAbs Binding to Off-target Cell Lines | | | | |
| --- | --- | --- | --- | --- |
| Cell Line | ATCC ID | Primary Site | CD20 expression level | Anti-CD20 VHH-huIgG1Fc mAb Binding |
| Raji | CCL-86 | Lymphoid | + | + |
| Daudi | CCL-213 | Lymphoid | + | + |
| Nalm.6 | CRL-3273 | Lymphoid | – | – |
| RPMI-8226 | CCL-155 | Lymphoid | very low | very weak |
| Jurkat | TIB-152 | Lymphoid | – | – |
| K562 | CCL-243 | Bone marrow | – | – |
| HL-60 | CCL-240 | Peripheral blood | – | – |
| THP-1 | TIB-85 | Peripheral blood | – | – |
| U87-MG | HTB-14 | Brain/Neuron | – | – |
| IMR-32 | CCL-127 | Brain/Neuron | – | – |
| FaDu | HTB-43 | Pharynx | – | – |
| A-253 | HTB-41 | Salivary gland | – | – |
| SK-BR-3 | HTB-30 | Breast | – | – |
| A549 | CCL-185 | Lung | – | – |
| NCI-H446 | HTB-171 | Lung | – | – |
| HepG2 | HB-8065 | Liver | – | – |
| NCI-N87 | CRL-5822 | Stomach | – | – |
| HEK-293T | 632180 | Kidney | – | – |
| PANC-1 | CRL-1469 | Pancreas | – | – |
| HCT 116 | CCL-247 | Colorectal | – | – |
| SK-OV-3 | HTB-77 | Ovary | – | – |
| Hela | CCL-2 | Cervix | – | – |

TABLE 11-continued

| | | | CD20 expression | Anti-CD20 VHH- |
|---|---|---|---|---|
| Cell Line | ATCC ID | Primary Site | level | huIgG1Fc mAb Binding |

Anti-CD20 VHH-huIgG1Fc mAbs Binding to Off-target Cell Lines

| BeWo | CCL-98 | Placenta | – | – |
| A375 | CRL-1619 | Skin | – | – |
| U-2 OS | HTB-96 | Bone | – | – |

6.6. Example 6—Generation and Characterization of Humanized CD20 VHH CARS

6.6.1. Humanization of Anti-CD20 VHH Antibodies

To reduce the immunogenicity in human, camelid VHH antibodies were humanized, since much of the immune response occurs against the non-human antibody constant region. When different framework regions are combined with the camelid CDRs, chimeric human and camelid antibodies specific for the same antigen can elicit different effector functions, extending their therapeutic benefits. Mono-specific camelid VHHs were humanized by using sequence-based approaches and framework shuffling to most homologous human germline sequence or related scaffold. The non-compatibility of camelid CDRs being supported by non-native human framework scaffold and elimination of key conformational residues were resolved by in silico CDR-grafting, homology structural modeling (tertiary conformation & fold), sequence alignment, structure based- VHH was performed using the modeling software MODELLER. According to alignment with human germline gene, IGHV3-64*04 was chosen as one human acceptor for anti-CD20 VHH domains. Relative solvent accessibility of the amino acids was calculated according to the three-dimensional structure of the protein. If one of the amino acids of VHH was exposed to a solvent, it would be replaced with the original amino acid. The exemplary humanized VHH domains (e.g., huVHH-253, huVHH-256, huVHH-260, huVHH-746, huVHH-750, huVHH-753, huVHH-836, huVHH-840, huVHH-843, huVHH-846, 2082H1, 2082H2, 2082H3, 2082H4, 2082H5 and 2082H6) generated herein are shown in Table 2, and the corresponding sequences are provided in the Sequence Listing provided herein.

6.6.2. Characterization of Humanized CD20 VHH CAR-T Cells

Exemplary humanized CD20 VHH CARs (see Table 12) were generated using the method described above.

TABLE 12

Exemplary Humanized CD20 VHH CAR Constructs

| Exemplary humanized CAR Code | Amino Acid Sequence | Signal Peptide | Extracellular antigen binding domain | Hinge & TM | Co-stimulatory signaling domain | Primary intracellular signaling domain |
|---|---|---|---|---|---|---|
| huVHH-253 CAR | SEQ ID NO: 88 | CD8α | huVHH-253 | CD8α | CD137 | CD3ζ |
| huVHH-256 CAR | SEQ ID NO: 89 | CD8α | huVHH-256 | CD8α | CD137 | CD3ζ |
| huVHH-260 CAR | SEQ ID NO: 90 | CD8α | huVHH-260 | CD8α | CD137 | CD3ζ |
| huVHH-746 CAR | SEQ ID NO: 91 | CD8α | huVHH-746 | CD8α | CD137 | CD3ζ |
| huVHH-750 CAR | SEQ ID NO: 92 | CD8α | huVHH-750 | CD8α | CD137 | CD3ζ |
| huVHH-753 CAR | SEQ ID NO: 93 | CD8α | huVHH-753 | CD8α | CD137 | CD3ζ |
| huVHH-836 CAR | SEQ ID NO: 94 | CD8α | huVHH-836 | CD8α | CD137 | CD3ζ |
| huVHH-840 CAR | SEQ ID NO: 95 | CD8α | huVHH-840 | CD8α | CD137 | CD3ζ |
| huVHH-843 CAR | SEQ ID NO: 96 | CD8α | huVHH-843 | CD8α | CD137 | CD3ζ |
| huVHH-846 CAR | SEQ ID NO: 97 | CD8α | huVHH-846 | CD8α | CD137 | CD3ζ | back mutation design and reintroduction of key conformational residues from camelid VHH antibody. The antibody humanization process may not only eliminate steric clashes but also restore function in relation to binding affinity to its antigen.

Universal humanized VHH framework h-NbBcII10FGLA (Protein Data Bank, PDB code: 3EAK, https://www.rcsb.org/structure/3EAK) designed by Cecile Vincke et al. was adopted for humanization design based on sequence homology. The homologous modeling of camelid The humanized CD20 VHH CAR-T cells were generated by lentivirus transduction in PCP-34, T2,111 human primary T cells and were assessed by in vitro efficacy study according to the standard method. The transduced T cells showed different CAR expression levels (%) with humanized CD20 VHH CAR. Exemplary humanized CD20 VHH CAR-T cells' viability was about 90%-96%, CAR+ (%) was about 12%-43% and the expansion folds were within 35-74 in a 7-day culture, indicating that there was no detectable negative effect of humanized VHH on the T cells' capability to proliferate and expand when compared to the un-transduced T cells (UnT).

Humanized CD20 VHH CAR-T cells generated as described above were counted and co-cultured with antigen specific cancer cell lines to assess the killing potency, parental camelid CD20 VHH CAR-T cells and CD20 scFv CAR-T cells were used as control and the un-transduced T cells (UnT) were used as non-targeting T cells control. Humanized CD20 VHH CAR-T cell killing assyas were conducted towards CD20 positive cell lines—Raji (ATCC #CCL-86), K562-CD20 and negative cell line—K562 (ATCC #CCL-243). All the cell lines were engineered in-house to express firefly luciferase as a reporter for cell viability/killing. The transduced cells were selected with puromycin and refreshed by the selection culture medium (Eagle's Minimum Essential Medium supplemented with 10% FBS and 2 μg/mL of puromycin) in every 2-3 days. Post three rounds of selection, the selected cell clones were harvested and preserved for further use. The cytotoxicity of humanized CD20 VHH CAR-T cells was measured at an effector cells to target cells ratio (E:T) of 15:1, 10:1, 5:1 or 2.5:1 for 24 hours. Assays were initiated by mixing the respective number of T cells with a constant number of target cells. The remaining luciferase activity per well was assessed by ONE-Glo luciferase assay (Promega, Cat. #E6110) to quantify the remaining viable target cells per well.

The results showed that the humanized CD20 VHH CAR-T cells (including huVHH-746 CAR-T cells, huVHH-750 CAR-T cells, huVHH-753 CAR-T cells, huVHH-253 CAR-T cells, huVHH-256 CAR-T cells, and huVHH-260 CAR-T cells) induced lysis of antigen specific target cells and exhibited higher potency or maintained potency against the target cells (FIGS. 13A-13B, FIGS. 13D-13E and FIGS. 13H-13I). No significant cytotoxicity effect was detected against negative cell line—K562.Luc or Nalm.6.Luc by humanized CD20 VHH CAR-T cells as compared to UnT control (FIG. 13C, FIGS. 13F-13G and FIGS. 13J-13K).

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

---

What is claimed:

1. An anti-CD20 single domain antibody (sdAb) comprising:

(i) a CDR1 comprising the amino acid sequence of SEQ ID NO: 1 or 195; a CDR2 comprising the amino acid sequence of SEQ ID NO: 2; and a CDR3 comprising the amino acid sequence of SEQ ID NO: 3;

(ii) a CDR1 comprising the amino acid sequence of SEQ ID NO: 4; a CDR2 comprising the amino acid sequence of SEQ ID NO: 5; and a CDR3 comprising the amino acid sequence of SEQ ID NO: 6;

(iii) a CDR1 comprising the amino acid sequence of SEQ ID NO: 1 or 195; a CDR2 comprising the amino acid sequence of SEQ ID NO: 7; and a CDR3 comprising the amino acid sequence of SEQ ID NO: 8;

(iv) a CDR1 comprising the amino acid sequence of SEQ ID NO: 4; a CDR2 comprising the amino acid sequence of SEQ ID NO: 9; and a CDR3 comprising the amino acid sequence of SEQ ID NO: 10;

(v) a CDR1 comprising the amino acid sequence of SEQ ID NO: 11 or 196; a CDR2 comprising the amino acid sequence of SEQ ID NO: 12; and a CDR3 comprising the amino acid sequence of SEQ ID NO: 8;

(vi) a CDR1 comprising the amino acid sequence of SEQ ID NO: 13; a CDR2 comprising the amino acid sequence of SEQ ID NO: 9; and a CDR3 comprising the amino acid sequence of SEQ ID NO: 10;

(vii) a CDR1 comprising the amino acid sequence of SEQ ID NO: 14 or 197; a CDR2 comprising the amino acid sequence of SEQ ID NO: 15; and a CDR3 comprising the amino acid sequence of SEQ ID NO: 16;

(viii) a CDR1 comprising the amino acid sequence of SEQ ID NO: 17; a CDR2 comprising the amino acid sequence of SEQ ID NO: 18; and a CDR3 comprising the amino acid sequence of SEQ ID NO: 19;

(ix) a CDR1 comprising the amino acid sequence of SEQ ID NO: 20 or 197; a CDR2 comprising the amino acid sequence of SEQ ID NO: 21; and a CDR3 comprising the amino acid sequence of SEQ ID NO: 16;

(x) a CDR1 comprising the amino acid sequence of SEQ ID NO: 22; a CDR2 comprising the amino acid sequence of SEQ ID NO: 23; and a CDR3 comprising the amino acid sequence of SEQ ID NO: 19;

(xi) a CDR1 comprising the amino acid sequence of SEQ ID NO: 24 or 198; a CDR2 comprising the amino acid sequence of SEQ ID NO: 25; and a CDR3 comprising the amino acid sequence of SEQ ID NO: 26;

(xii) a CDR1 comprising the amino acid sequence of SEQ ID NO: 27; a CDR2 comprising the amino acid sequence of SEQ ID NO: 28; and a CDR3 comprising the amino acid sequence of SEQ ID NO: 29;

(xiii) a CDR1 comprising the amino acid sequence of SEQ ID NO: 14 or 197; a CDR2 comprising the amino acid sequence of SEQ ID NO: 30; and a CDR3 comprising the amino acid sequence of SEQ ID NO: 16;

(xiv) a CDR1 comprising the amino acid sequence of SEQ ID NO: 17; a CDR2 comprising the amino acid sequence of SEQ ID NO: 31; and a CDR3 comprising the amino acid sequence of SEQ ID NO: 19;

(xv) a CDR1 comprising the amino acid sequence of SEQ ID NO: 1 or 195; a CDR2 comprising the amino acid sequence of SEQ ID NO: 32; and a CDR3 comprising the amino acid sequence of SEQ ID NO: 3;

(xvi) a CDR1 comprising the amino acid sequence of SEQ ID NO: 4; a CDR2 comprising the amino acid sequence of SEQ ID NO: 33; and a CDR3 comprising the amino acid sequence of SEQ ID NO: 6;

(xvii) a CDR1 comprising the amino acid sequence of SEQ ID NO: 20 or 197; a CDR2 comprising the amino acid sequence of SEQ ID NO: 34; and a CDR3 comprising the amino acid sequence of SEQ ID NO: 16;

(xviii) a CDR1 comprising the amino acid sequence of SEQ ID NO: 22; a CDR2 comprising the amino acid sequence of SEQ ID NO: 35; and a CDR3 comprising the amino acid sequence of SEQ ID NO: 19;

(xix) a CDR1 comprising the amino acid sequence of SEQ ID NO: 20 or 197; a CDR2 comprising the amino acid sequence of SEQ ID NO: 36; and a CDR3 comprising the amino acid sequence of SEQ ID NO: 16;

(xx) a CDR1 comprising the amino acid sequence of SEQ ID NO: 20 or 197; a CDR2 comprising the amino acid sequence of SEQ ID NO: 37; and a CDR3 comprising the amino acid sequence of SEQ ID NO: 16;

(xxi) a CDR1 comprising the amino acid sequence of SEQ ID NO: 20 or 197; a CDR2 comprising the amino acid sequence of SEQ ID NO: 38; and a CDR3 comprising the amino acid sequence of SEQ ID NO: 16;

(xxii) a CDR1 comprising the amino acid sequence of SEQ ID NO: 4; a CDR2 comprising the amino acid sequence of SEQ ID NO: 33; and a CDR3 comprising the amino acid sequence of SEQ ID NO: 39;

(xxiii) a CDR1 comprising the amino acid sequence of SEQ ID NO: 4; a CDR2 comprising the amino acid sequence of SEQ ID NO: 33; and a CDR3 comprising the amino acid sequence of SEQ ID NO: 40;

(xxiv) a CDR1 comprising the amino acid sequence of SEQ ID NO: 165 or 199; a CDR2 comprising the amino acid sequence of SEQ ID NO: 166; and a CDR3 comprising the amino acid sequence of SEQ ID NO: 167;

(xxv) a CDR1 comprising the amino acid sequence of SEQ ID NO: 168; a CDR2 comprising the amino acid sequence of SEQ ID NO: 169; and a CDR3 comprising the amino acid sequence of SEQ ID NO: 170;

(xxvi) a CDR1 comprising the amino acid sequence of SEQ ID NO: 171 or 200; a CDR2 comprising the amino acid sequence of SEQ ID NO: 172; and a CDR3 comprising the amino acid sequence of SEQ ID NO: 173;

(xxvii) a CDR1 comprising the amino acid sequence of SEQ ID NO: 174; a CDR2 comprising the amino acid sequence of SEQ ID NO: 175; and a CDR3 comprising the amino acid sequence of SEQ ID NO: 176;

(xxviii) a CDR1 comprising the amino acid sequence of SEQ ID NO: 177 or 197; a CDR2 comprising the amino acid sequence of SEQ ID NO: 178; and a CDR3 comprising the amino acid sequence of SEQ ID NO: 179; or (xxix) a CDR1 comprising the amino acid sequence of SEQ ID NO: 180; a CDR2 comprising the amino acid sequence of SEQ ID NO: 181; and a CDR3 comprising the amino acid sequence of SEQ ID NO: 182.

2. An anti-CD20 single domain antibody (sdAb) comprising:

(i) a CDR1, a CDR2, and a CDR3 having the amino acid sequences of the CDR1, CDR2, and CDR3, respectively, as set forth in SEQ ID NO: 41;

(ii) a CDR1, a CDR2, and a CDR3 having the amino acid sequences of the CDR1, CDR2, and CDR3, respectively, as set forth in SEQ ID NO: 42;

(iii) a CDR1, a CDR2, and a CDR3 having the amino acid sequences of the CDR1, CDR2, and CDR3, respectively, as set forth in SEQ ID NO: 43;

(iv) a CDR1, a CDR2, and a CDR3 having the amino acid sequences of the CDR1, CDR2, and CDR3, respectively, as set forth in SEQ ID NO: 44;

(v) a CDR1, a CDR2, and a CDR3 having the amino acid sequences of the CDR1, CDR2, and CDR3, respectively, as set forth in SEQ ID NO: 45;

(vi) a CDR1, a CDR2, and a CDR3 having the amino acid sequences of the CDR1, CDR2, and CDR3, respectively, as set forth in SEQ ID NO: 46;

(vii) a CDR1, a CDR2, and a CDR3 having the amino acid sequences of the CDR1, CDR2, and CDR3, respectively, as set forth in SEQ ID NO: 47;

(viii) a CDR1, a CDR2, and a CDR3 having the amino acid sequences of the CDR1, CDR2, and CDR3, respectively, as set forth in SEQ ID NO: 48;

(ix) a CDR1, a CDR2, and a CDR3 having the amino acid sequences of the CDR1, CDR2, and CDR3, respectively, as set forth in SEQ ID NO: 49;

(x) a CDR1, a CDR2, and a CDR3 having the amino acid sequences of the CDR1, CDR2, and CDR3, respectively, as set forth in SEQ ID NO: 50;

(xi) a CDR1, a CDR2, and a CDR3 having the amino acid sequences of the CDR1, CDR2, and CDR3, respectively, as set forth in SEQ ID NO: 51;

(xii) a CDR1, a CDR2, and a CDR3 having the amino acid sequences of the CDR1, CDR2, and CDR3, respectively, as set forth in SEQ ID NO: 52;

(xiii) a CDR1, a CDR2, and a CDR3 having the amino acid sequences of the CDR1, CDR2, and CDR3, respectively, as set forth in SEQ ID NO: 53;

(xiv) a CDR1, a CDR2, and a CDR3 having the amino acid sequences of the CDR1, CDR2, and CDR3, respectively, as set forth in SEQ ID NO: 54;

(xv) a CDR1, a CDR2, and a CDR3 having the amino acid sequences of the CDR1, CDR2, and CDR3, respectively, as set forth in SEQ ID NO: 55;

(xvi) a CDR1, a CDR2, and a CDR3 having the amino acid sequences of the CDR1, CDR2, and CDR3, respectively, as set forth in SEQ ID NO: 56;

(xvii) a CDR1, a CDR2, and a CDR3 having the amino acid sequences of the CDR1, CDR2, and CDR3, respectively, as set forth in SEQ ID NO: 57;

(xviii) a CDR1, a CDR2, and a CDR3 having the amino acid sequences of the CDR1, CDR2, and CDR3, respectively, as set forth in SEQ ID NO: 58;

(xix) a CDR1, a CDR2, and a CDR3 having the amino acid sequences of the CDR1, CDR2, and CDR3, respectively, as set forth in SEQ ID NO: 59;

(xx) a CDR1, a CDR2, and a CDR3 having the amino acid sequences of the CDR1, CDR2, and CDR3, respectively, as set forth in SEQ ID NO: 60;

(xxi) a CDR1, a CDR2, and a CDR3 having the amino acid sequences of the CDR1, CDR2, and CDR3, respectively, as set forth in SEQ ID NO: 61;

(xxii) a CDR1, a CDR2, and a CDR3 having the amino acid sequences of the CDR1, CDR2, and CDR3, respectively, as set forth in SEQ ID NO: 62;

(xxiii) a CDR1, a CDR2, and a CDR3 having the amino acid sequences of the CDR1, CDR2, and CDR3, respectively, as set forth in SEQ ID NO: 63;

(xxiv) a CDR1, a CDR2, and a CDR3 having the amino acid sequences of the CDR1, CDR2, and CDR3, respectively, as set forth in SEQ ID NO: 183;

(xxv) a CDR1, a CDR2, and a CDR3 having the amino acid sequences of the CDR1, CDR2, and CDR3, respectively, as set forth in SEQ ID NO: 184; or (xxvi) a CDR1, a CDR2, and a CDR3 having the amino acid sequences of the CDR1, CDR2, and CDR3, respectively, as set forth in SEQ ID NO: 185.

3. The anti-CD20 sdAb of claim 2, wherein the CDR1, CDR2 or CDR3 are determined according to the Kabat numbering scheme, the IMGT numbering scheme, the AbM numbering scheme, the Chothia numbering scheme, the Contact numbering scheme, or a combination thereof.

4. The anti-CD20 sdAb of claim 1, further comprising one or more FR regions as set forth in SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184 and/or SEQ ID NO: 185.

5. The anti-CD20 sdAb of claim 1, wherein anti-CD20 sdAb: (i) comprises the amino acid sequence of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184 or SEQ ID NO: 185; or (ii) consists of an amino acid sequence having at least 75%, 80%, 85%, 90%, 95%, 96%, 97%, 98%, 99%, or more sequence identity with the sequence of SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 63, SEQ ID NO: 183, SEQ ID NO: 184 or SEQ ID NO: 185.

6. The anti-CD20 sdAb of claim 1, wherein anti-CD20 sdAb is a camelid sdAb or a humanized sdAb.

7. The anti-CD20 sdAb of claim 1, wherein the anti-CD20 sdAb is genetically fused or chemically conjugated to an agent.

8. A chimeric antigen receptor (CAR), comprising:
(a) an extracellular antigen binding domain comprising the anti-CD20 sdAb of claim 1;
(b) a transmembrane domain; and
(c) an intracellular signaling domain.

9. The CAR of claim 8, wherein the extracellular antigen binding domain further comprises one or more additional antigen binding domain(s) binding to one or more antigen(s) selected from a group consisting of CD20, CD19, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

10. The CAR of claim 9, wherein the extracellular antigen binding domain comprises two or three of the anti-CD20 sdAbs.

11. The CAR of claim 8, further comprising a hinge domain located between the C-terminus of the extracellular antigen binding domain and the N-terminus of the transmembrane domain.

12. The CAR of claim 8, further comprising a signal peptide located at the N-terminus of the polypeptide.

13. A chimeric antigen receptor (CAR), comprising (i) an amino acid sequence selected from the group consisting of SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 189, SEQ ID NO: 190, and SEQ ID NO: 191; or (ii) an amino acid sequence having at least 75%, 80%, 85%, 90%, 95%, 96%, 97%, 98%, 99%, or more sequence identity with the sequence of SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 189, SEQ ID NO: 190, or SEQ ID NO: 191.

14. An isolated nucleic acid comprising a nucleic acid sequence encoding the CAR of claim 8.

15. A vector comprising the isolated nucleic acid of claim 14.

16. An engineered immune effector cell, comprising the CAR of claim 8.

17. The engineered immune effector cell of claim 16, wherein the immune effector cell is a T cell or B cell.

18. A pharmaceutical composition, comprising the engineered immune effector cell of claim 16, and a pharmaceutically acceptable excipient.

19. A method of treating a disease or disorder in a subject, comprising administering to the subject an effective amount of the engineered immune effector cell of claim 16, wherein the disease or disorder is a B cell associated disease or disorder and/or CD20 associated disease or disorder.

20. The method of claim 19, wherein the disease or disorder is selected from a group consisting of marginal zone lymphoma, diffuse large B cell lymphoma (DLBCL), mantle cell lymphoma (MCL), primary central nervous system (CNS) lymphoma, primary mediastinal B cell lymphoma (PMBL), small lymphocytic lymphoma (SLL), B cell prolymphocytic leukemia (B-PLL), follicular lymphoma (FL), burkitt lymphoma, primary intraocular lymphoma, chronic lymphocytic leukemia (CLL), acute lymphoblastic leukemia (ALL), hairy cell leukemia (HCL), precursor B lymphoblastic leukemia, non-hodgkin lymphoma (NHL), high-grade B-cell lymphoma (HGBL), and multiple myelomia (MM).

* * * * *